(12) United States Patent
Wang et al.

(10) Patent No.: US 11,111,245 B2
(45) Date of Patent: Sep. 7, 2021

(54) DERIVATIVES OF N-CYCLOALKYL/HETEROCYCLOALKYL-4-(IMIDAZO[1,2-A]PYRIDINE)PYRIMIDIN-2-AMINE AS THERAPEUTIC AGENTS

(71) Applicant: Aucentra Therapeutics Pty Ltd, Dulwich (AU)

(72) Inventors: Shudong Wang, Adelaide (AU); Sarah Al Haj Diab, St Peters (AU); Yi Long, Adelaide (AU)

(73) Assignee: Aucentra Therapeutics Pty Ltd, Dulwich (AU)

( * ) Notice: Subject to any disclaimer, the term of this patent is extended or adjusted under 35 U.S.C. 154(b) by 0 days.

(21) Appl. No.: 16/482,867

(22) PCT Filed: Feb. 1, 2018

(86) PCT No.: PCT/AU2018/000011
§ 371 (c)(1),
(2) Date: Aug. 1, 2019

(87) PCT Pub. No.: WO2018/141002
PCT Pub. Date: Aug. 9, 2018

(65) Prior Publication Data
US 2020/0231586 A1    Jul. 23, 2020

(30) Foreign Application Priority Data
Feb. 1, 2017    (AU) .............................. 2017900290

(51) Int. Cl.
*C07D 471/04*    (2006.01)
*A61K 31/437*    (2006.01)
*A61K 31/506*    (2006.01)
*A61P 35/00*    (2006.01)

(52) U.S. Cl.
CPC ............ *C07D 471/04* (2013.01); *A61P 35/00* (2018.01)

(58) Field of Classification Search
CPC .. C07D 471/04; A61K 31/437; A61K 31/506; A61P 35/00
See application file for complete search history.

(56) References Cited

U.S. PATENT DOCUMENTS

| 8,569,306 B2 | 10/2013 | Buettelmann et al. |
| 2010/0105655 A1 | 4/2010 | Ducray et al. |

FOREIGN PATENT DOCUMENTS

| WO | 97/22596 | 6/1997 |
| WO | 97/30035 | 8/1997 |
| WO | 97/32856 | 9/1997 |
| WO | 98/13354 | 4/1998 |
| WO | 99/02166 | 1/1999 |
| WO | 00/40529 | 7/2000 |
| WO | 00/41669 | 7/2000 |
| WO | 00/47212 | 8/2000 |
| WO | 01/92224 | 12/2001 |
| WO | 01/94341 | 12/2001 |
| WO | 02/04434 | 1/2002 |
| WO | 02/08213 | 1/2002 |
| WO | 03-000682 | 1/2003 |
| WO | 03-000689 | 1/2003 |
| WO | 03-031446 | 4/2003 |
| WO | 2006-038001 | 4/2006 |
| WO | 2010/009155 A2 | 1/2010 |
| WO | 2015-154039 | 10/2015 |
| WO | 2017/020065 | 2/2017 |

OTHER PUBLICATIONS

International Search Report and Written Opinion dated Oct. 22, 2018, from International Application No. PCT/AU2018/000011, 14 pages.
Alam, M. et al. "Synthesis and SAR of aminopyrimidines as novel c-Jun N-terminal kinase (JNK) inhibitors", Bioorganic & Medicinal Chemistry Letters, 2007, vol. 17, No. 12, pp. 3463-3467.
Palmer, W.S. et al. "Development of amino-pyrimidine inhibitors of c-Jun N-terminal kinase (JNK): Kinase profiling guided optimization of a 1,2,3-benzotriazole lead", Bioorganic & Medicinal Chemistry Letters, 2013, vol. 23, No. 5, pp. 1486-1492.
Buckley, G.M. et al. "IRAK-4 inhibitors. Part II A structured-based assessment of imidazo[1,2-alpyridine binding", Bioorganic & Medicinal Chemistry Letters, 2008, vol. 18, No. 11, pp. 3291-3295.

(Continued)

*Primary Examiner* — Bruck Kifle
(74) *Attorney, Agent, or Firm* — Meunier Carlin & Curfman LLC

(57) ABSTRACT

A novel class of inhibitors of protein kinases that are useful in the treatment of cell proliferative diseases and conditions, and especially those characterised by over-expression of one or more CDK enzyme and/or by one or more aberrant CDK activity, including certain cancers of lung, breast, brain, ovary, prostate, colorectal cancer and leukaemias. The inhibitors have the general structure (I).

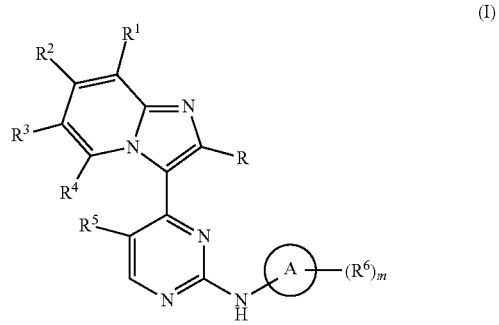

18 Claims, No Drawings

(56) References Cited

OTHER PUBLICATIONS

Wang, S. et al. "Cyclin-dependent kinase 9: a key transcriptional regulator and potential drug target in oncology, virology and cardiology", Trends in Pharmacological Sciences vol. 26, No. 6, pp. 302-313.

Gudmundsson et al., Bioorg Med Chem Lett 17(10):2735-2739, 2007.

European Search Report for Application No. 18748523.0, dated Nov. 3, 2020.

DERIVATIVES OF N-CYCLOALKYL/HETEROCYCLOALKYL-4-(IMIDAZO[1,2-A]PYRIDINE)PYRIMIDIN-2-AMINE AS THERAPEUTIC AGENTS

TECHNICAL FIELD

The present invention relates to a novel class of inhibitors of protein kinases useful in the treatment of proliferative cell diseases and conditions including cancers.

PRIORITY DOCUMENT

The present application claims priority from Australian Provisional Patent Application No 2017900290 titled "Pyrimidin-2-amine derivatives as therapeutic compounds" filed on 1 Feb. 2017, the content of which is hereby incorporated by reference in its entirety.

INCORPORATION BY REFERENCE

The following publication is referred to herein and its contents are hereby incorporated by reference in their entirety:

International Patent Publication No PCT/GB2009/051447 (WO 2010/049731) titled "Pyrazolo- and imidazopyrdinylpyrimidineamines as IGF-1R tyrosine kinase inhibitors" in the name of AstraZeneca AB.

BACKGROUND

Protein kinases regulate various biological functions, including DNA replication, transcription, translation, cell cycle progression, energy metabolism, migration, and cell growth, making them excellent targets for treating proliferative diseases and conditions including cancers. New compounds, which inhibit the activity of protein kinases and are effective as therapeutic anti-proliferative agents, are still needed.

Cyclin-dependent kinases (CDKs) are serine-threonine protein kinases that associated with various cyclin subunits. There are more than 20 CDKs which may be classified according to their main functions. That is, CDK1, CDK2, CDK3, CDK4 and CDK6 and their cyclin partners (eg cyclin A, B, D1, D2, D3, E and F) are known to be involved in the control of cell cycle progression, and are thus considered to be cell cycle regulators. On the other hand, CDK7, CDK8, CDK9 and CDK11 and their associated cyclin partners (eg cyclin C, H, K, L1, L2, T1 and T2), are considered to be transcriptional regulators. CDKs are thus involved in the regulation of cell-cycle control, apoptosis, neuronal physiology, differentiation, and transcription. As such, the use of CDK inhibitors in the treatment of various diseases, including cancers, cardiovascular disorders, inflammatory diseases, neurodegenerative diseases and viral diseases, is of considerable interest (Wang, S et al., *Trends Pharmacol Sci* 29(6):302-313, 2008).

Palbociclib (6-Acetyl-8-cyclopentyl-5-methyl-2-{[5-(1-piperazinyl)-2-pyridinyl]amino)}pyrido[2,3-d]pyrimidin-7(8H)-one), an inhibitor of CDK4 and CDK6, is one specific example of a CDK inhibitor that is now available for the treatment of a proliferative cell disease, particularly estrogen-positive, HER2-negative advanced breast cancer. However, numerous other CDK inhibitors have been described with potential as agents for treating proliferative cell diseases and conditions including cancers. For example, the present applicant has previously disclosed N-(pyridin-2-yl)-4-(thiazol-5-yl)pyrimidin-2-amine compounds (see International Patent Publication Nos WO 2017/020065). These compounds inhibit multiple protein kinases, particularly CDKs, including CDK4/cyclin D1 and CDK6/cyclin D3.

The present applicant has now identified a new class of N-cylcloalkyl/heterocycloalkyl-4-(imidazo[1,2-a]pyridine)pyrimidin-2-amine compounds, for use in the prevention and/or treatment of various diseases and conditions including proliferative diseases and conditions such as cancers.

SUMMARY

According to a first aspect of the present invention, there is provided a compound of formula I shown below:

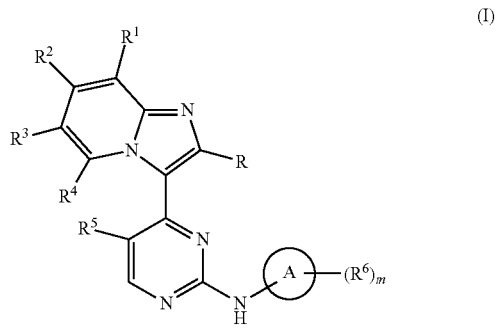

(I)

wherein:
A is a cycloalkyl or heterocycloalkyl, optionally substituted by one or more $R^6$ groups such that m is an integer from 0 to 5 inclusive, and wherein said heterocycloalkyl comprises at least one but no more than two heteroatoms selected from N, O and S; and wherein $R, R^1, R^2, R^3, R^4, R^5$ and $R^6$ are each independently selected from the group consisting of H, alkyl, alkyl-$R^9$, heteroalkyl, cycloalkyl, heterocycloalkyl, aryl, heteroaryl, $CH_2$-heteroaryl, aralkyl, halogen, $NO_2$, CN, $CF_3$, OH, O-alkyl, O-alkyl-$R^7$, O-heteroalkyl, O-cycloalkyl, O-heterocycloalkyl, O-aryl, O-heteroaryl, O—$R^7$, $NH_2$, NH-alkyl, NH-alkyl-$R^7$, NH-heteroalkyl, NH-cycloalkyl, NH-heterocycloalkyl, NH-aryl, NH-heteroaryl, NH—$R^7$, NHO-aryl, NH)-heteroaryl, $NHCH_2$-aryl, N-(alkyl)$_2$, N-(heteroalkyl)$_2$, N-(cycloalkyl)$_2$, N-(heterocycloalkyl)$_2$, N-(aryl)$_2$, N-(heteroaryl)$_2$, N—($R^7$)($R^8$), N-(alkyl)($R^7$), N-(heteroalkyl)($R^7$), N-(cycloalkyl)($R^7$), N-(heterocycloalkyl)($R^7$), N-(aryl)($R^7$), N-(heteroaryl)($R^7$), SH-alkyl, SH-alkyl-$R^7$, SH-heteroalkyl, SH-cycloalkyl, SH-heterocycloalkyl, SH-aryl, SH-heteroaryl, S-(alkyl)$_2$, S-heteroalkyl, S-(cycloalkyl)$_2$, S-(heterocycloalkyl)$_2$, S-(aryl)$_2$, S-(heteroaryl)$_2$, S-(alkyl)(aryl), SH—$R^7$, S—($R^7$)($R^8$), S-(alkyl)($R^7$), S-(heteroaryl)($R^7$), S-(cycloalkyl)($R^7$), S-(heterocycloalkyl)($R^7$), S-(aryl)($R^7$), S-(heteroaryl)($R^7$), COOH, $CONH_2$, CONH-alkyl, CONH-aryl, CON-(alkyl)($R^7$), CON(aryl)($R^7$), CON(heteroaryl)($R^7$), CONH—$R^7$, CON—($R^7$)($R^8$), $SO_3H$, $SO_2$-alkyl, $SO_2$-alkyl-$R^7$, $SO_2$-aryl, $SO_2$-aryl-$R^7$, $SO_2NH_2$, $SO_2NH$—$R^7$, $SO_2N$—($R^7$)($R^8$), CO-alkyl, CO-alkyl-$R^7$, CO-aryl, CO-aryl-$R^7$, CO—$R^7$, $COOR^7$, and $R^9$, and wherein $R^7$ and $R^8$ are each independently selected from the group consisting of H, alkyl, alkyl-$R^{10}$, heteroalkyl, cycloalkyl, heterocycloalkyl, aryl, heteroaryl, aralkyl, halogen, $NO_2$, CN, $CF_3$, OH, O-alkyl, O-alkyl-$R^{10}$, O-heteroalkyl, O-cycloalkyl, O-heterocycloalkyl, O-aryl, O-heteroaryl, O—$R^{10}$, $NH_2$, NH-alkyl, NH-alkyl-$R^{10}$, NH-heteroalkyl, NH-cycloalkyl, NH-heterocycloalkyl, NH-aryl, NH-heteroaryl, NH—$R^{10}$, N-(alkyl)$_2$, N-(heteroalkyl)$_2$, N-(cycloalkyl)$_2$, N-(heterocycloalkyl)$_2$, N-(aryl)$_2$, N-(heteroaryl)$_2$, N—(R$^{10}$)(R$^{11}$), N-(alkyl)(R$^{10}$), N-(heteroalkyl)(R$^{10}$), N-(cycloalkyl)(R$^{10}$), N-(heterocycloalkyl)(R$^{10}$), N-(aryl)(R$^{10}$), N-(heteroaryl)(R$^{10}$), SH-alkyl, SH-alkyl-R$^{10}$, SH-heteroalkyl, SH-cycloalkyl, SH-heterocycloalkyl, SH-aryl, SH-heteroaryl, S-(alkyl)$_2$, S-(cycloalkyl)$_2$, S-(heterocycloalkyl)$_2$, S-(aryl)$_2$, S-(heteroaryl)$_2$, S-(alkyl)(aryl), SH—R$^{10}$, S—(R$^{10}$)(R$^{11}$), S-(alkyl)(R$^{10}$), S-(heteroaryl)(R$^{10}$), S-(cycloalkyl)(R$^{10}$), S-(heterocycloalkyl)(R$^{10}$), S-(aryl)(R$^{10}$), S-(heteroaryl)(R$^{10}$), COOH, COO-alkyl, CONH$_2$, CONH-alkyl, CONH-aryl, CON-(alkyl)(R$^{10}$), CON(aryl)(R$^{10}$), CON(heteroaryl)(R$^{10}$), CONH—R$^{10}$, CON—(R$^{10}$)(R$^{11}$), SO$_3$H, SO$_2$-alkyl, SO$_2$-alkyl-R$^{10}$, SO$_2$-aryl, SO$_2$-aryl-R$^{10}$, SO$_2$NH$_2$, SO$_2$NH—R$^{10}$, SO$_2$N—(R$^{10}$)(R$^{11}$), CO-alkyl, CO-alkyl-R$^{10}$, CO-aryl, CO-aryl-R$^{10}$, CO—R$^{10}$, COOR$^{10}$, and R$^9$, and wherein said heterocycloalkyl and heteroaryl groups comprises at least one but no more than two heteroatoms selected from N, S and O, and wherein said alkyl, heteroalkyl, cycloalkyl, heterocycloalkyl, aralkyl, aryl and heteroaryl groups may be optionally substituted with one or more groups selected from halogen, CN, OH, O-methyl, NH$_2$, COOH, CONH$_2$, CF$_3$ and SO$_2$N(CH$_3$)$_2$; and
R$^9$, R$^{10}$ and R$^{11}$ are independently selected from water solubilising groups;
or a pharmaceutically acceptable salt, solvate or prodrug thereof.

In a second aspect, the present invention provides the use of a compound as defined in the first aspect or a pharmaceutically acceptable salt, solvate or prodrug thereof, for treating cancer or another proliferative cell disease or condition.

In a third aspect, the present invention provides a method of treating cancer or another proliferative cell disease or condition in a subject, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

In a fourth aspect, the present invention provides the use of a compound as defined in the first aspect, or a pharmaceutically acceptable salt, solvate or prodrug thereof, in the manufacture of a medicament for treating cancer or another proliferative cell disease or condition.

In a fifth aspect, the present invention provides a pharmaceutical composition or medicament comprising a compound as defined in the first aspect and a pharmaceutically acceptable carrier, diluent and/or excipient.

In a sixth aspect, the present invention provides a method for modulating protein kinase activity in a cell, comprising introducing to or contacting said cell with an effective amount of a compound as defined in the first aspect or a pharmaceutically acceptable salt, solvate or prodrug thereof.

In a seventh aspect, the present invention provides the use of a compound as defined in the first aspect or a pharmaceutically acceptable salt, solvate or prodrug thereof, for treating a disease or condition.

In an eighth aspect, the present invention provides a method of treating a disease or condition in a subject, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

In a ninth aspect, the present invention provides the use of a compound as defined in the first aspect, or a pharmaceutically acceptable salt, solvate or prodrug thereof, in the manufacture of a medicament for treating a disease or condition in a subject.

The disease or condition referred to in any of the above aspects may be characterised by over-expression of one or more CDK enzyme and/or by one or more aberrant CDK activity. Otherwise, said disease or condition may be one which may be beneficially treated by inhibiting one or more CDK (eg by inhibiting the activity and/or expression of one or more of CDK1, CDK2, CDK4, CDK6, CDK7 and CDK9, and/or the association of one or more of such CDK enzymes with their respective cyclin/mediator complex).

DETAILED DESCRIPTION

The present applicant has now identified a new class of N-cylcloalkyl/heterocycloalkyl-4-(imidazo[1,2-a]pyridine)pyrimidin-2-amine derivatives suitable for use in the prevention and/or treatment of various diseases and conditions including proliferative cell diseases and conditions such as cancers, which possess desirable biological activity (eg the compounds may inhibit cell proliferation by inhibiting the activity of CDKs, FMS-like tyrosine kinases (FLTs), aurora kinases and/or CDC-like kinases (CLKs)).

In a first aspect, the present invention provides a compound of formula I shown below:

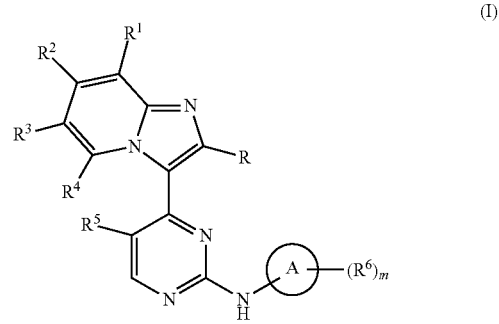

wherein:
A is a cycloalkyl or heterocycloalkyl, optionally substituted by one or more R$^6$ groups such that m is an integer from 0 to 5 inclusive, and wherein said heterocycloalkyl comprises at least one but no more than two heteroatoms selected from N, O and S; and wherein
R, R$^1$, R$^2$, R$^3$, R$^4$, R$^5$ and R$^6$ are each independently selected from the group consisting of H, alkyl, alkyl-R$^7$, heteroalkyl, cycloalkyl, heterocycloalkyl, aryl, heteroaryl, CH$_2$-heteroaryl, aralkyl, halogen, NO$_2$, CN, CF$_3$, OH, O-alkyl, O-alkyl-R$^7$, O-heteroalkyl, O-cycloalkyl, O-heterocycloalkyl, O-aryl, O-heteroaryl, O—R$^9$, NH$_2$, NH-alkyl, NH-alkyl-R$^7$, NH-heteroalkyl, NH-cycloalkyl, NH-heterocycloalkyl, NH-aryl, NH-heteroaryl, NH—R$^7$, NHO-aryl, NH)-heteroaryl, NHCH$_2$-aryl, N-(alkyl)$_2$, N-(heteroalkyl)$_2$, N-(cycloalkyl)$_2$, N-(heterocycloalkyl)$_2$, N-(aryl)$_2$, N-(heteroaryl)$_2$, N—(R$^7$)(R$^8$), N-(alkyl)(R$^7$), N-(heteroalkyl)(R$^7$), N-(cycloalkyl)(R$^7$), N-(heterocycloalkyl)(R$^7$), N-(aryl)(R$^7$), N-(heteroaryl)(R$^7$), SH-alkyl, SH-alkyl-R$^7$, SH-heteroalkyl, SH-cycloalkyl, SH-heterocycloalkyl, SH-aryl, SH-heteroaryl, S-(alkyl)$_2$, S-heteroalkyl, S-(cycloalkyl)$_2$, S-(heterocycloalkyl)$_2$, S-(aryl)$_2$, S-(heteroaryl)$_2$, S-(alkyl)(aryl), SH—R$^7$, S—(R$^7$)(R$^8$), S-(alkyl)(R$^7$), S-(heteroaryl)(R$^7$), S-(cycloalkyl)(R$^7$), S-(heterocycloalkyl)(R$^7$), S-(aryl)(R$^7$), S-(heteroaryl)(R$^7$), COOH, CONH$_2$, CONH-alkyl, CONH-aryl, CON-(alkyl)($R^7$), CON(aryl)($R^7$), CON(heteroaryl) ($R^7$), CONH—$R^7$, CON—($R^7$)($R^8$), $SO_3H$, $SO_2$-alkyl, $SO_2$-alkyl-$R^7$, $SO_2$-aryl, $SO_2$-aryl-$R^7$, $SO_2NH_2$, $SO_2NH$—$R^7$, $SO_2N$—($R^7$)($R^8$), CO-alkyl, CO-alkyl-$R^7$, CO-aryl, CO-aryl-$R^7$, CO—$R^7$, COO$R^7$, and $R^9$, and wherein $R^7$ and $R^9$ are each independently selected from the group consisting of H, alkyl, alkyl-$R^{10}$, heteroalkyl, cycloalkyl, heterocycloalkyl, aryl, heteroaryl, aralkyl, halogen, $NO_2$, CN, $CF_3$, OH, O-alkyl, O-alkyl-$R^{10}$, O-heteroalkyl, O-cycloalkyl, O-heterocycloalkyl, O-aryl, O-heteroaryl, O—$R^{10}$, $NH_2$, NH-alkyl, NH-alkyl-$R^{10}$, NH-heteroalkyl, NH-cycloalkyl, NH-heterocycloalkyl, NH-aryl, NH-heteroaryl, NH—$R^{10}$, N-(alkyl)$_2$, N-(heteroalkyl)$_2$, N-(cycloalkyl)$_2$, N-(heterocycloalkyl)$_2$, N-(aryl)$_2$, N-(heteroaryl)$_2$, N—($R^{10}$)($R^{11}$), N-(alkyl)($R^{10}$), N-(heteroalkyl)($R^{10}$), N-(cycloalkyl)($R^0$), N-(heterocycloalkyl)($R^{10}$), N-(aryl)($R^{10}$), N-(heteroaryl)($R^{10}$), SH-alkyl, SH-alkyl-$R^{10}$, SH-heteroalkyl, SH-cycloalkyl, SH-heterocycloalkyl, SH-aryl, SH-heteroaryl, S-(alkyl)$_2$, S-(cycloalkyl)$_2$, S-(heterocycloalkyl)$_2$, S-(aryl)$_2$, S-(heteroaryl)$_2$, S-(alkyl)(aryl), SH—$R^{10}$, S—($R^{10}$)($R^{11}$), S-(alkyl)($R^{10}$), S-(heteroaryl)($R^{10}$), S-(cycloalkyl)($R^{10}$), S-(heterocycloalkyl)($R^{10}$), S-(aryl)($R^{10}$), S-(heteroaryl)($R^{10}$), COOH, COO-alkyl, $CONH_2$, CONH-alkyl, CONH-aryl, CON-(alkyl)($R^{10}$), CON(aryl)($R^{10}$), CON(heteroaryl)($R^{10}$), CONH—$R^{10}$, CON—($R^{10}$)($R^{11}$), $SO_3H$, $SO_2$-alkyl, $SO_2$-alkyl-$R^{10}$, $SO_2$-aryl, $SO_2$-aryl-$R^{10}$, $SO_2NH_2$, $SO_2NH$—$R^{10}$, $SO_2N$—($R^{10}$)($R^{11}$), CO-alkyl, CO-alkyl-$R^{10}$, CO-aryl, CO-aryl-$R^{10}$, CO—$R^{10}$, and COO$R^{10}$, and $R^9$, and wherein said heterocycloalkyl and heteroaryl groups comprises at least one but no more than two heteroatoms selected from N, S and O, and wherein said alkyl, heteroalkyl, cycloalkyl, heterocycloalkyl, aralkyl, aryl and heteroaryl groups may be optionally substituted with one or more groups selected from halogen, CN, OH, O-methyl, $NH_2$, COOH, $CONH_2$, $CF_3$ and $SO_2N(CH_3)_2$; and $R^9$, $R^{10}$ and $R^{11}$ are independently selected from water solubilising groups;

or a pharmaceutically acceptable salt, solvate or prodrug thereof.

The compounds of formula I have been found to possess anti-proliferative activity and are therefore considered to be of use in the treatment of proliferative cell diseases and conditions such as cancers (including, for example, leukaemia and lymphoma) and other diseases and conditions associated with uncontrolled cell proliferation such as, for example, some cardiovascular diseases or conditions such as restenosis and cardiomyopathy, some auto-immune diseases such as glomerulonephritis and rheumatoid arthritis, dermatological conditions such as psoriasis, and fungal or parasitic disorders. As used herein, an anti-proliferative effect within the scope of the present invention may be demonstrated by the ability to inhibit cell proliferation in an in vitro whole cell assay. These assays, including methods for their performance, are described in more detail in the examples provided hereinafter.

The compounds of formula I may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of formula I may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

Thus, in a second aspect, the present invention provides the use of a compound as defined in the first aspect or a pharmaceutically acceptable salt, solvate or prodrug thereof, for treating cancer or another proliferative cell disease or condition.

In a third aspect, the present invention provides a method of treating cancer or another proliferative cell disease or condition in a subject, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

In a fourth aspect, the present invention provides the use of a compound as defined in the first aspect, or a pharmaceutically acceptable salt, solvate or prodrug thereof, in the manufacture of a medicament for treating cancer or another proliferative cell disease or condition.

In a fifth aspect, the present invention provides a pharmaceutical composition or medicament comprising a compound as defined in the first aspect and a pharmaceutically acceptable carrier, diluent and/or excipient.

In a sixth aspect, the present invention provides a method for modulating protein kinase activity in a cell, comprising introducing to or contacting said cell with an effective amount of a compound as defined in the first aspect or a pharmaceutically acceptable salt, solvate or prodrug thereof.

In a seventh aspect, the present invention provides the use of a compound as defined in the first aspect or a pharmaceutically acceptable salt, solvate or prodrug thereof, for treating a disease or condition in a subject.

In an eighth aspect, the present invention provides a method of treating a disease or condition in a subject, the method comprising administering to said subject a therapeutically effective amount of a compound as defined in the first aspect or a pharmaceutically acceptable salt, solvate or prodrug thereof, optionally in combination with a pharmaceutically acceptable carrier, diluent and/or excipient.

In a ninth aspect, the present invention provides the use of a compound as defined in the first aspect, or a pharmaceutically acceptable salt, solvate or prodrug thereof, in the manufacture of a medicament for treating a disease or condition in a subject.

In this specification, a number of terms are used which are well known to those skilled in the art. Nevertheless, for the purposes of clarity, a number of these terms are hereinafter defined.

As used herein, the term "treating" includes prophylaxis as well as the alleviation of established symptoms of a condition. As such, the act of "treating" a disease or condition therefore includes: (1) preventing or delaying the appearance of clinical symptoms of the disease or condition developing in a subject afflicted with or predisposed to the disease or condition; (2) inhibiting the disease or condition (ie arresting, reducing or delaying the development of the disease or condition or a relapse thereof (in case of a maintenance treatment) or at least one clinical or subclinical symptom thereof; and (3) relieving or attenuating the disease or condition (ie causing regression of the disease or condition or at least one of its clinical or subclinical symptoms).

As used herein, the term "alkyl" includes both straight chain and branched alkyl groups having from 1 to 8 carbon atoms (eg methyl, ethyl propyl, isopropyl, butyl, isobutyl, tert-butyl, pentyl, hexyl etc).

As used herein, the term "heteroalkyl" refers to both straight chain and branched alkyl groups wherein one or more carbon atoms are replaced by an O-, N- or S-atom (eg 1-methoxypropanyl, methyl propionate etc).

As used herein, the term "cycloalkyl" represents cyclic versions of alkyl (cyclopropyl, cyclopentyl, cyclohexyl etc), and may include fused rings. Cycloalkyl groups are unsubstituted, but may be substituted with those groups typically suitable for alkyl group substituents.

As used herein, the term "heterocycloalkyl" or "heterocyclic" represents a cycloalkyl containing at least one annular carbon and at least one annular heteroatom selected from the group consisting of N, O and S, wherein the ring is not aromatic but can contain unsaturations. The nitrogen and sulfur atoms in a heterocyclic group can be oxidised and the nitrogen atom(s) may optionally be quaternised. The heterocyclic group can be fused to an additional carbocyclic or heterocyclic ring. A heterocyclic group can be attached to the remainder of the molecule at an annular carbon or annular heteroatom. Additionally, heterocyclic main contain fused rings, but excludes fused systems containing a heteroaryl group as part of the fused ring system. Examples of heterocycloalkyl include, but are not limited to, 1-piperidinyl, 1-piperazinyl, morpholinyl, alkylpiperidinyl etc. Heterocycloalkyl moieties can be unsubstituted or substituted with various substituents known in the art, eg hydroxyl, halogen, alkylamino etc.

As used herein, the term "aryl" refers to a substituted (mono- or poly-) or unsubstituted monoaromatic or polyaromatic group, wherein said polyaromatic group may be fused or unfused. The term therefore includes groups having from 6 to 10 carbon atoms (eg phenyl, naphthyl etc). It is also to be understood that the term "aryl" is synonymous with the term "aromatic".

As used herein, the term "heteroaryl" refers to a substituted (mono- or poly-) or unsubstituted monoaromatic or polyaromatic group wherein polyaromatic group may be fused or unfused; and wherein at least one of the rings is an aromatic ring that contains from one to four heteroatoms selected from N, O and S as ring members (i.e. it contains at least one heteroaromatic ring); and wherein the nitrogen and sulfur atoms can be oxidised and the nitrogen atom(s) can be quaternised. A heteroaryl group can be attached to the remainder of the molecule through an annular carbon or annular heteroatom, and it can be attached through any ring of the heteroaryl moiety, if that moiety is bicyclic, tricyclic or a fused ring system. Illustrative examples of heteroaryl groups include 2-pyridyl, 3-pyridyl, 4-pyridyl, 4-pyrimidyl, 5-indolyl etc.

As used herein, the term "aralkyl" is used as a conjunction of the terms alkyl and aryl as defined above.

As used herein, the term "alicyclic" refers to a cyclic aliphatic group.

The term "aliphatic" takes its normal meaning in the art and includes non-aromatic groups such as alkanes, alkenes and alkynes and substituted derivatives thereof.

The term "halogen" refers to fluoro, chloro, bromo and iodo.

The term "derivative" as used herein, includes any chemical modification of an entity. Illustrative of such chemical modifications is the replacement of hydrogen by a halogen group, an alkyl group, an acyl group or an amino group.

As used herein, the phrase "manufacture of a medicament" includes the use of one or more of the compounds of formula I directly as the medicament or in any stage of the manufacture of a medicament comprising one or more of the compounds of formula I.

Some of the compounds of formula I may exist as single stereoisomers, racemates, and/or mixtures of enantiomers and/or diastereomers. All such single stereoisomers, racemates and mixtures thereof, are encompassed within the scope of the present invention. The isomeric forms such as diastereomers, enantiomers, and geometrical isomers can be separated by physical and/or chemical methods known to those skilled in the art.

The term "pharmaceutically acceptable salt" as used herein, refers to salts that retain the desired biological activity of the compounds of formula I, and include pharmaceutically acceptable acid addition salts and base addition salts. Suitable pharmaceutically acceptable acid addition salts of the compounds of formula I may be prepared from an inorganic acid or from an organic acid. Examples of such inorganic acids are hydrochloric, sulfuric and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic and arylsulfonic. Additional information on pharmaceutically acceptable salts can be found in Remington's Pharmaceutical Sciences, 19th Edition, Mack Publishing Co., Easton, Pa. 1995.

In the case of compounds of formula I that are solid, it will be understood by those skilled in the art that the compounds (or pharmaceutically acceptable salts, solvates or prodrugs thereof) may exist in different crystalline or polymorphic forms, all of which are encompassed within the scope of the present invention.

"Prodrug" means a compound that undergoes conversion to a compound of formula I within a biological system, usually by metabolic means (eg by hydrolysis, reduction or oxidation). For example, an ester prodrug of a compound of formula I containing a hydroxyl group may be convertible by hydrolysis in vivo to the compound of formula I. Suitable esters of the compounds of formula I containing a hydroxyl group may be, for example, acetates, citrates, lactates, tartrates, malonates, oxalates, salicylates, propionates, succinates, fumarates, maleates, methylene-bis-P-hydroxynaphthoates, gestisates, isethionates, di-p-toluoyltartrates, methanesulfonates, ethanesulfonates, benzenesulfonates, p-toluenesulfonates, cyclohexylsulfamates and quinates. As another example, an ester prodrug of a compound of formula I containing a carboxy group may be convertible by hydrolysis in vivo to the compound of formula I. Examples of ester prodrugs include those described by Leinweber F J, *Drug Metab Rev* 18:379-439 (1987). Similarly, an acyl prodrug of a compound of formula I containing an amino group may be convertible by hydrolysis in vivo to the compound of formula I. Examples of prodrugs for these and other functional groups, including amines, are provided in Prodrugs: challenges and rewards, Valentino J Stella (ed), Springer, 2007.

The term "therapeutically effective amount" or "effective amount" is an amount sufficient to effect beneficial or desired clinical results. A therapeutically effective amount can be administered in one or more administrations. Typically, a therapeutically effective amount is sufficient for treating a disease or condition or otherwise to palliate, ameliorate, stabilise, reverse, slow or delay the progression of a disease or condition such as, for example, cancer or another proliferative cell disease or condition. By way of example only, a therapeutically effective amount of a compound of formula I, or a pharmaceutically acceptable salt, solvate or prodrug thereof, may comprise between about 0.1 and about 250 mg/kg body weight per day, more preferably between about 0.1 and about 100 mg/kg body weight per day and, still more preferably between about 0.1 and about 25 mg/kg body weight per day. However, notwithstanding the above, it will be understood by those skilled in the art that the therapeutically effective amount may vary and depend upon a variety of factors including the activity of the particular compound (or salt, solvate or prodrug thereof), the metabolic stability and length of action of the particular compound (or salt, solvate or prodrug thereof), the age, body weight, sex, health, route and time of administration, rate of excretion of the particular compound (or salt, solvate or prodrug thereof), and the severity of, for example, the cancer or other proliferative cell disease or condition to be treated.

The compounds of formula I, and pharmaceutically acceptable salts, solvates and prodrugs thereof, are capable of inhibiting protein kinases, especially one or more of the following group: CDKs, FLT kinases, aurora kinases and/or CLKs and may show higher selectivity (to inhibit) CDKs over other protein kinases. As such, the compounds of formula I, and pharmaceutically acceptable salts, solvates and prodrugs thereof, which are believed to inhibit CDKs, have utility in both in vitro and in vivo applications (eg in vitro whole cell assays) and as the basis of a therapeutic method of treating cancer or another proliferative cell disease or condition in a subject. Moreover, the compounds of formula I are suitable for the treatment of other diseases or conditions in which one or more of the protein kinase targets outlined above are implicated.

The compounds of formula I preferably bear a fused heterocyclic group attached to the pyrimidine ring through one of the ring carbon atoms (particularly, the carbon at position 4). More specifically, compounds of formula I preferably bear an imidazo[1,2-a]pyridine group attached to the carbon at position 4 of the pyrimidine. Moreover, the compounds of formula I bear group A, which is preferably a 4- to 10-membered cycloalkyl or heterocycloalkyl group, attached to the pyrimidine ring at the carbon at position 3 through an amine group. Where the group A comprises a heterocycloalkyl group, then that heterocycloalkyl group will comprise at least one but no more than two heteroatoms selected from N, O and S as ring members. The group A is optionally substituted by one or more $R^6$ groups. In some embodiments, the group A is a 5- to 7-membered cycloalkyl or heterocycloalkyl group optionally substituted by one or more $R^6$ groups, such as a 6-membered cycloalkyl or heterocycloalkyl group optionally substituted by one or more $R^6$ groups such as, for example, a cyclohexyl group or piperidine group. In other embodiments, the group A is a 10-membered cycloalkyl group (eg an adamantane group) or heterocycloalkyl group optionally substituted by one or more $R^6$ groups.

In some embodiments, the compounds of formula I may preferably comprise at least one water solubilising group $R^9$, $R^{10}$ or $R^{11}$. Where present, $R^9$, $R^{10}$ and $R^{11}$ are preferably independently selected from water solubilising groups of the group consisting of:
(i) mono-, di- and poly-hydroxylated alicyclic groups, di- or poly-hydroxylated aliphatic or aryl groups; N-, O- and/or S-containing heterocyclic groups substituted with one or more hydroxyl or amino groups, aliphatic and aryl groups comprising one or more carboxamide, sulfoxide, sulfone or sulfonamide groups; and halogenated alkylcarbonyl groups;
(ii) COOH, $SO_3H$, $OSO_3H$, $PO_3H_2$ and $OPO_3H_2$;
(iii) $NHCO(CH_2)_m[NHCO(CH_2)_{m'}]_p[NHCO(CH_2)_{m''}]_qY$ and $NHCO(CH_2)$, $NH(CH_2)_tY$ wherein p and q are each independently selected from integers 0 or 1, and m, m', m", t and ' are each independently selected from integers 1 to 10, and Y is selected from:
(a) alicyclic, aryl and heterocyclic groups comprising one or more O-, S- or N-heteroatoms, which may further comprise an alkyl bridge (eg a —$CH_2$— or —$CH_2CH_2$— bridge),
(b) alicyclic groups comprising one or more of —O—, $NH_2$, —NH—, =N—, quaternary amine salt, and amidine, and
(c) morpholine, piperazine or 1,4-diazepane groups, each of which may be optionally substituted by one or more substituents selected from $SO_2$-alkyl, alkyl optionally substituted by one or more OH groups, CO-alkyl, aralkyl, COO-alkyl, and an ether group optionally substituted by one or more OH groups;
(iv) $(CH_2)_nNR^{12}COR^{13}$, $(CH_2)_nNR^{12}SO_2R^{13}$ and $SO_2R^{14}$, wherein $R^{12}$ is selected from H and alkyl, $R^{13}$ and $R^{14}$ are each independently selected from alkyl groups optionally comprising one or more heteroatoms and/or optionally substituted with one or more substituents independently selected from OH, $NH_2$, halogen and $NO_2$, and n and n' are each independently selected from integers 0, 1, 2 and 3;
(v) ether and polyether groups optionally substituted with one or more OH groups or one or more Y groups, wherein Y is as defined above at (iii);
(vi) $(CH_2)_rNH_2$, wherein r is selected from integers 0, 1, 2 and 3;
(vii) $(CH_2)_{r'}OH$, wherein r' is selected from integers 0, 1, 2 and 3;
(viii) $(CH_2)_{n''}NR^{15}COR^{16}$, wherein $R^{15}$ is H or alkyl, n" is selected from integers 0, 1, 2 and 3, and $R^{16}$ is an aryl group optionally substituted with one or more substituents selected from halogen, $NO_2$, OH, alkoxy, $NH_2$, COOH, $CONH_2$ and $CF_3$; and
(ix) $SO_2NR^{17}R^{18}$, wherein $R^{17}$ and $R^{18}$ are each independently selected from H, alkyl and aryl, with the proviso that at least one of $R^{17}$ and $R^{18}$ is other than H, or $R^{17}$ and $R^{18}$ together form a cyclic group optionally comprising one or more heteroatoms selected from N, O and S, and wherein said alkyl, aryl or cyclic group is optionally substituted by one or more substituents selected from halogen, $NO_2$, OH, alkoxy, $NH_2$, COOH, $CONH_2$ and $CF_3$.

In some embodiments, R, $R^1$, $R^2$, $R^3$ and $R^4$ are each independently selected from the group consisting of H, alkyl (eg a $C_{1-6}$ alkyl or, preferably, a $C_{1-3}$ alkyl such as methyl), cycloalkyl, heterocycloalkyl, aryl (eg phenyl), heteroaryl (eg pyridinyl, pyrimidinyl), $CH_2$-heteroaryl, halogen (especially Br or F), $NO_2$, $CF_3$, OH, O-alkyl (eg an O—$C_{1-6}$ alkyl, preferably, an O—$C_{1-3}$ alkyl such as O—$CH_3$), O-heteroalkyl, O—$C_{3-8}$ cycloalkyl (such as $O(C_5H_9)$; ie O-cyclopentyl), O-aryl, O-heteroaryl, $NH_2$, NH-alkyl (eg a NH—$C_{1-6}$ alkyl, preferably, a NH—$C_{1-3}$ alkyl such as NH—$CH_3$), NH-heteroalkyl (eg $N^1,N^1$-dimethylethane-1,2-diamine), NH-cycloalkyl (eg a NH—$C_{3-8}$ cycloalkyl such as $NH(C_5H_9)$; ie NH-cyclopentyl), NH-heterocycloalkyl (eg NH—$C_{3-8}$ heterocycloalkyl such as $NH(C_5H_{11}N)$; ie NH-piperidinamine), NH-aryl (eg NH-phenyl), NH-heteroaryl, NH—$C_{1-3}$O-aryl, NHO-aryl, NHO-heteroaryl, $NHCH_2$-aryl, $N(alkyl)_2$ (such as $N(CH_3)_2$), $N(cycloalkyl)_2$ (eg $N(C_5H_9)_2$), $N(heterocycloalkyl)_2$ (such as N-dipiperidinamine), N-(alkyl)(aryl), SH-alkyl (eg a SH—$C_{1-6}$ alkyl or, preferably, a SH—$C_{1-3}$ alkyl such as $SHCH_3$ and SHC (CH$_3$)), SH-aryl, SH-heteroaryl, S-heteroalkyl, S—C$_{3-8}$ cycloalkyl (such as S(C$_5$H$_9$); ie S-cyclopentyl), and R$^{11}$; wherein said heterocycloalkyl and heteroaryl groups comprises at least one but no more than two heteroatoms selected from N, S and O, and wherein said alkyl, heteroalkyl, cycloalkyl, heterocycloalkyl, aralkyl, aryl and heteroaryl groups may be optionally substituted with one or more groups selected from halogen, alkyl (eg methyl), CN, OH, O-methyl, O-ethyl, O—HCF$_2$, NH$_2$, COOH, CONH$_2$, heterocycloalkyl, CO-heterocycloalkyl, CF$_3$ and SO$_2$N(CH$_3$)$_2$.

In some embodiments, R is H.

In some embodiments, R$^1$ is heteroaryl (eg pyridine).

In some embodiments, R, R$^1$, R$^3$ and R$^4$ are all H, and R$^2$ is selected from the group consisting of H, alkyl (eg a C1-6 alkyl or, preferably, a C$_{1-3}$ alkyl such as methyl), cycloalkyl, heterocycloalkyl, aryl (eg phenyl), heteroaryl (eg pyridinyl, pyrimidinyl), halogen (especially Br or F), NO$_2$, CF$_3$, OH, O-alkyl (eg an O—C$_{1-6}$ alkyl, preferably, an O—C$_{1-3}$ alkyl such as O—CH$_3$), O-heteroalkyl, O—C$_{3-8}$ cycloalkyl (such as O(C$_5$H$_9$); ie O-cyclopentyl), O-aryl, O-heteroaryl, NH$_2$, NH-alkyl (eg a NH—C$_{1-6}$ alkyl, preferably, a NH—C$_{1-3}$ alkyl such as NH—CH$_3$), NH-heteroalkyl (eg N$^1$,N$^1$-dimethylethane-1,2-diamine), NH-cycloalkyl (eg a NH—C$_{3-8}$ cycloalkyl such as NH(C$_5$H$_9$); ie NH-cyclopentyl), NH-heterocycloalkyl (eg NH—C$_{3-8}$ heterocycloalkyl such as NH(C5H$_{11}$N); ie NH-piperidinamine), NH-aryl (eg NH-phenyl), NH-heteroaryl, N(alkyl)$_2$ (such as N(CH$_3$)$_2$), N(cycloalkyl)$_2$ (eg N(C$_5$H$_9$)$_2$), N(heterocycloalkyl)$_2$ (such as N-dipiperidinamine), N-(alkyl)(aryl), SH-alkyl (eg a SH—C$_{1-6}$ alkyl or, preferably, a SH—C$_{1-3}$ alkyl such as SHCH$_3$ and SHC(CH$_3$)), SH-aryl, SH-heteroaryl, S-heteroalkyl, S—C$_{3-8}$ cycloalkyl (such as S(C$_5$H$_9$); ie S-cyclopentyl), and R$^{11}$; wherein said heterocycloalkyl and heteroaryl groups comprises at least one but no more than two heteroatoms selected from N, S and O, and wherein said alkyl, heteroalkyl, cycloalkyl, heterocycloalkyl, aralkyl, aryl and heteroaryl groups may be optionally substituted with one or more groups selected from halogen, alkyl (eg methyl), CN, OH, O-methyl, O-ethyl, O—HCF$_2$, NH$_2$, COOH, CONH$_2$, heterocycloalkyl, CO-heterocycloalkyl, CF$_3$ and SO$_2$N(CH$_3$)$_2$.

In some embodiments, R, R$^1$, R$^2$ and R$^4$ are all H, and R$^3$ is selected from the group consisting of H, alkyl (eg a C$_{1-6}$ alkyl or, preferably, a C$_{1-3}$ alkyl such as methyl), cycloalkyl, heterocycloalkyl, aryl (eg phenyl), heteroaryl (eg pyridinyl, pyrimidinyl), halogen (especially Br or F), NO$_2$, CF$_3$, OH, O-alkyl (eg an O—C$_{1-6}$ alkyl, preferably, an O—C$_{1-3}$ alkyl such as O—CH$_3$), O-heteroalkyl, O—C$_{3-8}$ cycloalkyl (such as O(C$_5$H$_9$); ie O-cyclopentyl), O-aryl, O-heteroaryl, NH$_2$, NH-alkyl (eg a NH—C$_{1-6}$ alkyl, preferably, a NH—C$_{1-3}$ alkyl such as NH—CH$_3$), NH-heteroalkyl (eg N$^1$,N$^1$-dimethylethane-1,2-diamine), NH-cycloalkyl (eg a NH—C$_{3-8}$ cycloalkyl such as NH(C5H$_9$); ie NH-cyclopentyl), NH-heterocycloalkyl (eg NH—C$_{3-8}$ heterocycloalkyl such as NH(C5H$_{11}$N); ie NH-piperidinamine), NH-aryl (eg NH-phenyl), NH-heteroaryl, N(alkyl)$_2$ (such as N(CH$_3$)$_2$), N(cycloalkyl)$_2$ (eg N(C$_5$H$_9$)$_2$), N(heterocycloalkyl)$_2$ (such as N-dipiperidinamine), N-(alkyl)(aryl), SH-alkyl (eg a SH—C$_{1-6}$ alkyl or, preferably, a SH—C$_{1-3}$ alkyl such as SHCH$_3$ and SHC(CH$_3$)), SH-aryl, SH-heteroaryl, S-heteroalkyl, S—C$_{3-8}$ cycloalkyl (such as S(C$_5$H$_9$); ie S-cyclopentyl), and R$^{11}$; wherein said heterocycloalkyl and heteroaryl groups comprises at least one but no more than two heteroatoms selected from N, S and O, and wherein said alkyl, heteroalkyl, cycloalkyl, heterocycloalkyl, aralkyl, aryl and heteroaryl groups may be optionally substituted with one or more groups selected from halogen, alkyl (eg methyl), CN, OH, O-methyl, O-ethyl, O—HCF$_2$, NH$_2$, COOH, CONH$_2$, heterocycloalkyl, CO-heterocycloalkyl, CF$_3$ and SO$_2$N(CH$_3$)$_2$.

In some embodiments, R$^5$ is H, alkyl (eg a C$_{1-6}$ alkyl such as phenyl, or preferably, a C$_{1-3}$ alkyl such as methyl), O-alkyl (preferably, a C$_{1-6}$ alkoxy or, more preferably, a C$_{1-3}$ alkoxy such as methoxy or ethoxy), CN, or halogen (preferably F and Cl).

In some embodiments, m is an integer from 1 to 5 inclusive, but more preferably, m is an integer from 1, 2 and 3. Most preferably, m is 1. Where m is 2, 3, 4 or 5, it is to be understood that each of the R$^6$ groups may be the same or different.

In some embodiments, R$^6$ is independently selected from the group consisting of H, alkyl (eg a C$_{1-5}$ alkyl such as methyl, propyl, cyclopropylmethyl, cyclopentylmethyl), OH, halogen (preferably F), O-alkyl (preferably, a C$_{1-6}$ alkoxy or, more preferably, a C$_{1-3}$ alkoxy such as methoxy or ethoxy), CO$_2$-alkyl, COOH, C$_{1-3}$-heterocycloalkyl, O-heteroalkyl, NH$_2$, NH-alkyl (preferably, a C$_{1-6}$ alkyl or, more preferably, an NH—C$_{1-3}$ alkyl such as NH—CH$_3$), N-(alkyl)$_2$ (eg N(CH$_3$)$_2$ and N(C$_2$H$_5$)$_2$), NH-cycloalkyl (preferably, a NH—C$_{1-4}$ cycloalkyl such as azetidine), NH-heteroalkyl, NH—R$^7$ where R$^7$ is CO(NH-alkyl), SO$_2$-alkyl (preferably, an SO$_2$—C$_{1-3}$ alkyl such as SO$_2$-methyl), SO$_2$NH$_2$, NH-alkyl-R$^7$ where R$^7$ is CF$_3$, O-alkyl, CO(NH$_2$) or CO$_2$-alkyl, preferably a CO$_2$—C$_{1-3}$ alkyl (eg NH—CH$_2$—CO$_2$CH$_3$), N-(alkyl)(R$^7$) where R$^7$ is heteroalkyl such as a C$_{2-5}$ heteroalkyl (eg N(CH$_3$)(C$_2$H$_4$OCH$_3$), SO$_2$-alkyl (preferably, an SO$_2$—C$_{1-3}$ alkyl such as SO$_2$-methyl), alkyl-R$^7$ where R$^7$ is CO$_2$-alkyl, preferably a CO$_2$—C$_{1-3}$ alkyl (eg CH$_2$—CO$_2$CH$_3$), and COOR$^7$ where R$^7$ is preferably a C$_{1-3}$ alkyl or C$_{1-6}$ alkyl (eg tert-butyloxycarbonyl (Boc)); and wherein said heterocycloalkyl and heteroaryl groups comprises at least one but no more than two heteroatoms selected from N, S and O, and wherein said alkyl, heteroalkyl, cycloalkyl, heterocycloalkyl, aralkyl, aryl and heteroaryl groups may be optionally substituted with one or more groups selected from halogen, CN, carbonyl, OH, O-methyl, NH$_2$, COOH, CONH$_2$, and CF$_3$.

In some embodiments, A is a cyclopentane, cyclohexane, cycloheptane, tetrahydrofuran or tetrahydro-2H-pyran, diazaspiro[4.5]decan-1-one, quinuclidine, quinuclidin-3-amine, piperidine, or oxepane optionally substituted with at least one of R$^6$.

In some embodiments, A is cyclohexane, adamantane, tetrahydro-2H-pyran or piperidine optionally substituted with at least one of R$^6$.

In some preferred embodiments, the compounds of the present invention exhibit anti-proliferative activity in human cell lines, as measured by a standard cytotoxicity assay. Preferably, the compound exhibits an IC$_{50}$ value of less than 5 µM, even more preferably less than 1 µM as measured by the cell viability (MTT proliferation) assay described in Example 2 hereinafter. More preferably still, the compound exhibits an IC$_{50}$ value of less than 0.5 µM.

In some preferred embodiments, the compounds of the present invention inhibit one or more protein kinases, as measured by any standard assay well known to those skilled in the art. Preferably, the compound exhibits an IC$_{50}$ value of less than 1 µM or less than 0.5 µM as measured by the kinase assay described in Example 2 hereinafter, more preferably still less than 0.1 µM.

Particular examples of compounds according to the first aspect are shown in Table 1 below.

TABLE 1

Chemical structure of selected compounds of the present invention

| No. | Structure | Name | Mass |
|---|---|---|---|
| 1 | 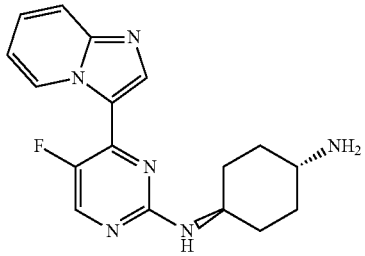 [SMILES: N[C@H]1CC[C@H](Nc2ncc(F)c(-c3cnc4ccccn34)n2)CC1] | (1r,4r)-N$^1$-(5-Fluoro-4-(imidazo[1,2-a]pyridin-3-yl)pyrimidin-2-yl)cyclohexane-1,4-diamine | 326.4 |
| 2 | 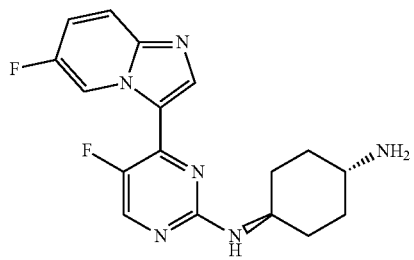 [SMILES: N[C@H]1CC[C@H](Nc2ncc(F)c(-c3cnc4ccc(F)cn34)n2)CC1] | (1r,4r)-N$^1$-(5-Fluoro-4-(6-fluoroimidazo[1,2-a]pyridin-3-yl)pyrimidin-2-yl)cyclohexane-1,4-diamine | 344.4 |
| 3 | 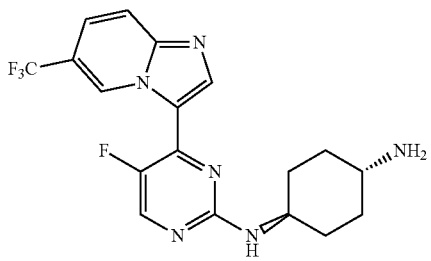 [SMILES: N[C@H]1CC[C@H](Nc2ncc(F)c(-c3cnc4ccc(C(F)(F)F)cn34)n2)CC1] | (1r,4r)-N$^1$-(5-Fluoro-4-(6-(trifluoromethyl)imidazo[1,2-a]pyridin-3-yl)pyrimidin-2-yl)cyclohexane-1,4-diamine | 394.4 |
| 4 | 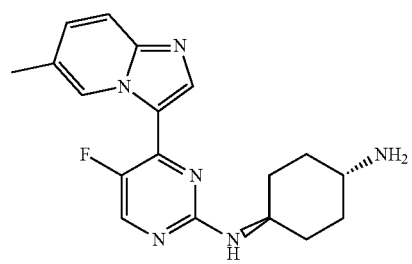 [SMILES: Cc1ccc2ncc(-c3nc(N[C@H]4CC[C@H](N)CC4)ncc3F)n2c1] | (1r,4r)-N$^1$-(5-Fluoro-4-(6-methylimidazo[1,2-a]pyridin-3-yl)pyrimidin-2-yl)cyclohexane-1,4-diamine | 340.4 |
| 5 | 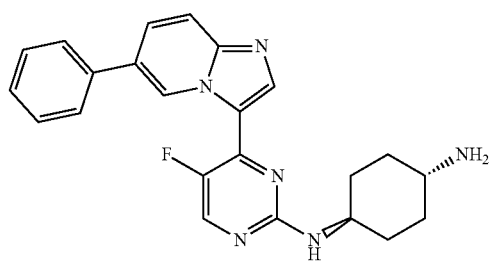 [SMILES: N[C@H]1CC[C@H](Nc2ncc(F)c(-c3cnc4ccc(-c5ccccc5)cn34)n2)CC1] | (1r,4r)-N$^1$-(5-Fluoro-4-(6-phenylimidazo[1,2-a]pyridin-3-yl)pyrimidin-2-yl)cyclohexane-1,4-diamine | 402.5 |

TABLE 1-continued

Chemical structure of selected compounds of the present invention

| No. | Structure | Name | Mass |
|---|---|---|---|
| 6 | 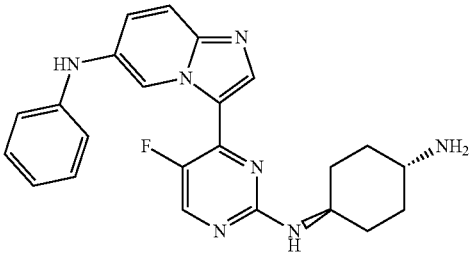 [SMILES: N[C@H]1CC[C@H](Nc2ncc(F)c(-c3cnc4ccc(Nc5ccccc5)cn34)n2)CC1] | (1r,4r)-N$^1$-(5-Fluoro-4-(6-(phenylamino)imidazo[1,2-a]pyridin-3-yl)pyrimidin-2-yl)cyclohexane-1,4-diamine | 417.5 |
| 7 | 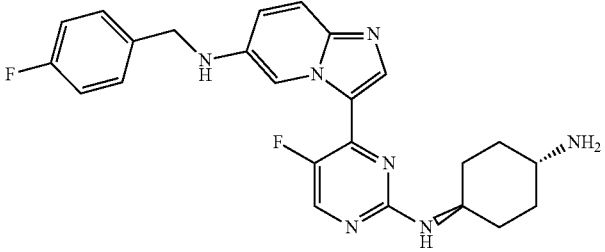 [SMILES: N[C@H]1CC[C@H](Nc2ncc(F)c(-c3cnc4ccc(NCc5ccc(F)cc5)cn34)n2)CC1] | (1r,4r)-N$^1$-(5-Fluoro-4-(6-((4-fluorobenzyl)amino)imidazo[1,2-a]pyridin-3-yl)pyrimidin-2-yl)cyclohexane-1,4-diamine | 449.5 |
| 8 | 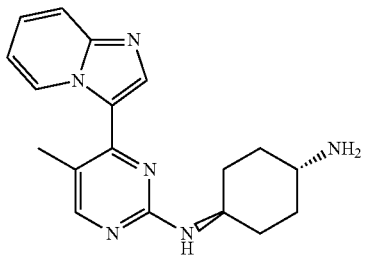 [SMILES: Cc1cnc(N[C@H]2CC[C@H](N)CC2)nc1-c1cnc2ccccn12] | (1r,4r)-N$^1$-(4-(Imidazo[1,2-a]pyridin-3-yl)-5-methylpyrimidin-2-yl)cyclohexane-1,4-diamine | 322.4 |
| 9 | 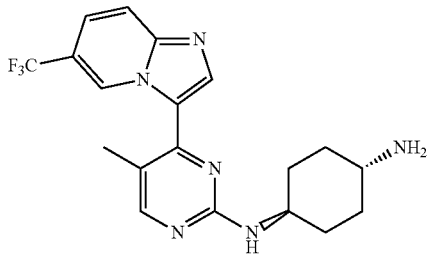 [SMILES: Cc1cnc(N[C@H]2CC[C@H](N)CC2)nc1-c1cnc2ccc(C(F)(F)F)cn12] | (1r,4r)-N$^1$-(5-Methyl-4-(6-(trifluoromethyl)imidazo[1,2-a]pyridin-3-yl)pyrimidin-2-yl)cyclohexane-1,4-diamine | 390.4 |
| 10 | 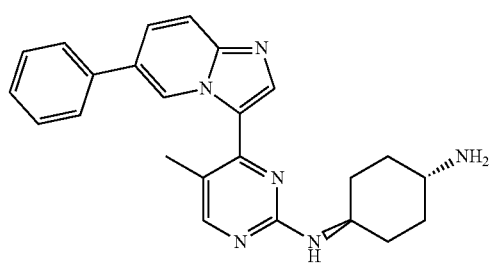 | (1r,4r)-N$^1$-(5-Methyl-4-(6-phenylimidazo[1,2-a]pyridin-3-yl)pyrimidin-2-yl)cyclohexane-1,4-diamine | 398.5 |

TABLE 1-continued

Chemical structure of selected compounds of the present invention

| No. | Structure | Name | Mass |
|---|---|---|---|
| 11 | 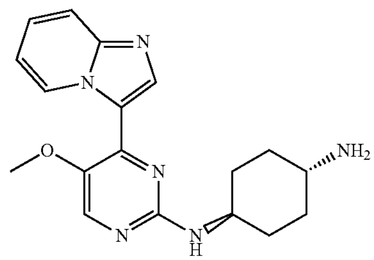 [SMILES: COc1cnc(N[C@H]2CC[C@H](N)CC2)nc1-c1cnc2ccccn12] | (1r,4r)-N[1]-(4-(Imidazo[1,2-a]pyridin-3-yl)-5-methoxypyrimidin-2-yl)cyclohexane-1,4-diamine | 338.4 |
| 12 | 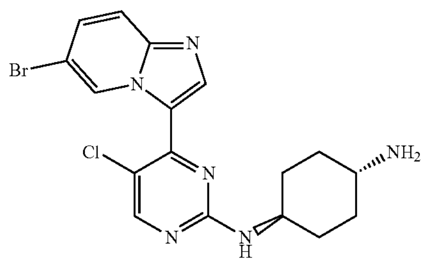 [SMILES: N[C@H]1CC[C@H](Nc2ncc(Cl)c(-c3cnc4ccc(Br)cn34)n2)CC1] | (1r,4r)-N[1]-(4-(6-Bromoimidazo[1,2-a]pyridin-3-yl)-5-chloropyrimidin-2-yl)cyclohexane-1,4-diamine | 421.7 |
| 13 | 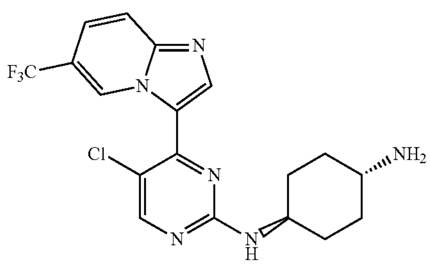 [SMILES: N[C@H]1CC[C@H](Nc2ncc(Cl)c(-c3cnc4ccc(C(F)(F)F)cn34)n2)CC1] | (1r,4r)-N[1]-(5-Chloro-4-(6-(trifluoromethyl)imidazo[1,2-a]pyridin-3-yl)pyrimidin-2-yl)cyclohexane-1,4-diamine | 410.8 |
| 14 | 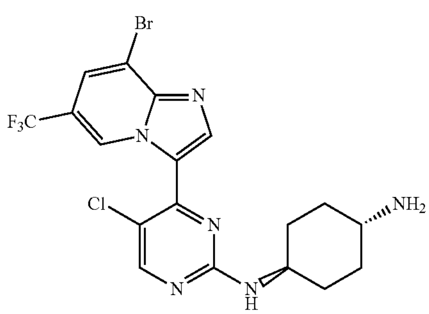 [SMILES: N[C@H]1CC[C@H](Nc2ncc(Cl)c(-c3cnc4c(Br)cc(C(F)(F)F)cn34)n2)CC1] | (1r,4r)-N[1]-(4-(8-Bromo-6-(trifluoromethyl)imidazo[1,2-a]pyridin-3-yl)-5-chloropyrimidin-2-yl)cyclohexane-1,4-diamine | 489.7 |
| 15 | 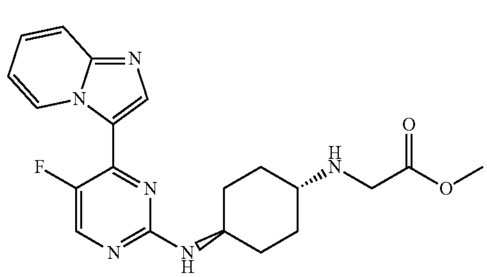 [SMILES: COC(=O)CN[C@H]1CC[C@H](Nc2ncc(F)c(-c3cnc4ccccn34)n2)CC1] | Methyl ((1r,4r)-4-((5-fluoro-4-(imidazo[1,2-a]pyridin-3-yl)pyrimidin-2-yl)amino)cyclohexyl)glycinate | 398.4 |

TABLE 1-continued

Chemical structure of selected compounds of the present invention

| No. | Structure | Name | Mass |
|---|---|---|---|
| 16 | 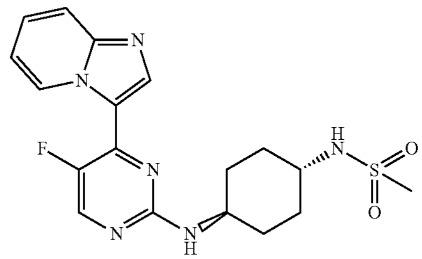 [SMILES: CS(=O)(=O)N[C@H]1CC[C@H](Nc2ncc(F)c(-c3cnc4ccccn34)n2)CC1] | N-((1r,4r)-4-((5-Fluoro-4-(imidazo[1,2-a]pyridin-3-yl)pyrimidin-2-yl)amino)cyclohexyl)methanesulfonamide | 404.5 |
| 17 | 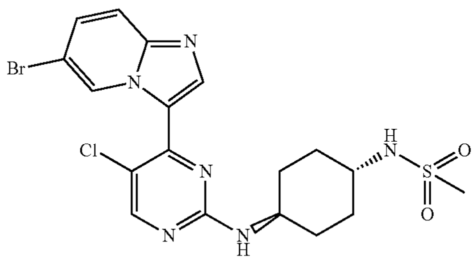 [SMILES: CS(=O)(=O)N[C@H]1CC[C@H](Nc2ncc(Cl)c(-c3cnc4ccc(Br)cn34)n2)CC1] | N-((1r,4r)-4-((4-(6-Bromoimidazo[1,2-a]pyridin-3-yl)-5-chloropyrimidin-2-yl)amino)cyclohexyl)methanesulfonamide | 499.8 |
| 18 | 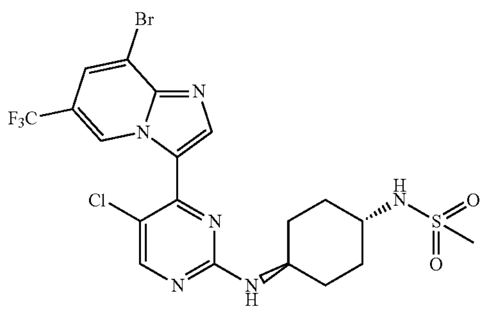 [SMILES: CS(=O)(=O)N[C@H]1CC[C@H](Nc2ncc(Cl)c(-c3cnc4c(Br)cc(C(F)(F)F)cn34)n2)CC1] | N-((1r,4r)-4-((4-(8-Bromo-6-(trifluoromethyl)imidazo[1,2-a]pyridin-3-yl)-5-chloropyrimidin-2-yl)amino)cyclohexyl)methanesulfonamide | 567.8 |
| 19 | 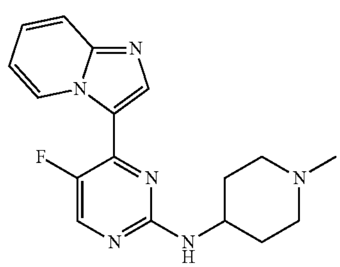 [SMILES: CN1CCC(Nc2ncc(F)c(-c3cnc4ccccn34)n2)CC1] | 5-Fluoro-4-(imidazo[1,2-a]pyridin-3-yl)-N-(1-methylpiperidin-4-yl)pyrimidin-2-amine | 326.4 |
| 20 | 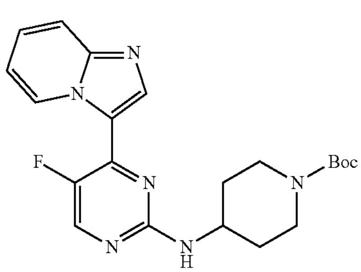 [SMILES: CC(C)(C)OC(=O)N1CCC(Nc2ncc(F)c(-c3cnc4ccccn34)n2)CC1] | tert-Butyl 4-((5-fluoro-4-(imidazo[1,2-a]pyridin-3-yl)pyrimidin-2-yl)amino)piperidine-1-carboxylate | 412.5 |

TABLE 1-continued

Chemical structure of selected compounds of the present invention

| No. | Structure | Name | Mass |
|---|---|---|---|
| 21 | 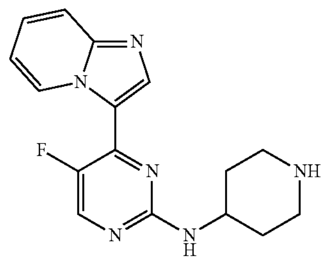 [SMILES: Fc1cnc(NC2CCNCC2)nc1-c1cnc2ccccn12] | 5-Fluoro-4-(imidazo[1,2-a]pyridin-3-yl)-N-(piperidin-4-yl)pyrimidin-2-amine | 312.4 |
| 22 | 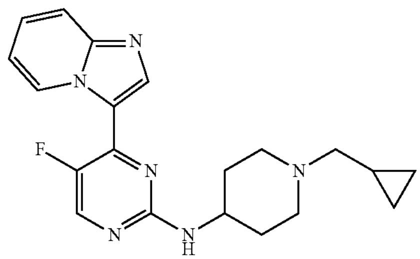 [SMILES: Fc1cnc(NC2CCN(CC3CC3)CC2)nc1-c1cnc2ccccn12] | N-(1-(Cyclopropylmethyl)piperidin-4-yl)-5-fluoro-4-(imidazo[1,2-a]pyridin-3-yl)pyrimidin-2-amine | 366.4 |
| 23 | 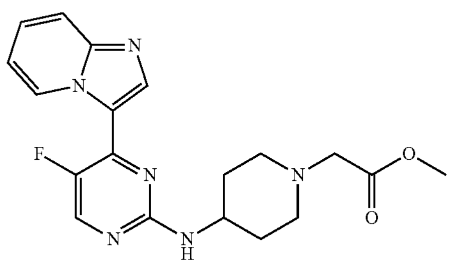 [SMILES: COC(=O)CN1CCC(Nc2ncc(F)c(-c3cnc4ccccn34)n2)CC1] | Methyl 2-(4-((5-fluoro-4-(imidazo[1,2-a]pyridin-3-yl)pyrimidin-2-yl)amino)piperidin-1-yl)acetate | 384.4 |
| 24 | 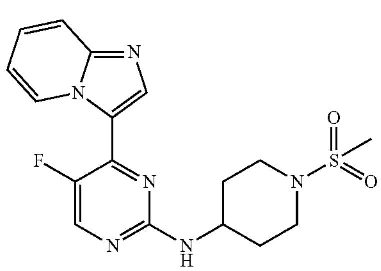 [SMILES: CS(=O)(=O)N1CCC(Nc2ncc(F)c(-c3cnc4ccccn34)n2)CC1] | 5-Fluoro-4-(imidazo[1,2-a]pyridin-3-yl)-N-(1-(methylsulfonyl)piperidin-4-yl)pyrimidin-2-amine | 390.4 |
| 25 | 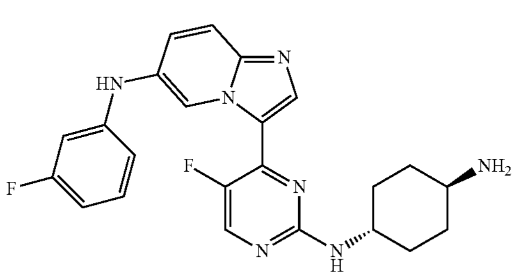 [SMILES: N[C@H]1CC[C@H](Nc2ncc(F)c(-c3cnc4ccc(Nc5cccc(F)c5)cn34)n2)CC1] | (1r,4r)-N$^1$-(5-Fluoro-4-(6-((3-fluorophenyl)amino)imidazo[1,2-a]pyridin-3-yl)pyrimidin-2-yl)cyclohexane-1,4-diamine | 435.5 |

TABLE 1-continued

Chemical structure of selected compounds of the present invention

| No. | Structure | Name | Mass |
|---|---|---|---|
| 26 | 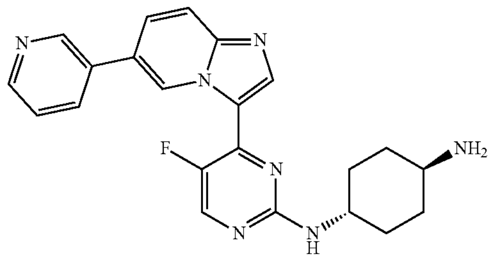 | (1r,4r)-N$^1$-(5-Fluoro-4-(6-(pyridin-3-yl)imidazo[1,2-a]pyridin-3-yl)pyrimidin-2-yl)cyclohexane-1,4-diamine | 403.5 |
| 27 | 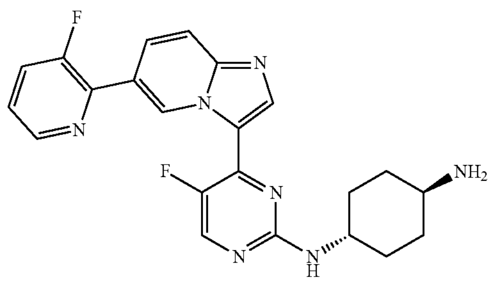 [SMILES: N[C@H]1CC[C@H](Nc2ncc(F)c(-c3cnc4ccc(-c5ncccc5F)cn34)n2)CC1] | (1r,4r)-N$^1$-(5-Fluoro-4-(6-(3-fluoropyridin-2-yl)imidazo[1,2-a]pyridin-3-yl)pyrimidin-2-yl)cyclohexane-1,4-diamine | 421.5 |
| 28 | 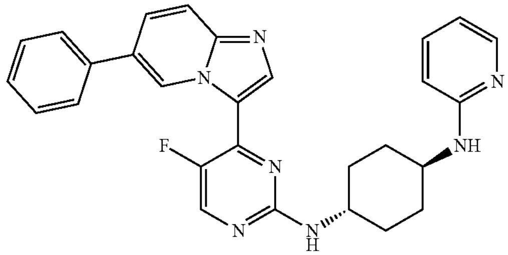 [SMILES: Fc1cnc(N[C@H]2CC[C@H](Nc3ccccn3)CC2)nc1-c1cnc2ccc(-c3ccccc3)cn12] | (1r,4r)-N$^1$-(5-Fluoro-4-(6-phenylimidazo[1,2-a]pyridin-3-yl)pyrimidin-2-yl)-N4-(pyridin-2-yl)cyclohexane-1,4-diamine | 479.6 |
| 29 | 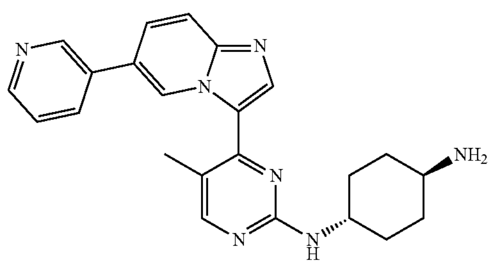 [SMILES: Cc1cnc(N[C@H]2CC[C@H](N)CC2)nc1-c1cnc2ccc(-c3cccnc3)cn12] | (1r,4r)-N$^1$-(5-Methyl-4-(6-(pyridin-3-yl)imidazo[1,2-a]pyridin-3-yl)pyrimidin-2-yl)cyclohexane-1,4-diamine | 399.5 |
| 30 | 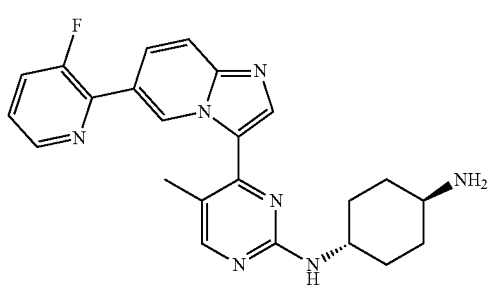 [SMILES: Cc1cnc(N[C@H]2CC[C@H](N)CC2)nc1-c1cnc2ccc(-c3ncccc3F)cn12] | (1r,4r)-N$^1$-(4-(6-(3-Fluoropyridin-2-yl)imidazo[1,2-a]pyridin-3-yl)-5-methylpyrimidin-2-yl)cyclohexane-1,4-diamine | 417.5 |

TABLE 1-continued

Chemical structure of selected compounds of the present invention

| No. | Structure | Name | Mass |
|---|---|---|---|
| 31 | 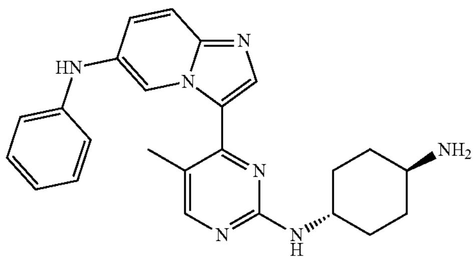 [SMILES: Cc1cnc(N[C@H]2CC[C@H](N)CC2)nc1-c1cnc2ccc(Nc3ccccc3)cn12] | (1r,4r)-N[1]-(5-Methyl-4-(6-(phenylamino)imidazo[1,2-a]pyridin-3-yl)pyrimidin-2-yl)cyclohexane-1,4-diamine | 413.5 |
| 32 | 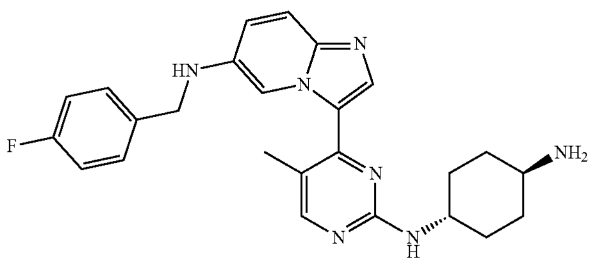 [SMILES: Cc1cnc(N[C@H]2CC[C@H](N)CC2)nc1-c1cnc2ccc(NCc3ccc(F)cc3)cn12] | (1r,4r)-N[1]-(4-(6-((4-Fluorobenzyl)amino)imidazo[1,2-a]pyridin-3-yl)-5-methylpyrimidin-2-yl)cyclohexane-1,4-diamine | 445.5 |
| 33 | 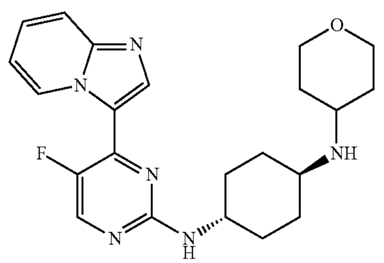 [SMILES: Fc1cnc(N[C@H]2CC[C@H](NC3CCOCC3)CC2)nc1-c1cnc2ccccn12] | (1r,4r)-N[1]-(5-Fluoro-4-(imidazo[1,2-a]pyridin-3-yl)pyrimidin-2-yl)-N4-(tetrahydro-2H-pyran-4-yl)cyclohexane-1,4-diamine | 410.5 |
| 34 | 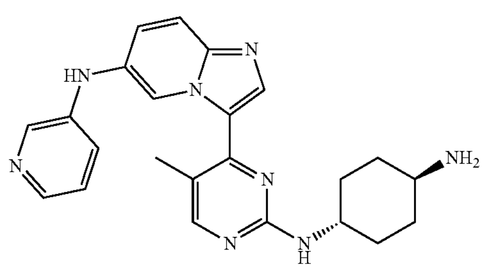 [SMILES: Cc1cnc(N[C@H]2CC[C@H](N)CC2)nc1-c1cnc2ccc(Nc3cccnc3)cn12] | (1r,4r)-N[1]-(5-Methyl-4-(6-(pyridin-3-ylamino)imidazo[1,2-a]pyridin-3-yl)pyrimidin-2-yl)cyclohexane-1,4-diamine | 414.5 |
| 35 | 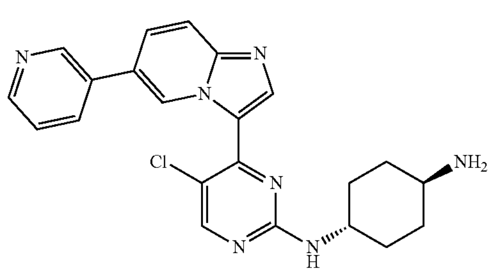 [SMILES: N[C@H]1CC[C@H](Nc2ncc(Cl)c(-c3cnc4ccc(-c5cccnc5)cn34)n2)CC1] | (1r,4r)-N[1]-(5-Chloro-4-(6-(pyridin-3-yl)imidazo[1,2-a]pyridin-3-yl)pyrimidin-2-yl)cyclohexane-1,4-diamine | 419.9 |

TABLE 1-continued

Chemical structure of selected compounds of the present invention

| No. | Structure | Name | Mass |
|---|---|---|---|
| 36 | 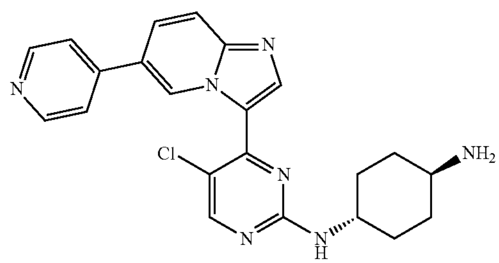 [SMILES: N[C@H]1CC[C@H](Nc2ncc(Cl)c(-c3cnc4ccc(-c5ccncc5)cn34)n2)CC1] | (1r,4r)-N[1]-(5-Chloro-4-(6-(pyridin-4-yl)imidazo[1,2-a]pyridin-3-yl)pyrimidin-2-yl)cyclohexane-1,4-diamine | 419.9 |
| 37 | 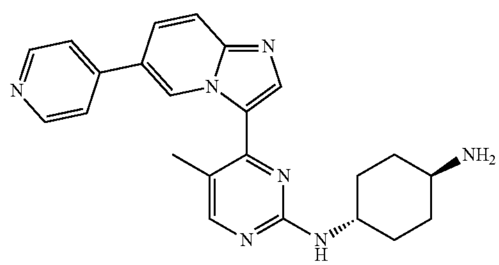 [SMILES: Cc1cnc(N[C@H]2CC[C@H](N)CC2)nc1-c1cnc2ccc(-c3ccncc3)cn12] | (1r,4r)-N[1]-(5-Methyl-4-(6-(pyridin-4-yl)imidazo[1,2-a]pyridin-3-yl)pyrimidin-2-yl)cyclohexane-1,4-diamine | 399.5 |
| 38 | 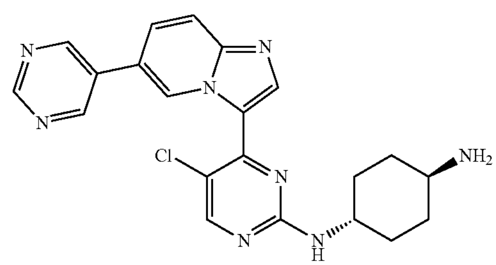 [SMILES: N[C@H]1CC[C@H](Nc2ncc(Cl)c(-c3cnc4ccc(-c5cncnc5)cn34)n2)CC1] | (1r,4r)-N[1]-(5-Chloro-4-(6-(pyrimidin-5-yl)imidazo[1,2-a]pyridin-3-yl)pyrimidin-2-yl)cyclohexane-1,4-diamine | 420.9 |
| 39 | 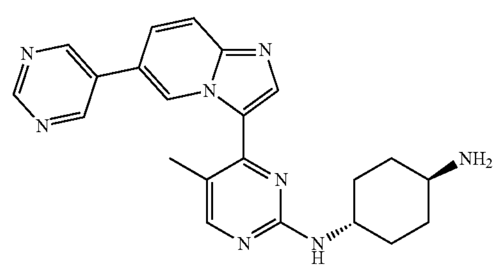 | (1r,4r)-N[1]-(5-Methyl-4-(6-(pyrimidin-5-yl)imidazo[1,2-a]pyridin-3-yl)pyrimidin-2-yl)cyclohexane-1,4-diamine | 400.5 |
| 40 | 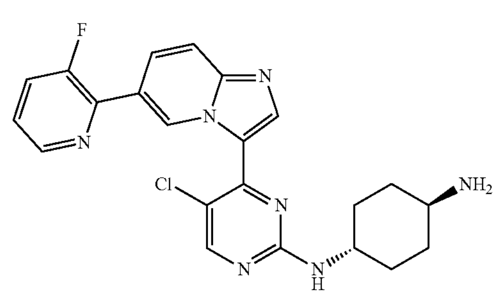 | (1r,4r)-N[1]-(5-Chloro-4-(6-(3-fluoropyridin-2-yl)imidazo[1,2-a]pyridin-3-yl)pyrimidin-2-yl)cyclohexane-1,4-diamine | 437.9 |

TABLE 1-continued

Chemical structure of selected compounds of the present invention

| No. | Structure | Name | Mass |
|---|---|---|---|
| 41 | 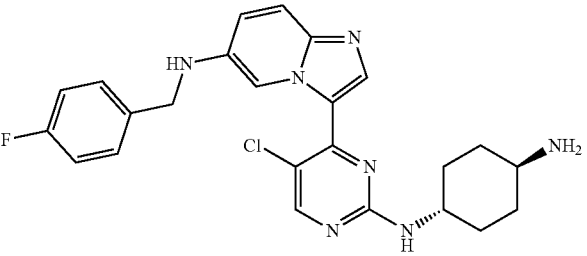 [SMILES: N[C@H]1CC[C@H](Nc2ncc(Cl)c(-c3cnc4ccc(NCc5ccc(F)cc5)cn34)n2)CC1] | (1r,4r)-N$^1$-(5-Chloro-4-(6-((4-fluorobenzyl)amino) imidazo[1,2-a]pyridin-3-yl)pyrimidin-2-yl)cyclohexane-1,4-diamine | 466.0 |
| 42 | 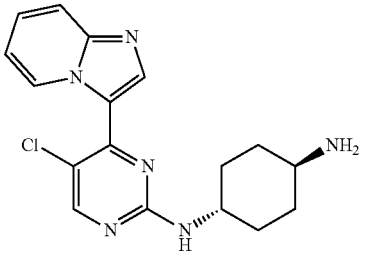 [SMILES: N[C@H]1CC[C@H](Nc2ncc(Cl)c(-c3cnc4ccccn34)n2)CC1] | (1r,4r)-N$^1$-(5-chloro-4-(imidazo[1,2-a]pyridin-3-yl) pyrimidin-2-yl)cyclohexane-1,4-diamine | 342.8 |
| 43 | 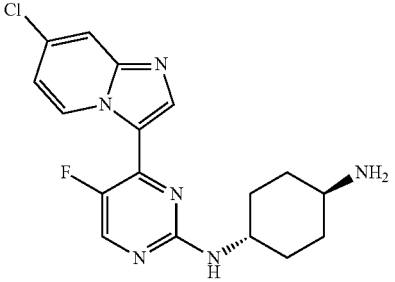 [SMILES: N[C@H]1CC[C@H](Nc2ncc(F)c(-c3cnc4cc(Cl)ccn34)n2)CC1] | (1r,4r)-N$^1$-(4-(7-Chloroimidazo[1,2-a]pyridin-3-yl)-5-fluoropyrimidin-2-yl)cyclohexane-1,4-diamine | 360.8 |
| 44 | 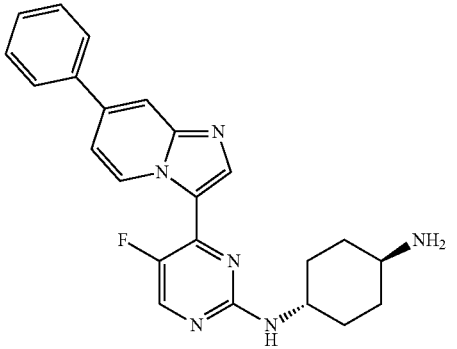 | (1r,4r)-N$^1$-(5-Fluoro-4-(7-phenylimidazo[1,2-a]pyridin-3-yl)pyrimidin-2-yl)cyclohexane-1,4-diamine | 402.5 |
| 45 | 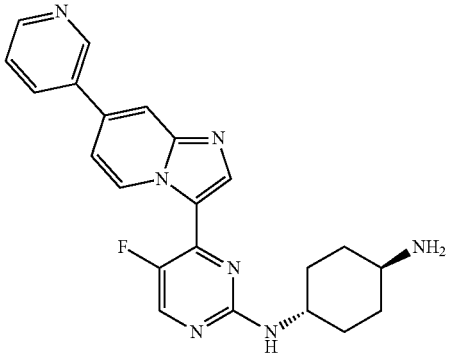 | (1r,4r)-N$^1$-(5-Fluoro-4-(7-(pyridin-3-yl)imidazo[1,2-a] pyridin-3-yl)pyrimidin-2-yl)cyclohexane-1,4-diamine | 403.5 |

TABLE 1-continued

Chemical structure of selected compounds of the present invention

| No. | Structure | Name | Mass |
|---|---|---|---|
| 46 | 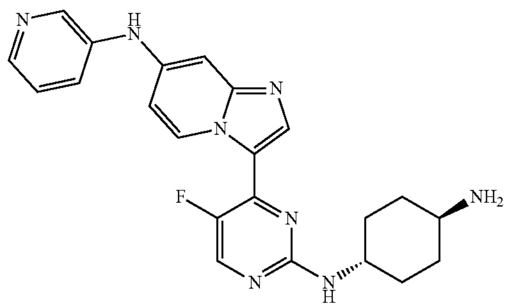 | (1r,4r)-N[1]-(5-Fluoro-4-(7-(pyridin-3-ylamino)imidazo[1,2-a]pyridin-3-yl)pyrimidin-2-yl)cyclohexane-1,4-diamine | 418.5 |
| 47 | 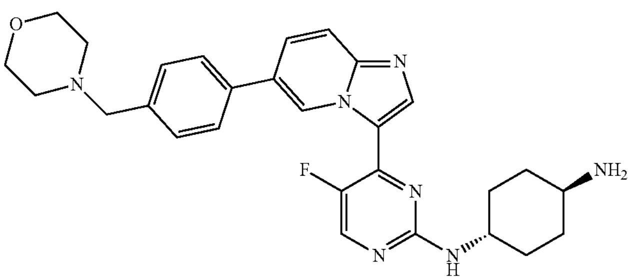 [SMILES: N[C@H]1CC[C@H](Nc2ncc(F)c(-c3cnc4ccc(-c5ccc(CN6CCOCC6)cc5)cn34)n2)CC1] | (1r,4r)-N[1]-(5-Fluoro-4-(6-(4-(morpholinomethyl)phenyl)imidazo[1,2-a]pyridin-3-yl)pyrimidin-2-yl)cyclohexane-1,4-diamine | 501.6 |
| 48 | 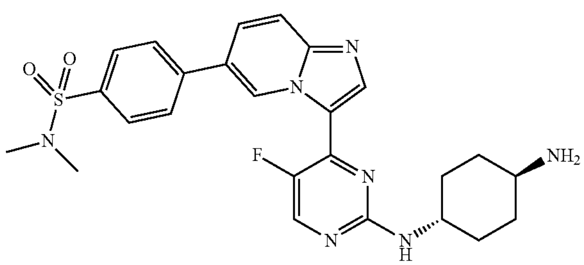 [SMILES: CN(C)S(=O)(=O)c1ccc(-c2ccc3ncc(-c4nc(N[C@H]5CC[C@H](N)CC5)ncc4F)n3c2)cc1] | 4-(3-(2-(((1r,4r)-4-Aminocyclohexyl)amino)-5-fluoropyrimidin-4-yl)imidazo[1,2-a]pyridin-6-yl)-N,N-dimethylbenzenesulfonamide | 509.6 |
| 49 | 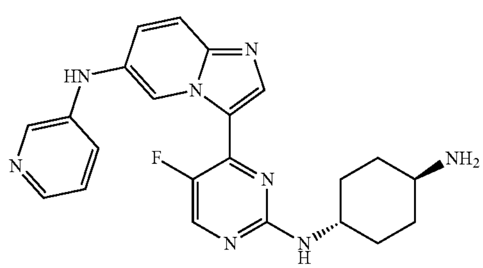 | (1r,4r)-N[1]-(5-Fluoro-4-(6-(pyridin-3-ylamino)imidazo[1,2-a]pyridin-3-yl)pyrimidin-2-yl)cyclohexane-1,4-diamine | 418.5 |
| 50 | 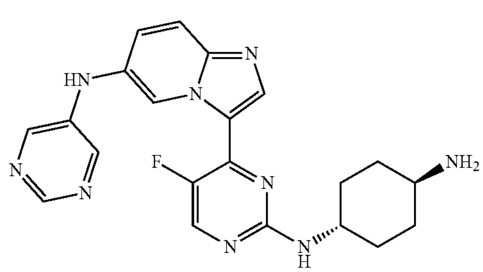 [SMILES: N[C@H]1CC[C@H](Nc2ncc(F)c(-c3cnc4ccc(Nc5cncnc5)cn34)n2)CC1] | (1r,4r)-N[1]-(5-Fluoro-4-(6-(pyrimidin-5-ylamino)imidazo[1,2-a]pyridin-3-yl)pyrimidin-2-yl)cyclohexane-1,4-diamine | 419.5 |

TABLE 1-continued

Chemical structure of selected compounds of the present invention

| No. | Structure | Name | Mass |
|---|---|---|---|
| 51 | 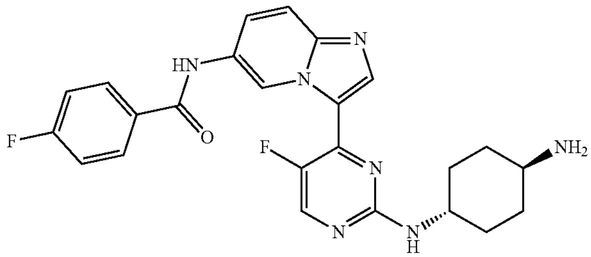 [SMILES: N[C@H]1CC[C@H](Nc2ncc(F)c(-c3cnc4ccc(NC(=O)c5ccc(F)cc5)cn34)n2)CC1] | N-(3-(2-(((1r,4r)-4-Aminocyclohexyl)amino)-5-fluoropyrimidin-4-yl)imidazo[1,2-a]pyridin-6-yl)-4-fluorobenzamide | 463.5 |
| 52 | 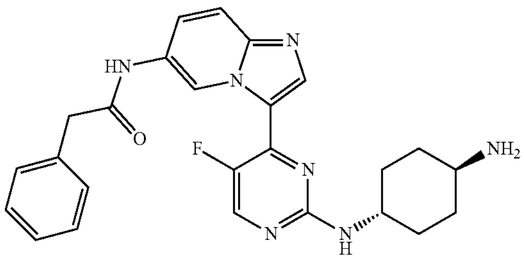 [SMILES: N[C@H]1CC[C@H](Nc2ncc(F)c(-c3cnc4ccc(NC(=O)Cc5ccccc5)cn34)n2)CC1] | N-(3-(2-(((1r,4r)-4-Aminocyclohexyl)amino)-5-fluoropyrimidin-4-yl)imidazo[1,2-a]pyridin-6-yl)-2-phenylacetamide | 459.3 |
| 53 | 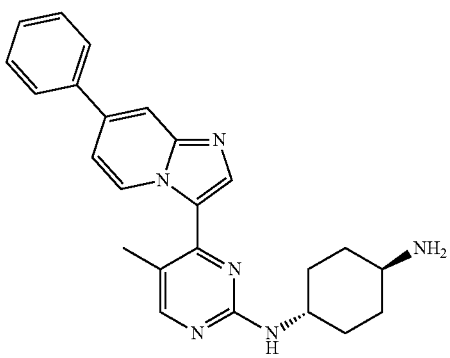 [SMILES: Cc1cnc(N[C@H]2CC[C@H](N)CC2)nc1-c1cnc2cc(-c3ccccc3)ccn12] | (1r,4r)-N¹-(5-Methyl-4-(7-phenylimidazo[1,2-a]pyridin-3-yl)pyrimidin-2-yl)cyclohexane-1,4-diamine | 398.5 |
| 54 | 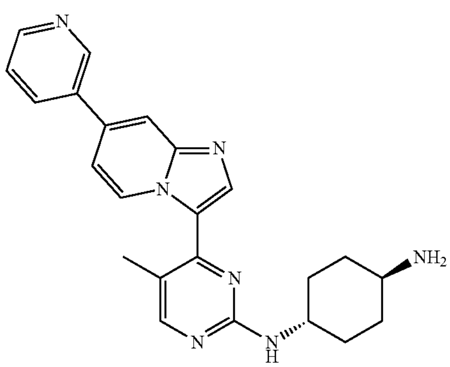 [SMILES: Cc1cnc(N[C@H]2CC[C@H](N)CC2)nc1-c1cnc2cc(-c3cccnc3)ccn12] | (1r,4r)-N¹-(5-Methyl-4-(7-(pyridin-3-yl)imidazo[1,2-a]pyridin-3-yl)pyrimidin-2-yl)cyclohexane-1,4-diamine | 399.5 |
| 55 | 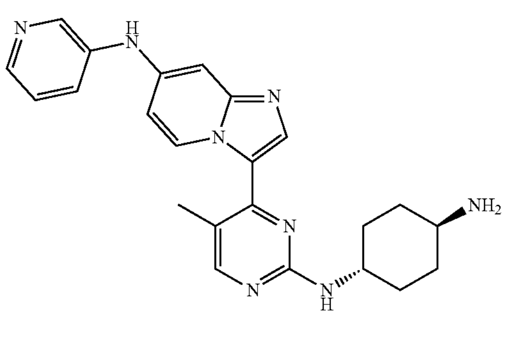 [SMILES: Cc1cnc(N[C@H]2CC[C@H](N)CC2)nc1-c1cnc2cc(Nc3cccnc3)ccn12] | (1r,4r)-N¹-(5-Methyl-4-(7-(pyridin-3-ylamino)imidazo[1,2-a]pyridin-3-yl)pyrimidin-2-yl)cyclohexane-1,4-diamine | 414.5 |

TABLE 1-continued

Chemical structure of selected compounds of the present invention

| No. | Structure | Name | Mass |
|---|---|---|---|
| 56 | 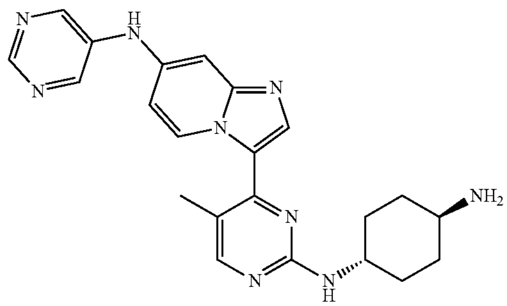 [SMILES: Cc1cnc(N[C@H]2CC[C@H](N)CC2)nc1-c1cnc2cc(Nc3cncnc3)ccn12] | (1r,4r)-N$^1$-(5-Methyl-4-(7-(pyrimidin-5-ylamino)imidazo[1,2-a]pyridin-3-yl)pyrimidin-2-yl)cyclohexane-1,4-diamine | 415.5 |
| 57 | 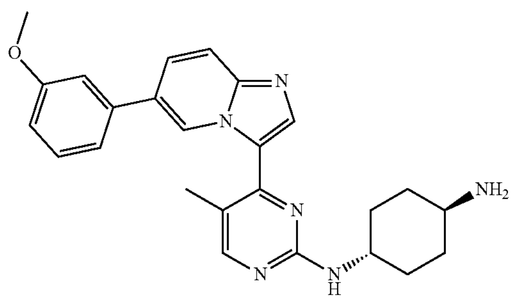 [SMILES: COc1cccc(-c2ccc3ncc(-c4nc(N[C@H]5CC[C@H](N)CC5)ncc4C)n3c2)c1] | (1r,4r)-N$^1$-(4-(6-(3-Methoxyphenyl)imidazo[1,2-a]pyridin-3-yl)-5-methylpyrimidin-2-yl)cyclohexane-1,4-diamine | 428.5 |
| 58 | 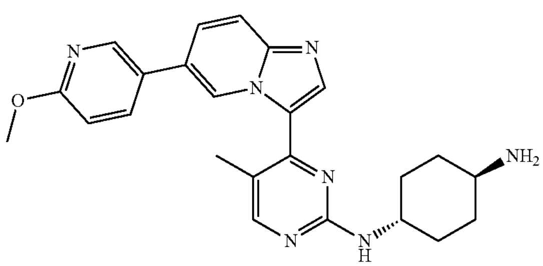 [SMILES: COc1ccc(-c2ccc3ncc(-c4nc(N[C@H]5CC[C@H](N)CC5)ncc4C)n3c2)cn1] | (1r,4r)-N$^1$-(4-(6-(6-Methoxypyridin-3-yl)imidazo[1,2-a]pyridin-3-yl)-5-methylpyrimidin-2-yl)cyclohexane-1,4-diamine | 429.5 |
| 59 | 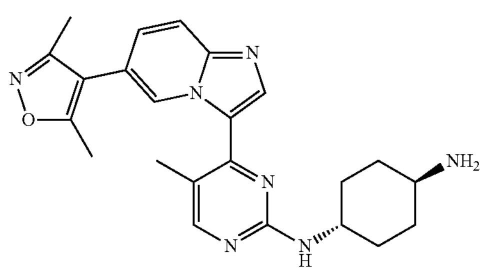 [SMILES: Cc1cnc(N[C@H]2CC[C@H](N)CC2)nc1-c1cnc2ccc(-c3c(C)noc3C)cn12] | (1r,4r)-N$^1$-(4-(6-(3,5-Dimethylisoxazol-4-yl)imidazo[1,2-a]pyridin-3-yl)-5-methylpyrimidin-2-yl)cyclohexane-1,4-diamine | 417.5 |
| 60 | 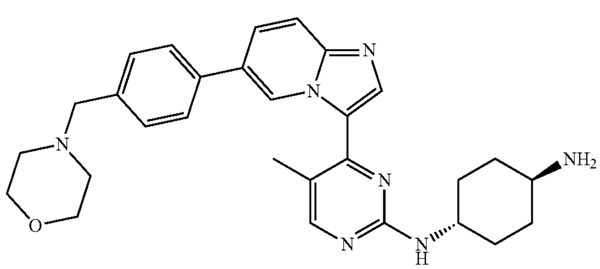 [SMILES: Cc1cnc(N[C@H]2CC[C@H](N)CC2)nc1-c1cnc2ccc(-c3ccc(CN4CCOCC4)cc3)cn12] | (1r,4r)-N$^1$-(5-Methyl-4-(6-(4-(morpholinomethyl)phenyl)imidazo[1,2-a]pyridin-3-yl)pyrimidin-2-yl)cyclohexane-1,4-diamine | 497.6 |

TABLE 1-continued

Chemical structure of selected compounds of the present invention

| No. | Structure | Name | Mass |
|---|---|---|---|
| 61 | 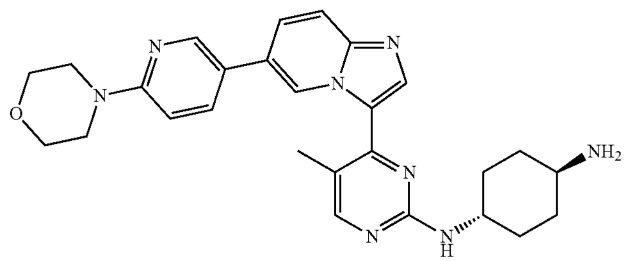 [SMILES: Cc1cnc(N[C@H]2CC[C@H](N)CC2)nc1-c1cnc2ccc(-c3ccc(N4CCOCC4)nc3)cn12] | (1r,4r)-N[1]-(5-Methyl-4-(6-(6-morpholinopyridin-3-yl)imidazo[1,2-a]pyridin-3-yl)pyrimidin-2-yl)cyclohexane-1,4-diamine | 484.6 |
| 62 | 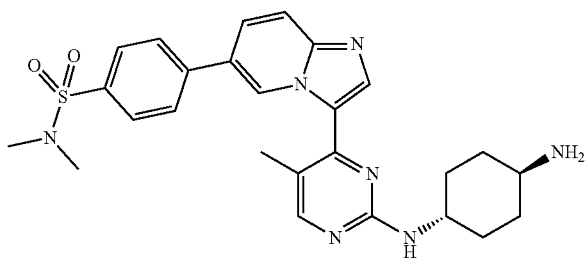 [SMILES: Cc1cnc(N[C@H]2CC[C@H](N)CC2)nc1-c1cnc2ccc(-c3ccc(S(=O)(=O)N(C)C)cc3)cn12] | 4-(3-(2-(((1r,4r)-4-Aminocyclohexyl)amino)-5-methylpyrimidin-4-yl)imidazo[1,2-a]pyridin-6-yl)-N,N-dimethylbenzenesulfonamide | 505.6 |
| 63 | 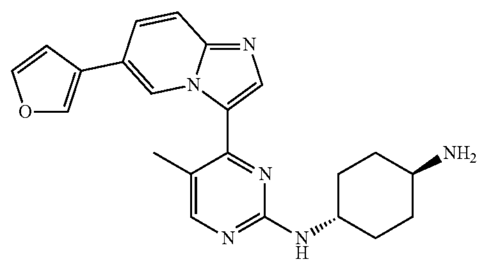 [SMILES: Cc1cnc(N[C@H]2CC[C@H](N)CC2)nc1-c1cnc2ccc(-c3ccoc3)cn12] | (1r,4r)-N[1]-(4-(6-(Furan-3-yl)imidazo[1,2-a]pyridin-3-yl)-5-methylpyrimidin-2-yl)cyclohexane-1,4-diamine | 388.5 |
| 64 | 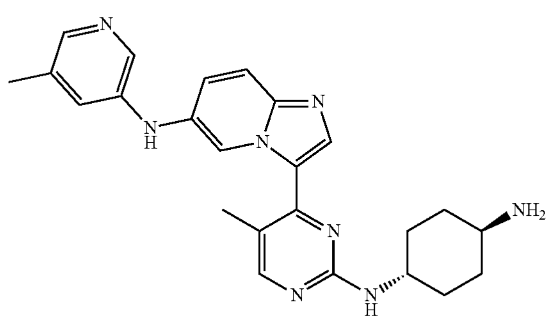 [SMILES: Cc1cncc(Nc2ccc3ncc(-c4nc(N[C@H]5CC[C@H](N)CC5)ncc4C)n3c2)c1] | (1r,4r)-N[1]-(5-Methyl-4-(6-((5-methylpyridin-3-yl)amino)imidazo[1,2-a]pyridin-3-yl)pyrimidin-2-yl)cyclohexane-1,4-diamine | 428.5 |
| 65 | 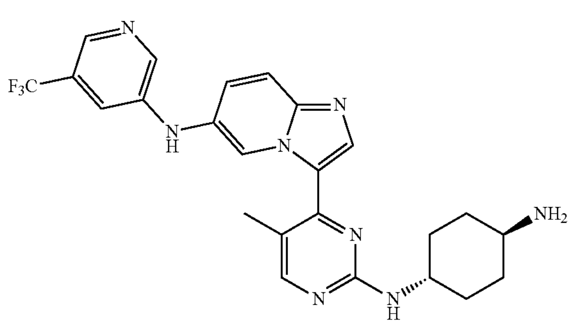 [SMILES: Cc1cnc(N[C@H]2CC[C@H](N)CC2)nc1-c1cnc2ccc(Nc3cncc(C(F)(F)F)c3)cn12] | (1r,4r)-N[1]-(5-Methyl-4-(6-((5-(trifluoromethyl)pyridin-3-yl)amino)imidazo[1,2-a]pyridin-3-yl)pyrimidin-2-yl)cyclohexane-1,4-diamine | 482.5 |

TABLE 1-continued

Chemical structure of selected compounds of the present invention

| No. | Structure | Name | Mass |
|---|---|---|---|
| 66 | 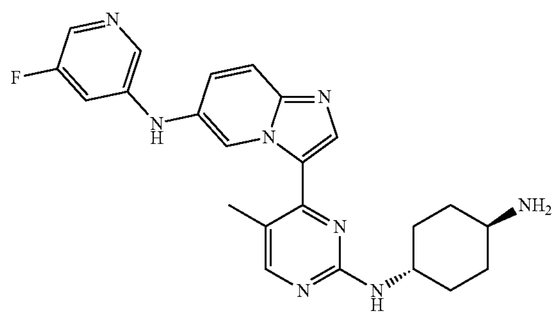 [SMILES: Cc1cnc(N[C@H]2CC[C@H](N)CC2)nc1-c1cnc2ccc(Nc3cncc(F)c3)cn12] | (1r,4r)-$N^1$-(4-(6-((5-Fluoropyridin-3-yl)amino)imidazo[1,2-a]pyridin-3-yl)-5-methylpyrimidin-2-yl)cyclohexane-1,4-diamine | 432.5 |
| 67 | 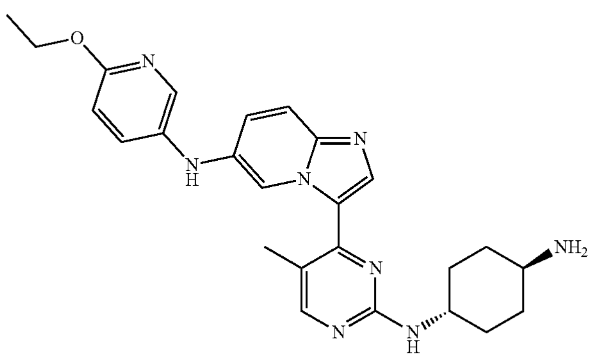 [SMILES: CCOc1ccc(Nc2ccc3ncc(-c4nc(N[C@H]5CC[C@H](N)CC5)ncc4C)n3c2)cn1] | (1r,4r)-$N^1$-(4-(6-((6-Ethoxypyridin-3-yl)amino)imidazo[1,2-a]pyridin-3-yl)-5-methylpyrimidin-2-yl)cyclohexane-1,4-diamine | 458.6 |
| 68 | 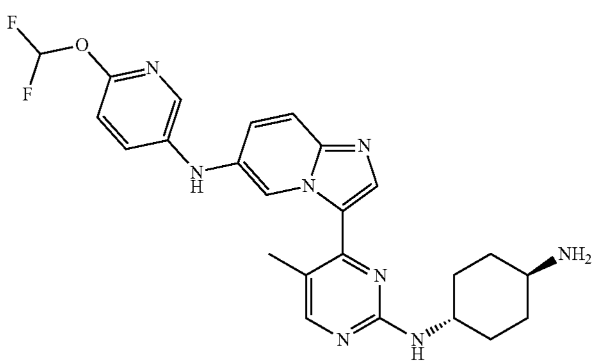 [SMILES: Cc1cnc(N[C@H]2CC[C@H](N)CC2)nc1-c1cnc2ccc(Nc3ccc(OC(F)F)nc3)cn12] | (1r,4r)-$N^1$-(4-(6-((6-(Difluoromethoxy)pyridin-3-yl)amino)imidazo[1,2-a]pyridin-3-yl)-5-methylpyrimidin-2-yl)cyclohexane-1,4-diamine | 480.5 |
| 69 | 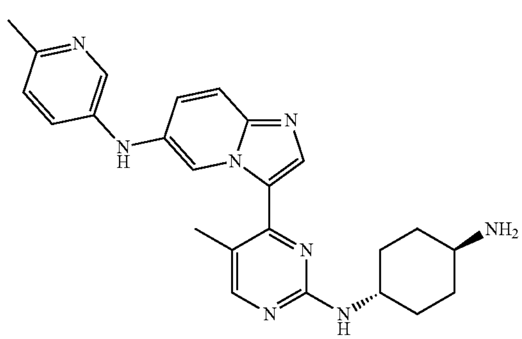 [SMILES: Cc1ccc(Nc2ccc3ncc(-c4nc(N[C@H]5CC[C@H](N)CC5)ncc4C)n3c2)cn1] | (1r,4r)-$N^1$-(5-Methyl-4-(6-((6-methylpyridin-3-yl)amino)imidazo[1,2-a]pyridin-3-yl)pyrimidin-2-yl)cyclohexane-1,4-diamine | 428.5 |

TABLE 1-continued

Chemical structure of selected compounds of the present invention

| No. | Structure | Name | Mass |
|---|---|---|---|
| 70 | 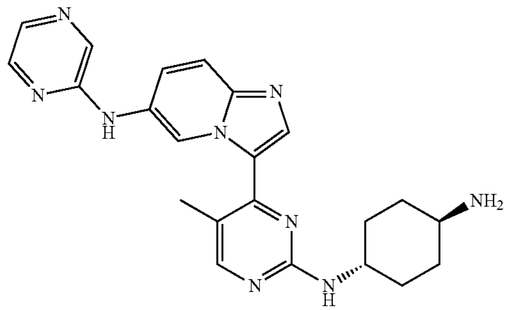 [SMILES: Cc1cnc(N[C@H]2CC[C@H](N)CC2)nc1-c1cnc2ccc(Nc3cnccn3)cn12] | (1r,4r)-N[1]-(5-Methyl-4-(6-(pyrazin-2-ylamino)imidazo[1,2-a]pyridin-3-yl)pyrimidin-2-yl)cyclohexane-1,4-diamine | 415.5 |
| 71 | 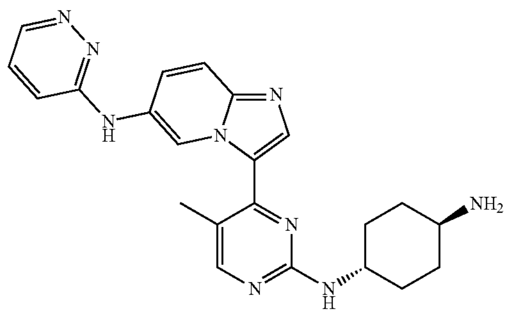 [SMILES: Cc1cnc(N[C@H]2CC[C@H](N)CC2)nc1-c1cnc2ccc(Nc3cccnn3)cn12] | (1r,4r)-N[1]-(5-Methyl-4-(6-(pyridazin-3-ylamino)imidazo[1,2-a]pyridin-3-yl)pyrimidin-2-yl)cyclohexane-1,4-diamine | 415.5 |
| 72 | 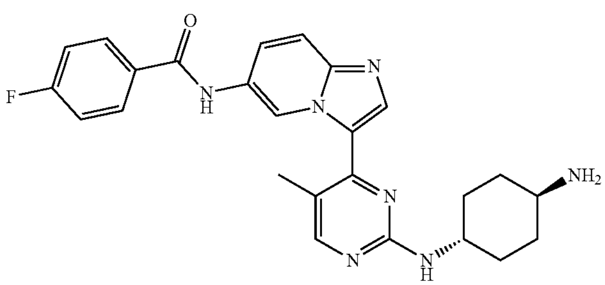 [SMILES: Cc1cnc(N[C@H]2CC[C@H](N)CC2)nc1-c1cnc2ccc(NC(=O)c3ccc(F)cc3)cn12] | N-(3-(2-(((1r,4r)-4-Aminocyclohexyl)amino)-5-methylpyrimidin-4-yl)imidazo[1,2-a]pyridin-6-yl)-4-fluorobenzamide | 459.5 |
| 73 | 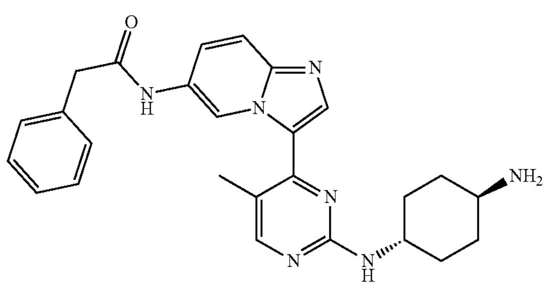 [SMILES: Cc1cnc(N[C@H]2CC[C@H](N)CC2)nc1-c1cnc2ccc(NC(=O)Cc3ccccc3)cn12] | N-(3-(2-(((1r,4r)-4-Aminocyclohexyl)amino)-5-methylpyrimidin-4-yl)imidazo[1,2-a]pyridin-6-yl)-2-phenylacetamide | 455.6 |
| 74 | 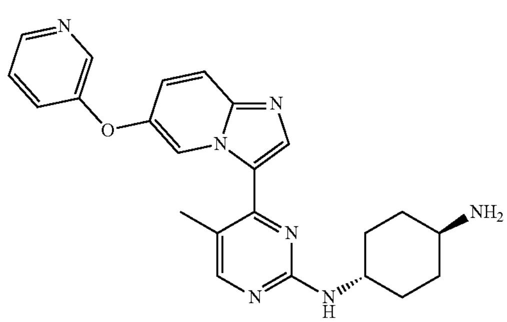 [SMILES: Cc1cnc(N[C@H]2CC[C@H](N)CC2)nc1-c1cnc2ccc(Oc3cccnc3)cn12] | (1r,4r)-N[1]-(5-Methyl-4-(6-(pyridin-3-yloxy)imidazo[1,2-a]pyridin-3-yl)pyrimidin-2-yl)cyclohexane-1,4-diamine | 415.5 |

TABLE 1-continued

Chemical structure of selected compounds of the present invention

| No. | Structure | Name | Mass |
|---|---|---|---|
| 75 | 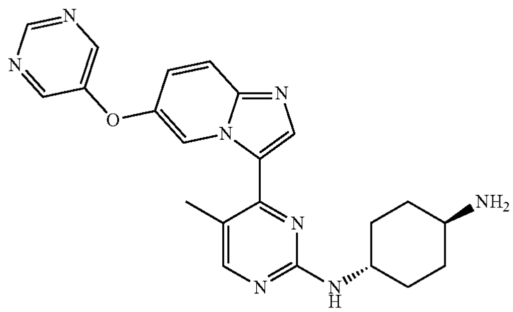 [SMILES: Cc1cnc(N[C@H]2CC[C@H](N)CC2)nc1-c1cnc2ccc(Oc3cncnc3)cn12] | (1r,4r)-N$^1$-(5-Methyl-4-(6-(pyrimidin-5-yloxy)imidazo[1,2-a]pyridin-3-yl)pyrimidin-2-yl)cyclohexane-1,4-diamine | 416.5 |
| 76 | 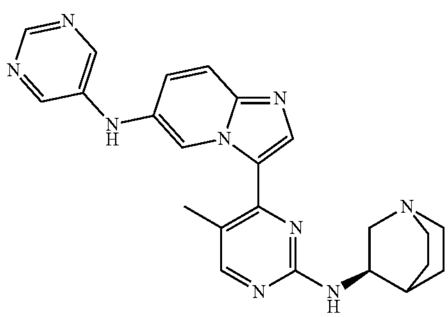 [SMILES: Cc1cnc(N[C@H]2CN3CCC2CC3)nc1-c1cnc2ccc(Nc3cncnc3)cn12] | (R)-N-(5-Methyl-4-(6-(pyrimidin-5-ylamino)imidazo[1,2-a]pyridin-3-yl)pyrimidin-2-yl)quinuclidin-3-amine | 427.5 |
| 77 | 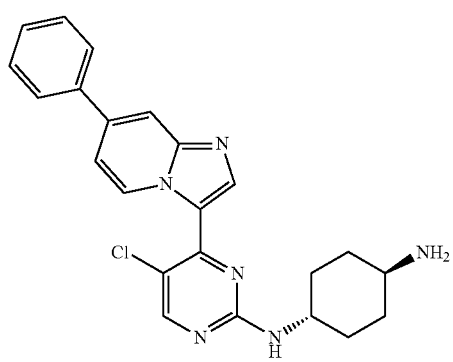 [SMILES: N[C@H]1CC[C@H](Nc2ncc(Cl)c(-c3cnc4cc(-c5ccccc5)ccn34)n2)CC1] | (1r,4r)-N$^1$-(5-Chloro-4-(7-phenylimidazo[1,2-a]pyridin-3-yl)pyrimidin-2-yl)cyclohexane-1,4-diamine | 418.9 |
| 78 | 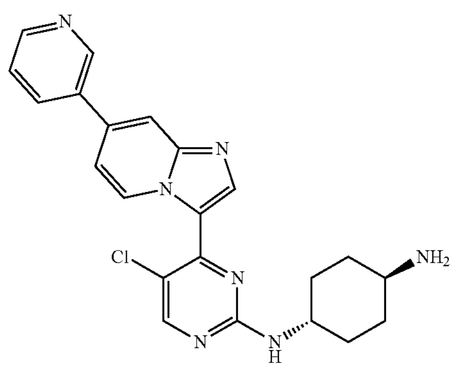 [SMILES: N[C@H]1CC[C@H](Nc2ncc(Cl)c(-c3cnc4cc(-c5cccnc5)ccn34)n2)CC1] | (1r,4r)-N$^1$-(5-Chloro-4-(7-(pyridin-3-yl)imidazo[1,2-a]pyridin-3-yl)pyrimidin-2-yl)cyclohexane-1,4-diamine | 419.2 |

TABLE 1-continued

Chemical structure of selected compounds of the present invention

| No. | Structure | Name | Mass |
|---|---|---|---|
| 79 | 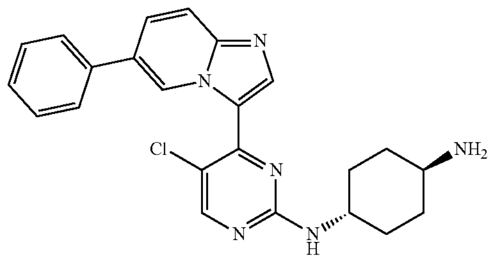 [SMILES: N[C@H]1CC[C@H](Nc2ncc(Cl)c(-c3cnc4ccc(-c5ccccc5)cn34)n2)CC1] | (1r,4r)-N$^1$-(5-Chloro-4-(6-phenylimidazo[1,2-a]pyridin-3-yl)pyrimidin-2-yl)cyclohexane-1,4-diamine | 418.9 |
| 80 | 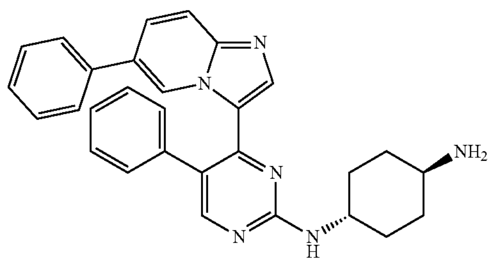 [SMILES: N[C@H]1CC[C@H](Nc2ncc(-c3ccccc3)c(-c3cnc4ccc(-c5ccccc5)cn34)n2)CC1] | (1r,4r)-N$^1$-(5-Phenyl-4-(6-phenylimidazo[1,2-a]pyridin-3-yl)pyrimidin-2-yl)cyclohexane-1,4-diamine | 460.6 |
| 81 | 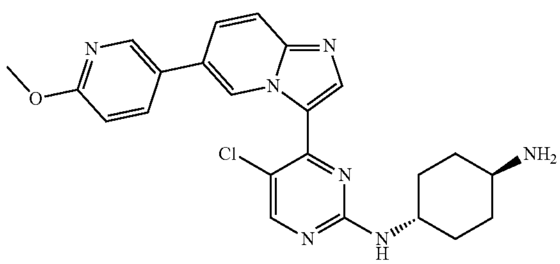 [SMILES: COc1ccc(-c2ccc3ncc(-c4nc(N[C@H]5CC[C@H](N)CC5)ncc4Cl)n3c2)cn1] | (1r,4r)-N$^1$-(5-Chloro-4-(6-(6-methoxypyridin-3-yl)imidazo[1,2-a]pyridin-3-yl)pyrimidin-2-yl)cyclohexane-1,4-diamine | 449.9 |
| 82 | 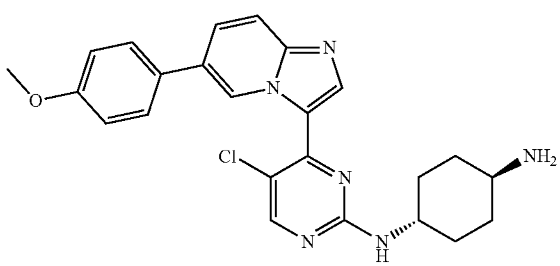 [SMILES: COc1ccc(-c2ccc3ncc(-c4nc(N[C@H]5CC[C@H](N)CC5)ncc4Cl)n3c2)cc1] | (1r,4r)-N$^1$-(5-Chloro-4-(6-(4-methoxyphenyl)imidazo[1,2-a]pyridin-3-yl)pyrimidin-2-yl)cyclohexane-1,4-diamine | 449.0 |
| 83 | 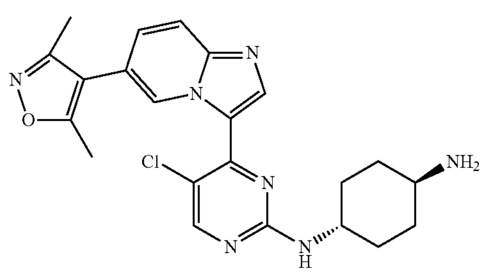 [SMILES: Cc1noc(C)c1-c1ccc2ncc(-c3nc(N[C@H]4CC[C@H](N)CC4)ncc3Cl)n2c1] | (1r,4r)-N$^1$-(5-Chloro-4-(6-(3,5-dimethylisoxazol-4-yl)imidazo[1,2-a]pyridin-3-yl)pyrimidin-2-yl)cyclohexane-1,4-diamine | 437.9 |

TABLE 1-continued

Chemical structure of selected compounds of the present invention

| No. | Structure | Name | Mass |
|---|---|---|---|
| 84 | 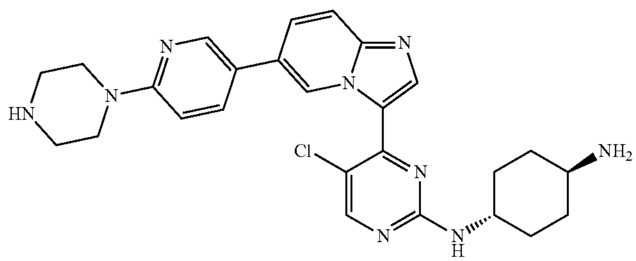 [SMILES: N[C@H]1CC[C@H](Nc2ncc(Cl)c(-c3cnc4ccc(-c5ccc(N6CCNCC6)nc5)cn34)n2)CC1] | (1r,4r)-N[1]-(5-Chloro-4-(6-(6-(piperazin-1-yl)pyridin-3-yl)imidazo[1,2-a]pyridin-3-yl)pyrimidin-2-yl)cyclohexane-1,4-diamine | 504.0 |
| 85 | 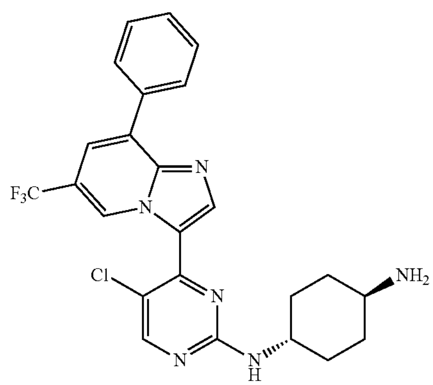 [SMILES: N[C@H]1CC[C@H](Nc2ncc(Cl)c(-c3cnc4c(-c5ccccc5)cc(C(F)(F)F)cn34)n2)CC1] | (1r,4r)-N[1]-(5-Chloro-4-(8-phenyl-6-(trifluoromethyl)imidazo[1,2-a]pyridin-3-yl)pyrimidin-2-yl)cyclohexane-1,4-diamine | 486.9 |
| 86 | 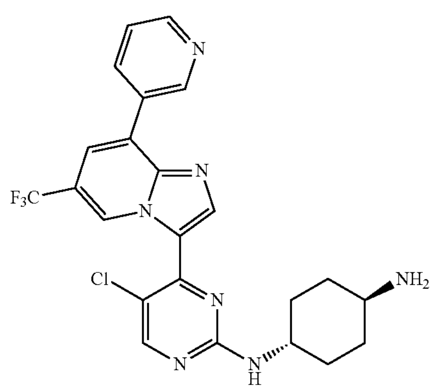 | (1r,4r)-N[1]-(5-Chloro-4-(8-(pyridin-3-yl)-6-(trifluoromethyl)imidazo[1,2-a]pyridin-3-yl)pyrimidin-2-yl)cyclohexane-1,4-diamine | 487.9 |
| 87 | 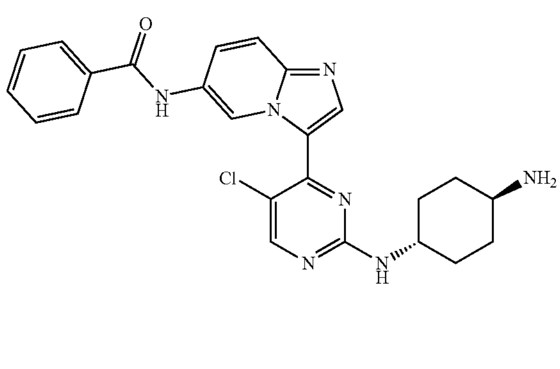 [SMILES: N[C@H]1CC[C@H](Nc2ncc(Cl)c(-c3cnc4ccc(NC(=O)c5ccccc5)cn34)n2)CC1] | N-(3-(2-(((1r,4r)-4-Aminocyclohexyl)amino)-5-chloropyrimidin-4-yl)imidazo[1,2-a]pyridin-6-yl)benzamide | 462.0 |

TABLE 1-continued

Chemical structure of selected compounds of the present invention

| No. | Structure | Name | Mass |
|---|---|---|---|
| 88 | 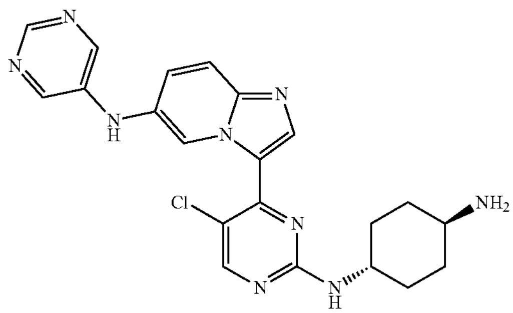 [SMILES: N[C@H]1CC[C@H](Nc2ncc(Cl)c(-c3cnc4ccc(Nc5cncnc5)cn34)n2)CC1] | (1r,4r)-N$^1$-(5-Chloro-4-(6-(pyrimidin-5-ylamino)imidazo[1,2-a]pyridin-3-yl)pyrimidin-2-yl)cyclohexane-1,4-diamine | 435.9 |
| 89 | 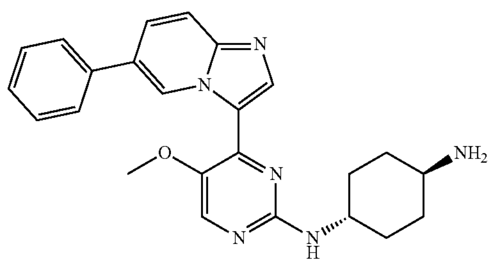 [SMILES: COc1cnc(N[C@H]2CC[C@H](N)CC2)nc1-c1cnc2ccc(-c3ccccc3)cn12] | (1r,4r)-N$^1$-(5-Methoxy-4-(6-phenylimidazo[1,2-a]pyridin-3-yl)pyrimidin-2-yl)cyclohexane-1,4-diamine | 414.5 |
| 90 | 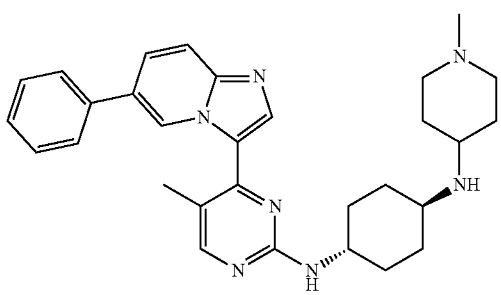 [SMILES: Cc1cnc(N[C@H]2CC[C@H](NC3CCN(C)CC3)CC2)nc1-c1cnc2ccc(-c3ccccc3)cn12] | (1r,4r)-N$^1$-(5-Methyl-4-(6-phenylimidazo[1,2-a]pyridin-3-yl)pyrimidin-2-yl)-N4-(1-methylpiperidin-4-yl)cyclohexane-1,4-diamine | 495.7 |
| 91 | 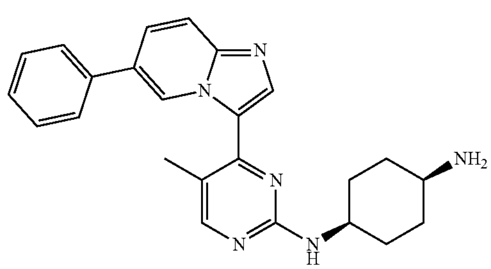 [SMILES: Cc1cnc(N[C@H]2CC[C@@H](N)CC2)nc1-c1cnc2ccc(-c3ccccc3)cn12] | (1s,4s)-N$^1$-(5-Methyl-4-(6-phenylimidazo[1,2-a]pyridin-3-yl)pyrimidin-2-yl)cyclohexane-1,4-diamine | 398.5 |
| 92 | 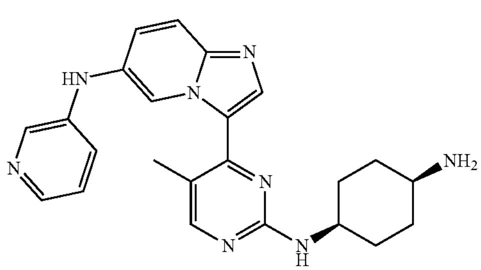 [SMILES: Cc1cnc(N[C@H]2CC[C@@H](N)CC2)nc1-c1cnc2ccc(Nc3cccnc3)cn12] | (1s,4s)-N$^1$-(5-Methyl-4-(6-(pyridin-3-ylamino)imidazo[1,2-a]pyridin-3-yl)pyrimidin-2-yl)cyclohexane-1,4-diamine | 414.5 |

TABLE 1-continued

Chemical structure of selected compounds of the present invention

| No. | Structure | Name | Mass |
|---|---|---|---|
| 93 | 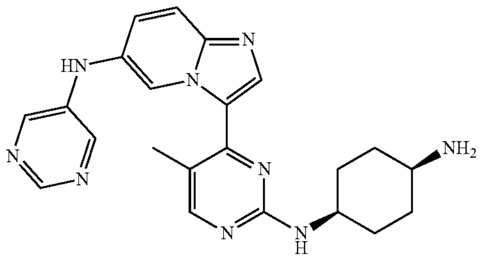 [SMILES: Cc1cnc(N[C@H]2CC[C@@H](N)CC2)nc1-c1cnc2ccc(Nc3cncnc3)cn12] | (1s,4s)-N[1]-(5-Methyl-4-(6-(pyrimidin-5-ylamino)imidazo[1,2-a]pyridin-3-yl)pyrimidin-2-yl)cyclohexane-1,4-diamine | 415.5 |
| 94 | 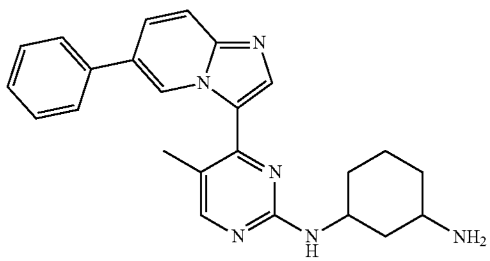 [SMILES: Cc1cnc(NC2CCCC(N)C2)nc1-c1cnc2ccc(-c3ccccc3)cn12] | N[1]-(5-Methyl-4-(6-phenylimidazo[1,2-a]pyridin-3-yl)pyrimidin-2-yl)cyclohexane-1,3-diamine | 398.5 |
| 95 | 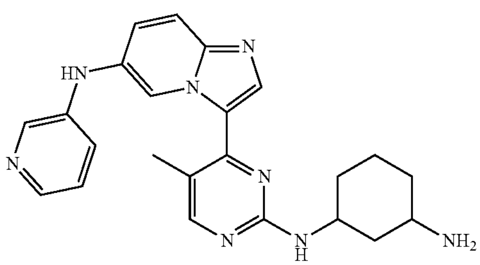 [SMILES: Cc1cnc(NC2CCCC(N)C2)nc1-c1cnc2ccc(Nc3cccnc3)cn12] | N[1]-(5-Methyl-4-(6-(pyridin-3-ylamino)imidazo[1,2-a]pyridin-3-yl)pyrimidin-2-yl)cyclohexane-1,3-diamine | 414.5 |
| 96 | 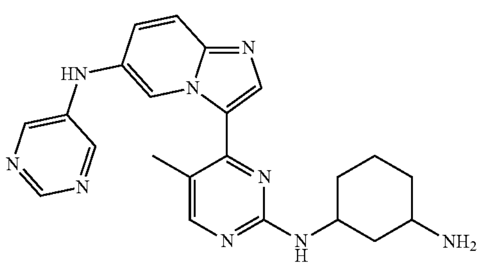 [SMILES: Cc1cnc(NC2CCCC(N)C2)nc1-c1cnc2ccc(Nc3cncnc3)cn12] | N[1]-(5-Methyl-4-(6-(pyrimidin-5-ylamino)imidazo[1,2-a]pyridin-3-yl)pyrimidin-2-yl)cyclohexane-1,3-diamine | 415.5 |
| 97 | 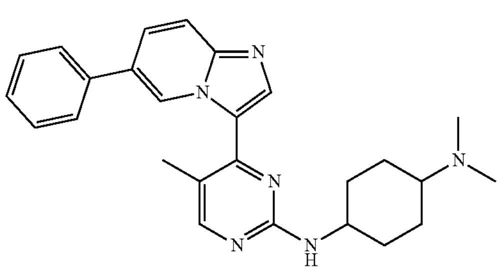 [SMILES: Cc1cnc(NC2CCC(N(C)C)CC2)nc1-c1cnc2ccc(-c3ccccc3)cn12] | N[1],N[1]-Dimethyl-N[4]-(5-methyl-4-(6-phenylimidazo[1,2-a]pyridin-3-yl)pyrimidin-2-yl)cyclohexane-1,4-diamine | 426.6 |

TABLE 1-continued

Chemical structure of selected compounds of the present invention

| No. | Structure | Name | Mass |
|---|---|---|---|
| 98 | 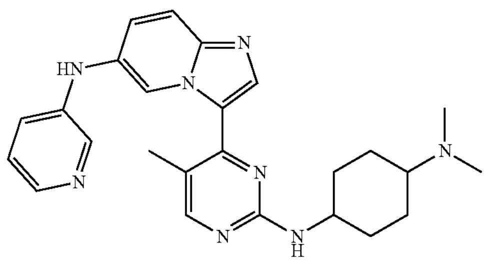 [SMILES: Cc1cnc(NC2CCC(N(C)C)CC2)nc1-c1cnc2ccc(Nc3cccnc3)cn12] | $N^1,N^1$-Dimethyl-$N^4$-(5-Methyl-4-(6-(pyridin-3-ylamino)imidazo[1,2-a]pyridin-3-yl)pyrimidin-2-yl)cyclohexane-1,4-diamine | 442.6 |
| 99 | 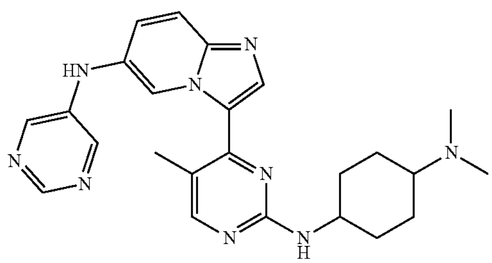 [SMILES: Cc1cnc(NC2CCC(N(C)C)CC2)nc1-c1cnc2ccc(Nc3cncnc3)cn12] | $N^1,N^1$-dimethyl-$N^4$-(5-Methyl-4-(6-(pyrimidin-5-ylamino)imidazo[1,2-a]pyridin-3-yl)pyrimidin-2-yl)cyclohexane-1,4-diamine | 443.6 |
| 100 | 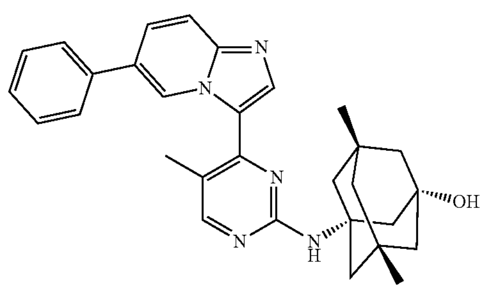 [SMILES: Cc1cnc(N[C@]23C[C@@]4(C)C[C@](C)(C[C@](O)(C4)C2)C3)nc1-c1cnc2ccc(-c3ccccc3)cn12] | (1s,3R,5S,7r)-3,5-Dimethyl-7-((5-methyl-4-(6-phenylimidazo[1,2-a]pyridin-3-yl)pyrimidin-2-yl)amino)adamantan-1-ol | 479.6 |
| 101 | 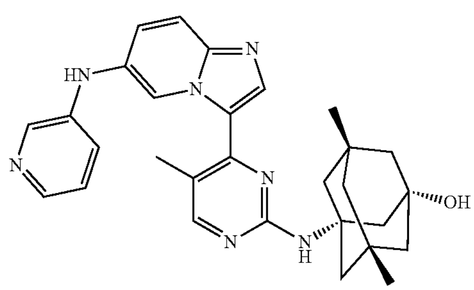 [SMILES: Cc1cnc(N[C@]23C[C@@]4(C)C[C@](C)(C[C@](O)(C4)C2)C3)nc1-c1cnc2ccc(Nc3cccnc3)cn12] | (1s,3R,5S,7r)-3,5-Dimethyl-7-((5-methyl-4-(6-(pyridin-3-ylamino)imidazo[1,2-a]pyridin-3-yl)pyrimidin-2-yl)amino)adamantan-1-ol | 495.6 |
| 102 | 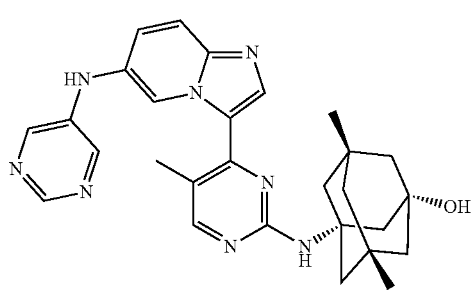 [SMILES: Cc1cnc(N[C@]23C[C@@]4(C)C[C@](C)(C[C@](O)(C4)C2)C3)nc1-c1cnc2ccc(Nc3cncnc3)cn12] | (1s,3R,5S,7r)-3,5-Dimethyl-7-((5-methyl-4-(6-(pyrimidin-5-ylamino)imidazo[1,2-a]pyridin-3-yl)pyrimidin-2-yl)amino)adamantan-1-ol | 496.6 |

TABLE 1-continued

Chemical structure of selected compounds of the present invention

| No. | Structure | Name | Mass |
|---|---|---|---|
| 103 | 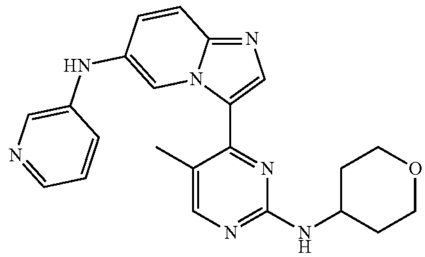 [SMILES: Cc1cnc(NC2CCOCC2)nc1-c1cnc2ccc(Nc3cccnc3)cn12] | 3-(5-Methyl-2-((tetrahydro-2H-pyran-4-yl)amino)pyrimidin-4-yl)-N-(pyridin-3-yl)imidazo[1,2-a]pyridin-6-amine | 401.5 |
| 104 | 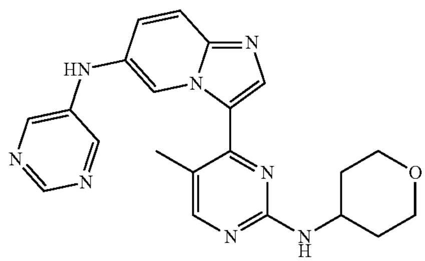 [SMILES: Cc1cnc(NC2CCOCC2)nc1-c1cnc2ccc(Nc3cncnc3)cn12] | 3-(5-Methyl-2-((tetrahydro-2H-pyran-4-yl)amino)pyrimidin-4-yl)-N-(pyrimidin-5-yl)imidazo[1,2-a]pyridin-6-amine | 402.5 |
| 105 | 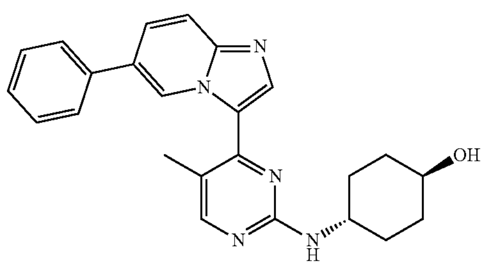 [SMILES: Cc1cnc(N[C@H]2CC[C@H](O)CC2)nc1-c1cnc2ccc(-c3ccccc3)cn12] | (1r,4r)-4-((5-Methyl-4-(6-phenylimidazo[1,2-a]pyridin-3-yl)pyrimidin-2-yl)amino)cyclohexan-1-ol | 399.5 |
| 106 | 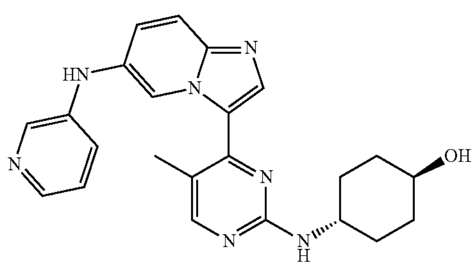 [SMILES: Cc1cnc(N[C@H]2CC[C@H](O)CC2)nc1-c1cnc2ccc(Nc3cccnc3)cn12] | (1r,4r)-4-((5-Methyl-4-(6-(pyridin-3-ylamino)imidazo[1,2-a]pyridin-3-yl)pyrimidin-2-yl)amino)cyclohexan-1-ol | 415.5 |
| 107 | 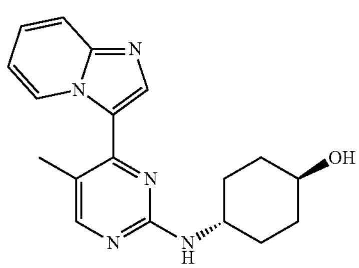 [SMILES: Cc1cnc(N[C@H]2CC[C@H](O)CC2)nc1-c1cnc2ccccn12] | (1r,4r)-4-((4-(Imidazo[1,2-a]pyridin-3-yl)-5-methylpyrimidin-2-yl)amino)cyclohexan-1-ol | 323.4 |

TABLE 1-continued

Chemical structure of selected compounds of the present invention

| No. | Structure | Name | Mass |
|---|---|---|---|
| 108 | 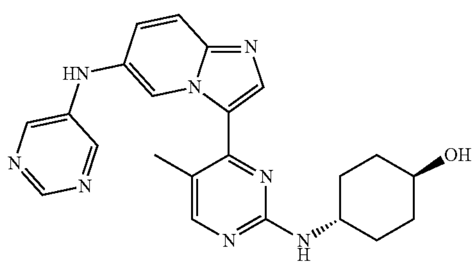 [SMILES: Cc1cnc(N[C@H]2CC[C@H](O)CC2)nc1-c1cnc2ccc(Nc3cncnc3)cn12] | (1r,4r)-4-((5-Methyl-4-(6-(pyrimidin-5-ylamino)imidazo[1,2-a]pyridin-3-yl)pyrimidin-2-yl)amino)cyclohexan-1-ol | 416.5 |
| 109 | 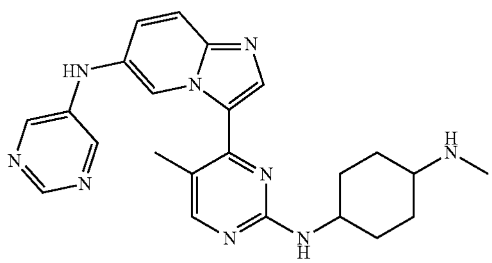 | $N^1$-Methyl-$N^4$-(5-Methyl-4-(6-(pyrimidin-5-ylamino)imidazo[1,2-a]pyridin-3-yl)pyrimidin-2-yl)cyclohexane-1,4-diamine | 429.5 |
| 110 | 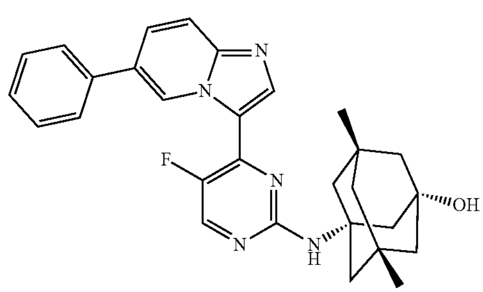 [SMILES: C[C@]12C[C@]3(C)C[C@](O)(C1)C[C@](Nc1ncc(F)c(-c4cnc5ccc(-c6ccccc6)cn45)n1)(C2)C3] | (1s,3r,5R,7S)-3-((5-Fluoro-4-(6-phenylimidazo[1,2-a]pyridin-3-yl)pyrimidin-2-yl)amino)-5,7-dimethyladamantan-1-ol | 483.6 |
| 111 | 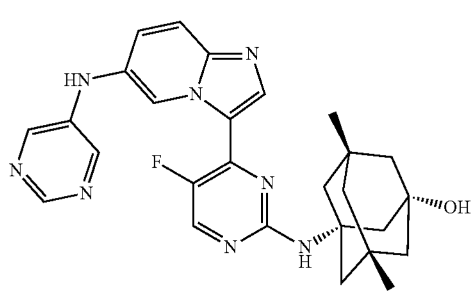 [SMILES: C[C@]12C[C@]3(C)C[C@](O)(C1)C[C@](Nc1ncc(F)c(-c4cnc5ccc(Nc6cncnc6)cn45)n1)(C2)C3] | (1s,3r,5R,7S)-3-((5-Fluoro-4-(6-(pyrimidin-5-ylamino)imidazo[1,2-a]pyridin-3-yl)pyrimidin-2-yl)amino)-5,7-dimethyladamantan-1-ol | 500.6 |
| 112 | 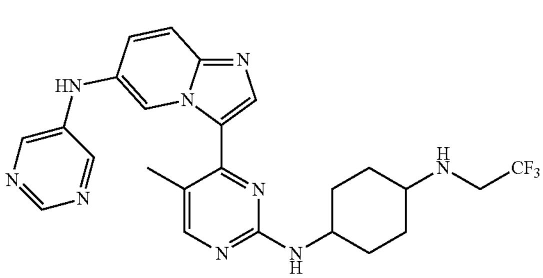 [SMILES: Cc1cnc(NC2CCC(NCC(F)(F)F)CC2)nc1-c1cnc2ccc(Nc3cncnc3)cn12] | $N^1$-(5-Methyl-4-(6-(pyrimidin-5-ylamino)imidazo[1,2-a]pyridin-3-yl)pyrimidin-2-yl)-$N^4$-(2,2,2-trifluoroethyl)cyclohexane-1,4-diamine | 497.5 |

TABLE 1-continued

Chemical structure of selected compounds of the present invention

| No. | Structure | Name | Mass |
|---|---|---|---|
| 113 | 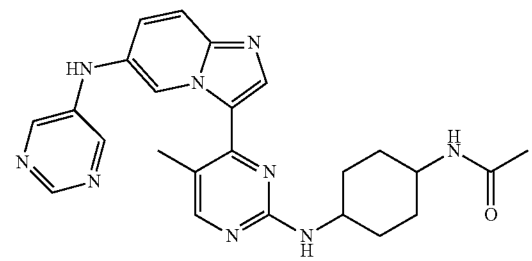 [SMILES: CC(=O)NC1CCC(Nc2ncc(C)c(-c3cnc4ccc(Nc5cncnc5)cn34)n2)CC1] | N-(4-((5-Methyl-4-(6-(pyrimidin-5-ylamino)imidazo[1,2-a]pyridin-3-yl)pyrimidin-2-yl)amino)cyclohexyl)acetamide | 457.5 |
| 114 | 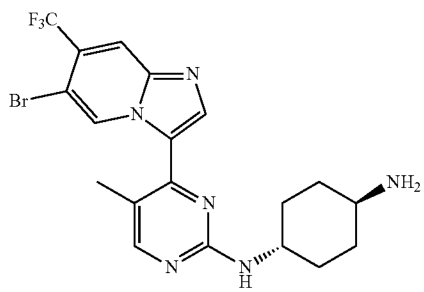 [SMILES: Cc1cnc(N[C@H]2CC[C@H](N)CC2)nc1-c1cnc2cc(C(F)(F)F)c(Br)cn12] | (1r,4r)-N$^1$-(4-(6-Bromo-7-(trifluoromethyl)imidazo[1,2-a]pyridin-3-yl)-5-methylpyrimidin-2-yl)cyclohexane-1,4-diamine | 469.3 |
| 115 | 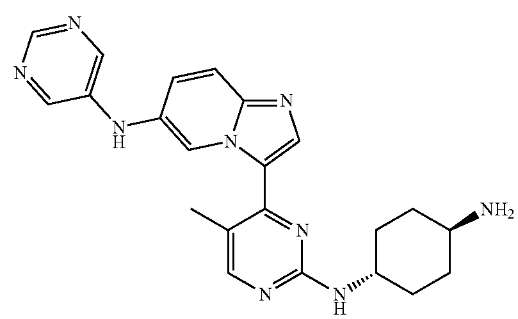 [SMILES: Cc1cnc(N[C@H]2CC[C@H](N)CC2)nc1-c1cnc2ccc(Nc3cncnc3)cn12] | (1r,4r)-N$^1$-(5-Methyl-4-(6-(pyrimidin-5-ylamino)imidazo[1,2-a]pyridin-3-yl)pyrimidin-2-yl)cyclohexane-1,4-diamine | 415.5 |
| 116 | 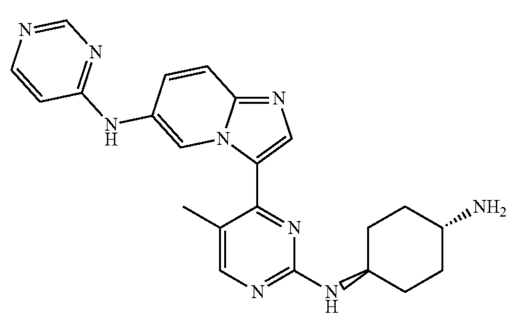 [SMILES: Cc1cnc(N[C@H]2CC[C@H](N)CC2)nc1-c1cnc2ccc(Nc3ccncn3)cn12] | (1r,4r)-N$^1$-(5-Methyl-4-(6-(pyrimidin-4-ylamino)imidazo[1,2-a]pyridin-3-yl)pyrimidin-2-yl)cyclohexane-1,4-diamine | 415.5 |
| 117 | 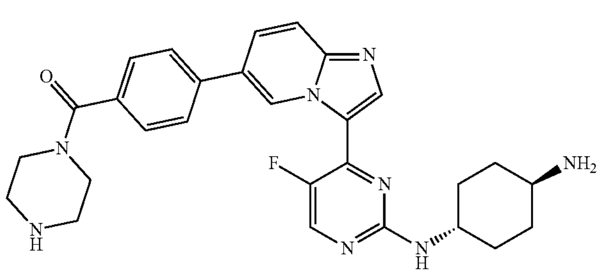 [SMILES: N[C@H]1CC[C@H](Nc2ncc(F)c(-c3cnc4ccc(-c5ccc(C(=O)N6CCNCC6)cc5)cn34)n2)CC1] | (4-(3-(2-(((1r,4r)-4-Aminocyclohexyl)amino)-5-fluoropyrimidin-4-yl)imidazo[1,2-a]pyridin-6-yl)phenyl)(piperazin-1-yl)methanone | 514.6 |

TABLE 1-continued

Chemical structure of selected compounds of the present invention

| No. | Name | Mass |
|---|---|---|
| 118 | (1r,4r)-N[1]-(5-Chloro-4-(7-(pyrimidin-5-ylamino)imidazo[1,2-a]pyridin-3-yl)pyrimidin-2-yl)cyclohexane-1,4-diamine | 435.9 |
| 119 | 3-(2-(((1r,4r)-4-(Aziridin-1-yl)cyclohexyl)amino)-5-methylpyrimidin-4-yl)-N-(pyrimidin-5-yl)imidazo[1,2-a]pyridin-7-amine | 441.5 |
| 120 | N[1]-(4-(6-((5-Fluoropyridin-3-yl)amino)imidazo[1,2-a]pyridin-3-yl)-5-methylpyrimidin-2-yl)-N[4],N[4]-dimethylcyclohexane-1,4-diamine | 460.6 |
| 121 | (1r,4r)-N[1]-Isopropyl-N[4]-(5-methyl-4-(6-(pyrimidin-5-ylamino)imidazo[1,2-a]pyridin-3-yl)pyrimidin-2-yl)cyclohexane-1,4-diamine | 457.6 |
| 122 | (1r,4r)-N[1]-(5-Methyl-4-(6-(methyl(pyridin-3-yl)amino)imidazo[1,2-a]pyridin-3-yl)pyrimidin-2-yl)cyclohexane-1,4-diamine | 428.5 |

TABLE 1-continued

Chemical structure of selected compounds of the present invention

| No. | Structure | Name | Mass |
|---|---|---|---|
| 123 | 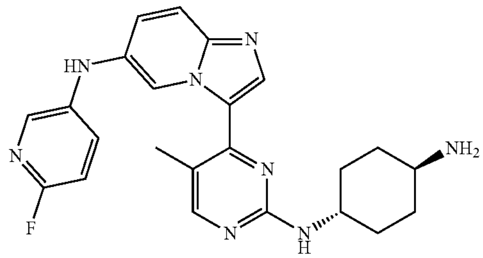 [SMILES: Cc1cnc(N[C@H]2CC[C@H](N)CC2)nc1-c1cnc2ccc(Nc3ccc(F)nc3)cn12] | (1r,4r)-N¹-(4-(6-((6-Fluoropyridin-3-yl)amino)imidazo[1,2-a]pyridin-3-yl)-5-methylpyrimidin-2-yl)cyclohexane-1,4-diamine | 432.5 |
| 124 | 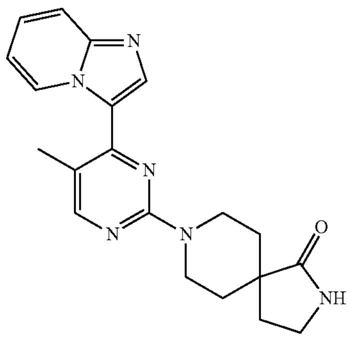 [SMILES: Cc1cnc(N2CCC3(CCNC3=O)CC2)nc1-c1cnc2ccccn12] | 8-(4-(Imidazo[1,2-a]pyridin-3-yl)-5-methylpyrimidin-2-yl)-2,8-diazaspiro[4.5]decan-1-one | 362.4 |
| 125 | 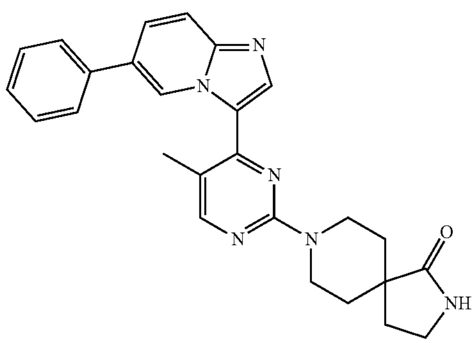 [SMILES: Cc1cnc(N2CCC3(CCNC3=O)CC2)nc1-c1cnc2ccc(-c3ccccc3)cn12] | 8-(5-Methyl-4-(6-phenylimidazo[1,2-a]pyridin-3-yl)pyrimidin-2-yl)-2,8-diazaspiro[4.5]decan-1-one | 438.5 |
| 126 | 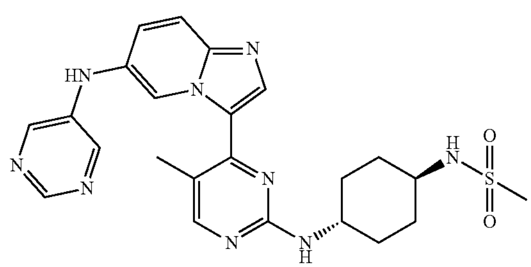 [SMILES: Cc1cnc(N[C@H]2CC[C@H](NS(C)(=O)=O)CC2)nc1-c1cnc2ccc(Nc3cncnc3)cn12] | N-((1r,4r)-4-((5-Methyl-4-(6-(pyrimidin-5-ylamino)imidazo[1,2-a]pyridin-3-yl)pyrimidin-2-yl)amino)cyclohexyl)methanesulfonamide | 493.6 |
| 127 | 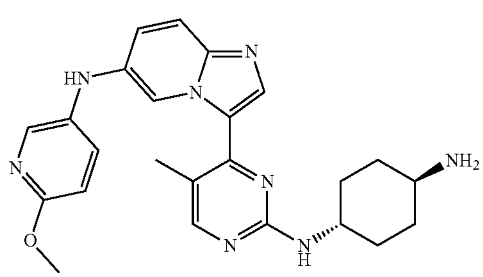 [SMILES: COc1ccc(Nc2ccc3ncc(-c4nc(N[C@H]5CC[C@H](N)CC5)ncc4C)n3c2)cn1] | (1r,4r)-N¹-(4-(6-((6-Methoxypyridin-3-yl)amino)imidazo[1,2-a]pyridin-3-yl)-5-methylpyrimidin-2-yl)cyclohexane-1,4-diamine | 444.5 |

TABLE 1-continued

Chemical structure of selected compounds of the present invention

| No. | Structure | Name | Mass |
|---|---|---|---|
| 128 | 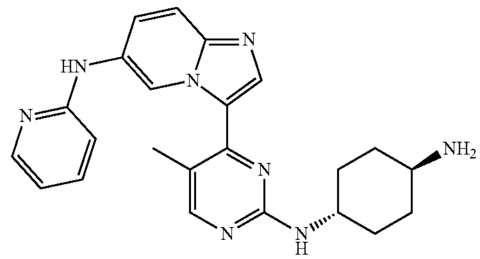 [SMILES: Cc1cnc(N[C@H]2CC[C@H](N)CC2)nc1-c1cnc2ccc(Nc3ccccn3)cn12] | (1r,4r)-$N^1$-(5-Methyl-4-(6-(pyridin-2-ylamino)imidazo[1,2-a]pyridin-3-yl)pyrimidin-2-yl)cyclohexane-1,4-diamine | 414.5 |
| 129 | 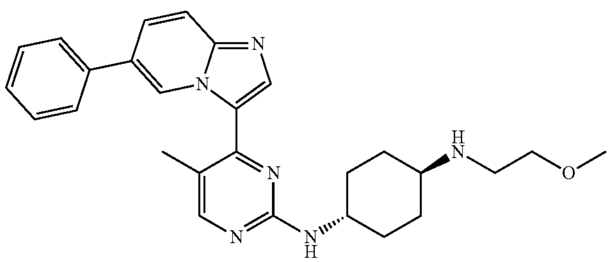 [SMILES: COCCN[C@H]1CC[C@H](Nc2ncc(C)c(-c3cnc4ccc(-c5ccccc5)cn34)n2)CC1] | (1r,4r)-$N^1$-(2-Methoxyethyl)-$N^4$-(5-methyl-4-(6-phenylimidazo[1,2-a]pyridin-3-yl)pyrimidin-2-yl)cyclohexane-1,4-diamine | 456.6 |
| 130 | 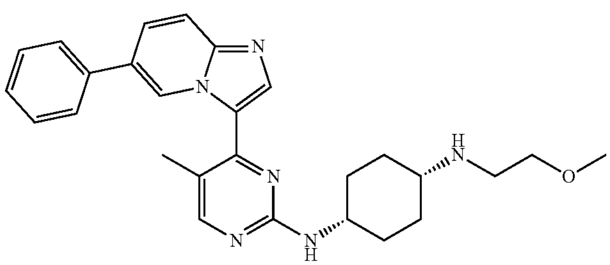 [SMILES: COCCN[C@H]1CC[C@@H](Nc2ncc(C)c(-c3cnc4ccc(-c5ccccc5)cn34)n2)CC1] | (1s,4s)-$N^1$-(2-Methoxyethyl)-$N^4$-(5-methyl-4-(6-phenylimidazo[1,2-a]pyridin-3-yl)pyrimidin-2-yl)cyclohexane-1,4-diamine | 456.6 |
| 131 | 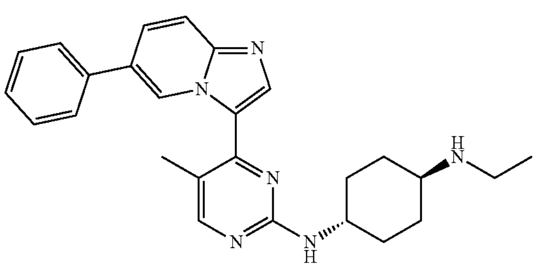 [SMILES: CCN[C@H]1CC[C@H](Nc2ncc(C)c(-c3cnc4ccc(-c5ccccc5)cn34)n2)CC1] | (1r,4r)-$N^1$-Ethyl-$N^4$-(5-methyl-4-(6-phenylimidazo[1,2-a]pyridin-3-yl)pyrimidin-2-yl)cyclohexane-1,4-diamine | 426.6 |
| 132 | 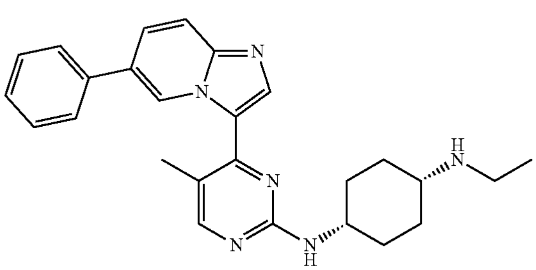 [SMILES: CCN[C@H]1CC[C@@H](Nc2ncc(C)c(-c3cnc4ccc(-c5ccccc5)cn34)n2)CC1] | (1s,4s)-$N^1$-ethyl-$N^4$-(5-Methyl-4-(6-phenylimidazo[1,2-a]pyridin-3-yl)pyrimidin-2-yl)cyclohexane-1,4-diamine | 426.6 |

TABLE 1-continued

Chemical structure of selected compounds of the present invention

| No. | Structure | Name | Mass |
| --- | --- | --- | --- |
| 133 | 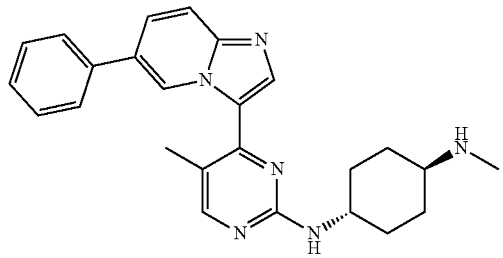 [SMILES: CN[C@H]1CC[C@H](Nc2ncc(C)c(-c3cnc4ccc(-c5ccccc5)cn34)n2)CC1] | (1r,4r)-N[1]-Methyl-N[4]-(5-methyl-4-(6-phenylimidazo[1,2-a]pyridin-3-yl)pyrimidin-2-yl)cyclohexane-1,4-diamine | 412.5 |
| 134 | 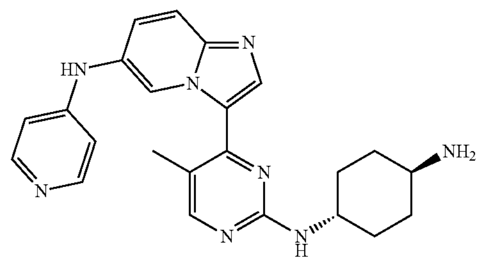 [SMILES: Cc1cnc(N[C@H]2CC[C@H](N)CC2)nc1-c1cnc2ccc(Nc3ccncc3)cn12] | (1r,4r)-N[1]-(5-Methyl-4-(6-(pyridin-4-ylamino)imidazo[1,2-a]pyridin-3-yl)pyrimidin-2-yl)cyclohexane-1,4-diamine | 414.5 |
| 135 | 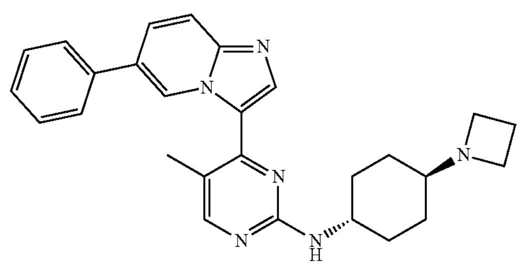 [SMILES: Cc1cnc(N[C@H]2CC[C@H](N3CCC3)CC2)nc1-c1cnc2ccc(-c3ccccc3)cn12] | N-((1r,4r)-4-(Azetidin-1-yl)cyclohexyl)-5-methyl-4-(6-phenylimidazo[1,2-a]pyridin-3-yl)pyrimidin-2-amine | 438.6 |
| 136 | 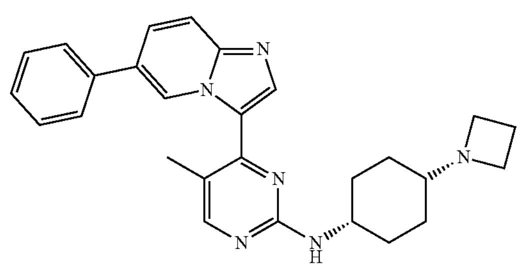 | N-((1s,4s)-4-(Azetidin-1-yl)cyclohexyl)-5-methyl-4-(6-phenylimidazo[1,2-a]pyridin-3-yl)pyrimidin-2-amine | 438.6 |
| 137 | 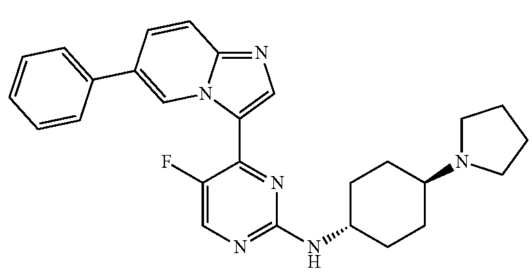 | 5-Fluoro-4-(6-phenylimidazo[1,2-a]pyridin-3-yl)-N-((1r,4r)-4-(pyrrolidin-1-yl)cyclohexyl)pyrimidin-2-amine | 456.6 |

TABLE 1-continued

Chemical structure of selected compounds of the present invention

| No. | Structure | Name | Mass |
|---|---|---|---|
| 138 | 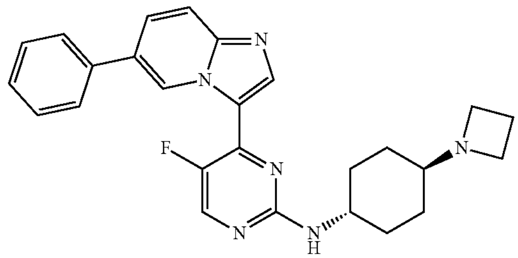 [SMILES: Fc1cnc(N[C@H]2CC[C@H](N3CCC3)CC2)nc1-c1cnc2ccc(-c3ccccc3)cn12] | N-((1r,4r)-4-(Azetidin-1-yl)cyclohexyl)-5-fluoro-4-(6-phenylimidazo[1,2-a]pyridin-3-yl)pyrimidin-2-amine | 442.5 |
| 139 | 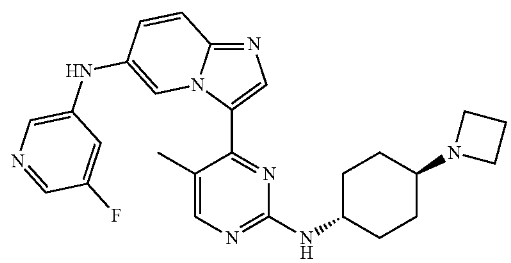 [SMILES: Cc1cnc(N[C@H]2CC[C@H](N3CCC3)CC2)nc1-c1cnc2ccc(Nc3cncc(F)c3)cn12] | 3-(2-(((1r,4r)-4-(Azetidin-1-yl)cyclohexyl)amino)-5-methylpyrimidin-4-yl)-N-(5-fluoropyridin-3-yl)imidazo[1,2-a]pyridin-6-amine | 472.6 |
| 140 | 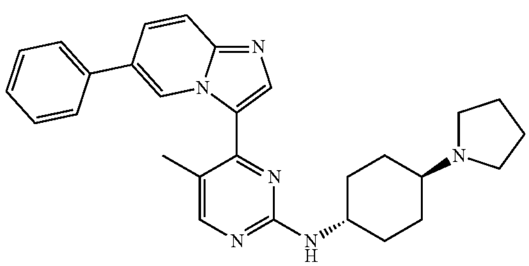 [SMILES: Cc1cnc(N[C@H]2CC[C@H](N3CCCC3)CC2)nc1-c1cnc2ccc(-c3ccccc3)cn12] | 5-Methyl-4-(6-phenylimidazo[1,2-a]pyridin-3-yl)-N-((1r,4r)-4-(pyrrolidin-1-yl)cyclohexyl)pyrimidin-2-amine | 452.6 |
| 141 | 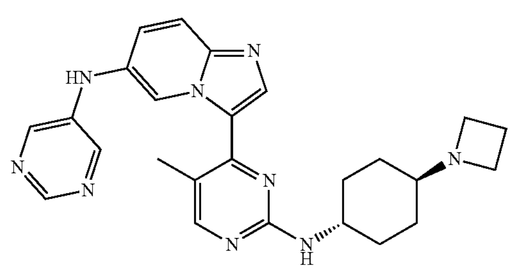 [SMILES: Cc1cnc(N[C@H]2CC[C@H](N3CCC3)CC2)nc1-c1cnc2ccc(Nc3cncnc3)cn12] | 3-(2-(((1r,4r)-4-(Azetidin-1-yl)cyclohexyl)amino)-5-methylpyrimidin-4-yl)-N-(pyrimidin-5-yl)imidazo[1,2-a]pyridin-6-amine | 455.6 |
| 142 | 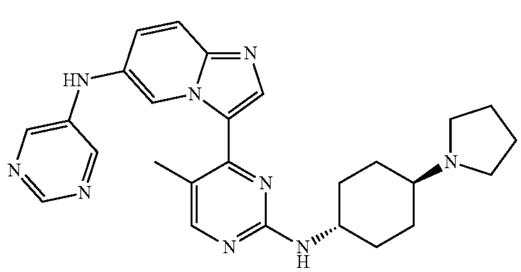 [SMILES: Cc1cnc(N[C@H]2CC[C@H](N3CCCC3)CC2)nc1-c1cnc2ccc(Nc3cncnc3)cn12] | 3-(5-Methyl-2-(((1r,4r)-4-(pyrrolidin-1-yl)cyclohexyl)amino)pyrimidin-4-yl)-N-(pyrimidin-5-yl)imidazo[1,2-a]pyridin-6-amine | 469.6 |

TABLE 1-continued

Chemical structure of selected compounds of the present invention

| No. | Structure | Name | Mass |
|---|---|---|---|
| 143 | 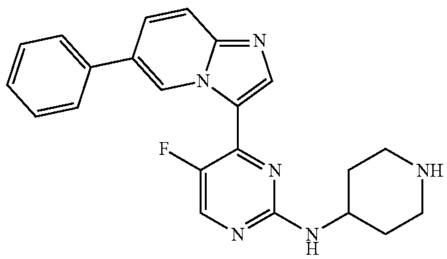 [SMILES: Fc1cnc(NC2CCNCC2)nc1-c1cnc2ccc(-c3ccccc3)cn12] | 5-Fluoro-4-(6-phenylimidazo[1,2-a]pyridin-3-yl)-N-(piperidin-4-yl)pyrimidin-2-amine | 388.5 |
| 144 | 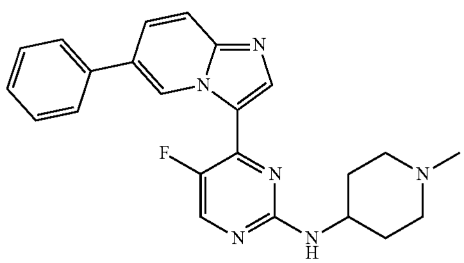 [SMILES: CN1CCC(Nc2ncc(F)c(-c3cnc4ccc(-c5ccccc5)cn34)n2)CC1] | 5-Fluoro-N-(1-Methylpiperidin-4-yl)-4-(6-phenylimidazo[1,2-a]pyridin-3-yl)pyrimidin-2-amine | 402.5 |
| 145 | 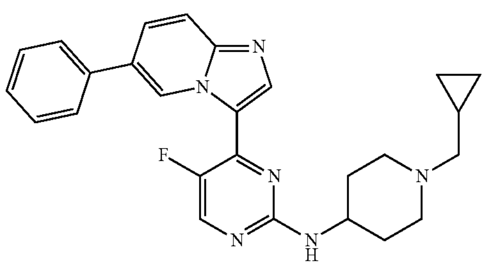 [SMILES: Fc1cnc(NC2CCN(CC3CC3)CC2)nc1-c1cnc2ccc(-c3ccccc3)cn12] | N-(1-(Cyclopropylmethyl)piperidin-4-yl)-5-fluoro-4-(6-phenylimidazo[1,2-a]pyridin-3-yl)pyrimidin-2-amine | 442.5 |
| 146 | 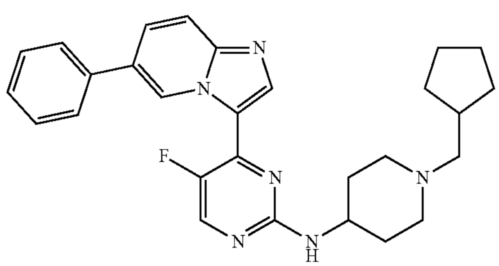 [SMILES: Fc1cnc(NC2CCN(CC3CCCC3)CC2)nc1-c1cnc2ccc(-c3ccccc3)cn12] | N-(1-(Cyclopentylmethyl)piperidin-4-yl)-5-fluoro-4-(6-phenylimidazo[1,2-a]pyridin-3-yl)pyrimidin-2-amine | 470.6 |
| 147 | 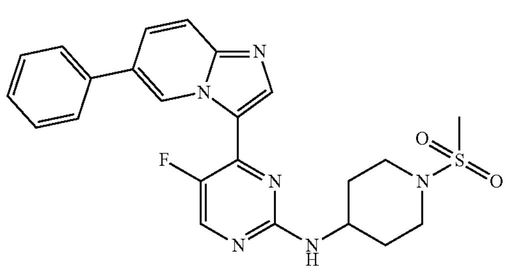 | 5-Fluoro-N-(1-(methylsulfonyl)piperidin-4-yl)-4-(6-phenylimidazo[1,2-a]pyridin-3-yl)pyrimidin-2-amine | 466.5 |

TABLE 1-continued

Chemical structure of selected compounds of the present invention

| No. | Structure | Name | Mass |
|---|---|---|---|
| 148 | 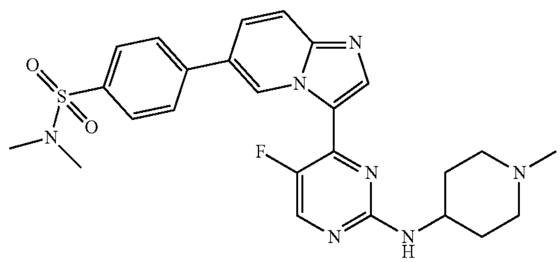 | 4-(3-(5-Fluoro-2-((1-methylpiperidin-4-yl)amino)pyrimidin-4-yl)imidazo[1,2-a]pyridin-6-yl)-N,N-dimethylbenzenesulfonamide | 509.2 |
| 149 | 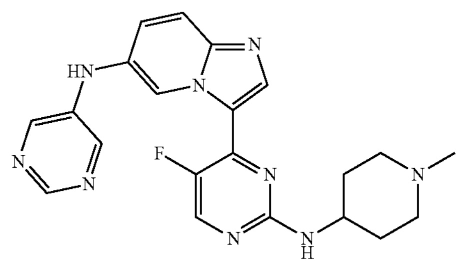 [SMILES: CN1CCC(Nc2ncc(F)c(-c3cnc4ccc(Nc5cncnc5)cn34)n2)CC1] | 3-(5-Fluoro-2-((1-methylpiperidin-4-yl)amino)pyrimidin-4-yl)-N-(pyrimidin-5-yl)imidazo[1,2-a]pyridin-6-amine | 419.5 |
| 150 | 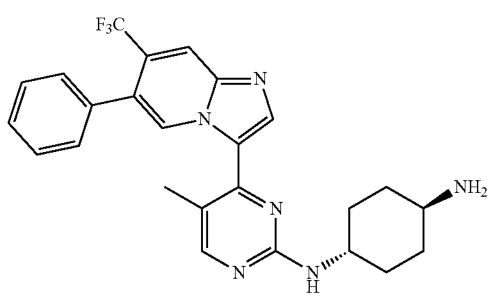 [SMILES: Cc1cnc(N[C@H]2CC[C@H](N)CC2)nc1-c1cnc2cc(C(F)(F)F)c(-c3ccccc3)cn12] | (1r,4r)-N1-(5-Methyl-4-(6-phenyl-7-(trifluoromethyl)imidazo[1,2-a]pyridin-3-yl)pyrimidin-2-yl)cyclohexane-1,4-diamine | 466.5 |
| 151 | 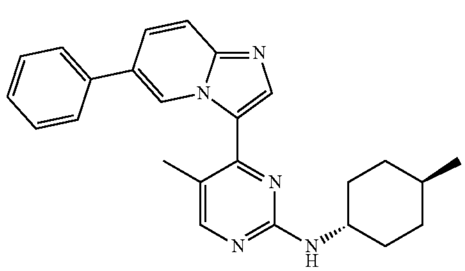 [SMILES: Cc1cnc(N[C@H]2CC[C@H](C)CC2)nc1-c1cnc2ccc(-c3ccccc3)cn12] | 5-Methyl-N-((1r,4r)-4-methylcyclohexyl)-4-(6-phenylimidazo[1,2-a]pyridin-3-yl)pyrimidin-2-amine | 397.5 |
| 152 | 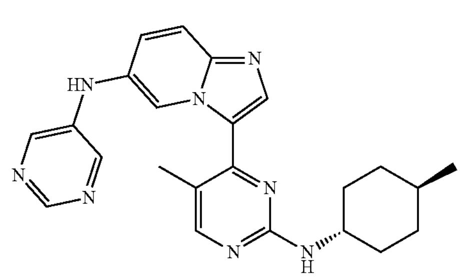 [SMILES: Cc1cnc(N[C@H]2CC[C@H](C)CC2)nc1-c1cnc2ccc(Nc3cncnc3)cn12] | 3-(5-Methyl-2-(((1r,4r)-4-methylcyclohexyl)amino)pyrimidin-4-yl)-N-(pyrimidin-5-yl)imidazo[1,2-a]pyridin-6-amine | 414.5 |

TABLE 1-continued

Chemical structure of selected compounds of the present invention

| No. | Structure | Name | Mass |
|---|---|---|---|
| 153 | 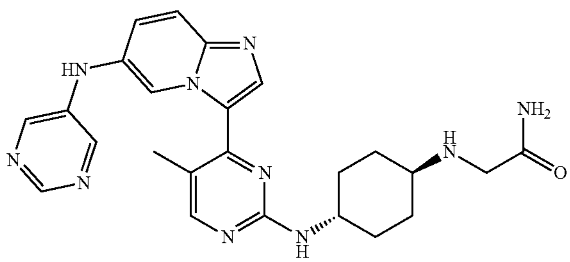 [SMILES: Cc1cnc(N[C@H]2CC[C@H](NCC(N)=O)CC2)nc1-c1cnc2ccc(Nc3cncnc3)cn12] | 2-(((1r,4r)-4-((5-Methyl-4-(6-(pyrimidin-5-ylamino) imidazo[1,2-a]pyridin-3-yl)pyrimidin-2-yl)amino) cyclohexyl)amino)acetamide | 472.6 |
| 154 | 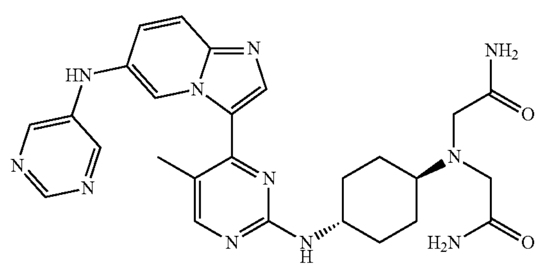 [SMILES: Cc1cnc(N[C@H]2CC[C@H](N(CC(N)=O)CC(N)=O)CC2)nc1-c1cnc2ccc(Nc3cncnc3)cn12] | 2,2'-(((1r,4r)-4-((5-Methyl-4-(6-(pyrimidin-5-ylamino) imidazo[1,2-a]pyridin-3-yl)pyrimidin-2-yl)amino) cyclohexyl)azanediyl)diacetamide | 529.6 |
| 155 | 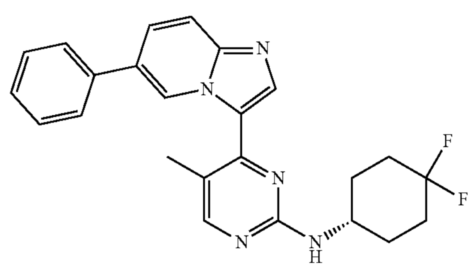 | N-(4,4-Difluorocyclohexyl)-5-methyl-4-(6-phenylimidazo [1,2-a]pyridin-3-yl)pyrimidin-2-amine | 419.5 |
| 156 | 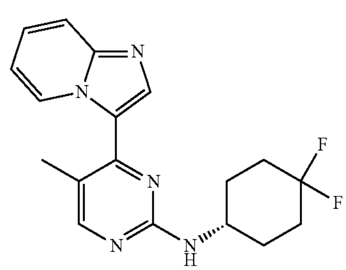 | N-(4,4-Difluorocyclohexyl)-4-(imidazo[1,2-a]pyridin-3-yl)-5-methylpyrimidin-2-amine | 343.4 |
| 157 | 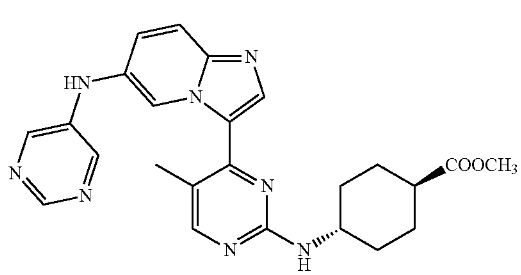 [SMILES: COC(=O)[C@H]1CC[C@H](Nc2ncc(C)c(-c3cnc4ccc(Nc5cncnc5)cn34)n2)CC1] | Methyl (1r,4r)-4-((5-methyl-4-(6-(pyrimidin-5-ylamino) imidazo[1,2-a]pyridin-3-yl)pyrimidin-2-yl)amino) cyclohexane-1-carboxylate | 458.5 |

TABLE 1-continued

Chemical structure of selected compounds of the present invention

| No. | Structure | Name | Mass |
|---|---|---|---|
| 158 | 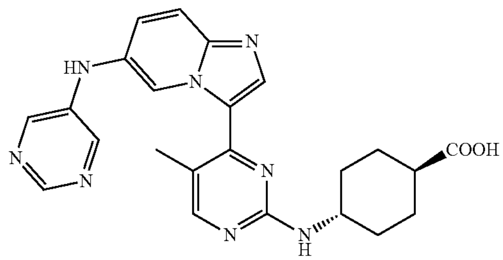 [SMILES: Cc1cnc(N[C@H]2CC[C@H](C(=O)O)CC2)nc1-c1cnc2ccc(Nc3cncnc3)cn12] | (1r,4r)-4-((5-Methyl-4-(6-(pyrimidin-5-ylamino)imidazo[1,2-a]pyridin-3-yl)pyrimidin-2-yl)amino)cyclohexane-1-carboxylic acid | 444.5 |
| 159 | 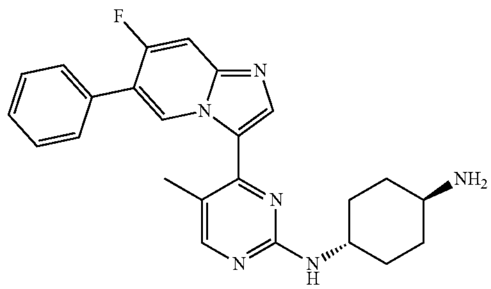 [SMILES: Cc1cnc(N[C@H]2CC[C@H](N)CC2)nc1-c1cnc2cc(F)c(-c3ccccc3)cn12] | (1r,4r)-$N^1$-(4-(7-Fluoro-6-phenylimidazo[1,2-a]pyridin-3-yl)-5-methylpyrimidin-2-yl)cyclohexane-1,4-diamine | 416.5 |
| 160 | 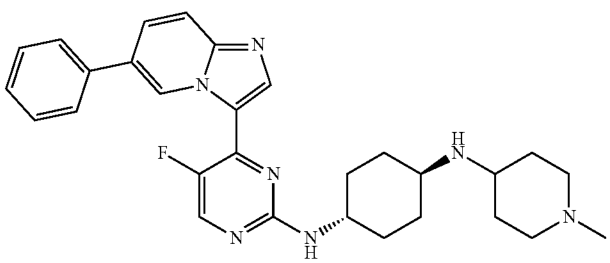 [SMILES: CN1CCC(N[C@H]2CC[C@H](Nc3ncc(F)c(-c4cnc5ccc(-c6ccccc6)cn45)n3)CC2)CC1] | (1r,4r)-$N^1$-(5-Fluoro-4-(6-phenylimidazo[1,2-a]pyridin-3-yl)pyrimidin-2-yl)-$N^4$-(1-methylpiperidin-4-yl)cyclohexane-1,4-diamine | 499.6 |
| 161 | 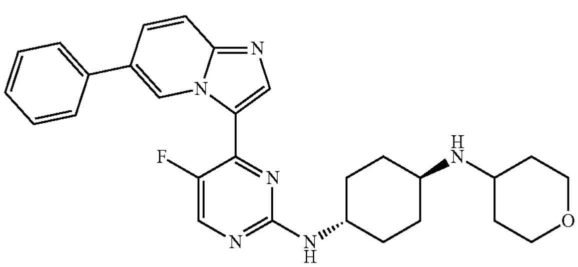 [SMILES: Fc1cnc(N[C@H]2CC[C@H](NC3CCOCC3)CC2)nc1-c1cnc2ccc(-c3ccccc3)cn12] | (1r,4r)-$N^1$-(5-fluoro-4-(6-phenylimidazo[1,2-a]pyridin-3-yl)pyrimidin-2-yl)-$N^4$-(tetrahydro-2H-pyran-4-yl)cyclohexane-1,4-diamine | 486.6 |
| 163 | 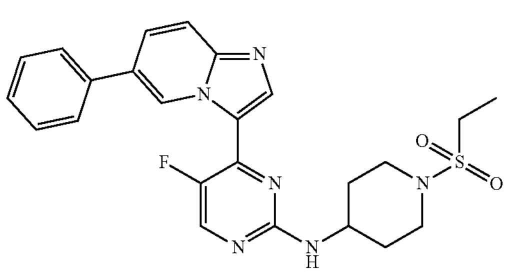 [SMILES: CCS(=O)(=O)N1CCC(Nc2ncc(F)c(-c3cnc4ccc(-c5ccccc5)cn34)n2)CC1] | N-(1-(Ethylsulfonyl)piperidin-4-yl)-5-fluoro-4-(6-phenylimidazo[1,2-a]pyridin-3-yl)pyrimidin-2-amine | 480.6 |

TABLE 1-continued

Chemical structure of selected compounds of the present invention

| No. | Structure | Name | Mass |
|---|---|---|---|
| 165 | 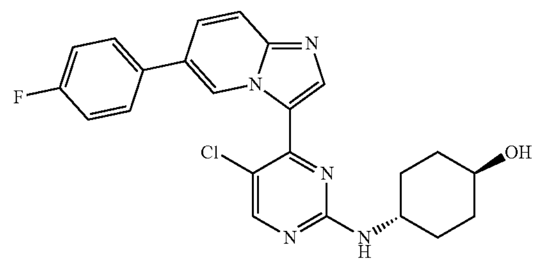 [SMILES: O[C@H]1CC[C@H](Nc2ncc(Cl)c(-c3cnc4ccc(-c5ccc(F)cc5)cn34)n2)CC1] | (1r,4r)-4-((5-Chloro-4-(6-(4-fluorophenyl)imidazo[1,2-a]pyridin-3-yl)pyrimidin-2-yl)amino)cyclohexan-1-ol | 437.9 |
| 166 | 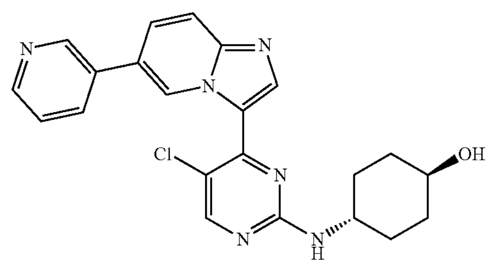 [SMILES: O[C@H]1CC[C@H](Nc2ncc(Cl)c(-c3cnc4ccc(-c5cccnc5)cn34)n2)CC1] | (1r,4r)-4-((5-Chloro-4-(6-(pyridin-3-yl)imidazo[1,2-a]pyridin-3-yl)pyrimidin-2-yl)amino)cyclohexan-1-ol | 420.9 |
| 167 | 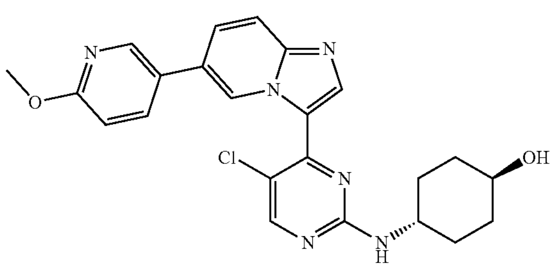 [SMILES: COc1ccc(-c2ccc3ncc(-c4nc(N[C@H]5CC[C@H](O)CC5)ncc4Cl)n3c2)cn1] | (1r,4r)-4-((5-Chloro-4-(6-(6-methoxypyridin-3-yl)imidazo[1,2-a]pyridin-3-yl)pyrimidin-2-yl)amino)cyclohexan-1-ol | 450.9 |
| 168 | 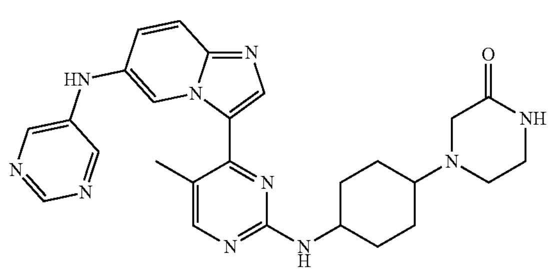 [SMILES: Cc1cnc(NC2CCC(N3CCNC(=O)C3)CC2)nc1-c1cnc2ccc(Nc3cncnc3)cn12] | 4-(4-((5-Methyl-4-(6-(pyrimidin-5-ylamino)imidazo[1,2-a]pyridin-3-yl)pyrimidin-2-yl)amino)cyclohexyl)piperazin-2-one | 498.6 |
| 169 | 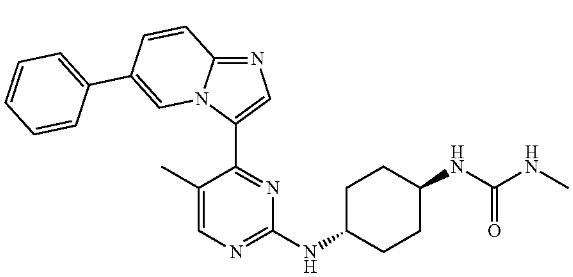 [SMILES: CNC(=O)N[C@H]1CC[C@H](Nc2ncc(C)c(-c3cnc4ccc(-c5ccccc5)cn34)n2)CC1] | 1-Methyl-3-((1r,4r)-4-((5-methyl-4-(6-phenylimidazo[1,2-a]pyridin-3-yl)pyrimidin-2-yl)amino)cyclohexyl)urea | 455.6 |

TABLE 1-continued

Chemical structure of selected compounds of the present invention

| No. | Structure | Name | Mass |
|---|---|---|---|
| 170 | 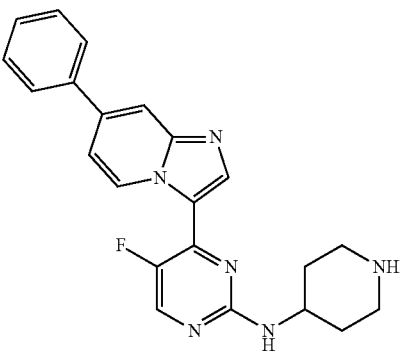 [SMILES: Fc1cnc(NC2CCNCC2)nc1-c1cnc2cc(-c3ccccc3)ccn12] | 5-Fluoro-4-(7-phenylimidazo[1,2-a]pyridin-3-yl)-N-(piperidin-4-yl)pyrimidin-2-amine | 388.5 |
| 171 | 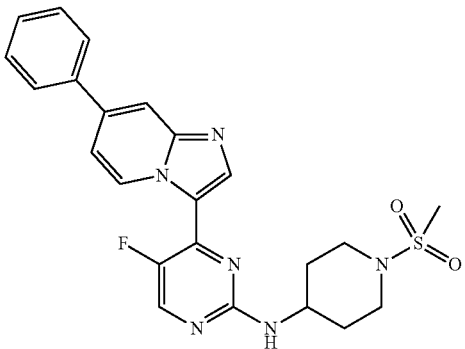 [SMILES: CS(=O)(=O)N1CCC(Nc2ncc(F)c(-c3cnc4cc(-c5ccccc5)ccn34)n2)CC1] | 5-Fluoro-N-(1-(methylsulfonyl)piperidin-4-yl)-4-(7-phenylimidazo[1,2-a]pyridin-3-yl)pyrimidin-2-amine | 466.5 |
| 172 | 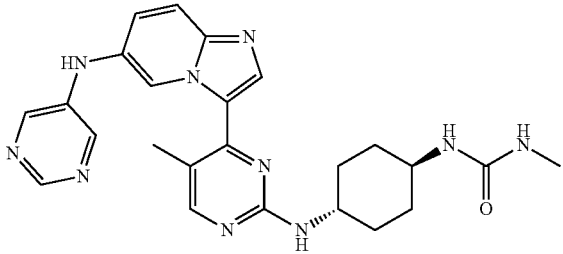 [SMILES: CNC(=O)N[C@H]1CC[C@H](Nc2ncc(C)c(-c3cnc4ccc(Nc5cncnc5)cn34)n2)CC1] | 1-Methyl-3-((1r,4r)-4-((5-methyl-4-(6-(pyrimidin-5-ylamino)imidazo[1,2-a]pyridin-3-yl)pyrimidin-2-yl)amino)cyclohexyl)urea | 472.6 |
| 173 | 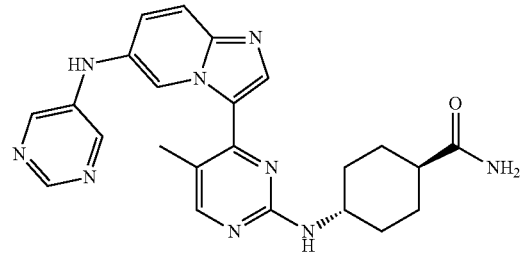 [SMILES: Cc1cnc(N[C@H]2CC[C@H](C(N)=O)CC2)nc1-c1cnc2ccc(Nc3cncnc3)cn12] | (1r,4r)-4-((5-Methyl-4-(6-(pyrimidin-5-ylamino)imidazo[1,2-a]pyridin-3-yl)pyrimidin-2-yl)amino)cyclohexane-1-carboxamide | 443.2 |
| 174 | 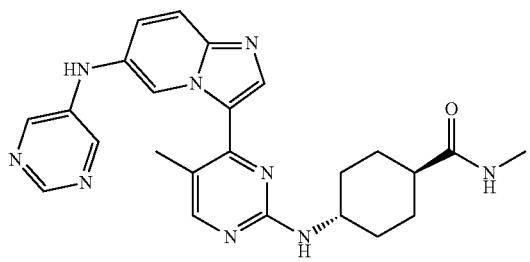 [SMILES: CNC(=O)[C@H]1CC[C@H](Nc2ncc(C)c(-c3cnc4ccc(Nc5cncnc5)cn34)n2)CC1] | (1r,4r)-N-Methyl-4-((5-methyl-4-(6-(pyrimidin-5-ylamino)imidazo[1,2-a]pyridin-3-yl)pyrimidin-2-yl)amino)cyclohexane-1-carboxamide | 457.2 |

TABLE 1-continued

Chemical structure of selected compounds of the present invention

| No. | Structure | Name | Mass |
|---|---|---|---|
| 175 | 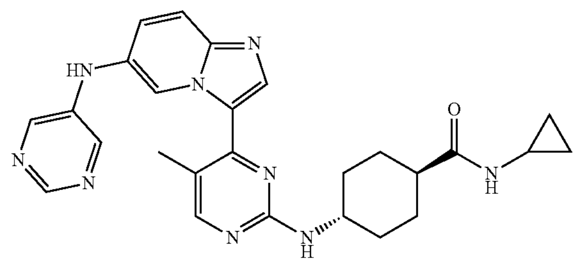 [SMILES: Cc1cnc(N[C@H]2CC[C@H](C(=O)NC3CC3)CC2)nc1-c1cnc2ccc(Nc3cncnc3)cn12] | (1r,4r)-N-Cyclopropyl-4-((5-methyl-4-(6-(pyrimidin-5-ylamino)imidazo[1,2-a]pyridin-3-yl)pyrimidin-2-yl)amino)cyclohexane-1-carboxamide | 483.2 |
| 176 | 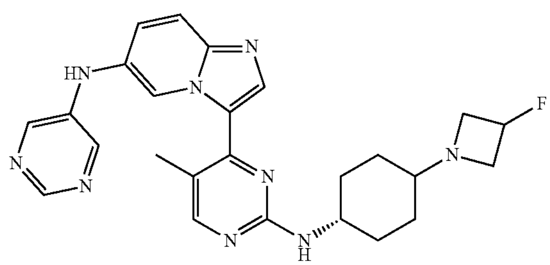 | 3-(2-((4-(3-Fluoroazetidin-1-yl)cyclohexyl)amino)-5-methylpyrimidin-4-yl)-N-(pyrimidin-5-yl)imidazo[1,2-a]pyridin-6-amine | 473.2 |
| 177 | 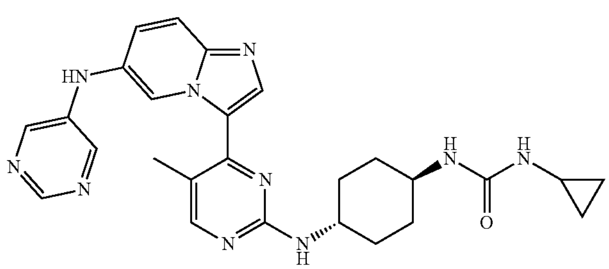 [SMILES: Cc1cnc(N[C@H]2CC[C@H](NC(=O)NC3CC3)CC2)nc1-c1cnc2ccc(Nc3cncnc3)cn12] | 1-Cyclopropyl-3-((1r,4r)-4-((5-methyl-4-(6-(pyrimidin-5-ylamino)imidazo[1,2-a]pyridin-3-yl)pyrimidin-2-yl)amino)cyclohexyl)urea | 498.3 |
| 178 | 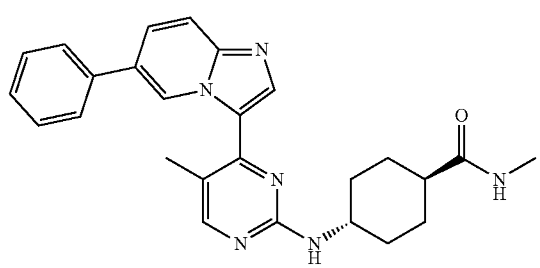 [SMILES: CNC(=O)[C@H]1CC[C@H](Nc2ncc(C)c(-c3cnc4ccc(-c5ccccc5)cn34)n2)CC1] | (1r,4r)-N-Methyl-4-((5-methyl-4-(6-phenyl imidazo[1,2-a]pyridin-3-yl)pyrimidin-2-yl)amino)cyclohexane-1-carboxamide | 440.2 |
| 179 | 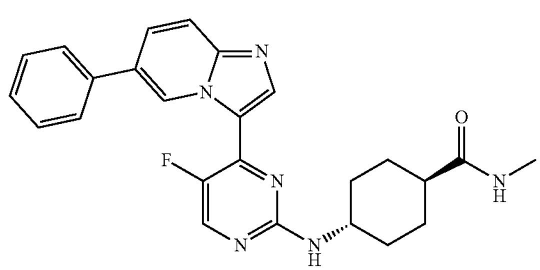 [SMILES: CNC(=O)[C@H]1CC[C@H](Nc2ncc(F)c(-c3cnc4ccc(-c5ccccc5)cn34)n2)CC1] | (1r,4r)-4-((5-fluoro-4-(6-phenylimidazo[1,2-a]pyridin-3-yl)pyrimidin-2-yl)amino)-N-methylcyclohexane-1-carboxamide | 444.2 |

TABLE 1-continued

Chemical structure of selected compounds of the present invention

| No. | Structure | Name | Mass |
|---|---|---|---|
| 180 | 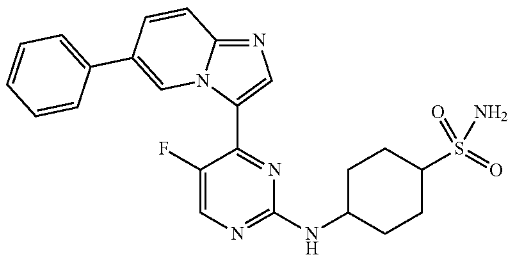 [SMILES: NS(=O)(=O)C1CCC(Nc2ncc(F)c(-c3cnc4ccc(-c5ccccc5)cn34)n2)CC1] | 4-((5-Fluoro-4-(6-phenylimidazo[1,2-a]pyridin-3-yl)pyrimidin-2-yl)amino)cyclohexane-1-sulfonamide | 466.2 |
| 181 | 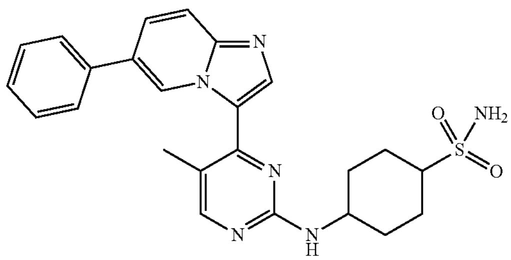 [SMILES: Cc1cnc(NC2CCC(S(N)(=O)=O)CC2)nc1-c1cnc2ccc(-c3ccccc3)cn12] | 4-((5-Methyl-4-(6-phenylimidazo[1,2-a]pyridin-3-yl)pyrimidin-2-yl)amino)cyclohexane-1-sulfonamide | 462.2 |

The compounds (and pharmaceutically acceptable salts, solvates and prodrugs thereof) may be administered in combination with one or more additional agent(s) for the treatment of cancer or another proliferative disease or condition. For example, the compounds may be used in combination with other anti-cancer agents in order to inhibit more than one cancer signalling pathway simultaneously so as to make cancer cells more susceptible to anti-cancer therapies (eg treatments with other anti-cancer agents, chemotherapy, radiotherapy or a combination thereof). As such, the compounds of formula I may be used in combination with one or more of the following categories of anti-cancer agents:

- other anti-proliferative/antineoplastic drugs and combinations thereof, as used in medical oncology, such as alkylating agents (eg cis-platin, oxaliplatin, carboplatin, cyclophosphamide, nitrogen mustard, melphalan, chlorambucil, busulphan, temozolamide and nitrosoureas); antimetabolites (eg gemcitabine and antifolates such as fluoropyrimidines like 5-fluorouracil and tegafur, raltitrexed, methotrexate, cytosine arabinoside, fludarabine and hydroxyurea); antitumour antibiotics (eg anthracyclines such as adriamycin, bleomycin, doxorubicin, daunomycin, epirubicin, idarubicin, mitomycin-C, dactinomycin and mithramycin); antimitotic agents (eg vinca alkaloids such as vincristine, vinblastine, vindesine and vinorelbine and taxoids including taxol and taxotere and polokinase inhibitors); and topoisomerase inhibitors (eg epipodophyllotoxins such as etoposide and teniposide, amsacrine, topotecan and camptothecin);
- cytostatic agents such as antioestrogens (eg tamoxifen, fulvestrant, toremifene, raloxifene, droloxifene and iodoxyfene), antiandrogens (eg bicalutamide, flutamide, nilutamide and cyproterone acetate), LHRH antagonists or LHRH agonists (eg goserelin, leuprorelin and buserelin), progestogens (eg megestrol acetate), aromatase inhibitors (eg as anastrozole, letrozole, vorazole and exemestane) and inhibitors of 5α-reductase such as finasteride;
- anti-invasion agents (eg c-Src kinase family inhibitors such as 4-(6-chloro-2,3-methylenedioxyanilino)-7-[2-(4-methylpiperazin-1-yl)ethoxy]-5-tetrahydropyran-4-yloxyquinazoline (AZD0530; International Patent Publication No WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib) and bosutinib (SKI-606)), and metalloproteinase inhibitors including marimastat, inhibitors of urokinase plasminogen activator receptor function or antibodies to heparanase;
- inhibitors of growth factor function (eg growth factor antibodies and growth factor receptor antibodies such as the anti-erbB2 antibody trastuzumab (Herceptin™), the anti-EGFR antibody panitumumab, the anti-erbB1 antibody cetuximab (Erbitux, C225) and any growth factor or growth factor receptor antibodies disclosed by Stern et al. Critical reviews in oncology/haematology, 2005, Vol. 54, pp 11-29). Such inhibitors also include tyrosine kinase inhibitors such as inhibitors of the epidermal growth factor family (eg EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN 107); inhibitors of serine/threonine kinases (eg Ras/Raf signalling inhibitors such as farnesyl transferase inhibitors including sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (eg AZD1152, PH739358, VX-680, MLN8054, R763, MP235, MP529, VX-528 and AX39459) and cyclin dependent kinase inhibitors such as CDK2 and/or CDK9 inhibitors;

anti-angiogenic agents such as those which inhibit the effects of vascular endothelial growth factor (eg the anti-vascular endothelial cell growth factor antibody bevacizumab (Avastin™) and VEGF receptor tyrosine kinase inhibitors such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within International Patent Publication No WO 00/47212), compounds such as those disclosed in International Patent Publication Nos WO97/22596, WO 97/30035, WO 97/32856 and WO 98/13354, and compounds that work by other mechanisms (eg linomide, inhibitors of integrin αvβ3 function and angiostatin);

vascular damaging agents such as Combretastatin A4 and compounds disclosed in International Patent Publication Nos WO 99/02166, WO 00/40529, WO 00/41669, WO 01/92224, WO 02/04434 and WO 02/08213;

an endothelin receptor antagonist such as zibotentan (ZD4054) or atrasentan;

antisense therapies such as those which are directed to the targets listed above, such as ISIS 2503, an anti-ras antisense;

gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and immunotherapy approaches, including for example ex vivo and in vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Where used in combination with other anti-cancer agents, a compound of the present invention and the other anti-cancer agent can be administered in the same pharmaceutical composition or in separate pharmaceutical compositions. If administered in separate pharmaceutical compositions, the compound and the other anti-cancer agent may be administered simultaneously or sequentially in any order (eg within seconds or minutes or even hours (eg 2 to 48 hours).

The present invention is typically applied to the treatment of cancer or another proliferative cell disease or condition in a human subject. However, the subject may also be selected from, for example, livestock animals (eg cows, horses, pigs, sheep and goats), companion animals (eg dogs and cats) and exotic animals (eg non-human primates, tigers, elephants etc).

Cancers and other proliferative cell diseases and conditions that may be treated in accordance with the present invention include biliary tract cancer, brain cancer (including glioblastomas and medulloblastomas), breast cancer, cervical cancer; choriocarcinoma, colonic cancer, endometrial cancer, oesophageal cancer, gastric cancer, haematological neoplasms (including acute lymphocytic leukemia (ALL)), chronic lymphocytic leukemia (CLL) and chronic myelogenous leukemia (CML), acute myeloid leukaemia (AML), multiple myeloma, AIDS-associated leukemias and adult T-cell leukemia lymphoma, intraepithelial neoplasms (including Bowen's disease and Paget's disease), liver cancer, lung cancer, lymphomas (including Hodgkin's disease and lymphocytic lymphomas), neuroblastomas, oral cancer (including squamous cell carcinoma), ovarian cancer (including those arising from epithelial cells, stromal cells, germ cells, and mesenchymal cells), pancreatic cancer, prostate cancer, colorectal cancer, sarcomas (including leiomyosarcoma, rhabdomyosarcoma, liposarcoma, fibrosarcoma, and osteosarcoma), skin cancer (including melanoma, Kaposi's sarcoma, basocellular cancer, and squamous cell cancer), testicular cancer (including germinal tumours such as seminoma, non-seminoma teratomas, and choriocarcinomas), stromal tumours, germ cell tumours, thyroid cancer (including thyroid adenocarcinoma and medullar carcinoma), and renal cancer (including adenocarcinoma and Wilms' tumour).

In some embodiments, the compounds of the present invention are used to treat cancers characterised by over-expression of CDKs, for example, chronic lymphocytic leukaemia (CLL), lymphoma, leukaemia, breast cancer, lung cancer, prostate cancer, colon cancer, melanoma, pancreatic cancer, ovarian cancer, squamous cancer, carcinoma of head and neck, endometrial cancer, and oesophageal carcinoma (reviewed in Lapenna et al., *Nat Rev Drug Discov* 8(7):547-66 (2009) and Asghar et al., *Nat Rev Drug Discov* 14(2): 130-46 (2015)). CDKs and/or cyclin over-expression may be determined by, for example, assessing the amount of mRNA encoding CDK and/or cyclin in a suitable sample using any of the techniques well known to those skilled in the art (eg quantitative amplification techniques such as qPCR).

In a preferred embodiment, the compounds of the present invention are used to a disease or condition characterised by over-expression of one or more CDK enzyme and/or by one or more aberrant CDK activity. Otherwise, said disease or condition may be one which may be beneficially treated by inhibiting one or more CDK (eg by inhibiting the activity and/or expression of one or more of CDK1, CDK2, CDK4, CDK6, CDK7 and CDK9, and/or the association of one or more of such CDK enzymes with their respective cyclin/mediator complex). The compounds of the present invention may therefore be used to treat diseases or conditions including, for example, viral disorders, eg human cytomegalovirus (HCMV), herpes simplex virus type 1 (HSV-1), human immunodeficiency virus type 1 (HIV-1), and varicella zoster virus (VZV) (Yamamoto et al., *J Clin Invest* 124(8): 3479-3488 (2014)), cardiovascular diseases, eg ischaemic heart disease (known also as myocardial infarction or angina), hypertension, heart failure, restenosis and cardiomyopathy (Trifonov et al., *Curr Opin Biotechnol.* 24(S 1): S 114-S 115 (2013)), cancers, eg chronic lymphocytic leukaemia (CLL) (Walsby et al., *Oncotarget* 5(2):375-85 (2014)), lymphoma (Gregory et al., *Leukemia* 29(6): 1437-1441 (2015)), leukaemia (Walsby et al., *Leukemia* 25(3):411-419 (2011)), breast cancer (Mita et al., *Clin Breast Cancer* 14(3): 169-176 (2014)), lung cancer (Stephenson et al., *Lung Cancer* 83(2): 219-223 (2014)), prostate cancer (reviewed in Rahaman et al., *Endocr Relat Cancer* pii: ERC-16-0299 (2016)), melanoma (Desai et al., *PLoS One* 8(3):e59588 (2013)), pancreatic cancer (Hu et al., *Mol Cancer Ther* 14(7):1532-1539 (2015)), ovarian cancer (Lam et al., *Oncotarget* 5(17):7691-

7704 (2014)), hepatocarcinoma (Li et al., *Curr Cancer Drug Targets* 15(3): 196-204 (2015)), oesophageal carcinoma, neuroblastoma and primary neuroectodermal tumor (de Falco et al., *Cancer Biol Ther* 4(3):277-281 (2005)), rhabdomyosarcoma (Simone et al., *Cell Death and Differ* 14(1): 192-195 (2007)) and carcinoma of head and neck (Gary et al., *Oncotarget* 7(25):38598-38611 (2016)). The level of CDK may be determined by, for example, assessing the amount of mRNA encoding CDK and/or cyclin in a suitable sample using any of the techniques well known to those skilled in the art (eg quantitative amplification techniques such as qPCR).

In some embodiments, the compounds of the present invention are used to treat cancers characterised by over-expression of Flt kinases such as Flt3 and/or mutations, eg acute myeloid leukaemia (reviewed in Hitoshi et al., *Nagoya J Med Sci* 77(1-2):7-17 (2015) and Wander et al., *Ther Adv Hematol* 5(3):65-77 (2014)).

In some embodiments, the compounds of the present invention are used to treat conditions characterised by over-expression of CLKs, eg in Alzheimer's disease (AD) and in diseases involving abnormal pre-mRNA splicing (Jain et al., *Curr Drug Targets* 15(5):539-50 (2014)). CLKs are serine-arginine protein kinases and are elements of the splicing machinery. Inhibitors of CLKs modulate pre-mRNA splicing, thereby impeding cell growth and inducing apoptosis (Araki et al., *PLoS One* 10(1): e0116929 (2015)).

In some embodiments, the compounds of the present invention are used to treat cancers characterised by over-expression of aurora kinases. Aurora kinases are key mitotic regulators, they control multiple steps of mitosis, including centrosome duplication, formation of a bipolar mitotic spindle, chromosome alignment on the mitotic spindle and the fidelity-monitoring spindle checkpoint (reviewed in Macarulla et al., *Recent Pat Anticancer Drug Discov* (2): 114-22 (2008)). Aurora kinase inhibitors are used to treat cancers, eg childhood acute leukaemia (Hartsink Segers et al., *Leukemia* 27(3): 560-568 (2013)), lung cancer (Chinn et al., *J Cancer Res Clin Oncol* 140(7):1137-1349 (2014)), prostate cancer (Paller et al., *Cancer Med* 3(5):1322-1335 (2014)), advanced solid tumours (Schwartz et al., *Invest New Drugs* 31(2):370-80 (2013)), and neuroblastoma (Michaelis et al., *PLoS One* 9(9): e108758 (2014)).

The compounds of the present invention may be formulated into a pharmaceutical composition with a pharmaceutically acceptable carrier, diluent and/or excipient. Examples of suitable carriers and diluents are well known to those skilled in the art, and are described in, for example, Remington's Pharmaceutical Sciences, Mack Publishing Co., Easton, Pa. 1995. Examples of suitable excipients for the various different forms of pharmaceutical compositions described herein may be found in the Handbook of Pharmaceutical Excipients, $2^{nd}$ Edition, (1994), Edited by A Wade and PJ Weller. Examples of suitable carriers include lactose, starch, glucose, methyl cellulose, magnesium stearate, mannitol, sorbitol and the like. Examples of suitable diluents include ethanol, glycerol and water. The choice of carrier, diluent and/or excipient may be made with regard to the intended route of administration and standard pharmaceutical practice.

A pharmaceutical composition comprising a compound of the present invention may further comprise any suitable binders, lubricants, suspending agents, coating agents and solubilising agents. Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilising agents, dyes and even flavouring agents may be provided in the pharmaceutical composition. Examples of preservatives include sodium benzoate, sorbic acid and esters of p-hydroxybenzoic acid. Anti-oxidants and suspending agents may be also used.

A pharmaceutical composition comprising a compound of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration. For oral administration, particular use may be made of compressed tablets, pills, tablets, gellules, drops, and capsules. For other forms of administration, a pharmaceutical composition may comprise solutions or emulsions which may be injected intravenously, intraarterially, intrathecally, subcutaneously, intradermally, intraperitoneally or intramuscularly, and which are prepared from sterile or sterilisable solutions. A pharmaceutical composition comprising a compound of the present invention may also be in form of suppositories, pessaries, suspensions, emulsions, lotions, ointments, creams, gels, sprays, solutions or dusting powders. A pharmaceutical composition may be formulated in unit dosage form (ie in the form of discrete portions containing a unit dose, or a multiple or sub-unit of a unit dose).

The compounds of the present invention may be provided as a pharmaceutically acceptable salt including, for example, suitable acid addition or base salts thereof. A review of suitable pharmaceutical salts may be found in Berge et al., *J Pharm Sci* 66:1-19 (1977). Salts are formed, for example with strong inorganic acids such as mineral acids (eg sulfuric acid, phosphoric acid or hydrohalic acids), with strong organic carboxylic acids, such as alkanecarboxylic acids of 1 to 4 carbon atoms which are unsubstituted or substituted (eg by halogen), such as acetic acid, with saturated or unsaturated dicarboxylic acids (eg oxalic, malonic, succinic, maleic, fumaric, phthalic or tetraphthalic acid), with hydroxycarboxylic acids (eg ascorbic, glycolic, lactic, malic, tartaric or citric acid), with amino acids (eg aspartic or glutamic acid), with benzoic acid, or with organic sulfonic acids (eg ($C_1$-$C_4$)-alkyl- or aryl-sulfonic acids which are unsubstituted or substituted by, for example, halogen) such as methane- or p-toluene sulfonic acid).

The compounds of the present invention may be provided in their various crystalline forms, polymorphic forms and (an)hydrous forms. In this regard, it is well known to those skilled in the art that chemical compounds may be isolated in any of such forms by slightly varying the method of purification and or isolation from the solvents used in the synthetic preparation of such compounds.

The present invention further provides a method of synthesising a compound according to the present invention, or a pharmaceutically acceptable salt, solvate or prodrug thereof.

With regard to the description of the synthetic methods described below and in the referenced synthetic methods that are used to prepare starting materials, it will be understood by those skilled in the art that all proposed reaction conditions, including choice of solvent, reaction atmosphere, reaction temperature, duration of the experiment and workup procedures, can be readily selected. Moreover, it will be understood by those skilled in the art that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the examples hereinafter. Alternatively, necessary starting materials may be obtainable by analogous procedures to those illustrated which are within the ordinary skill of those skilled in the art. Further, it will be appreciated that during the synthesis of the compounds, in the processes described below, or during the synthesis of certain starting materials, it may be desirable to protect certain substituent groups to prevent their undesired reaction. Those skilled in the art will readily recognise when such protection is required, and how such protecting groups may be put in place, and later removed. Examples of protecting groups are described in, for example, Protective Groups in Organic Synthesis by Theodora Green (publisher: John Wiley & Sons). Protecting groups may be removed by any convenient method well known to those skilled in the art as appropriate for the removal of the protecting group in question, such methods being chosen so as to effect removal of the protecting group with the minimum disturbance of groups elsewhere in the molecule. Thus, if reactants include, for example, groups such as amino, carboxyl or hydroxyl, it may be desirable to protect the group in some of the reactions mentioned herein.

The compounds of the present invention may be prepared by, for example, the general synthetic methodologies described in International Patent Publication No WO 2010/049731, which is herein incorporated by reference.

In a further aspect of the present invention, a method of synthesising a compound of the present invention (or a pharmaceutically acceptable salt, solvate or prodrug thereof) is provided wherein the method comprises the steps of:

a) brominating a compound of formula III

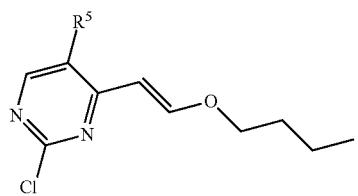

III wherein $R^5$ is as defined in the first aspect, b) thereafter conducting a one pot cyclocondensation with a compound selected from pyridin-2-amines, pyridazin-3-amine, pyrazin-2-amines and 1-aminopyridin-1-iums, to form a compound of formula V;

c) aminating the compound of formula V,

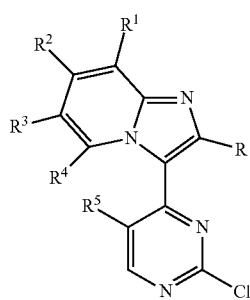

V wherein R, $R^1$, $R^2$, $R^3$, $R^4$ and $R^5$ are as defined in the first aspect, by reacting the compound of formula III with a compound of formula VI:

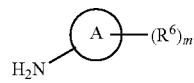

VI wherein $R^6$ is as defined in the first aspect; and if necessary, d) removing any protecting groups present, and/or forming a pharmaceutically acceptable salt, solvate or prodrug thereof.

The cyclocondensation reaction of step b) may be conducted in the presence of a suitable solvent or solvent mixture. Those skilled in the art will be able to readily select a suitable solvent or solvent mixture for use in this reaction. Examples of suitable solvents include dioxane, water, etc.

In addition, those skilled in the art will be able to readily select appropriate reaction conditions for the condensation reaction of step b). However, typically, the reaction will be carried out in anhydrous conditions and in the presence of an inert atmosphere, such as argon or nitrogen.

The bromination reaction of step a) may be carried out at room temperature for a suitable time period of, for example, 30 minutes to 2 hours, whereas the subsequent condensation reaction of step b) may be carried out at an elevated temperature, for example, within the range of 60 to 100° C. for a suitable time period of, for example, 20 minutes to 10 hours. Suitably, the bromination reaction of step a) is carried out at room temperature for 30 minutes to 2 hours, and then the condensation reaction of step b) will be conducted by adding the required compound (ie a compound selected from pyridin-2-amines, pyridazin-3-amine, pyrazin-2-amines and 1-aminopyridin-1-iums) and normal heating at 60 to 100° C. for 20 minutes to 10 hours.

The coupling reaction of step c) may be conducted in the presence of a suitable solvent or solvent mixture. Again, those skilled in the art will be able to readily select a suitable solvent or solvent mixture for use in this reaction. Examples of suitable solvents include alcohols, acetonitrile, halogenated solvents, etc.

In addition, those skilled in the art will be able to select appropriate reaction conditions to use in the coupling reaction of step c). However, typically, the reaction will be carried out in anhydrous conditions and in the presence of an inert atmosphere, such as argon or nitrogen. The reaction may also be carried out an elevated temperature, such as, for example, within the range of 80 to 180° C. for a suitable time period of, for example, 20 minutes to 48 hours. Suitably, the reaction is carried out under microwave heating, for example, at 80 to 180° C. for 20 minutes to 1.5 hour.

The resultant compound of formula I can be isolated and purified using techniques well known to those skilled in the art.

The method of synthesising a compound of the present invention (or a pharmaceutically acceptable salt, solvate or prodrug thereof) may further comprise:

e) subjecting the compound of formula I to a salt exchange (particularly in situations where the compound is formed as a mixture of different salt forms).

The salt exchange may comprise immobilising the compound on a suitable solid support or resin, and eluting the compound with an appropriate acid to yield salt of the compound of formula I.

An example of a particularly suitable method for synthesising a compound of the present invention is shown as Scheme 1 below.

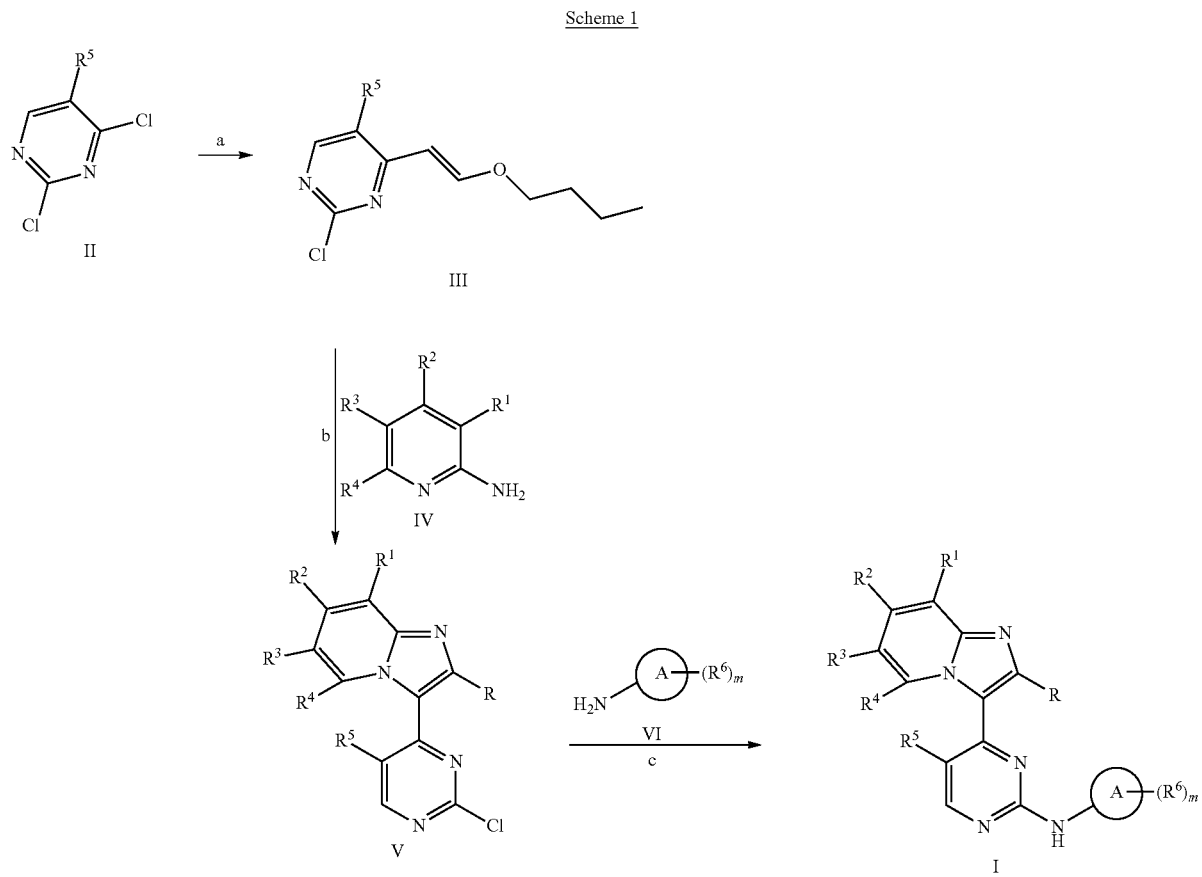

Scheme 1

General reaction conditions: (a) 1-(vinyloxy)butane, Pd(OAc)$_2$, base, PEG400, heating; (b) (i) N-bromosuccimide, dioxane/water, room temperature; (ii) IV, heating; (c) base, 2-methoxyethanol, heating.

The invention is hereinafter described with reference to the following, non-limiting examples.

EXAMPLES

Example 1 Synthesis

General $^1$H spectra were recorded at 298 K on a Bruker AVANCE III HD 500 spectrometer and were analysed using Bruker Topspin 3.2 software. $^1$H-NMR signals are reported with chemical shift values δ (ppm), multiplicity (s=singlet, d=doublet, t=triplet, q=quartet, dd=doublet of doublets, m=multiplet and br=broad), relative integral, coupling constants J (Hz) and assignments. High resolution mass spectra were recorded on an AB SCIEX TripleTOF 5600 mass spectrometer (Concord, ON, Canada), and ionisation of all samples was carried out using ESI.

General Synthetic Procedure A:

i. A suspension of 2-chloro-4-heteroarylpyrimidine (1.00 eq.), (1r,4r)-cyclohexane-1,4-diamine (3.00 eq.) and K$_2$CO$_3$ (3.00 eq.) in 2-methoxyethan-1-ol was heated at 90° C. for overnight, concentrated under reduced pressure and purified by flash column chromatography starting with 100% DCM ramping to 9% MeOH+1.0% NH$_3$ (32% in water).

ii. A microwave tube was charged with 2-chloro-4-heteroarylpyrimidine (1.00 eq.), (1r,4r)-cyclohexane-1,4-diamine (3.00 eq.) and Et$_3$N (1 mL.) in 2-methoxyethan-1-ol (4 mL). The reaction mixture was heated at 180° C. for 1 h, concentrated under reduced pressure and purified by flash column chromatography starting with 100% DCM ramping to 9% MeOH+1% NH$_3$ (32% in water).

General Synthetic Procedure B:

A microwave-tube was charged with aryl halide (1.00 eq.), amine (1.00 eq.), Cs$_2$CO$_3$ (2.00 eq.), Pd$_2$(dba)$_3$ (0.05 eq.), xantphos (0.05 eq.) and dioxane (3 mL). The reaction mixture was heated under microwave at 170° C. for 2 h. Amine (1.00 eq.), Cs$_2$CO$_3$ (2.00 eq.), Pd$_2$(dba)$_3$ (0.05 eq.), xantphos (0.05 eq.) were re-added for incomplete reactions and the latter were heated under microwave at 170° C. for 2 h again. The reaction mixtures were concentrated under reduced pressure and purified by flash column chromatography starting with 100% DCM ramping to 7% MeOH+1% NH$_3$ (32% in water) to afford the desired product. Compounds showing purity <94% were further purified using preparative HPLC.

General Synthetic Procedure C:

A microwave tube was charged with aryl halide (1.00 eq.), boronic acid/ester (1.00 eq.), Na$_2$CO$_3$ (2.00 eq.), Pd(PPh$_3$)$_4$ (0.05 eq.) and MeCN/water (4 mL; 3:1). The reaction mixture was heated under microwave at 130° C. for 60 min, concentrated under reduced pressure and purified by flash column chromatography starting with 100% DCM ramping to 7% MeOH+1% $NH_3$ (32% in water) to afford the desired product. Compounds showing purity <94% were further purified using preparative HPLC.

General Synthetic Procedure D:

A solution of amine derivative (1.00 eq.), the corresponding ketone (1.00-5.00 eq.), $Et_3N$ in the amine is a salt (1.50 eq.) in DCE was stirred at rt for 1 h. AcOH (2.50 eq.) and sodium triacetoxyborohydride (2.00 eq.) were added. The reaction was stirred at rt overnight, quenched by adding saturated $NaHCO_3$, and extracted with DCM. Organic extracts were combined, concentrated under reduced pressure and purified by flash column chromatography starting with 100% DCM ramping to 7% MeOH+0.5% $NH_3$ (32% in water) to afford the desired product. Compounds showing purity <94% were further purified using preparative HPLC.

General Synthetic Procedure E:

A suspension of the cyclohexane-1,4-diamine derivative (1.00 eq.), the corresponding haloalkane (1.10 eq), $K_2CO_3$ (0.25 eq.), KI (1.30 eq) in MeCN was heated at reflux for 3-10 h. The reaction mixture was filtered, concentrated under reduced pressure and purified by flash column chromatography starting with 100% DCM ramping to 7% MeOH+0.5% $NH_3$ (32% in water) to afford the desired product. Compounds showing purity <94% were further purified using preparative HPLC.

The following compounds were synthesised in accordance with the procedures set above:

(1r,4r)-$N^1$-(5-Fluoro-4-(imidazo[1,2-a]pyridin-3-yl)pyrimidin-2-yl)cyclohexane-1,4-diamine (1)

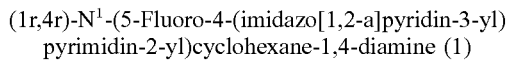

A suspension of the corresponding 2,4-dichloro-5-fluoropyrimidine (2.20 g, 13.2 mmol), 1-(vinyloxy)butane (5.0 mL 39 mmol), triethylamine (1.93 mL, 13.7 mmol) in PEG400 (6 mL) as stirred and degassed over 30 min. $Pd(OAc)_2$ (150 mg, 0.67 mmol) was added and the reaction mixture stirred under nitrogen at 80° C. for 12-48 h. The mixture was cooled, diluted with $Et_2O$ and water. Organic phase was separated and the aqueous phase extracted with $Et_2O$. Organic extracts were combined, washed with brine and purified by flash column chromatography starting with 100% petroleum ether ramping to 100% DCM to give (E)-4-(2-butoxyvinyl)-2-chloro-5-fluoropyrimidine as a yellow liquid (900 mg, 30%). $^1$H-NMR ($CDCl_3$): δ 0.94 (t, 3H, J=7.0 Hz), 1.39-1.46 (m, 2H), 1.68-1.74 (m, 2H), 3.98 (t, 2H, J=6.5 Hz), 5.87 (d, 1H, J=12.5 Hz), 7.96 (d, 1H, J=12.5 Hz), 8.18 (d, 1H, J=2.0 Hz). MS (ESI) m/z $[M+H]^+$ 231.0665. N-Bromosuccinimide (0.83 g, 4.67 mmol) was added to a stirred solution of (E)-4-(2-butoxyvinyl)-2-chloro-5-fluoropyrimidine (0.90 g, 3.90 mmol) in 20 mL of dioxane/water (3:1), and the resulting solution stirred for 1 h. Pyridin-2-amine (0.37 g, 3.90 mmol) was added, and the reaction mixture heated at 85° C. for 2.5 h. Dioxane was evaporated and the residue was triturated with EtOAc, the resulting solid was filtered, washed with EtOAc and purified by flash column chromatography starting with 100% petroleum ether ramping to 100% DCM to give 3-(2-chloro-5-fluoropyrimidin-4-yl)imidazo[1,2-a]pyridine as a white powder (0.80 g, 93%). $^1$H-NMR (DMSO-$d_6$): δ 7.35 (t, 1H, J=7.0 Hz), 7.65 (t, 1H, J=8.0 Hz), 7.88 (d, 1H, J=9.0 Hz), 8.51 (d, 1H, J=4.0 Hz), 8.85 (d, 1H, J=3.0 Hz), 9.73 (d, 1H, J=7.0 Hz). HRMS (ESI) m/z $[M+H]^+$ calcd. for $C_{11}H_7ClFN_4^+$, 249.0338; found 249.0309. 3-(2-Chloro-5-fluoropyrimidin-4-yl)imidazo[1,2-a]pyridine (0.45 g, 1.80 mmol) and (1r,4r)-cyclohexane-1,4-diamine (0.64 g, 5.60 mmol) were reacted according to general synthetic procedure A(i) to give 1 as a yellow solid (0.33 g, 56%). $^1$H-NMR ($CDCl_3$): δ 1.30-1.33 (m, 4H), 1.96-1.98 (m, 2H), 2.20-2.22 (m, 2H), 2.76-2.79 (m, 1H), 3.74-3.75 (m, 1H), 5.01 (s, 1H), 7.00 (d, 1H, J=6.5 Hz), 7.40 (t, 1H, J=7.0 Hz), 7.76 (d, 1H, J=8.0 Hz), 8.18 (s, 1H), 8.47 (s, 1H), 10.02 (s, 1H) (two primary amine protons ($NH_2$) signals not observed). MS (ESI) m/z $[M+H]^+$ 327.1851.

(1r,4r)-$N^1$-(5-Fluoro-4-(6-fluoroimidazo[1,2-a]pyridin-3-yl)pyrimidin-2-yl)cyclohexane-1,4-diamine (2)

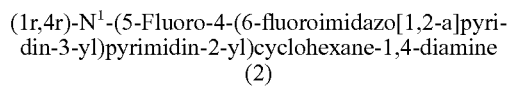

3-(2-Chloro-5-fluoropyrimidin-4-yl)-6-fluoroimidazo[1,2-a]pyridine (0.30 g, 1.59 mmol) and (1r,4r)-cyclohexane-1,4-diamine (0.39 g, 4.78 mmol) were reacted according to general synthetic procedure A(i) to give 2 as a yellow solid (0.22 g, 40%). H-NMR ($CDCl_3$): δ 1.31-1.39 (m, 4H), 1.98 (s, 2H), 2.23 (s, 2H), 2.74-2.79 (m, 1H), 3.74-3.80 (m, 1H), 5.03 (d, 1H, J=7.0 Hz), 7.33 (td, 1H, J=8.0 & 2.5 Hz), 7.74 (dd, 1H, J=9.5 & 5.0 Hz), 8.21 (d, 1H, J=3.5 Hz), 8.49 (d, 1H, J=3.5 Hz), 10.08 (s, 1H). HRMS (ESI) m/z $[M+H]^+$ 345.1582.

(1r,4r)-$N^1$-(5-Fluoro-4-(6-(trifluoromethyl)imidazo[1,2-a]pyridin-3-yl)pyrimidin-2-yl)cyclohexane-1,4-diamine (3). 3-(2-Chloro-5-fluoropyrimidin-4-yl)-6-(trifluoromethyl) imidazo[1,2-a]pyridine (0.50 g, 1.58 mmol) and (1r,4r)-cyclohexane-1,4-diamine (0.66 g, 4.75 mmol) were reacted according to general synthetic procedure A(i) to give 3 as a yellow solid (0.20 g, 32%). $^1$H-NMR ($CDCl_3$): δ 1.25-1.37 (m, 4H), 1.95 (d, 2H, J=8.5 Hz), 2.18 (d, 2H, J=8.5 Hz), 2.72-2.74 (m, 1H), 3.78-3.82 (m, 1H), 5.00 (d, 1H, J=7.5 Hz), 7.55 (dd, 1H, J=9.5 & 1.5 Hz), 7.87 (d, 1H, J=9.0 Hz), 8.24 (d, 1H, J=3.5 Hz), 8.54 (d, 1H, J=4.0 Hz), 10.49 (s, 1H). HRMS (ESI) m/z $[M+H]^+$ 395.2399.

(1r,4r)-$N^1$-(5-Fluoro-4-(6-methylimidazo[1,2-a]pyridin-3-yl)pyrimidin-2-yl)cyclohexane-1,4-diamine (4)

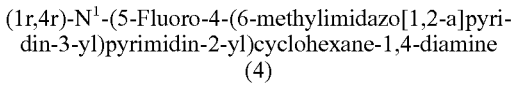

N-Bromosuccinimide (0.70 g, 3.91 mmol) was added to a stirred solution of (E)-4-(2-butoxyvinyl)-2-chloro-5-fluoropyrimidine (0.90 g, 3.90 mmol) in 10 mL of dioxane/water (3:1), and the resulting solution stirred for 1 h. 5-Methylpyridin-2-amine (0.42 g, 3.91 mmol) was added, and the reaction mixture heated at 85° C. for 2.5 h. Dioxane was evaporated and the residue was triturated with EtOAc, the resulting solid was filtered, washed with EtOAc to give 3-(2-chloro-5-fluoropyrimidin-4-yl)-6-methylimidazo[1,2-a]pyridine as a white powder (0.20 g, 20%). $^1$H-NMR (DMSO-$d_6$): δ 2.42 (s, 3H), 7.53 (dd, 1H, J=9.0 & 1.0 Hz), 7.79 (d, 1H, J=9.0 Hz), 8.45 (d, 1H, J=4.0 Hz), 8.83 (d, 1H, J=3.5 Hz), 9.54 (s, 1H). HRMS (ESI) m/z $[M+H]^+$ 263.0498. 3-(2-Chloro-5-fluoropyrimidin-4-yl)-6-methylimidazo[1,2-a]pyridine (0.15 g, 0.57 mmol) and (1r,4r)-cyclohexane-1,4-diamine (0.20 g, 1.72 mmol) were reacted according to general synthetic procedure A(ii) to give 4 as a yellow solid (0.12 g, 62%). $^1$H-NMR ($CDCl_3$): δ 1.29-1.36 (m, 4H), 1.97 (d, 2H, J=9.0 Hz), 2.23 (d, 2H, J=9.0 Hz), 2.44 (s, 3H), 2.76-2.78 (m, 1H), 3.78-3.80 (m, 1H), 4.98 (d, 1H, J=7.5 Hz), 7.25 (dd, 1H, J=9.0 & 1.0 Hz), 7.66 (d, 1H, J=9.0 Hz), 8.17 (d, 1H, J=4.0 Hz ( ), 8.42 (d, 1H, J=4.0 Hz), 9.79 (s, 1H). HRMS (ESI) m/z $[M+H]^+$ 341.1830.

(1r,4r)-$N^1$-(5-Fluoro-4-(6-phenylimidazo[1,2-a]pyridin-3-yl)pyrimidin-2-yl)cyclohexane-1,4-diamine (5)

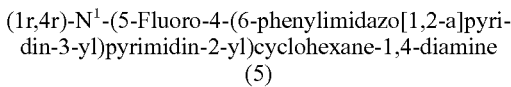

3-(2-Chloro-5-fluoropyrimidin-4-yl)-6-phenylimidazo[1,2-a]pyridine (0.45 g, 1.39 mmol) and (1r,4r)-cyclohexane- 1,4-diamine (0.48 g, 4.17 mmol) were reacted according to general synthetic procedure A(ii) to give 5 as a white solid (0.20 g, 36%). $^1$H-NMR (CDCl$_3$): δ 1.07 (s, 2H), 1.17-1.26 (m, 4H), 1.82 (d, 2H, J=9.5 Hz), 2.09 (d, 2H, J=11.0 Hz), 2.61 (br, 1H), 2.62 (br, 1H), 4.84 (br, 1H), 5.83 (br, 1H), 6.94 (t, 1H, J=7.0 Hz), 7.02 (d, 2H, J=6.5 Hz), 7.27-7.30 (m, 2H), 7.70 (d, 1H, J=9.0 Hz), 8.16 (d, 1H, J=3.5 Hz), 8.42 (d, 1H, J=4.0 Hz), 10.04 (s, 1H). HRMS (ESI) m/z [M+H]$^+$ 403.1958.

(1r,4r)-N$^1$-(5-Fluoro-4-(6-(phenylamino)imidazo[1,2-a]pyridin-3-yl)pyrimidin-2-yl)cyclohexane-1,4-diamine (6)

6-Nitro-N-phenylpyridin-3-amine: Microwave tubes were charged each with 5-bromo-2-nitropyridine (0.50 g, 2.47 mmol), aniline (3.53 μL, 3.74 mmol), Cs$_2$CO$_3$ (1.60 g, 4.95 mmol), Pd$_2$dba$_3$ (0.12 g, 0.12 mmol) and xantphos (0.07 g, 0.12 mmol) in dioxane (7 mL). Reaction mixtures were heated under microwave at 160° C. for 1 h, combined, concentrated under reduced pressure and purified by flash column chromatography starting with 100% DCM ramping to 2% MeOH to give a black solid that was washed with MeOH to yield 6-nitro-N-phenylpyridin-3-amine as a brown solid (2.00 g, 63%). $^1$H-NMR (DMSO-d$_6$): δ 7.14 (t, 1H, J=7.5 Hz), 7.30 (d, 2H, J=7.5 Hz), 7.42 (d, 2H, J=7.5 Hz), 7.57 (dd, 1H, J=9.0 & 2.5 Hz), 8.20 (d, 1H, J=9.0 Hz), 8.22 (d, 1H, J=2.5 Hz), 9.49 (s, 1H). HRMS (ESI) m/z [M+H]$^+$ 216.0684. N$^5$-Phenylpyridine-2,5-diamine: To a solution of 6-nitro-N-phenylpyridin-3-amine (1.00 g, 4.65 mmol)) in MeOH (20 mL) was added 10% Pd/C (49.0 mg, 0.46 mmol). The reaction mixture was stirred and bubbled with H$_2$ at room temperature for 3-10 h. The solids were filtered off and washed with MeOH. The filtrate and MeOH washing were combined and concentrated under reduced pressure to give N$^5$-phenylpyridine-2,5-diamine as a white powder (0.85 g, 99%). $^1$H-NMR (CDCl$_3$): δ 4.35 (s, 2H), 5.33 (s, 1H), 6.52 (d, 1H, J=8.5 Hz), 6.79-6.83 (m, 3H), 7.20 (t, 2H, J=8.0 Hz), 7.34 (dd, 1H, J=9.0 & 2.5 Hz), 7.96 (d, 1H, J=2.5 Hz). HRMS (ESI) m/z [M+H]$^+$186.0997. 3-(2-Chloro-5-fluoropyrimidin-4-yl)-N-phenylimidazo[1,2-a]pyridin-6-amine: N-Bromosuccinimide (0.56 g, 3.13 mmol) was added to a stirred solution of (E)-4-(2-butoxyvinyl)-2-chloro-5-fluoropyrimidine (0.80 g, 3.48 mmol) in 10 mL of dioxane/water (3:1), and the resulting solution stirred for 1 h. N$^5$-Phenylpyridine-2,5-diamine (0.55 g, 2.96 mmol) was added, and the reaction mixture heated at 85° C. for 2.5 h. Dioxane was evaporated and the residue was triturated with EtOAc, the resulting solid was filtered, washed with EtOAc and used for next reaction without further purification to give 3-(2-chloro-5-fluoropyrimidin-4-yl)-N-phenylimidazo[1,2-a]pyridin-6-amine as a brown powder (1.00 g, 85%). $^1$H-NMR (DMSO-d$_6$): δ 7.01 (t, 1H, J=7.5 Hz), 7.29 (dd, 2H, J=8.5 & 1.0 Hz), 7.38 (dt, 2H, J=7.5 & 1.5 Hz), 7.78 (dd, 1H, J=9.5 & 2.5 Hz), 7.97 (d, 1H, J=9.5 Hz), 8.83 (d, 1H, J=3.5 Hz), 8.91 (s, 1H), 9.02 (d, 1H, J=3.0 Hz), 9.87 (d, 1H, J=1.5 Hz). HRMS (ESI) m/z [M+H]$^+$ 340.0692. 3-(2-Chloro-5-fluoropyrimidin-4-yl)-N-phenylimidazo[1,2-a]pyridin-6-amine (0.34 g, 1.00 mmol) and (1r,4r)-cyclohexane-1,4-diamine (0.34 g, 3.00 mmol) were reacted according to general synthetic procedure A(ii) to give 6 as a white solid (0.11 g, 27%). $^1$H-NMR (CDCl$_3$): δ 0.78 (s, 2H), 1.16-1.26 (m, 4H), 1.72 (d, 2H, J=10.5 Hz), 2.12 (d, 2H, J=11.5 Hz), 2.49-2.54 (m, 1H), 3.66-3.68 (m, 1H), 4.92 (d, 1H, J=8.0 Hz), 7.45 (t, 1H, J=7.0 Hz), 7.54 (t, 2H, J=7.5 Hz), 7.61-7.64 (m, 3H), 7.84 (dd, 1H, J=9.0 & 1.0 Hz), 8.20 (d, 1H, J=3.5 Hz), 8.50 (d, 1H, J=3.5 Hz), 10.01 (s, 1H), 10.04 (s, 1H). HRMS (ESI) m/z [M+H]$^+$ 418.2133.

(1r,4r)-N$^1$-(5-Fluoro-4-(6-((4-fluorobenzyl)amino)imidazo[1,2-a]pyridin-3-yl)pyrimidin-2-yl)cyclohexane-1,4-diamine (7)

A solution of 5-bromo-2-nitropyridine (5.00 g, 24.6 mmol), DIPEA (8.75 mL, 50 mmol) and (4-fluorophenyl)methanamine (5.50 mL, 50 mmol) in DMSO (20 mL) was heated at 150° C. for 24 h. Water (100 mL) was added and the mixture was extracted with EtOAc (3×250 mL). The organic layers were combined, concentrated under reduced pressure and purified by flash column chromatography starting with 100% DCM ramping to 20% EtOAc to give N-(4-fluorobenzyl)-6-nitropyridin-3-amine as a yellow solid (3.50 g, 58%). $^1$H-NMR (DMSO-d$_6$): (4.44 (d, 2H, J=6.0 Hz), 7.07 (dd, 1H, J=9.0 & 2.0 Hz), 7.19 (t, 2H, J=8.5 Hz), 7.39-7.42 (m, 2H), 7.93-7.94 (m, 2H), 8.10 (d, 1H, J=9.0 Hz). HRMS (ESI) m/z [M+H]$^+$ 248.0799. To a solution of N-(4-fluorobenzyl)-6-nitropyridin-3-amine (1.21 g, 4.90 mmol) in MeOH (20 mL) was added 10% Pd/C (51.9 mg, 0.49 mmol). The reaction mixture was stirred and bubbled with H$_2$ at room temperature for 10 h. The solids were filtered off and washed with MeOH. The filtrate and MeOH washing were combined and concentrated under reduced pressure to give N$^5$-(4-fluorobenzyl)pyridine-2,5-diamine as a white powder (1.00 g, 94%). $^1$H-NMR (CDCl$_3$): δ 4.03 (s, 2H), 4.23 (s, 2H), 6.43 (d, 1H, J=9.0 Hz), 6.87 (dd, 1H, J=8.5 & 3.0 Hz), 7.02 (t, 2H, J=8.0 Hz), 7.31 (t, 2H, J=8.5 Hz), 7.58 (d, 1H, J=2.5 Hz) (one secondary amine proton (NH) signal not observed). HRMS (ESI) m/z [M+H]$^+$ 218.1056. N-Bromosuccinimide (0.30 g, 1.69 mmol) was added to a stirred solution of (E)-4-(2-butoxyvinyl)-2-chloro-5-fluoropyrimidine (0.39 g, 1.69 mmol) in 5 mL of dioxane/water (3:1), and the resulting solution stirred for 1 h. N$^5$-(4-Fluorobenzyl)pyridine-2,5-diamine (0.43 g, 19.8 mmol) was added, and the reaction mixture heated at 85° C. for 2.5 h. Dioxane was evaporated and the residue was triturated with EtOAc, the resulting solid was filtered, washed with EtOAc, and purified by flash column chromatography starting with 100% petroleum ether ramping to 100% DCM to give 3-(2-chloro-5-fluoropyrimidin-4-yl)-N-(4-fluorobenzyl)imidazo[1,2-a]pyridin-6-amine as a brown powder (0.14 g, 23%). $^1$H-NMR (CDCl$_3$): δ 4.17 (s, 1H), 4.39 (s, 2H), 7.02-7.08 (m, 3H), 7.46 (t, 2H, J=8.5 Hz), 7.62 (d, 1H, J=9.0 Hz), 8.38 (d, 1H, J=3.5 Hz), 8.44 (d, 1H, J=3.0 Hz), 9.28 (d, 1H, J=2.0 Hz). HRMS (ESI) m/z [M+H]$^+$ 372.0746. 3-(2-Chloro-5-fluoropyrimidin-4-yl)-N-(4-fluorobenzyl)imidazo[1,2-a]pyridin-6-amine (0.10 g, 0.26 mmol) and (1r,4r)-cyclohexane-1,4-diamine (0.09 g, 0.80 mmol) were reacted according to general synthetic procedure A(ii) to give 7 as a white solid (0.03 g, 26%). $^1$H-NMR (CDCl$_3$): δ 1.19-1.27 (m, 4H), 1.89 (d, 2H, J=11.5 Hz), 2.13 (d, 2H, J=11.5 Hz), 2.67-2.71 (m, 1H), 3.77-3.79 (m, 1H), 3.91 (s, 1H), 4.37 (d, 2H, J=4.5 Hz), 4.56 (br, 1H), 6.99 (dd, 1H, J=9.0 & 2.5 Hz), 7.09 (t, 2H, J=8.5 Hz), 7.41 (t, 2H, J=7.5 Hz), 7.60 (dd, 1H, J=9.0 & 0.5 Hz), 8.15 (d, 1H, J=4.0 Hz), 8.34 (d, 1H, J=4.5 Hz), 9.26 (s, 1H) (two primary amine protons (NH$_2$) signals not observed). HRMS (ESI) m/z [M+H]$^+$ 450.2196.

(1r,4r)-N$^1$-(4-(Imidazo[1,2-a]pyridin-3-yl)-5-methylpyrimidin-2-yl)cyclohexane-1,4-diamine (8)

3-(2-Chloro-5-methylpyrimidin-4-yl)imidazo[1,2-a]pyridine (0.17 g, 0.70 mmol) and (1r,4r)-cyclohexane-1,4-diamine (0.24 g, 2.10 mmol) were reacted according to general synthetic procedure A(i) to give 8 as an orange powder (0.06 g, 27%). $^1$H-NMR (CDCl$_3$): δ 1.26-1.36 (m, 4H), 1.95 (apparent s, 2H), 2.18 (br, 2H), 2.39 (s, 3H), 2.74-2.78 (m, 1H), 3.79-3.83 (m, 1H), 4.88 (d, 1H, J=7.5 Hz), 6.93 (t, 1H, J=7.0 Hz), 7.35 (t, 1H, J=8.0 Hz), 7.73 (d, 1H, J=8.5 Hz), 8.14 (s, 1H), 8.20 (s, 1H), 9.76 (s, 1H) (two primary amine protons (NH$_2$) signals not observed). HRMS (ESI) m/z [M+H]$^+$ 323.1928.

(1r,4r)-N$^1$-(5-Methyl-4-(6-(trifluoromethyl)imidazo[1,2-a]pyridin-3-yl)pyrimidin-2-yl)cyclohexane-1,4-diamine (9)

3-(2-Chloro-5-methylpyrimidin-4-yl)-6-(trifluoromethyl)imidazo[1,2-a]pyridine (0.11 g, 0.35 mmol) and (1r,4r)-cyclohexane-1,4-diamine (0.15 g, 1.05 mmol) were reacted according to synthetic procedure A(i) to give 9 as a white powder (0.06 g, 44%). $^1$H-NMR (CDCl$_3$): δ 1.21-1.31 (m, 4H), 1.89 (d, 2H, J=10.5 Hz), 2.12 (d, 2H, J=11.0 Hz), 2.36 (s, 3H), 2.65-2.698 (m, 1H), 3.74-3.78 (m, 1H), 5.12 (d, 1H, J=6.5 Hz), 7.45 (d, 1H, J=9.5 Hz), 7.79 (d, 1H, J=9.5 Hz), 8.17 (s, 1H), 8.20 (s, 1H), 10.14 (s, 1H). HRMS (ESI) m/z [M+H]$^+$ 391.1804.

(1r,4r)-N$^1$-(5-Methyl-4-(6-phenylimidazo[1,2-a]pyridin-3-yl)pyrimidin-2-yl)cyclohexane-1,4-diamine (10)

A suspension of 2,4-dichloro-5-methylpyrimidine (5.00 g, 30.7 mmol), 1-(vinyloxy)butane (11.9 mL, 92 mmol), diisopropylethylamine (5.60 mL, 32.2 mmol) in PEG400 (15 mL, 43.0 mmol) was stirred and degassed over 30 min. Pd(OAc)$_2$ (482 mg, 2.15 mmol) was added and the reaction mixture stirred at 80° C. for 96 h. The mixture was cooled, diluted with Et$_2$O and water. Organic phase was separated and the aqueous phase extracted with Et$_2$O. Organic extracts were combined, washed with brine and purified by flash column chromatography starting with 100% petroleum ether ramping to 100% DCM to give (E)-4-(2-butoxyvinyl)-2-chloro-5-methylpyrimidine as an orange liquid (1.00 g, 15%). $^1$H-NMR (CDCl$_3$): δ 0.95 (t, 3H, J=7.0 Hz), 1.39-1.47 (m, 2H), 1.68-1.73 (m, 2H), 2.15 (s, 3H), 3.98 (t, 2H, J=6.5 Hz), 5.79 (d, 1H, J=12.0 Hz), 7.95 (d, 1H, J=11.5 Hz), 8.14 (s, 1H). MS (ESI) m/z [M+H]$^+$ 227.1035. N-Bromosuccinimide (1.67 g, 9.38 mmol) was added to a stirred solution of give (E)-4-(2-butoxyvinyl)-2-chloro-5-methylpyrimidine (2.20 g, 9.73 mmol), in 10 mL of dioxane/water (3:1), and the resulting solution stirred for 1 h. 5-Bromopyridin-2-amine (1.52 g, 8.79 mmol) was added, and the reaction mixture heated at 80° C. for 2 h. The reaction was allowed to cool to room temperature, and the precipitate was filtered and washed with MeOH to give 6-bromo-3-(2-chloro-5-methylpyrimidin-4-yl)imidazo[1,2-a]pyridine as a beige powder (1.30 g, 42%). $^1$H-NMR (DMSO-d$_6$): δ 7.74 (d, 1H, J=9.5 Hz), 7.85 (d, 1H, J=9.5 Hz), 8.50 (s, 1H), 8.74 (s, 1H), 9.83 (s, 1H). HRMS (ESI) m/z [M($^{81}$Br)+H]$^+$325.9694. 6-Bromo-3-(2-chloro-5-methylpyrimidin-4-yl)imidazo[1,2-a]pyridine (1.15 g, 3.58 mmol) and (1r,4r)-cyclohexane-1,4-diamine (1.02 g, 8.95 mmol) were reacted according to general synthetic procedure A(ii) to give (1r,4r)-N$^1$-(4-(6-bromoimidazo[1,2-a]pyridin-3-yl)-5-methylpyrimidin-2-yl)cyclohexane-1,4-diamine as a white solid (1.10 g, 77%). $^1$H-NMR (DMSO-d$_6$): δ 1.26-1.38 (m, 4H), 1.92 (d, 2H, J=12.0 Hz), 2.22 (d, 2H, J=10.5 Hz), 2.69-2.73 (m, 1H), 3.79-3.83 (m, 1H), 5.08 (d, 1H, J=8.0 Hz), 7.38 (dd, 1H, J=9.5 & 1.5 Hz), 7.60 (d, 1H, J=9.0 Hz), 8.09 (s, 1H), 8.17 (s, 1H), 9.96 (s, 1H). HRMS (ESI) m/z [M($^{81}$Br)+H]$^+$ 403.1070. (1r,4r)-N$^1$-(4-(6-bromoimidazo[1,2-a]pyridin-3-yl)-5-methylpyrimidin-2-yl)cyclohexane-1,4-diamine (0.50 g, 12.5 mmol) and 4,4,5,5-tetramethyl-2-phenyl-1,3,2-dioxaborolane (0.26 mg, 12.5 mmol) were reacted according to general synthetic procedure C to give 10 as a white solid (0.38 g, 76%). $^1$H-NMR (CDCl$_3$): δ 0.78 (s, 2H, NH$_2$), 1.16-1.27 (m, 4H), 1.68 (d, 2H, J=10.5 Hz), 2.08 (d, 2H, J=11.5 Hz), 2.41 (s, 3H), 2.49-2.54 (m, 1H), 3.65-3.69 (m, 1H), 4.85 (d, 1H, J=7.5 Hz), 7.42 (t, 1H, J=7.5 Hz), 7.50 (t, 2H, J=7.5 Hz), 7.57-7.61 (m, 3H), 7.80 (d, 1H, J=9.5 Hz), 8.16 (s, 1H), 8.20 (s, 1H), 9.98 (s, 1H). HRMS (ESI) m/z [M+H]$^+$399.2294.

(1r,4r)-N$^1$-(4-(Imidazo[1,2-a]pyridin-3-yl)-5-methoxypyrimidin-2-yl)cyclohexane-1,4-diamine (11)

3-(2-Chloro-5-methoxypyrimidin-4-yl)imidazo[1,2-a]pyridine (250 mg, 0.95 mmol) and (1r,4r)-cyclohexane-1,4-diamine (438 mg, 3.80 mmol) were reacted according to synthetic procedure A(ii) to give 11 as a yellow powder (0.13 g, 40%). $^1$H-NMR (DMSO-d$_6$): δ 1.23-1.45 (m, 4H), 1.88-2.07 (m, 4H), 2.77 (br s, 1H), 2.93 (br s, 1H), 3.92 (s, 3H), 6.93 (d, 1H, J=7.5 Hz), 7.14 (t, 1H, J=6.5 Hz), 7.51 (t, 1H, J=8.0 Hz), 7.77 (d, 1H, J=9.0 Hz), 8.25 (s, 1H), 8.43 (br s, 2H), 8.56 (s, 1H), 10.24 (br s, 1H). HRMS (ESI) m/z [M+H]$^+$ 339.1928.

(1r,4r)-N$^1$-(4-(6-Bromoimidazo[1,2-a]pyridin-3-yl)-5-chloropyrimidin-2-yl)cyclohexane-1,4-diamine (12)

6-Bromo-3-(2,5-dichloropyrimidin-4-yl)imidazo[1,2-a]pyridine (300 mg, 0.88 mmol) and (1r,4r)-cyclohexane-1,4-diamine (201 mg, 1.76 mmol) were reacted according to synthetic procedure A(ii) to give 12 as a white powder (198 mg g, 53%). $^1$H-NMR (DMSO-d$_6$): δ 1.33-1.37 (m, 4H), 1.94-1.96 (m, 2H), 2.18-2.20 (m, 2H), 2.74 (br s, 1H), 3.80 (br s, 1H), 5.09 (br s, 1H), 7.45 (d, 1H, J=9.0 Hz), 7.65 (d, 1H, J=9.0 Hz), 8.30 (s, 1H), 8.76 (s, 1H), 9.99 (s, 1H). HRMS (ESI) m/z [M($^{81}$Br)+H]$^+$423.0510.

(1r,4r)-N$^1$-(5-Chloro-4-(6-(trifluoromethyl)imidazo[1,2-a]pyridin-3-yl)pyrimidin-2-yl)cyclohexane-1,4-diamine (13)

3-(2,5-Dichloropyrimidin-4-yl)-6-(trifluoromethyl)imidazo[1,2-a]pyridine (250 mg, 0.75 mmol) and (1r,4r)-cyclohexane-1,4-diamine (171 mg, 1.50 mmol) were reacted according to synthetic procedure A(ii) to give 13 as a yellow powder (140 mg, 45%). $^1$H-NMR (DMSO-d$_6$): δ 1.05-1.07 (m, 2H), 1.31-1.38 (m, 2H), 1.76-1.78 (m, 2H), 1.90-1.92 (m, 2H), 2.22 (br s, 2H), 2.56 (s, 1H), 3.63 (s, 1H), 7.55 (d, 1H, J=8.0 Hz), 7.75 (d, 1H, J=9.0 Hz), 7.99 (d, 1H, J=9.5 Hz), 8.46 (s, 1H), 8.67 (s, 1H), 10.06 (s, 1H). HRMS (ESI) m/z [M+H]$^+$ 411.1306.

(1r,4r)-N$^1$-(4-(8-Bromo-6-(trifluoromethyl)imidazo[1,2-a]pyridin-3-yl)-5-chloropyrimidin-2-yl)cyclohexane-1,4-diamine (14)

8-Bromo-3-(2,5-dichloropyrimidin-4-yl)-6-(trifluoromethyl)imidazo[1,2-a]pyridine (300 mg, 0.73 mmol) and (1r,4r)-cyclohexane-1,4-diamine (167 mg, 1.46 mmol) were reacted according to synthetic procedure A(ii) to give 14 as a white powder (155 mg g, 43%). $^1$H-NMR (CDCl$_3$):

(1.23-1.30 (m, 4H), 1.90-1.92 (m, 2H), 2.11-2.13 (m, 2H), 2.67-2.31 (m, 1H), 3.71-3.74 (m, 1H), 5.26 (br s, 1H), 7.77 (s, 1H), 8.33 (s, 1H), 8.78 (s, 1H), 10.09 (s, 1H). HRMS (ESI) m/z [M($^{79}$Br)+H]$^+$489.0419, m/z [M($^{81}$Br)+H]$^+$ found 491.0399.

Methyl ((1r,4r)-4-((5-fluoro-4-(imidazo[1,2-a]pyridin-3-yl)pyrimidin-2-yl)amino)cyclohexyl) glycinate (15)

A solution of (1r,4r)-N$^1$-(5-fluoro-4-(imidazo[1,2-a]pyridin-3-yl)pyrimidin-2-yl)cyclohexane-1,4-diamine (0.17 g, 0.52 mmol), methyl 2-bromoacetate (0.15 mL, 1.56 mmol) and Et$_3$N (0.13 mL, 1.56 mmol) in THF (4 mL) was stirred at rt for 48 h. The reaction mixture was concentrated under reduced pressure and purified by flash column chromatography starting with 100% DCM and ramping to 4% MeOH in DCM to give 15 as a yellow solid (42.0 mg, 20%). $^1$H-NMR (CDCl$_3$): δ 1.29-1.39 (m, 5H), 2.02 (d, 2H, J=12.0 Hz), 2.25 (d, 2H, J=10.0 Hz), 2.52-2.55 (m, 1H), 3.48 (s, 2H), 3.72-3.78 (m, 4H), 5.02 (d, 1H, J=7.5 Hz), 7.01 (t, 1H, J=7.0 Hz), 7.41 (t, 1H, J=7.5 Hz), 7.76 (d, 1H, J=9.0 Hz), 8.18 (d, 1H, J=4.0 Hz), 8.47 (d, 1H, J=4.0 Hz), 10.02 (d, 1H, J=7.0 Hz). HRMS (ESI) m/z [M+H]$^+$ 399.1878.

N-((1r,4r)-4-((5-Fluoro-4-(imidazo[1,2-a]pyridin-3-yl)pyrimidin-2-yl)amino)cyclohexyl)methanesulfonamide (16)

To a solution of (1r,4r)-N$^1$-(5-fluoro-4-(imidazo[1,2-a]pyridin-3-yl)pyrimidin-2-yl)cyclohexane-1,4-diamine (0.20 g, 0.61 mmol) and Et$_3$N (0.10 mL, 1.22 mmol) in DCM (5 mL) cooled in an ice bath was added methanesulfonyl chloride (0.10 mL, 1.22 mmol). The reaction mixture was stirred at rt for 48 h, concentrated under reduced pressure and purified by flash column chromatography starting with 100% DCM and ramping to 3% MeOH in DCM to give 16 as a white powder (0.07 g, 28%). $^1$H-NMR (DMSO-d$_6$): δ 1.38 (s, 4H), 1.98 (s, 2H), 2.02 (s, 2H), 2.93 (s, 3H), 3.16 (s, 1H), 3.61 (s, 1H), 7.04 (d, 1H, J=7.5 Hz), 7.18 (t, 1H, J=7.0 Hz), 7.36 (d, 1H, J=7.5 Hz), 7.56 (t, 1H, J=7.5 Hz), 7.82 (t, 1H, J=9.0 Hz), 8.35 (d, 1H, J=4.0 Hz), 8.39 (d, 1H, J=4.0 Hz), 10.17 (s, 1H). HRMS (ESI) m/z [M+H]$^+$ 405.1792.

N-((1r,4r)-4-((4-(6-Bromoimidazo[1,2-a]pyridin-3-yl)-5-chloropyrimidin-2-yl)amino)cyclohexyl)methanesulfonamide (17)

To a solution of N$^1$-(4-(6-bromoimidazo[1,2-a]pyridin-3-yl)-5-chloropyrimidin-2-yl) cyclo-hexane-1,4-diamine (100 mg, 0.24 mmol) in pyridine (1 mL) and DCM (4 mL) added methanesulfonyl chloride (54.7 mg, 0.48 mmol) at 0° C. and the resulting solution was stirred at room temperature for 2 h. The reaction residue was filtered and washed with DCM (5 mL) and EtOAc (10 mL) to give 17 as a yellow solid (110 mg, 92%). H-NMR (DMSO-d$_6$): δ 1.41-1.46 (m, 2H), 1.95-1.97 (m, 2H), 2.92 (s, 3H), 3.14 (s, 1H), 3.66 (s, 1H), 3.71-3.76 (m, 4H), 7.06 (br s, 1H), 7.62 (br s, 1H), 7.72 (d, 1H, J=9.0 Hz), 7.82 (d, 1H, J=9.0 Hz), 8.43 (s, 1H), 8.74 (s, 1H), 9.95 (s, 1H). HRMS (ESI) m/z [M($^{79}$Br)+H]$^+$499.0313, m/z [M($^{81}$Br)+H]$^+$501.0283.

N-((1r,4r)-4-((4-(8-Bromo-6-(trifluoromethyl)imidazo[1,2-a]pyridin-3-yl)-5-chloropyrimidin-2-yl) amino)cyclohexyl)methanesulfonamide (18)

To a solution of N$^1$-(4-(8-bromo-6-(trifluoromethyl)imidazo[1,2-a]pyridin-3-yl)-5-chloro-pyrimidin-2-yl)cyclohexane-1,4-diamine (100 mg, 0.20 mmol) in pyridine (1 mL) and DCM (4 mL) added methanesulfonyl chloride (45.8 mg, 0.40 mmol) at 0° C. and the resulting solution was stirred at room temperature for 2 h. The reaction residue was filtered and washed with DCM (5 mL) and EtOAc (10 mL) to give 18 as a pale white solid (98 mg, 86%). $^1$H-NMR (CDCl$_3$): δ 1.24-1.28 (m, 2H), 1.37-1.44 (m, 2H), 1.91-1.95 (m, 4H), 2.90 (s, 3H), 3.09 (s, 1H), 3.60 (s, 1H), 7.06 (d, 1H, J=5.0 Hz), 7.77 (d, 1H, J=7.0 Hz), 8.20 (s, 1H), 8.48 (s, 1H), 8.66 (s, 1H), 10.02 (s, 1H). HRMS (ESI) m/z [M+H]$^+$ 567.0187.

5-Fluoro-4-(imidazo[1,2-a]pyridin-3-yl)-N-(1-methylpiperidin-4-yl)pyrimidin-2-amine (19)

3-(2-Chloro-5-fluoropyrimidin-4-yl)imidazo[1,2-a]pyridine (0.25 g, 1.00 mmol) and 1-methylpiperidin-4-amine (0.38 mL, 3.00 mmol) were reacted according to synthetic procedure A(i) to give 19 as a yellow solid (0.19 g, 58%). $^1$H-NMR (CDCl$_3$): δ 1.60-1.67 (m, 2H), 2.13-2.21 (m, 4H), 2.33 (s, 3H), 2.87 (d, 2H, J=9.5 Hz), 3.81-3.82 (m, 1H), 5.07 (d, 1H, J=7.0 Hz), 7.01 (t, 1H, J=7.0 Hz), 7.40 (t, 1H, J=7.5 Hz), 7.77 (d, 1H, J=9.0 Hz), 8.20 (d, 1H, J=3.5 Hz), 8.47 (d, 1H, J=4.0 Hz), 10.01 (d, 1H, J=7.0 Hz). HRMS (ESI) m/z [M+H]$^+$ 327.1804.

tert-Butyl 4-((5-fluoro-4-(imidazo[1,2-a]pyridin-3-yl)pyrimidin-2-yl)amino)piperidine-1-carboxylate (20)

3-(2-Chloro-5-fluoropyrimidin-4-yl)imidazo[1,2-a]pyridine (0.55 g, 2.21 mmol) and tert-butyl 4-aminopiperidine-1-carboxylate (1.33 g, 6.34 mmol) were reacted according to synthetic procedure A(i) to give 20 as a white solid (0.48 g, 53%). $^1$H-NMR (CDCl$_3$): δ 1.48 (s, 11H), 2.12 (d, 2H, J=11.0 Hz), 2.99 (t, 2H, J=11.5 Hz), 3.93-3.99 (m, 1H), 4.11 (s, 2H), 5.05 (d, 1H, J=7.5 Hz), 7.01 (t, 1H, J=7.0 Hz), 7.40 (t, 1H, J=7.5 Hz), 7.77 (d, 1H, J=9.0 Hz), 8.20 (d, 1H, J=3.5 Hz), 8.47 (d, 1H, J=4.0 Hz), 9.99 (d, 1H, J=7.0 Hz). HRMS (ESI) m/z [M+H]$^+$ 413.2178.

5-Fluoro-4-(imidazo[1,2-a]pyridin-3-yl)-N-(piperidin-4-yl)pyrimidin-2-amine (21)

A solution of tert-butyl 4-((5-fluoro-4-(imidazo[1,2-a]pyridin-3-yl)pyrimidin-2-yl)amino)piperidine-1-carboxylate (100 mg, 0.24 mmol) in 2M HCl (2 mL) and EtOH (2 mL) was stirred at room temperature for 48 h, basified with 2M (NaOH) to pH 10, and purified by flash column chromatography starting with 100% DCM ramping to 6% MeOH+1.0% NH$_3$ (32% in water) to give 21 as a white solid (70 mg, 93%). $^1$H-NMR (CDCl$_3$): δ 1.43-1.50 (m, 2H), 2.15 (d, 2H, J=10.5 Hz), 2.78 (t, 2H, J=10.5 Hz), 3.17 (d, 2H, J=12.5 Hz), 3.48 (s, 1H), 3.88-3.96 (m, 1H), 5.09 (d, 1H, J=7.0 Hz), 7.00 (t, 1H, J=7.0 Hz), 7.40 (t, 1H, J=7.5 Hz), 7.77 (d, 1H, J=8.5 Hz), 8.20 (d, 1H, J=3.5 Hz), 8.47 (d, 1H, J=3.5 Hz), 10.02 (d, 1H, J=5.0 Hz). HRMS (ESI) m/z [M+H]$^+$ 313.1246.

N-(1-(Cyclopropylmethyl)piperidin-4-yl)-5-fluoro-4-(imidazo[1,2-a]pyridin-3-yl)pyrimidin-2-amine (22)

A suspension of 5-fluoro-4-(imidazo[1,2-a]pyridin-3-yl)-N-(piperidin-4-yl)pyrimidin-2-amine (350 mg, 1.12 mmol), (bromomethyl)cyclopropane (338 μL, 3.33 mmol), triethylamine (0.25 mL, 1.78 mmol) in DMF (7 mL) was stirred at 90° C. overnight, concentrated under reduced pressure and purified by flash column chromatography starting with 100% DCM ramping to 2% MeOH to give 22 as a white powder (70 mg, 17%). $^1$H-NMR (CDCl$_3$): δ 0.11-0.14 (m, 2H), 0.52-0.60 (m, 2H), 0.87-0.93 (m, 2H), 1.63-1.69 (m, 2H), 2.16 (d, 2H, J=11.5 Hz), 2.22 (t, 2H, J=10.5 Hz), 2.30 (d, 2H, J=6.5 Hz), 3.08 (d, 2H, J=9.0 Hz), 3.80-3.86 (m, 1H), 5.08 (d, 1H, J=7.0 Hz), 7.00 (t, 1H, J=7.0 Hz), 7.40 (t, 1H, J=7.5 Hz), 7.77 (d, 1H, J=9.0 Hz), 8.20 (d, 1H, J=3.5 Hz), 8.48 (d, 1H, J=4.0 Hz), 10.08 (d, 1H, J=7.0 Hz). HRMS (ESI) m/z [M+H]$^+$ 367.2450.

Methyl 2-(4-((5-fluoro-4-(imidazo[1,2-a]pyridin-3-yl)pyrimidin-2-yl)amino)piperidin-1-yl)acetate (23)

A suspension of 5-fluoro-4-(imidazo[1,2-a]pyridin-3-yl)-N-(piperidin-4-yl)pyrimidin-2-amine (350 mg, 1.12 mmol), methyl 2-bromoacetate (318 μL, 3.37 mmol), triethylamine (0.25 mL, 1.78 mmol) in THF (7 mL) was stirred at room temperature overnight, concentrated under reduced pressure and purified by flash column chromatography starting with 100% DCM ramping to 2% MeOH to give 23 as an orange powder (60 mg, 14%). $^1$H-NMR (CDCl$_3$): δ 1.67-1.74 (m, 2H), 2.15 (d, 2H, J=11.0 Hz), 2.43 (t, 2H, J=11.0 Hz), 2.98 (d, 2H, J=12.0 Hz), 3.74 (s, 3H), 3.74 (s, 2H), 3.81-3.87 (m, 1H), 5105 (d, 1H, J=7.0 Hz), 7.10 (t, 1H, J=6.5 Hz), 7.40 (t, 1H, J=7.0 Hz), 7.76 (d, 1H, J=9.0 Hz), 8.19 (d, 1H, J=3.5 Hz), 8.40 (d, 1H, J=4.0 Hz), 10.0 (d, 1H, J=7.0 Hz). HRMS (ESI) m/z [M+H]$^+$ 385.2190.

5-Fluoro-4-(imidazo[1,2-a]pyridin-3-yl)-N-(1-(methylsulfonyl)piperidin-4-yl)pyrimidin-2-amine (24)

To a solution of 5-fluoro-4-(imidazo[1,2-a]pyridin-3-yl)-N-(piperidin-4-yl)pyrimidin-2-amine (283 mg, 0.91 mmol) and triethylamine (133 μL, 0.93 mmol) in DCM (7 mL) cooled on an ice bath was added methanesulfonyl chloride (105 μL, 1.82 mmol). The reaction was allowed to warm to room temperature, stirred overnight, and filtered. The filtrate was purified by flash column chromatography starting with 100% DCM ramping to 2% MeOH to give 24 as a white solid (40 mg, 11%). $^1$H-NMR (DMSO-d$_6$): δ 1.56-1.62 (m, 2H), 2.07 (d, 2H, J=11.5 Hz), 2.91 (s, 5H), 3.60 (d, 2H, J=12.0 Hz), 3.82-3.85 (m, 1H), 7.24 (s, 1H), 7.48 (d, 1H, J=7.5 Hz), 7.55-7.58 (m, 1H), 7.82 (d, 1H, J=9.0 Hz), 8.37 (d, 1H, J=4.0 Hz), 8.42 (d, 1H, J=4.0 Hz), 10.13 (s, 1H). HRMS (ESI) m/z [M+H]$^+$ 391.1777.

(1r,4r)-N$^1$-(5-Fluoro-4-(6-((3-fluorophenyl)amino)imidazo[1,2-a]pyridin-3-yl)pyrimidin-2-yl)cyclohexane-1,4-diamine (25)

(1r,4r)-N$^1$-(4-(6-Bromoimidazo[1,2-a]pyridin-3-yl)-5-fluoropyrimidin-2-yl)cyclohexane-1,4-diamine (291 mg, 0.72 mmol) and 3-fluoroaniline (69 μL, 0.72 mmol) were coupled according to general procedure B. The product was further purified by preparative HPLC to afford 25 as a yellow solid (30.0 mg, 10%). $^1$H-NMR (DMSO-d$_6$): δ 1.13 (s, 4H), 1.94 (s, 4H), 2.84 (s, 1H), 3.61 (s, 1H), 6.59 (s, 1H), 6.81 (dt, 1H, J=12.0 & 2.0 Hz), 6.85 (d, 1H, J=8.0 Hz), 7.13 (d, 1H, J=7.0 Hz), 7.24 (d, 1H, J=8.0 Hz), 7.48 (d, 1H, J=9.0 Hz), 7.78 (d, 1H, J=9.5 Hz), 8.29 (d, 1H, J=4.5 Hz), 8.40 (d, 1H, J=4.0 Hz), 8.77 (s, 1H, NH), 9.95 (s, 1H). HRMS (ESI) m/z [M+H]$^+$ 436.2059.

(1r,4r)-N$^1$-(5-Fluoro-4-(6-(pyridin-3-yl)imidazo[1,2-a]pyridin-3-yl)pyrimidin-2-yl)cyclohexane-1,4-diamine (26)

(1r,4r)-N$^1$-(4-(6-Bromoimidazo[1,2-a]pyridin-3-yl)-5-fluoropyrimidin-2-yl)cyclohexane-1,4-diamine (200 mg, 0.49 mmol) and 3-(4,4,5,5-tetramethyl-1,3,2-dioxaborolan-2-yl)pyridine (100 mg, 0.49 mmol) were reacted according to general synthetic procedure C. The product was further purified by preparative HPLC to give 26 as a yellow solid (100 mg, 50%). $^1$H-NMR (CDCl$_3$): δ 0.90 (s, 2H), 1.23 (d, 2H, J=10.5 Hz), 1.67-1.75 (m, 4H), 2.10 (d, 2H, J=9.5 Hz), 2.57 (s, 1H), 3.70 (s, 1H), 5.105 (d, 1H, J=5.0 Hz), 7.47 (t, 1H, J=6.0 Hz), 7.53 (d, 1H, J=8.5 Hz), 7.86 (d, 1H, J=8.5 Hz), 7.92 (d, 1H, J=5.0 Hz), 8.20 (s, 1H), 8.51 (s, 1H), 8.69 (s, 1H), 8.91 (s, 1H), 10.26 (s, 1H). HRMS (ESI) m/z [M+H]$^+$ 404.1998.

(1r,4r)-N$^1$-(5-Fluoro-4-(6-(3-fluoropyridin-2-yl)imidazo[1,2-a]pyridin-3-yl)pyrimidin-2-yl)cyclohexane-1,4-diamine (27)

(1r,4r)-N$^1$-(4-(6-Bromoimidazo[1,2-a]pyridin-3-yl)-5-fluoropyrimidin-2-yl)cyclohexane-1,4-diamine (187 mg, 0.46 mmol) and 3-fluoro-2-(4,4,5,5-tetramethyl-1,3,2-dioxaborolan-2-yl)pyridine (103 mg, 0.46 mmol) were reacted according to general synthetic procedure C to give 27 as a yellow solid (90 mg, 47%). $^1$H-NMR (CDCl$_3$): δ 1.11-1.36 (m, 2H), 1.25-1.33 (m, 2H), 1.84 (d, 1H, J=12.5 Hz), 2.23 (d, 1H, J=11.0 Hz), 2.66-2.71 (m, 1H), 3.87-3.89 (m, 1H), 5.02 (d, 1H, J=7.5 Hz), 6.96 (dd, 1H, J=8.0 & 2.5 Hz), 7.66 (dd, 1H, J=7.5 & 1.5 Hz), 7.83 (d, 1H, J=9.5 Hz), 7.92-7.95 (m, 2H), 8.23 (d, 1H, J=3.5 Hz), 8.47 (d, 1H, J=3.5 Hz), 10.69 (s, 1H). HRMS (ESI) m/z [M+H]$^+$ 422.1905.

(1r,4r)-N$^1$-(5-Fluoro-4-(6-phenylimidazo[1,2-a]pyridin-3-yl)pyrimidin-2-yl)-N4-(pyridin-2-yl)cyclohexane-1,4-diamine (28)

3-(2-Chloro-5-fluoropyrimidin-4-yl)-6-phenylimidazo[1,2-a]pyridine (200 mg, 0.62 mmol) and (1r,4r)-N$^1$-(pyridin-2-yl)cyclohexane-1,4-diamine (236 mg, 1.20 mmol) were reacted according to general synthetic procedure A(ii) to give 28 as a yellow solid (90.0 mg, 30%). $^1$H-NMR (DMSO-d$_6$): δ 0.93 (br s, 2H), 1.37-1.41 (m, 2H), 1.90 (br s, 2H), 2.00-2.022 (m, 2H), 3.53-3.56 (m, 1H), 3.70-3.72 (m, 1H), 6.44-6.47 (m, 2H), 7.30-7.37 (m, 2H), 7.47 (t, 1H, J=7.5 Hz), 7.57 (t, 2H, J=7.5 Hz), 7.76-7.85 (m, 3H), 7.92-7.95 (m, 2H), 8.38 (s, 1H), 8.45 (s, 1H), 10.15 (s, 1H) (one secondary amine proton (NH) signal not observed). HRMS (ESI) m/z [M+H]$^+$ 480.2309.

(1r,4r)-N$^1$-(5-Methyl-4-(6-(pyridin-3-yl)imidazo[1,2-a]pyridin-3-yl)pyrimidin-2-yl)cyclohexane-1,4-diamine (29)

(1r,4r)-N$^1$-(4-(6-Bromoimidazo[1,2-a]pyridin-3-yl)-5-methylpyrimidin-2-yl) cyclohexane-1,4-diamine (146 mg, 0.37 mmol) and 3-(4,4,5,5-tetramethyl-1,3,2-dioxaborolan-2-yl) pyridine (76 mg, 0.37 mmol) were reacted according to general synthetic procedure C. The product was further purified by preparative HPLC to give 29 as a yellow solid (50 mg, 34%). $^1$H-NMR (CDCl$_3$): δ 1.25-1.30 (m, 4H), 1.98 (apparent s, 2H), 2.10 (apparent s, 2H), 2.41 (s, 3H), 3.00 (s, 1H), 3.82 (s, 1H), 5.18 (s, 1H), 7.46 (t, 1H, J=6.0 Hz), 7.53 (d, 1H, J=9.0 Hz), 7.85 (d, 1H, J=9.0 Hz), 7.89 (d, 1H, J=7.5 Hz), 8.17 (s, 1H), 8.21 (s, 1H), 8.66 (d, 1H, J=4.0 Hz), 8.87 (s, 1H), 9.80 (s, 1H) HRMS (ESI) m/z [M+H]$^+$ 400.2250.

(1r,4r)-N$^1$-(4-(6-(3-Fluoropyridin-2-yl)imidazo[1,2-a]pyridin-3-yl)-5-methylpyrimidin-2-yl)cyclohexane-1,4-diamine (30)

(1r,4r)-N$^1$-(4-(6-Bromoimidazo[1,2-a]pyridin-3-yl)-5-methylpyrimidin-2-yl)cyclohexane-1,4-diamine (195 mg, 0.49 mmol) and 3-fluoro-2-(4,4,5,5-tetramethyl-1,3,2-dioxaborolan-2-yl)pyridine (162 mg, 0.73 mmol) were reacted according to general synthetic procedure C to give 30 as a white solid (40 mg, 20%). $^1$H-NMR (CDCl$_3$): δ 0.98 (s, 2H), 1.18-1.26 (m, 2H), 1.64 (s, 2H), 1.73 (d, 2H, J=11.0 Hz), 2.14 (d, 2H, J=11.0 Hz), 2.34 (s, 3H), 2.57-2.61 (m, 1H), 3.77-3.82 (m, 1H), 5.14 (d, 1H, J=8.0 Hz), 6.87 (dd, 1H, J=8.0 & 3.0 Hz), 7.54 (dd, 1H, J=7.5 & 1.5 Hz), 7.73 (d, 1H, J=9.5 Hz), 7.81-7.87 (m, 2H), 8.06 (s, 1H), 8.18 (s, 1H), 10.30 (s, 1H). HRMS (ESI) m/z [M+H]$^+$418.2155.

(1r,4r)-N$^1$-(5-Methyl-4-(6-(phenylamino)imidazo[1,2-a]pyridin-3-yl)pyrimidin-2-yl)cyclohexane-1,4-diamine (31)

(1r,4r)-N$^1$-(4-(6-Bromoimidazo[1,2-a]pyridin-3-yl)-5-methylpyrimidin-2-yl)cyclohexane-1,4-diamine (200 mg, 0.50 mmol) and aniline (47 μL, 0.50 mmol) were reacted according to general synthetic procedure A. The product was further purified by preparative HPLC to give 31 as a yellow solid (45 mg, 22%). $^1$H-NMR (DMSO-d$_6$): δ 1.26 (apparent s, 4H), 1.88-1.92 (m, 4H), 2.31 (s, 3H), 2.80 (s, 1H), 3.60 (s, 1H), 6.69 (s, 1H), 6.84 (t, 1H, J=7.5 Hz), 7.08 (d, 2H, J=7.0 Hz), 7.24 (t, 2H, J=7.5 Hz), 7.35 (d, 1H, J=9.5 Hz), 7.70 (d, 1H, J=9.0 Hz), 8.16 (s, 1H), 8.21 (s, 1H), 8.44 (s, 1H), 9.57 (s, 1H). HRMS (ESI) m/z [M+H]$^+$ 414.2407.

(1r,4r)-N$^1$-(4-(6-((4-Fluorobenzyl)amino)imidazo[1,2-a]pyridin-3-yl)-5-methylpyrimidin-2-yl)cyclohexane-1,4-diamine (32)

3-(2-Chloro-5-methylpyrimidin-4-yl)-N-(4-fluorobenzyl)imidazo[1,2-a]pyridin-6-amine (0.25 g, 0.68 mmol) and (1r,4r)-cyclohexane-1,4-diamine (0.23 g, 2.04 mmol) were reacted according to general synthetic procedure A(ii) to give 32 as a beige solid (0.90 g, 30%). $^1$H-NMR (CDCl$_3$): δ 1.21 (s, 4H), 1.58 (s, 2H), 1.86 (s, 2H), 2.09 (s, 2H), 2.30 (s, 3H), 2.67 (s, 1H), 3.81 (s, 1H), 3.96 (s, 1H), 4.27 (s, 2H), 4.68 (s, 1H), 6.92 (s, 1H), 7.03 (s, 2H), 7.35 (s, 2H), 7.51 (s, 1H), 7.93 (s, 1H), 8.15 (s, 1H), 8.83 (s, 1H). HRMS (ESI) m/z [M+H]$^+$ 446.2469.

(1r,4r)-N$^1$-(5-Fluoro-4-(imidazo[1,2-a]pyridin-3-yl)pyrimidin-2-yl)-N4-(tetrahydro-2H-pyran-4-yl)cyclohexane-1,4-diamine (33)

To a solution (1r,4r)-N$^1$-(5-fluoro-4-(imidazo[1,2-a]pyridin-3-yl)pyrimidin-2-yl)cyclohexane-1,4-diamine (80.0 mg, 0.25 mmol) in THF (6 mL) and AcOH (0.2 mL) was added tetrahydro-4H-pyran-4-one (23 μL, 0.25 mmol), and the reaction mixture stirred for 30 min at rt. Sodium triacetoxyborohydride (62.4 mg, 0.29 mmol) was added and the reaction mixture stirred at room temperature overnight. Saturated NaHCO$_3$ (20 mL) and DCM (100 mL) were added. Organic phase was separated and the aqueous phase was extracted with DCM (2×100 mL). Organic extracts were combined and purified by flash column chromatography starting with 100% DCM ramping to 7% MeOH+1% NH$_3$ (32% in water) to afford 33 as a yellow solid (20.0 mg, 20%). $^1$H-NMR (CDCl$_3$): δ 1.26-1.33 (m, 2H), 1.70-1.85 (m, 4H), 1.97 (d, 2H, J=11.5 Hz), 2.19 (d, 2H, J=11.5 Hz), 2.29 (d, 2H, J=12.0 Hz), 3.05 (t, 1H, J=12.0 Hz), 3.22 (t, 1H, J=12.5 Hz), 3.38 (t, 2H, J=12.0 Hz), 3.80-3.82 (m, 1H), 4.01 (d, 2H, J=11.5 Hz), 5.07 (s, 1H), 7.11 (t, 1H, J=7.0 Hz), 7.41 (t, 1H, J=7.5 Hz), 7.76 (d, 1H, J=9.0 Hz), 8.16 (d, 1H, J=3.5 Hz), 8.46 (d, 1H, J=3.5 Hz), 9.98 (d, 1H, J=7.0 Hz). HRMS (ESI) m/z [M+H]$^+$ 411.2310.

(1r,4r)-N$^1$-(5-Methyl-4-(6-(pyridin-3-ylamino)imidazo[1,2-a]pyridin-3-yl)pyrimidin-2-yl)cyclohexane-1,4-diamine (34)

(1r,4r)-N$^1$-(4-(6-Bromoimidazo[1,2-a]pyridin-3-yl)-5-methylpyrimidin-2-yl)cyclohexane-1,4-diamine (225 mg, 0.56 mmol) and pyridin-3-amine (53 mg, 0.56 mmol) were reacted according to general synthetic procedure B. The product was further purified by preparative HPLC to give 34 as an orange solid (85 mg, 37%). H-NMR (MeOD-d$_4$): δ 1.37-1.42 (m, 4H), 1.99 (s, 2H), 2.10 (s, 2H), 2.38 (s, 3H), 3.08 (s, 1H), 3.72 (s, 1H), 7.32 (t, 1H, J=8.0 Hz), 7.43 (d, 1H, J=9.0 Hz), 7.56 (d, 1H, J=8.0 Hz), 7.68 (d, 1H, J=9.5 Hz), 8.05 (d, 1H, J=4.5 Hz), 8.12 (s, 1H), 8.22 (s, 1H), 8.35 (s, 1H), 8.51 (s, 1H), 9.70 (s, 1H). HRMS (ESI) m/z [M+H]$^+$ 415.2360.

(1r,4r)-N$^1$-(5-Chloro-4-(6-(pyridin-3-yl)imidazo[1,2-a]pyridin-3-yl)pyrimidin-2-yl)cyclohexane-1,4-diamine (35)

(1r,4r)-N$^1$-(4-(6-Bromoimidazo[1,2-a]pyridin-3-yl)-5-chloropyrimidin-2-yl)cyclohexane-1,4-diamine (150 mg, 0.36 mmol) and 3-(4,4,5,5-tetramethyl-1,3,2-dioxaborolan-2-yl)pyridine (74 mg, 0.36 mmol) were reacted according to general synthetic procedure C. The product was further purified by preparative HPLC to give 35 as a white solid (100 mg, 66%). $^1$H-NMR (DMSO-d$_6$): δ 0.46 (s, 2H), 1.21 (s, 2H), 1.44 (s, 2H), 1.83 (s, 2H), 2.31 (s, 1H), 3.51 (s, 1H), 7.47 (s, 1H), 7.54 (t, 1H, J=5.0 Hz), 7.84 (d, 1H, J=9.5 Hz), 7.91 (d, 1H, J=9.0 Hz), 8.18 (d, 1H, J=7.0 Hz), 8.43 (s, 1H), 8.61 (s, 1H), 8.64 (d, 1H, J=4.0 Hz), 8.98 (s, 1H), 9.88 (s, 1H) (two primary amine protons (NH$_2$) signals not observed). HRMS (ESI) m/z [M+H]$^+$ 420.1700.

(1r,4r)-N$^1$-(5-Chloro-4-(6-(pyridin-4-yl)imidazo[1,2-a]pyridin-3-yl)pyrimidin-2-yl)cyclohexane-1,4-diamine (36)

(1r,4r)-N$^1$-(4-(6-Bromoimidazo[1,2-a]pyridin-3-yl)-5-chloropyrimidin-2-yl)cyclohexane-1,4-diamine (150 mg, 0.36 mmol) and 4-(4,4,5,5-tetramethyl-1,3,2-dioxaborolan-2-yl)pyridine (74 mg, 0.36 mmol) were reacted according to general synthetic procedure C. The product was further purified by preparative HPLC to give 36 as a white solid (110 mg, 73%). $^1$H-NMR (DMSO-d$_6$): δ 0.49 (s, 1H), 1.25 (s, 3H), 1.49 (s, 2H), 1.88 (s, 2H), 2.35 (s, 1H), 3.43 (s, 1H), 7.51 (s, 1H), 7.82 (s, 2H), 7.89-7.94 (m, 2H), 8.45 (s, 1H), 8.61 (s, 1H), 8.71 (s, 2H), 9.88 (s, 1H) (two primary amine protons (NH$_2$) signals not observed). HRMS (ESI) m/z [M+H]$^+$ 420.1700.

(1r,4r)-N$^1$-(5-Methyl-4-(6-(pyridin-4-yl)imidazo[1,2-a]pyridin-3-yl)pyrimidin-2-yl)cyclohexane-1,4-diamine (37)

(1r,4r)-N$^1$-(4-(6-Bromoimidazo[1,2-a]pyridin-3-yl)-5-methylpyrimidin-2-yl)cyclohexane-1,4-diamine (158 mg, 0.39 mmol) and 4-(4,4,5,5-tetramethyl-1,3,2-dioxaborolan-2-yl)pyridine (121 mg, 0.59 mmol) were reacted according to general synthetic procedure C to give 37 as a yellow solid (74 mg, 48%). $^1$H-NMR (CDCl$_3$): δ 0.77 (s, 2H), 1.11-1.19 (m, 2H), 1.64 (s, 4H), 2.01 (d, 2H, J=11.5 Hz), 2.34 (s, 3H), 2.49-2.53 (m, 1H), 3.60-3.64 (m, 1H), 5.23 (d, 1H, J=8.0 Hz), 7.46 (d, 2H, J=4.5 Hz), 7.52 (d, 1H, J=9.0 Hz), 7.78 (d, 1H, J=9.0 Hz), 8.11 (s, 1H), 8.16 (s, 1H), 8.86 (d, 2H, J=4.5 Hz), 9.96 (s, 1H). HRMS (ESI) m/z [M+H]⁺ 400.2248.

(1r,4r)-N¹-(5-Chloro-4-(6-(pyrimidin-5-yl)imidazo[1,2-a]pyridin-3-yl)pyrimidin-2-yl) cyclohexane-1,4-diamine (38)

(1r,4r)-N¹-(4-(6-Bromoimidazo[1,2-a]pyridin-3-yl)-5-chloropyrimidin-2-yl)cyclohexane-1,4-diamine (220 mg, 0.52 mmol) and 5-(4,4,5,5-tetramethyl-1,3,2-dioxaborolan-2-yl)pyrimidine (110 mg, 0.53 mmol) were reacted according to general synthetic procedure C to give 38 as a yellow solid (110 mg, 50%). ¹H-NMR (DMSO-d₆): δ 1.20-1.26 (m, 4H), 1.43 (d, 2H, J=11.0 Hz), 1.81 (d, 2H, J=11.0 Hz), 2.35 (m, 1H), 3.65 (m, 1H), 7.49 (br s, 1H), 7.91 (d, 1H, J=9.0 Hz), 7.95 (d, 1H, J=9.0 Hz), 8.44 (s, 1H), 8.61 (s, 1H), 9.25 (s, 2H), 9.28 (s, 1H), 9.95 (s, 1H). HRMS (ESI) m/z [M+H]⁺421.1667.

(1r,4r)-N¹-(5-Methyl-4-(6-(pyrimidin-5-yl)imidazo[1,2-a]pyridin-3-yl)pyrimidin-2-yl) cyclohexane-1,4-diamine (39)

(1r,4r)-N¹-(4-(6-Bromoimidazo[1,2-a]pyridin-3-yl)-5-methylpyrimidin-2-yl)cyclohexane-1,4-diamine (210 mg, 0.52 mmol) and 5-(4,4,5,5-tetramethyl-1,3,2-dioxaborolan-2-yl)pyrimidine (110 mg, 0.53 mmol) were reacted according to general synthetic procedure C to give 39 as a yellow solid (120 mg, 58%). ¹H-NMR (DMSO-d₆): δ 1.22-1.28 (m, 4H), 1.55 (d, 2H, J=11.0 Hz), 1.88 (d, 2H, J=11.5 Hz), 2.35 (s, 3H), 2.97 (m, 1H), 3.58 (m, 1H), 7.02 (s, 1H), 7.88 (d, 1H, J=9.0 Hz), 7.93 (d, 1H, J=9.0 Hz), 8.28 (m, 2H), 9.25 (s, 2H), 9.26 (s, 1H), 9.98 (s, 1H). HRMS (ESI) m/z [M+H]⁺401.2203.

(1r,4r)-N¹-(5-Chloro-4-(6-(3-fluoropyridin-2-yl)imidazo[1,2-a]pyridin-3-yl)pyrimidin-2-yl)cyclohexane-1,4-diamine (40)

(1r,4r)-N¹-(4-(6-Bromoimidazo[1,2-a]pyridin-3-yl)-5-chloropyrimidin-2-yl)cyclohexane-1,4-diamine (162 mg, 0.39 mmol) and 3-fluoro-2-(4,4,5,5-tetramethyl-1,3,2-dioxaborolan-2-yl)pyridine (86 mg, 0.39 mmol) were reacted according to general synthetic procedure C. The product was further purified by preparative HPLC to give 40 as a white solid (60 mg, 35%). ¹H-NMR (DMSO-d₆): δ 0.95 (s, 2H), 1.35 (d, 2H, J=11.5 Hz), 1.73 (s, 2H), 2.04 (d, 2H, J=9.5 Hz), 2.78 (s, 1H), 3.74 (s, 1H), 7.21 (d, 1H, J=8.0 Hz), 7.57 (s, 1H), 7.91 (d, 1H, J=9.0 Hz), 8.06 (d, 1H, J=6.5 Hz), 8.13-8.17 (m, 2H), 8.40 (s, 1H), 8.50 (s, 1H), 10.14 (s, 1H) (two primary amine protons (NH₂) signals not observed). HRMS (ESI) m/z [M+H]⁺ 438.1610.

(1r,4r)-N¹-(5-Chloro-4-(6-((4-fluorobenzyl)amino)imidazo[1,2-a]pyridin-3-yl)pyrimidin-2-yl)cyclohexane-1,4-diamine (41)

3-(2,5-Dichloropyrimidin-4-yl)-N-(4-fluorobenzyl)imidazo[1,2-a]pyridin-6-amine (200 mg, 0.52 mmol) and (1r,4r)-cyclohexane-1,4-diamine (177 mg, 1.55 mmol) were reacted according to general synthetic procedure A(ii) to give 41 as a beige solid (140 mg, 58%). ¹H-NMR (DMSO-d₆): δ 1.11 (s, 2H), 1.35 (d, 2H, J=11.5 Hz), 1.56 (s, 2H), 1.79 (s, 2H), 1.94 (d, 2H, J=10.5 Hz), 3.35 (s, 1H), 3.75 (s, 1H), 4.36 (s, 2H), 6.30 (s, 1H), 7.16-7.22 (m, 4H), 7.46 (t, 2H, J=7.0 Hz), 7.57 (d, 1H, J=9.5 Hz), 8.37 (s, 2H), 8.85 (s, 1H). HRMS (ESI) m/z [M+H]⁺ 466.1920.

(1r,4r)-N¹-(5-chloro-4-(imidazo[1,2-a]pyridin-3-yl)pyrimidin-2-yl)cyclohexane-1,4-diamine (42)

3-(2,5-Dichloropyrimidin-4-yl)imidazo[1,2-a]pyridine (0.50 g, 1.90 mmol) and (1r,4r)-cyclohexane-1,4-diamine (0.65 g, 5.70 mmol) were reacted according to general synthetic procedure A(ii) to give 42 as a yellow solid (0.28 g, 43%). ¹H-NMR (CDCl₃): δ 1.25-1.30 (m, 4H), 1.80 (d, 2H, J 8.5), 2.08 (d, 2H, J=8.5 Hz), 2.62 (m, 1H), 3.67 (m, 1H), 5.05 (s, 1H), 7.56 (d, 1H, J=6.5 Hz), 7.91 (t, 1H, J=7.0 Hz), 8.34 (d, 1H, J=8.0 Hz), 8.81 (s, 1H), 9.06 (s, 1H), 9.96 (s, 1H). HRMS (ESI) m/z [M+H]⁺ 343.1453.

(1r,4r)-N¹-(4-(7-Chloroimidazo[1,2-a]pyridin-3-yl)-5-fluoropyrimidin-2-yl)cyclohexane-1,4-diamine (43)

7-Chloro-3-(2-chloro-5-fluoropyrimidin-4-yl)imidazo[1,2-a]pyridine (1.50 g, 5.32 mmol) and (1r,4r)-cyclohexane-1,4-diamine (1.82 g, 16.0 mmol) were reacted according to general synthetic procedure A(ii). The product was repurified by preparative HPLC to give 43 as a yellow powder (0.90 g, 47%). ¹H-NMR (DMSO-d₆): δ 1.32-1.48 (m, 4H), 1.99-2.07 (m, 4H), 2.95-2.98 (m, 1H), 3.63-3.67 (m, 1H), 7.25 (s, 1H), 7.45 (d, 1H, J=7.0), 8.03 (s, 1H), 8.38 (s, 1H), 8.44 (s, 1H), 10.10 (s, 1H) (two primary amine protons (NH₂) signals not observed). HRMS (ESI) m/z [M+H]⁺ 361.1342.

(1r,4r)-N¹-(5-Fluoro-4-(7-phenylimidazo[1,2-a]pyridin-3-yl)pyrimidin-2-yl)cyclohexane-1,4-diamine (44)

(1r,4r)-N¹-(4-(7-Chloroimidazo[1,2-a]pyridin-3-yl)-5-fluoropyrimidin-2-yl)cyclohexane-1,4-diamine (150 mg, 0.42 mmol) and 4,4,5,5-tetramethyl-2-phenyl-1,3,2-dioxaborolane (85.0 mg, 0.42 mmol) were reacted according to general synthetic procedure C. The product was further purified by preparative HPLC to give 44 as a yellow solid (50 mg, 30%). ¹H-NMR (DMSO-d₆): δ 1.37-1.44 (m, 4H), 2.02-2.09 (m, 4H), 2.99-3.04 (m, 1H), 3.767-3.70 (m, 1H), 7.44 (d, 1H, J=6.0 Hz), 7.50 (t, 1H, J=7.0 Hz), 7.57 (t, 2H, J=7.5 Hz), 7.95 (d, 2H, J=7.0 Hz), 8.16 (s, 1H), 8.40-8.41 (m, 3H) (two primary amine protons (NH₂) signals not observed). HRMS (ESI) m/z [M+H]⁺ 403.2046.

(1r,4r)-N¹-(5-Fluoro-4-(7-(pyridin-3-yl)imidazo[1,2-a]pyridin-3-yl)pyrimidin-2-yl)cyclohexane-1,4-diamine (45)

(1r,4r)-N¹-(4-(7-Chloroimidazo[1,2-a]pyridin-3-yl)-5-fluoropyrimidin-2-yl)cyclohexane-1,4-diamine (150 mg, 0.42 mmol) and 3-(4,4,5,5-tetramethyl-1,3,2-dioxaborolan-2-yl)pyridine (86.0 mg, 0.42 mmol) were reacted according to general synthetic procedure C. The product was further purified by preparative HPLC to give 45 as a yellow solid (100 mg, 59%). ¹H-NMR (DMSO-d₆): δ 1.36-1.55 (m, 6H), 2.01-2.09 (m, 4H), 2.98-3.00 (m, 1H), 3.65-3.68 (m, 1H), 7.45 (d, 1H, J=7.0 Hz), 7.59 (t, 2H, J=6.5 Hz), 8.31 (s, 1H), 8.37-8.44 (m, 4H), 8.69 (d, 1H, J=4.0 Hz), 9.17 (s, 1H). HRMS (ESI) m/z [M+H]⁺ 404.1997.

(1r,4r)-N¹-(5-Fluoro-4-(7-(pyridin-3-ylamino)imidazo[1,2-a]pyridin-3-yl)pyrimidin-2-yl)cyclohexane-1,4-diamine (46)

(1r,4r)-N¹-(4-(7-Chloroimidazo[1,2-a]pyridin-3-yl)-5-fluoropyrimidin-2-yl)cyclohexane-1,4-diamine (200 mg, 0.56 mmol) and pyridin-3-amine (53 mg, 0.56 mmol) were reacted according to general synthetic procedure B to give 46 as a yellow solid (75 mg, 54%). ¹H-NMR (CDCl₃): δ 1.326-1.35 (m, 4H), 1.94-1.96 (m, 2H), 2.19-2.21 (m, 2H), 2.77-2.79 (m, 1H), 3.68-3.71 (m, 1H), 5.00 (d, 1H, J=7.5 Hz), 6.70 (d, 1H, J=7.5 Hz), 7.03 (s, 1H), 7.19 (s, 1H), 7.27-7.28 (m, 1H), 7.62 (d, 1H, J=8.0 Hz), 8.11 (d, 1H, J=3.0 Hz), 8.32 (s, 2H), 8.51 (s, 1H), 9.83 (d, 1H, J=7.5 Hz) (two primary amine protons (NH₂) signals not observed). HRMS (ESI) m/z [M+H]⁺ 419.2105.

(1r,4r)-N¹-(5-Fluoro-4-(6-(4-(morpholinomethyl)phenyl)imidazo[1,2-a]pyridin-3-yl)pyrimidin-2-yl)cyclohexane-1,4-diamine (47)

(1r,4r)-N¹-(4-(6-Bromoimidazo[1,2-a]pyridin-3-yl)-5-fluoropyrimidin-2-yl)cyclohexane-1,4-diamine (100 mg, 0.25 mmol) and 4-(4-(4,4,5,5-tetramethyl-1,3,2-dioxaborolan-2-yl)benzyl)morpholine (76.0 mg, 0.25 mmol) were reacted according to general synthetic procedure C. The product was further purified by preparative HPLC to give 47 as a yellow solid (65.0 mg, 52%). ¹H-NMR (CDCl₃): δ 1.26-1.33 (m, 2H), 1.46-1.47 (m, 2H), 2.09-2.11 (m, 2H), 2.22 (d, 2H, J=10.0 Hz), 2.55-2.58 (m, 4H), 3.03-3.07 (m, 1H), 3.62-6.35 (m, 2H), 3.2-3.77 (m, 5H), 5.08-5.10 (m, 1H), 7.49 (d, 2H, J=7.0 Hz), 7.56 (d, 2H, J=7.0 Hz), 7.60 (d, 1H, J=9.0 Hz), 7.81 (d, 1H, J=9.0 Hz), 8.17 (s, 1H), 8.47 (s, 1H), 10.04 (s, 1H) (two primary amine protons (NH₂) signals not observed). HRMS (ESI) m/z [M+H]⁺ 502.2730.

4-(3-(2-(((1r,4r)-4-Aminocyclohexyl)amino)-5-fluoropyrimidin-4-yl)imidazo[1,2-a]pyridin-6-yl)-N,N-dimethylbenzenesulfonamide (48)

(1r,4r)-N¹-(4-(6-Bromoimidazo[1,2-a]pyridin-3-yl)-5-fluoropyrimidin-2-yl)cyclohexane-1,4-diamine (100 mg, 0.25 mmol) and N,N-dimethyl-4-(4,4,5,5-tetramethyl-1,3,2-dioxaborolan-2-yl)benzenesulfonamide (78.0 mg, 0.25 mmol) were reacted according to general synthetic procedure C. The product was repurified by preparative HPLC to give 48 as a yellow solid (60 mg, 47%). ¹H-NMR (DMSO-d₆): δ 1.34-1.37 (d, 4H, J=11.5 Hz), 1.86-1.89 (m, 2H), 1.98-2.01 (m, 2H), 2.71 (s, 7H), 3.66-3.68 (m, 1H), 7.34 (s, 1H), 7.91-7.97 (m, 4H), 8.08 (d, 2H, J=6.5 Hz), 8.38 (s, 1H), 8.47 (s, 1H), 10.19 (s, 1H) (two primary amine protons (NH₂) signals not observed). HRMS (ESI) m/z [M+H]⁺ 510.2085.

(1r,4r)-N¹-(5-Fluoro-4-(6-(pyridin-3-ylamino)imidazo[1,2-a]pyridin-3-yl)pyrimidin-2-yl)cyclohexane-1,4-diamine (49)

(1r,4r)-N¹-(4-(6-Bromoimidazo[1,2-a]pyridin-3-yl)-5-fluoropyrimidin-2-yl)cyclohexane-1,4-diamine (200 mg, 0.50 mmol) and pyridin-3-amine (46 mg, 0.50 mmol) were reacted according to general synthetic procedure B to give 49 as a yellow solid (60 mg, 29%). ¹H-NMR (MeOD-d₄): δ 1.38-1.45 (m, 4H), 2.07 (d, 2H, J=10.0 Hz), 2.19 (d, 2H, J=10.5 Hz), 3.11-3.16 (m, 1H), 3.67-3.72 (m. 1H), 7.35 (dd, 1H, J=7.5 & 4.5 Hz), 7.49 (d, 1H, J=9.5 Hz), 7.56 (d, 1H, J=7.0 Hz), 7.70 (d, 1H, J=9.5 Hz), 8.08 (d, 1H, J=4.0 Hz), 8.23 (d, 1H, J=3.0 Hz), 8.28 (d, 1H, J=3.5 Hz), 8.40 (s, 1H), 8.48 (s, 1H), 10.08 (s, 1H) (two primary amine protons (NH₂) and one secondary amine proton (NH) signals not observed). HRMS (ESI) m/z [M+H]⁺ 419.2105.

(1r,4r)-N¹-(5-Fluoro-4-(6-(pyrimidin-5-ylamino)imidazo[1,2-a]pyridin-3-yl)pyrimidin-2-yl)cyclohexane-1,4-diamine (50)

(1r,4r)-N¹-(4-(6-Bromoimidazo[1,2-a]pyridin-3-yl)-5-fluoropyrimidin-2-yl)cyclohexane-1,4-diamine (200 mg, 0.50 mmol) and pyrimidin-5-amine (47 mg, 0.50 mmol) were reacted according to general synthetic procedure B to give 50 as a yellow solid (65 mg, 31%). ¹H-NMR (DMSO-d₆): δ 1.24-1.30 (m, 4H), 1.86-1.96 (m, 4H), 2.85-2.88 (m, 1H), 3.54-3.60 (m, 1H), 7.26 (d, 1H, J=7.0 Hz), 7.53 (d, 1H, J=8.5 Hz), 7.81 (d, 1H, J=9.0 Hz), 8.30 (d, 1H, J=3.0 Hz), 8.41 (d, 1H, J=2.0 Hz), 8.50 (s, 1H), 8.57 (s, 2H), 8.65 (s, 1H), 9.08 (s, 1H) (two primary amine protons (NH₂) signals not observed). HRMS (ESI) m/z [M+H]⁺ 420.2060.

N-(3-(2-(((1r,4r)-4-Aminocyclohexyl)amino)-5-fluoropyrimidin-4-yl)imidazo[1,2-a]pyridin-6-yl)-4-fluorobenzamide (51)

N-(3-(2-Chloro-5-fluoropyrimidin-4-yl)imidazo[1,2-a]pyridin-6-yl)-4-fluorobenzamide (0.20 g, 0.52 mmol) and (1r,4r)-cyclohexane-1,4-diamine (0.18 g, 1.55 mmol) were reacted according to general synthetic procedure A(ii). The product was further purified by preparative HPLC to give 51 as a yellow solid (0.05 g, 21%). ¹H-NMR (DMSO-d₆): δ 1.19-1.29 (m, 4H), 1.73-1.74 (m, 2H), 2.01 (d, 2H, J=9.5 Hz), 3.90-3.92 (m, 1H), 7.15 (d, 1H, J=7.5 Hz), 7.42 (t, 2H, J=8.0 Hz), 7.77-7.85 (m, 2H), 8.17 (t, 2H, J=6.5 Hz), 8.32 (s, 1H), 8.42 (s, 1H), 10.60 (s, 1H). HRMS (ESI) m/z [M+H]⁺ 464.2010.

N-(3-(2-(((1r,4r)-4-Aminocyclohexyl)amino)-5-fluoropyrimidin-4-yl)imidazo[1,2-a]pyridin-6-yl)-2-phenylacetamide (52)

N-(3-(2-Chloro-5-fluoropyrimidin-4-yl)imidazo[1,2-a]pyridin-6-yl)-2-phenylacetamide (300 mg, 0.79 mmol) and (1r,4r)-cyclohexane-1,4-diamine (270 mg, 2.37 mmol) were reacted according to general synthetic procedure A(ii). The product was repurified by flash column chromatography to give 52 as a yellow solid (50.0 mg, 14%). ¹H-NMR (DMSO-d₆): δ 1.26-1.28 (m, 4H), 1.75-1.78 (m, 2H), 1.95-1.97 (m, 2H), 2.63-2.67 (m, 1H), 3.79 (s, 2H), 3.95-3.98 (m, 1H), 7.01 (s, 1H), 7.27 (t, 1H, J=6.5 Hz), 7.34-7.41 (m, 5H), 7.79 (d, 1H, J=9.5 Hz, 8.28 (d, 1H, J=3.5 Hz), 8.40 (d, 1H, J=3.0 Hz), 10.56 (s, 2H). HRMS (ESI) m/z [M+H]⁺ 460.2259.

(1r,4r)-N¹-(5-Methyl-4-(7-phenylimidazo[1,2-a]pyridin-3-yl)pyrimidin-2-yl)cyclohexane-1,4-diamine (53)

(1r,4r)-N¹-(4-(7-Chloroimidazo[1,2-a]pyridin-3-yl)-5-methylpyrimidin-2-yl)cyclohexane-1,4-diamine (150 mg, 0.42 mmol) and 4,4,5,5-tetramethyl-2-phenyl-1,3,2-dioxaborolane (83.0 mg, 0.42 mmol) were reacted according to general synthetic procedure C. The product was further purified by preparative HPLC to give 53 as a yellow solid (90 mg, 67%). ¹H-NMR (DMSO-d₆): δ 1.34-1.41 (m, 2H), 1.48 (s, 2H), 2.00-2.08 (m, 4H), 2.37 (s, 3H), 2.94-2.97 (m, 1H), 3.74-3.76 (m, 1H), 7.11 (d, 1H, J=7.5 Hz), 7.46-7.49

(m, 2H), 7.56 (t, 2H, J=7.5 Hz), 7.94 (d, 2H, J=7.0 Hz), 8.11 (s, 1H), 8.26 (s, 1H), 8.32 (s, 1H), 8.46 (s, 1H). HRMS (ESI) m/z [M+H]$^+$ 399.2298.

(1r,4r)-N$^1$-(5-Methyl-4-(7-(pyridin-3-yl)imidazo[1,2-a]pyridin-3-yl)pyrimidin-2-yl)cyclohexane-1,4-diamine (54)

(1r,4r)-N$^1$-(4-(7-Chloroimidazo[1,2-a]pyridin-3-yl)-5-methylpyrimidin-2-yl)cyclohexane-1,4-diamine (150 mg, 0.42 mmol) and 3-(4,4,5,5-tetramethyl-1,3,2-dioxaborolan-2-yl)pyridine (86.0 mg, 0.42 mmol) were reacted according to general synthetic procedure C. The product was further purified by preparative HPLC to give 54 as a yellow solid (65.0 mg, 39%). $^1$H-NMR (DMSO-d$_6$): δ 1.34-1.41 (m, 2H), 1.47 (s, 2H), 2.00-2.08 (m, 4H), 2.37 (s, 3H), 2.97 (br, 1H), 3.72 (br, 1H), 7.13 (d, 1H, J=7.5 Hz), 7.57-7.59 (m, 2H), 8.25 (s, 1H), 8.27 (s, 1H), 8.34-8.36 (m, 2H), 8.42 (s, 1H), 8.67 (d, 1H, J=4.0 Hz), 9.16 (s, 1H) (two primary amine protons (NH$_2$) signals not observed). HRMS (ESI) m/z [M+H]$^+$ 400.2250.

(1r,4r)-N$^1$-(5-Methyl-4-(7-(pyridin-3-ylamino)imidazo[1,2-a]pyridin-3-yl)pyrimidin-2-yl)cyclohexane-1,4-diamine (55)

(1r,4r)-N$^1$-(4-(7-Chloroimidazo[1,2-a]pyridin-3-yl)-5-methylpyrimidin-2-yl)cyclohexane-1,4-diamine (150 mg, 0.42 mmol) and pyridin-3-amine (40.0 mg, 0.42 mmol) were reacted according to general synthetic procedure B. The product was further purified by preparative HPLC to give 55 as a yellow solid (40.0 mg, 23%). $^1$H-NMR (MeOD-d$_4$): δ 1.44-1.57 (m, 4H), 2.11 (d, 2H, J=11.5 Hz), 2.23 (d, 2H, J=12.0 Hz), 2.39 (s, 3H), 3.05 (br, 1H), 3.80 (br, 1H), 6.91 (d, 1H, J=7.5 Hz), 7.15 (s, 1H), 7.48 (dd, 1H, J=7.5 & 5.0 Hz), 7.83 (d, 1H, J=7.5 Hz), 8.07 (s, 1H), 8.16 (s, 1H), 8.26 (d, 1H, J=4.5 Hz), 8.50 (s, 1H), 8.58 (s, 1H), 9.85 (d, 1H, J=6.0 Hz) (two primary amine protons (NH$_2$) and one secondary amine proton (NH) signals not observed). HRMS (ESI) m/z [M+H]$^+$ 415.2357.

(1r,4r)-N$^1$-(5-Methyl-4-(7-(pyrimidin-5-ylamino)imidazo[1,2-a]pyridin-3-yl)pyrimidin-2-yl)cyclohexane-1,4-diamine (56)

(1r,4r)-N$^1$-(4-(7-Chloroimidazo[1,2-a]pyridin-3-yl)-5-methylpyrimidin-2-yl)cyclohexane-1,4-diamine (200 mg, 0.56 mmol) and pyrimidin-5-amine (53.0 mg, 0.56 mmol) were reacted according to general synthetic procedure B. The product was further purified by preparative HPLC to give 56 as a yellow solid (80.0 mg, 34%). $^1$H-NMR (MeOD-d$_4$): δ 1.44-1.57 (m, 4H), 2.11 (d, 2H, J=11.5 Hz), 2.23 (d, 2H, J=12.0 Hz), 2.39 (s, 3H), 3.05 (br, 1H), 3.80 (br, 1H), 6.91 (d, 1H, J=7.5 Hz), 7.15 (s, 1H), 7.48 (dd, 1H, J=7.5 & 5.0 Hz), 7.83 (d, 1H, J=7.5 Hz), 8.07 (s, 1H), 8.16 (s, 1H), 8.26 (d, 1H, J=4.5 Hz), 8.50 (s, 1H), 8.58 (s, 1H), 9.85 (d, 1H, J=6.0 Hz) (two primary amine protons (NH$_2$) and one secondary amine proton (NH) signals not observed). HRMS (ESI) m/z [M+H]$^+$ 416.2310.

(1r,4r)-N$^1$-(4-(6-(3-Methoxyphenyl)imidazo[1,2-a]pyridin-3-yl)-5-methylpyrimidin-2-yl)cyclohexane-1,4-diamine (57)

(1r,4r)-N$^1$-(4-(6-Bromoimidazo[1,2-a]pyridin-3-yl)-5-methylpyrimidin-2-yl)cyclohexane-1,4-diamine (150 mg, 0.38 mmol) and (3-methoxyphenyl)boronic acid (57 mg, 0.38 mmol) were reacted according to general synthetic procedure C to give 57 as a brown solid (70 mg, 43%). $^1$H-NMR (CDCl$_3$): δ 0.73 (s, 2H), 1.10-1.16 (m, 2H), 1.64 (br, 2H), 1.89-2.04 (m, 4H), 2.36 (s, 3H), 2.47 (br, 1H), 3.62 (br, 1H), 3.82 (s, 3H), 5.14 (d, 1H, J=7.5 Hz), 6.91 (d, 1H, J=8.0 Hz), 7.07 (s, 1H), 7.16 (d, 1H, J=7.0 Hz), 7.36 (t, 1H, J=8.0 Hz), 7.53 (d, 1H, J=9.0 Hz), 7.74 (d, 1H, J=9.0 Hz), 8.12 (s, 1H), 8.15 (s, 1H), 9.97 (s, 1H). HRMS (ESI) m/z [M+H]$^+$ 429.2402

(1r,4r)-N$^1$-(4-(6-(6-Methoxypyridin-3-yl)imidazo[1,2-a]pyridin-3-yl)-5-methylpyrimidin-2-yl)cyclohexane-1,4-diamine (58)

(1r,4r)-N$^1$-(4-(6-Bromoimidazo[1,2-a]pyridin-3-yl)-5-methylpyrimidin-2-yl)cyclohexane-1,4-diamine (150 mg, 0.39 mmol) and (6-methoxypyridin-3-yl)boronic acid (91 mg, 0.59 mmol) were reacted according to general synthetic procedure C to give 58 as a yellow solid (135 mg, 81%). $^1$H-NMR (CDCl$_3$): δ 0.84 (s, 2H), 1.11-1.18 (m, 2H), 1.69 (d, 2H, J=10.0 Hz), 1.93 (br, 2H), 2.03 (d, 2H, J=11.5 Hz), 2.34 (s, 3H), 2.49-2.53 (m, 1H), 3.61-3.67 (m, 1H), 3.94 (s, 3H), 5.17 (d, 1H, J=7.5 Hz), 6.82 (d, 1H, J=8.5 Hz), 7.44 (d, 1H, J=9.0 Hz), 7.71-7.75 (m, 2H), 8.11 (s, 1H), 8.14 (s, 1H), 8.34 (s, 1H), 9.88 (s, 1H). HRMS (ESI) m/z [M+H]$^+$ 430.2355.

(1r,4r)-N$^1$-(4-(6-(3,5-Dimethylisoxazol-4-yl)imidazo[1,2-a]pyridin-3-yl)-5-methylpyrimidin-2-yl)cyclohexane-1,4-diamine (59)

(1r,4r)-N$^1$-(4-(6-Bromoimidazo[1,2-a]pyridin-3-yl)-5-methylpyrimidin-2-yl)cyclohexane-1,4-diamine (210 mg, 0.52 mmol) and 3,5-dimethyl-4-(4,4,5,5-tetramethyl-1,3,2-dioxaborolan-2-yl)isoxazole (116 mg, 0.52 mmol) were reacted according to general synthetic procedure C to give 59 as a pale yellow solid (92 mg, 42%). $^1$H-NMR (DMSO-d$_6$): δ 1.18-1.24 (m, 4H), 1.70 (d, 2H, J=11.0 Hz), 1.83 (d, 2H, J=11.0 Hz), 2.24 (s, 3H), 2.34 (s, 3H), 2.43 (s, 3H), 2.90 (m, 1H), 3.49 (m, 1H), 6.95 (s, 1H), 7.51 (d, 1H, J=9.0 Hz), 7.85 (d, 1H, J=9.0 Hz), 8.24 (s, 1H), 8.29 (s, 1H), 9.87 (s, 1H). HRMS (ESI) m/z [M+H]$^+$ 418.2357.

(1r,4r)-N$^1$-(5-Methyl-4-(6-(4-(morpholinomethyl)phenyl)imidazo[1,2-a]pyridin-3-yl)pyrimidin-2-yl)cyclohexane-1,4-diamine (60)

(1r,4r)-N$^1$-(4-(6-Bromoimidazo[1,2-a]pyridin-3-yl)-5-methylpyrimidin-2-yl)cyclohexane-1,4-diamine and (150 mg, 0.38 mmol) 4-(4-(4,4,5,5-tetramethyl-1,3,2-dioxaborolan-2-yl)benzyl)morpholine (114 mg, 0.38 mmol) were reacted according to general synthetic procedure C. The product was further purified by preparative HPLC to give 60 as a yellow solid (130 mg, 69%). $^1$H-NMR (CDCl$_3$): δ 1.19-1.30 (m, 4H), 1.93 (br, 2H), 2.05 (br, 2H), 2.31 (s, 3H), 2.72 (br, 4H), 2.97 (br, 1H), 3.74-3.81 (m, 7H), 5.81 (br, 1H), 7.44-7.51 (m, 4H), 7.54 (d, 1H, J=9.0 Hz), 7.78 (d, 1H, J=9.0 Hz), 8.06 (s, 1H), 8.18 (s, 1H), 9.61 (s, 1H) (two primary amine protons (NH$_2$) signals not observed). HRMS (ESI) m/z [M+H]$^+$ 498.2980.

(1r,4r)-N$^1$-(5-Methyl-4-(6-(6-morpholinopyridin-3-yl)imidazo[1,2-a]pyridin-3-yl)pyrimidin-2-yl)cyclohexane-1,4-diamine (61)

(1r,4r)-N$^1$-(4-(6-Bromoimidazo[1,2-a]pyridin-3-yl)-5-methylpyrimidin-2-yl)cyclohexane-1,4-diamine (150 mg, 0.38 mmol) and 4-(5-(4,4,5,5-tetramethyl-1,3,2-dioxaborolan-2-yl)pyridin-2-yl)morpholine (109 mg, 0.52 mmol) were reacted according to general synthetic procedure C to give 61 as a white solid (90 mg, 49%). $^1$H-NMR (DMSO-$d_6$): δ 0.66 (s, 2H), 1.22-1.27 (m, 4H), 1.57 (br, 2H), 1.90 (d, 2H, J=11.0 Hz), 2.14 (d, 2H, J=11.0 Hz), 2.35 (s, 3H), 3.49-3.59 (m, 5H), 3.72-3.74 (m, 4H), 6.92 (d, 1H, J=6.0 Hz), 6.99 (d, 1H, J=8.5 Hz), 7.72 (d, 1H, J=9.5 Hz), 7.83 (d, 1H, J=9.0 Hz), 7.93 (d, 1H, J=8.0 Hz), 8.25 (s, 2H), 8.51 (s, 1H), 9.98 (s, 1H). HRMS (ESI) m/z [M+H]$^+$ 485.2777.

4-(3-(2-(((1r,4r)-4-Aminocyclohexyl)amino)-5-methylpyrimidin-4-yl)imidazo[1,2-a]pyridin-6-yl)-N,N-dimethylbenzenesulfonamide (62)

(1r,4r)-N$^1$-(4-(6-Bromoimidazo[1,2-a]pyridin-3-yl)-5-methylpyrimidin-2-yl)cyclohexane-1,4-diamine (200 mg, 0.50 mmol) and N,N-dimethyl-4-(4,4,5,5-tetramethyl-1,3,2-dioxaborolan-2-yl)benzenesulfonamide (156 mg, 0.50 mmol) were reacted according to general synthetic procedure C to give 62 as a white solid (160 mg, 67%). $^1$H-NMR (CDCl$_3$): δ 0.86 (s, 2H), 1.19-1.26 (m, 2H), 1.23 (d, 2H, J=8.0 Hz), 2.07 (d, 2H, J=11.5 Hz), 2.40 (s, 3H), 2.58-2.62 (m, 1H), 2.79 (s, 6H), 3.67-3.72 (m, 1H), 4.85 (d, 1H, J=7.5 Hz), 7.58 (d, 1H, J=9.5 Hz), 7.76 (d, 2H, J=8.0 Hz), 7.84 (d, 1H, J=9.5 Hz), 7.91 (d, 2H, J=8.0 Hz), 8.15 (s, 1H), 8.24 (s, 1H), 9.92 (s, 1H). HRMS (ESI) m/z [M+H]$^+$ 506.2339.

(1r,4r)-N$^1$-(4-(6-(Furan-3-yl)imidazo[1,2-a]pyridin-3-yl)-5-methylpyrimidin-2-yl)cyclohexane-1,4-diamine (63)

(1r,4r)-N$^1$-(4-(6-Bromoimidazo[1,2-a]pyridin-3-yl)-5-methylpyrimidin-2-yl)cyclohexane-1,4-diamine (100 mg, 0.25 mmol) and 2-(furan-3-yl)-4,4,5,5-tetramethyl-1,3,2-dioxaborolane (28 mg, 0.25 mmol) were reacted according to general synthetic procedure C to give 63 as an orange solid (80 mg, 82%). $^1$H-NMR (CDCl$_3$): δ 1.03-1.05 (m, 2H), 1.21-1.28 (m, 2H), 1.43 (s, 2H), 1.80 (d, 2H, J=11.5 Hz), 2.13 (d, 2H, J=11.0 Hz), 2.37 (s, 3H), 2.61-2.65 (m, 1H), 3.75-3.78 (m, 1H), 4.99 (d, 1H, J=7.5 Hz), 6.67 (s, 1H), 7.44 (d, 1H, J=9.0 Hz), 7.52 (s, 1H), 7.70-7.72 (m, 2H), 8.08 (s, 1H), 8.20 (s, 1H), 9.76 (s, 1H). HRMS (ESI) m/z [M+H]$^+$ 389.2091.

(1r,4r)-N$^1$-(5-Methyl-4-(6-((5-methylpyridin-3-yl)amino)imidazo[1,2-a]pyridin-3-yl)pyrimidin-2-yl)cyclohexane-1,4-diamine (64)

(1r,4r)-N$^1$-(4-(6-Bromoimidazo[1,2-a]pyridin-3-yl)-5-methyl pyrimidin-2-yl)cyclohexane-1,4-diamine (200 mg, 0.50 mmol) and 5-methylpyridin-3-amine (54 mg, 0.50 mmol) were reacted according to general synthetic procedure B. The product was further purified by preparative HPLC to give 64 as an orange solid (65 mg, 30%). $^1$H-NMR (MeOD-$d_4$): δ 1.37-1.42 (m, 4H), 2.03 (br, 2H), 2.08 (br, 2H), 2.31 (s, 3H), 2.36 (s, 3H), 3.10 (br, 1H), 3.71 (br, 1H), 7.36 (s, 1H), 7.44 (d, 1H, J=9.0 Hz), 7.67 (d, 1H, J=9.5 Hz), 7.91 (s, 1H), 8.12 (s, 1H), 8.19 (s, 2H), 8.32 (s, 2H), 9.76 (s, 1H) (two primary amine protons (NH$_2$) signals not observed). HRMS (ESI) m/z [M+H]$^+$ 429.2511.

(1r,4r)-N$^1$-(5-Methyl-4-(6-((5-(trifluoromethyl)pyridin-3-yl)amino)imidazo[1,2-a]pyridin-3-yl)pyrimidin-2-yl)cyclohexane-1,4-diamine (65)

(1r,4r)-N$^1$-(4-(6-Bromoimidazo[1,2-a]pyridin-3-yl)-5-methylpyrimidin-2-yl)cyclohexane-1,4-diamine (200 mg, 0.50 mmol) and 5-(trifluoromethyl)pyridin-3-amine (81 mg, 0.50 mmol) were reacted according to general synthetic procedure B to give 65 as a yellow solid (70 mg, 29%). $^1$H-NMR (MeOD-$d_4$): δ 1.08-1.11 (m, 2H), 1.27-1.34 (m, 2H), 1.81-1.83 (m, 2H), 2.01 (d, 2H, J=11.0 Hz), 2.40 (s, 3H), 2.61-2.64 (m, 1H), 3.66-3.68 (m, 1H), 7.48 (d, 1H, J=9.0 Hz), 7.59 (s, 1H), 7.75 (d, 1H, J=9.5 Hz), 8.18-8.21 (m, 2H), 8.30 (s, 1H), 8.56 (s, 1H), 9.95 (s, 1H) (two primary amine protons (NH$_2$) and two secondary amine protons (NH) signals not observed). HRMS (ESI) m/z [M+H]$^+$ 483.2229.

(1r,4r)-N$^1$-(4-(6-((5-Fluoropyridin-3-yl)amino)imidazo[1,2-a]pyridin-3-yl)-5-methylpyrimidin-2-yl)cyclohexane-1,4-diamine (66)

(1r,4r)-N$^1$-(4-(6-Bromoimidazo[1,2-a]pyridin-3-yl)-5-methylpyrimidin-2-yl)cyclohexane-1,4-diamine (200 mg, 0.50 mmol) and 5-fluoropyridin-3-amine (56 mg, 0.50 mmol) were reacted according to general synthetic procedure B to give 66 as a yellow solid (80 mg, 37%). $^1$H-NMR (MeOD-$d_4$): δ 1.41-1.48 (m, 4H), 2.05-2.16 (m, 4H), 2.40 (s, 3H), 3.10-3.14 (m, 1H), 3.75-3.78 (m, 1H), 7.32 (d, 1H, J=10.5 Hz), 7.48 (d, 1H, J=9.0 Hz), 7.73 (d, 1H, J=9.5 Hz), 7.94 (s, 1H), 8.16 (s, 1H), 8.22 (s, 1H), 8.24 (s, 1H), 8.31 (s, 2H), 9.77 (s, 1H) (two primary amine protons (NH$_2$) signals not observed). HRMS (ESI) m/z [M+H]$^+$ 433.2268.

(1r,4r)-N$^1$-(4-(6-((6-Ethoxypyridin-3-yl)amino)imidazo[1,2-a]pyridin-3-yl)-5-methylpyrimidin-2-yl)cyclohexane-1,4-diamine (67)

(1r,4r)-N$^1$-(4-(6-Bromoimidazo[1,2-a]pyridin-3-yl)-5-methylpyrimidin-2-yl)cyclohexane-1,4-diamine (750 mg, 1.87 mmol) and 5-ethoxypyridin-3-amine (259 mg, 1.87 mmol) were reacted according to general synthetic procedure B to give 67 as a yellow solid (200 mg, 23%). $^1$H-NMR (MeOD-$d_4$): δ 1.24-1.33 (m, 4H), 1.40 (t, 3H, J=7.0 Hz), 1.91-1.93 (m, 2H), 2.03 (d, 2H, J=8.5 Hz), 2.37 (s, 3H, CH$_3$), 2.72-2.75 (m, 1H), 3.61-3.64 (m, 1H), 4.30 (q, 2H, J=7.0 Hz), 6.79 (d, 1H, J=9.0 Hz), 7.33 (d, 1H, J=9.0 Hz), 7.61 (d, 2H, J=9.0 Hz), 8.00 (s, 1H), 8.06 (s, 1H), 8.18 (s, 1H), 9.54 (s, 1H) (two primary amine protons (NH$_2$) signals not observed). HRMS (ESI) m/z [M+H]$^+$ 459.2620.

(1r,4r)-N$^1$-(4-(6-((6-(Difluoromethoxy)pyridin-3-yl)amino)imidazo[1,2-a]pyridin-3-yl)-5-methylpyrimidin-2-yl)cyclohexane-1,4-diamine (68)

(1r,4r)-N$^1$-(4-(6-Bromoimidazo[1,2-a]pyridin-3-yl)-5-methylpyrimidin-2-yl)cyclohexane-1,4-diamine (200 mg, 0.50 mmol) and 5-(difluoromethoxy)pyridin-3-amine (80 mg, 0.50 mmol) were reacted according to general synthetic procedure B to give 68 as a brown solid (80 mg, 33%). $^1$H-NMR (MeOD-$d_4$): δ 1.38-1.48 (m, 4H), 2.06-2.14 (m, 4H), 2.37 (s, 3H), 3.10-3.13 (m, 1H), 3.70-3.74 (m, 1H), 6.96 (d, 1H, J=8.5 Hz), 7.38 (d, 1H, J=8.5 Hz), 7.44 (t, 1H, J=74 Hz), 7.65 (d, 1H, J=8.5 Hz), 7.69 (dd, 1H, J=8.5 & 1.5 Hz), 8.09 (s, 2H), 8.21 (s, 1H), 8.50 (s, 1H), 9.62 (s, 1H) (two primary amine protons (NH$_2$) and one secondary amine proton (NH) signals not observed). HRMS (ESI) m/z [M+H]$^+$ 481.2275.

(1r,4r)-N$^1$-(5-Methyl-4-(6-((6-methylpyridin-3-yl)amino)imidazo[1,2-a]pyridin-3-yl)pyrimidin-2-yl)cyclohexane-1,4-diamine (69)

(1r,4r)—N$^1$-(4-(6-Bromoimidazo[1,2-a]pyridin-3-yl)-5-methylpyrimidin-2-yl)cyclohexane-1,4-diamine (200 mg, 0.50 mmol) and 6-methylpyridin-3-amine (54 mg, 0.50 mmol) were reacted according to general synthetic procedure B to give 69 as a brown solid (55 mg, 26%). $^1$H-NMR (MeOD-d$_4$): δ 1.37-1.41 (m, 4H), 2.03-2.08 (m, 4H), 2.36 (s, 3H), 2.49 (s, 3H), 3.08-3.11 (m, 1H), 3.68-3.71 (m, 1H), 7.22 (d, 1H, J=8.5 Hz), 7.42 (d, 1H, J=9.5 Hz), 7.54 (d, 1H, J=8.0 Hz), 7.66 (d, 1H, J=9.5 Hz), 8.11 (s, 1H), 8.20 (s, 1H), 8.25 (s, 1H), 8.30 (s, 2H), 9.69 (s, 1H) (two primary amine protons (NH$_2$) signals not observed). HRMS (ESI) m/z [M+H]$^+$ 429.2515.

(1r,4r)-N$^1$-(5-Methyl-4-(6-(pyrazin-2-ylamino)imidazo[1,2-a]pyridin-3-yl)pyrimidin-2-yl)cyclohexane-1,4-diamine (70)

(1r,4r)-N$^1$-(4-(6-Bromoimidazo[1,2-a]pyridin-3-yl)-5-methylpyrimidin-2-yl)cyclohexane-1,4-diamine (200 mg, 0.50 mmol) and pyrazin-2-amine (47 mg, 0.50 mmol) were reacted according to general synthetic procedure B to give 70 as a brown solid (60 mg, 29%). $^1$H-NMR (DMSO-d$_6$): δ 1.21 (br, 2H), 1.51 (br, 2H), 1.89 (br, 2H), 2.32 (br, 5H), 3.34 (br, 1H), 3.67 (br, 1H), 6.80 (s, 1H), 7.47 (br, 1H), 7.73 (d, 1H, J=9.5 Hz), 7.96 (s, 1H), 8.08 (s, 1H), 8.13 (s, 1H), 8.26 (s, 1H), 8.30 (s, 1H), 9.63 (s, 1H), 10.43 (s, 1H) (two primary amine protons (NH$_2$) signals not observed). HRMS (ESI) m/z [M+H]$^+$ 416.2310.

(1r,4r)-N$^1$-(5-Methyl-4-(6-(pyridazin-3-ylamino)imidazo[1,2-a]pyridin-3-yl)pyrimidin-2-yl)cyclohexane-1,4-diamine (71)

(1r,4r)-N$^1$-(4-(6-Bromoimidazo[1,2-a]pyridin-3-yl)-5-methylpyrimidin-2-yl)cyclohexane-1,4-diamine (200 mg, 0.50 mmol) and pyridazin-3-amine (47 mg, 0.50 mmol) were reacted according to general synthetic procedure B to give 71 as an orange solid (60 mg, 29%). $^1$H-NMR (CDCl$_3$): δ 1.18 (s, 2H), 1.39 (br, 2H), 1.83 (br, 4H), 2.10-2.12 (m, 2H), 2.36 (s, 3H), 2.68 (br, 1H), 3.80 (br, 1H), 6.01 (s, 1H), 6.99 (d, 1H, J=9.0 Hz), 7.20-7.26 (m, 2H), 7.57 (d, 1H, J=9.0 Hz), 8.16 (s, 2H), 8.38 (s, 1H), 8.66 (d, 1H, J=4.0 Hz), 11.6 (s, 1H). HRMS (ESI) m/z [M+H]$^+$ 416.2309.

N-(3-(2-(((1r,4r)-4-Aminocyclohexyl)amino)-5-methylpyrimidin-4-yl)imidazo[1,2-a]pyridin-6-yl)-4-fluorobenzamide (72)

N-(3-(2-Chloro-5-methylpyrimidin-4-yl)imidazo[1,2-a]pyridin-6-yl)-4-fluorobenzamide (0.20 g, 0.52 mmol) and (1r,4r)-cyclohexane-1,4-diamine (0.12 g, 1.05 mmol) were reacted according to general synthetic procedure A(ii). The product was further purified by preparative HPLC to give 72 as a yellow solid (0.06 g, 25%). $^1$H-NMR (DMSO-d$_6$): δ 1.32 (br, 4H), 1.86, 1.86 (br, 2H), 2.03 (br, 2H), 2.31 (s, 3H), 2.88 (br, 1H), 3.91 (s, 1H), 6.95 (s, 1H), 7.40 (t, 2H, J=8.5 Hz), 7.70 (d, 1H, J=9.0 Hz), 8.11-8.15 (m, 3H), 8.28 (s, 1H), 8.40 (s, 1H), 10.31 (s, 1H), 10.7 (s, 1H) (two primary amine protons (NH$_2$) signals not observed). HRMS (ESI) m/z [M+H]$^+$ 460.2257.

N-(3-(2-(((r,4r)-4-Aminocyclohexyl)amino)-5-methylpyrimidin-4-yl)imidazo[1,2-a]pyridin-6-yl)-2-phenylacetamide (73)

N-(3-(2-Chloro-5-methylpyrimidin-4-yl)imidazo[1,2-a]pyridin-6-yl)-2-phenylacetamide (0.20 g, 0.53 mmol) and (1r,4r)-cyclohexane-1,4-diamine (0.12 g, 1.05 mmol) were reacted according to general synthetic procedure A(ii) to give 73 as a yellow solid (0.70 g, 29%). $^1$H-NMR (MeOD-d$_4$): δ 1.35-1.50 (m, 4H), 2.00 (d, 2H, J=8.5 Hz), 2.25 (d, 2H, J=10.0 Hz), 2.51 (s, 3H), 2.79 (br, 1H), 3.93 (s, 2H), 4.03 (s, 1H), 7.45 (t, 1H, J=7.0 Hz), 7.51-7.57 (m, 4H), 7.62 (d, 1H, J=9.0 Hz), 7.82 (d, 1H, J=9.5 Hz), 8.26 (s, 1H), 8.35 (s, 1H), 10.59 (s, 1H) (two primary amine protons (NH$_2$) and two secondary amine protons (NH) signals not observed). HRMS (ESI) m/z [M+H]$^+$ 456.2508.

(1r,4r)-N$^1$-(5-Methyl-4-(6-(pyridin-3-yloxy)imidazo[1,2-a]pyridin-3-yl)pyrimidin-2-yl)cyclohexane-1,4-diamine (74)

3-(2-Chloro-5-methylpyrimidin-4-yl)-7-(pyridin-3-yloxy)imidazo[1,2-a]pyridine (110 mg, 0.33 mmol) and (1r,4r)-cyclohexane-1,4-diamine (114 mg, 1.00 mmol) were reacted according to synthetic procedure A(ii) to give 74 as a beige powder (80.0 mg, 58%). $^1$H-NMR (DMSO-d$_6$): δ 0.91 (s, 2H), 1.24-1.31 (m, 2H), 1.69 (br, 2H), 1.85-1.87 (m, 2H), 2.35 (s, 3H), 2.47 (br, 2H), 3.35 (br, 1H), 3.52 (br, 1H), 6.90 (s, 1H), 7.41-7.45 (m, 2H), 7.50 (d, 1H, J=7.5 Hz), 7.86 (d, 1H, J=9.0 Hz), 8.24 (s, 1H), 8.31 (s, 1H), 8.37 (d, 1H, J=3.0 Hz), 8.49 (s, 1H), 9.86 (s, 1H). HRMS (ESI) m/z [M+H]$^+$ 416.2197.

(1r,4r)-N$^1$-(5-Methyl-4-(6-(pyrimidin-5-yloxy)imidazo[1,2-a]pyridin-3-yl)pyrimidin-2-yl)cyclohexane-1,4-diamine (75).

3-(2-Chloro-5-methylpyrimidin-4-yl)-6-(pyrimidin-5-yloxy)imidazo[1,2-a]pyridine (200 mg, 0.60 mmol) and (1r,4r)-cyclohexane-1,4-diamine (137 mg, 1.20 mmol) were reacted according to general synthetic procedure A(ii) to give 75 as a white powder (80.0 mg, 32%). $^1$H-NMR (MeOD-d$_4$): δ 1.45 (q, 2H, J=12.5 Hz), 1.57 (q, 2H, J=12.0 Hz), 2.11 (d, 2H, J=11.0 Hz), 2.20 (d, 2H, J=11.5 Hz), 2.42 (s, 3H), 3.15 (t, 1H, J=12.0 Hz), 3.78 (t, 1H, J=11.0 Hz), 7.51 (d, 1H, J=9.5 Hz), 7.83 (d, 1H, J=9.5 Hz), 8.25 (s, 1H), 8.28 (s, 1H), 8.53 (s, 1H), 8.69 (s, 2H), 8.99 (s, 1H), 9.87 (s, 1H), (two primary amine protons (NH$_2$) signals not observed). HRMS (ESI) m/z [M+H]$^+$ 417.2148.

(R)—N-(5-Methyl-4-(6-(pyrimidin-5-ylamino)imidazo[1,2-a]pyridin-3-yl)pyrimidin-2-yl) quinuclidin-3-amine (76)

(R)—N-(4-(6-Bromoimidazo[1,2-a]pyridin-3-yl)-5-methylpyrimidin-2-yl) quinuclidin-3-amine (220 mg, 0.54 mmol) and pyrimidin-5-amine (51.0 mg, 0.54 mmol) were reacted according to general synthetic procedure B. The product was further purified by preparative HPLC to give 76 as a yellow solid (95.0 mg, 41%). $^1$H-NMR (MeOD-d$_4$): δ 1.44-1.47 (m, 1H), 1.79-1.81 (m, 1H), 1.91-1.93 (m, 1H), 2.23-2.27 (s, 1H), 2.43 (s, 3H), 2.54-2.57 (m, 1H), 3.21 (t, 1H, J=10.5 Hz), 3.37-3.46 (m, 2H), 3.71 (dd, 1H, J=14.5 & 2.5 Hz), 3.75-3.77 (m, 1H), 4.30-4.32 (m, 1H), 4.60 (d, 1H, J=14.5 Hz), 7.46 (t, 1H, J=9.0 Hz), 7.76 (t, 1H, J=9.0 Hz), 8.16 (s, 1H), 8.38 (s, 1H), 8.54 (s, 1H), 8.59 (s, 2H), 8.68 (s, 1H), 9.58 (s, 1H) (one secondary amine proton (NH) signal not observed). HRMS (ESI) m/z [M+H]$^+$ 428.2307.

(1r,4r)-N$^1$-(5-Chloro-4-(7-phenylimidazo[1,2-a]pyridin-3-yl)pyrimidin-2-yl)cyclohexane-1,4-diamine (77)

(1r,4r)-N$^1$-(4-(7-Bromoimidazo[1,2-a]pyridin-3-yl)-5-chloropyrimidin-2-yl)cyclohexane-1,4-diamine (150 mg, 0.36 mmol) and 4,4,5,5-tetramethyl-2-phenyl-1,3,2-dioxaborolane (73.0 mg, 0.36 mmol) were reacted according to general synthetic procedure C. The product was further purified by preparative HPLC to give 77 as a yellow solid (125 mg, 83%). $^1$H-NMR (DMSO-$d_6$): δ 1.38-1.53 (m, 4H), 2.00-2.06 (m, 4H), 2.93-2.96 (m, 1H), 3.68-3.71 (m, 1H), 7.49 (t, 1H, J=7.0 Hz), 7.57 (t, 2H, J=7.5 Hz), 7.63 (s, 1H), 7.95 (s, 2H), 8.15 (s, 1H), 8.43 (s, 1H), 8.48 (s, 1H), 8.77 (s, 1H), 9.99 (s, 1H) (two primary amine protons (NH$_2$) signals not observed). HRMS (ESI) m/z [M+H]$^+$ 419.1749.

(1r,4r)-N$^1$-(5-Chloro-4-(7-(pyridin-3-yl)imidazo[1,2-a]pyridin-3-yl)pyrimidin-2-yl)cyclohexane-1,4-diamine (78)

(1r,4r)-N$^1$-(4-(7-Bromoimidazo[1,2-a]pyridin-3-yl)-5-chloropyrimidin-2-yl)cyclohexane-1,4-diamine (150 mg, 0.36 mmol) and 3-(4,4,5,5-tetramethyl-1,3,2-dioxaborolan-2-yl)pyridine (73.0 mg, 0.36 mmol) were reacted according to general synthetic procedure C to give 78 as a yellow solid (135 mg, 89%). $^1$H-NMR (DMSO-$d_6$): δ 1.17-1.23 (m, 2H), 1.34-1.38 (m, 2H), 1.82-1.85 (m, 2H), 1.97-1.99 (m, 2H), 2.52-2.55 (m, 1H), 3.65-3.68 (m, 1H), 7.53-7.58 (m, 3H), 8.26 (s, 1H), 8.35 (d, 1H, J=4.5 Hz), 8.42 (s, 1H), 8.68 (s, 1H), 8.77 (s, 1H), 9.16 (s, 1H), 9.99 (s, 1H) (two primary amine protons (NH$_2$) signals not observed). HRMS (ESI) m/z [M+H]$^+$ 420.1703.

(1r,4r)-N$^1$-(5-Chloro-4-(6-phenylimidazo[1,2-a]pyridin-3-yl)pyrimidin-2-yl)cyclohexane-1,4-diamine (79) and (1r,4r)-N$^1$-(5-Phenyl-4-(6-phenylimidazo[1,2-a]pyridin-3-yl)pyrimidin-2-yl)cyclohexane-1,4-diamine (80)

(1r,4r)-N$^1$-(4-(6-Bromoimidazo[1,2-a]pyridin-3-yl)-5-chloropyrimidin-2-yl)cyclohexane-1,4-diamine (150 mg, 0.36 mmol) and 4,4,5,5-tetramethyl-2-phenyl-1,3,2-dioxaborolane (99.0 mg, 0.48 mmol) were reacted according to general synthetic procedure C. The products were further purified by preparative HPLC to give: 79 as a white solid (90 mg, 60%). $^1$H-NMR (CDCl$_3$): δ 1.19-1.23 (m, 4H), 1.93-1.95 (m, 2H), 2.12-2.14 (m, 2H), 2.89-2.91 (m, 1H), 3.72-3.76 (m, 1H), 5.18 (s, 1H), 7.42 (t, 1H, J=7.0 Hz), 7.48 (t, 2H, J=7.5 Hz), 7.56 (d, 2H, J=7.5 Hz), 7.60 (d, 1H, J=9.0 Hz), 7.83 (d, 1H, J=9.0 Hz), 8.31 (s, 1H), 8.36 (s, 1H), 9.73 (s, 1H) (two primary amine protons (NH$_2$) signals not observed). HRMS (ESI) m/z [M+H]$^+$ 419.1752. 80 as a white solid (25 mg, 15%). $^1$H-NMR (CDCl$_3$): δ 1.22-1.24 (m, 4H), 1.98-2.01 (m, 2H), 2.14-2.16 (m, 2H), 2.92-2.94 (m, 1H), 3.81-3.83 (m, 1H), 5.40 (s, 1H), 7.13 (s, 1H), 7.23 (d, 1H, J=6.0 Hz), 7.33-7.38 (m, 4H), 7.43-7.50 (m, 5H), 7.67 (d, 1H, J=9.0 Hz), 8.22 (s, 1H), 8.44 (s, 1H), 9.54 (s, 1H) (two primary amine protons (NH$_2$) signals not observed). HRMS (ESI) m/z [M+H]$^+$ 461.2454.

(1r,4r)-N$^1$-(5-Chloro-4-(6-(6-methoxypyridin-3-yl)imidazo[1,2-a]pyridin-3-yl)pyrimidin-2-yl)cyclohexane-1,4-diamine (81)

(1r,4r)-N$^1$-(4-(6-Bromoimidazo[1,2-a]pyridin-3-yl)-5-chloropyrimidin-2-yl)cyclohexane-1,4-diamine (150 mg, 0.36 mmol) and 2-methoxy-5-(4,4,5,5-tetramethyl-1,3,2-dioxaborolan-2-yl)pyridine (55.0 mg, 0.36 mmol) were reacted according to general synthetic procedure C. The product was further purified by preparative HPLC to give 81 as a white solid (50 mg, 31%). $^1$H-NMR (DMSO-$d_6$): δ 0.80-0.82 (m, 1H), 1.22-1.32 (m, 3H), 1.61-1.63 (s, 1H), 1.89-1.92 (m, 3H), 2.79-2.81 (m, 1H), 3.90-3.92 (m, 4H), 6.95 (d, 1H, J=8.5 Hz), 7.81 (d, 1H, J=9.0 Hz), 7.87 (d, 1H, J=9.0 Hz), 8.10 (d, 1H, J=7.0 Hz), 8.40 (s, 1H), 8.45 (s, 1H), 8.52 (s, 1H), 8.57 (s, 1H), 9.69 (s, 1H) (two primary amine protons (NH$_2$) signals not observed). HRMS (ESI) m/z [M+H]$^+$ 450.1809.

(1r,4r)-N$^1$-(5-Chloro-4-(6-(4-methoxyphenyl)imidazo[1,2-a]pyridin-3-yl)pyrimidin-2-yl)cyclohexane-1,4-diamine (82)

(1r,4r)-N$^1$-(4-(6-Bromoimidazo[1,2-a]pyridin-3-yl)-5-chloropyrimidin-2-yl)cyclohexane-1,4-diamine (220 mg, 0.52 mmol) and 2-(4-methoxyphenyl)-4,4,5,5-tetramethyl-1,3,2-dioxaborolane (122 mg, 0.52 mmol) were reacted according to general synthetic procedure C to give 82 as a yellow solid (80 mg, 34%). $^1$H-NMR (CDCl$_3$): δ 1.21-1.27 (m, 4H), 1.95 (d, 2H, J=10.5 Hz), 2.14 (d, 2H, J=11.0 Hz), 2.86 (s, 1H), 3.75 (s, 1H), 3.86 (s, 3H), 5.08 (s, 1H), 7.03 (d, 2H, J=7.5 Hz), 7.49 (d, 2H, J=7.5 Hz), 7.56 (d, 1H, J=9.0 Hz), 7.79 (d, 1H, J=9.0 Hz), 8.31 (s, 1H), 8.39 (s, 1H, J=4.0 Hz), 9.71 (s, 1H). HRMS (ESI) m/z [M+H]$^+$ 449.1859.

(1r,4r)-N$^1$-(5-Chloro-4-(6-(3,5-dimethylisoxazol-4-yl)imidazo[1,2-a]pyridin-3-yl)pyrimidin-2-yl)cyclohexane-1,4-diamine (83)

(1r,4r)-N$^1$-(4-(6-Bromoimidazo[1,2-a]pyridin-3-yl)-5-chloropyrimidin-2-yl)cyclohexane-1,4-diamine (220 mg, 0.52 mmol) and 3,5-dimethyl-4-(4,4,5,5-tetramethyl-1,3,2-dioxaborolan-2-yl)isoxazole (116 mg, 0.52 mmol) were reacted according to general synthetic procedure C to give 83 as a pale yellow solid (85 mg, 37%). $^1$H-NMR (DMSO-$d_6$): δ 1.22-1.28 (m, 4H), 1.61 (d, 2H, J=10.5 Hz), 1.84 (d, 2H, J=11.0 Hz), 2.26 (s, 3H), 2.45 (s, 3H), 2.65 (m, 1H), 3.65 (m, 1H), 7.52 (br s, 1H), 7.58 (d, 1H, J=9.0 Hz), 7.90 (d, 1H, J=9.0 Hz), 8.43 (s, 1H), 8.73 (s, 1H), 9.85 (s, 1H). HRMS (ESI) m/z [M+H]$^+$ 438.1831.

(1r,4r)-N$^1$-(5-Chloro-4-(6-(6-(piperazin-1-yl)pyridin-3-yl)imidazo[1,2-a]pyridin-3-yl)pyrimidin-2-yl)cyclohexane-1,4-diamine (84)

(1r,4r)-N$^1$-(4-(6-Bromoimidazo[1,2-a]pyridin-3-yl)-5-chloropyrimidin-2-yl)cyclohexane-1,4-diamine (150 mg, 0.36 mmol) and tert-butyl 4-(5-(4,4,5,5-tetramethyl-1,3,2-dioxaborolan-2-yl)pyridin-2-yl)piperazine-1-carboxylate (140.0 mg, 0.36 mmol) were reacted according to general synthetic procedure C to give tert-butyl 4-(5-(3-(2-(((1r,4r)-4-aminocyclohexyl)amino)-5-chloropyrimidin-4-yl)imidazo[1,2-a]pyridin-6-yl)pyridin-2-yl)piperazine-1-carboxylate (130 mg). The latter was heated at reflux in 3M HCl (4 mL) and MeOH (4 mL) for 6 h, basified with 2M NaOH, and extracted with DCM (3×100 mL). Organic extracts were combined, concentrated under reduced pressure and purified by preparative HPLC to give 84 as a yellow solid (60 mg, 33%). $^1$H-NMR (DMSO-$d_6$): δ 0.98-102 (m, 1H), 1.35-1.37 (m, 2H), 1.74-1.76 (m, 1H), 1.90-1.96 (m, 3H), 2.81-2.92 (m, 5H), 3.59-3.66 (m, 5H), 6.96 (d, 1H, J=8.5 Hz), 7.80-7.86 (m, 2H), 7.95 (d, 1H, J=8.5 Hz), 8.38 (s, 2H), 8.47 (s, 1H), 8.54 (s, 1H), 9.63 (s, 1H) (two primary amine protons (NH$_2$) and one secondary amine proton (NH) signals not observed). HRMS (ESI) m/z [M+H]$^+$ 504.2387.

(1r,4r)-N$^1$-(5-Chloro-4-(8-phenyl-6-(trifluoromethyl)imidazo[1,2-a]pyridin-3-yl)pyrimidin-2-yl)cyclohexane-1,4-diamine (85)

(1r,4r)-N$^1$-(4-(8-Bromo-6-(trifluoromethyl)imidazo[1,2-a]pyridin-3-yl)-5-chloropyrimidin-2-yl)cyclohexane-1,4-diamine (150 mg, 0.31 mmol) and 4,4,5,5-tetramethyl-2-phenyl-1,3,2-dioxaborolane (63.0 mg, 0.31 mmol) were reacted according to general synthetic procedure C. The product was further purified by preparative HPLC to give 85 as a yellow solid (60 mg, 40%). $^1$H-NMR (DMSO-$d_6$): δ 1.32-1.43 (m, 4H), 1.96-2.02 (m, 4H), 2.89-2.91 (m, 1H), 3.65-3.68 (m, 1H), 7.52 (d, 1H, J=7.5 Hz), 7.57 (t, 2H, J=7.0 Hz), 7.66 (d, 1H, J=7.5 Hz), 7.89 (s, 1H), 8.13 (d, 2H, J=7.0 Hz), 8.44 (s, 1H), 8.51 (s, 1H), 9.96 (s, 1H) (two primary amine protons (NH$_2$) signals not observed). HRMS (ESI) m/z [M+H]$^+$ 487.1623.

(1r,4r)-N$^1$-(5-Chloro-4-(8-(pyridin-3-yl)-6-(trifluoromethyl)imidazo[1,2-a]pyridin-3-yl)pyrimidin-2-yl)cyclohexane-1,4-diamine (86)

(1r,4r)-N$^1$-(4-(8-Bromo-6-(trifluoromethyl)imidazo[1,2-a]pyridin-3-yl)-5-chloropyrimidin-2-yl)cyclohexane-1,4-diamine (128 mg, 0.26 mmol) and 3-(4,4,5,5-tetramethyl-1,3,2-dioxaborolan-2-yl)pyridine (51.0 mg, 0.25 mmol) were reacted according to general synthetic procedure C to give 86 as a yellow solid (71 mg, 56%). $^1$H-NMR (DMSO-$d_6$): δ 1.06-1.08 (m, 2H), 1.38 (q, 2H, J=12.0 Hz), 1.48 (s, 2H), 1.79 (d, 2H, J=10.5 Hz), 1.93 (d, 2H, J=10.5 Hz), 2.53-2.55 (m, 1H), 3.65-3.68 (m, 1H), 7.60-7.62 (m, 2H), 8.07 (s, 1H), 8.50 (s, 1H), 8.54 (d, 2H, J=8.0 Hz), 8.71-8.72 (m, 1H), 9.30 (s, 1H), 10.09 (s, 1H). HRMS (ESI) m/z [M+H]$^+$ 488.1577.

N-(3-(2-(((1r,4r)-4-Aminocyclohexyl)amino)-5-chloropyrimidin-4-yl)imidazo[1,2-a]pyridin-6-yl)benzamide (87)

N-(3-(2,5-Dichloropyrimidin-4-yl)imidazo[1,2-a]pyridin-6-yl)benzamide (220 mg, 0.57 mmol) and (1r,4r)-cyclohexane-1,4-diamine (196 mg, 1.72 mmol) were reacted according to general synthetic procedure A(ii) to give 87 as a beige solid (90.0 mg, 34%). $^1$H-NMR (DMSO-$d_6$): δ 0.93-1.02 (m, 4H), 1.24-1.26 (m, 2H), 1.56 (s, 2H), 1.95 (d, 2H, J=11.0 Hz), 2.32-2.35 (m, 1H), 3.87-3.90 (m, 1H), 7.41 (s, 1H), 7.59 (t, 2H, J=7.5 Hz), 7.65 (t, 1H, J=7.0 Hz), 7.70 (s, 1H), 7.83 (d, 1H, J=9.0 Hz), 8.05 (d, 2H, J=7.5 Hz), 8.43 (s, 1H), 8.60 (s, 1H), 10.51 (s, 2H). HRMS (ESI) m/z [M+H]$^+$ 462.1810.

(1r,4r)-N$^1$-(5-Chloro-4-(6-(pyrimidin-5-ylamino)imidazo[1,2-a]pyridin-3-yl)pyrimidin-2-yl)cyclohexane-1,4-diamine (88)

(1r,4r)-N$^1$-(4-(6-Bromoimidazo[1,2-a]pyridin-3-yl)-5-chloropyrimidin-2-yl)cyclohexane-1,4-diamine (200 mg, 0.48 mmol) and pyrimidin-5-amine (45.0 mg, 0.48 mmol) were reacted according to general synthetic procedure B to give 88 as a yellow solid (90.0 mg, 43%). $^1$H-NMR (DMSO-$d_6$): δ 1.25-1.36 (m, 4H), 1.74 (d, 2H, J=16.5 Hz), 1.96-1.98 (m, 2H), 2.77-2.79 (m, 1H), 3.50-3.52 (m, 1H), 7.45-7.48 (m, 2H), 7.79 (d, 1H, J=8.0 Hz), 8.43 (s, 1H), 8.46 (s, 1H), 8.60 (s, 2H), 8.65 (s, 1H), 8.99 (s, 1H), 9.74 (s, 1H) (two primary amine protons (NH$_2$) signals not observed). HRMS (ESI) m/z [M+H]$^+$ 436.1763.

(1r,4r)-N$^1$-(5-Methoxy-4-(6-phenylimidazo[1,2-a]pyridin-3-yl)pyrimidin-2-yl)cyclohexane-1,4-diamine (89)

(1r,4r)-N$^1$-(4-(6-Bromoimidazo[1,2-a]pyridin-3-yl)-5-methoxypyrimidin-2-yl)cyclohexane-1,4-diamine (100 mg, 0.24 mmol) and 4,4,5,5-tetramethyl-2-phenyl-1,3,2-dioxaborolane (50 mg, 0.24 mmol) were reacted according to general synthetic procedure C. The product was further purified by preparative HPLC to give 89 as a yellow powder (50 mg, 50%). $^1$H-NMR (DMSO-$d_6$): δ 1.12-1.15 (m, 2H), 1.32 (q, 2H, J=12.0 Hz), 1.84 (d, 2H, J=11.5 Hz), 1.99 (d, 2H, J=11.5 Hz), 2.79-2.82 (m, 1H), 3.62-3.64 (m, 1H), 3.94 (s, 3H), 6.81 (d, 1H, J=7.5 Hz), 7.48 (t, 1H, J=7.0 Hz), 7.56 (t, 2H, J=7.0 Hz), 7.77 (d, 2H, J=7.5 Hz), 7.80 (d, 1H, J=9.5 Hz), 7.87 (d, 1H, J=9.0 Hz), 8.31 (s, 1H), 8.51 (s, 1H), 10.15 (s, 1H) (two primary amine protons (NH$_2$) signals not observed). HRMS (ESI) m/z [M+H]$^+$ 415.2246.

(1r,4r)-N$^1$-(5-Methyl-4-(6-phenylimidazo[1,2-a]pyridin-3-yl)pyrimidin-2-yl)-N4-(1-methylpiperidin-4-yl)cyclohexane-1,4-diamine (90)

To a solution of (1r,4r)-N$^1$-(5-methyl-4-(6-phenylimidazo[1,2-a]pyridin-3-yl)pyrimidin-2-yl)cyclohexane-1,4-diamine (200 mg, 0.50 mmol) in THF (6 mL) and AcOH (0.2 mL) was added 1-methylpiperidin-4-one (62 μL, 0.50 mmol), and the reaction mixture stirred for 30 min at rt. Sodium triacetoxyborohydride (212 mg, 1.00 mmol) was added and the reaction mixture stirred at room temperature overnight. Saturated NaHCO$_3$ (20 mL) and DCM (100 mL) were added. Organic phase was separated and the aqueous phase was extracted with DCM (2×100 mL). Organic extracts were combined and purified by flash column chromatography starting with 100% DCM ramping to 7% MeOH+1% NH$_3$ (32% in water) to afford 90 as a white solid (90.0 mg, 36%). $^1$H-NMR (CDCl$_3$): δ 0.68-0.72 (m, 2H), 1.12 (q, 2H, J=11.5 Hz), 1.30 (q, 2H, J=10.5 Hz), 1.76 (t, 4H, J=12.5 Hz), 1.92 (t, 2H, J=11.0 Hz), 2.04 (d, 2H, J=10.5 Hz), 2.22 (s, 3H), 2.36-2.41 (m, 5H), 2.78 (d, 2H, J=11.0 Hz), 3.62-3.64 (m, 1H), 5.07 (d, 1H, J=7.5 Hz), 7.36 (t, 1H, J=7.0 Hz), 7.44 (t, 2H, J=7.5 Hz), 7.52-7.55 (m, 3H), 7.74 (d, 1H, J=9.0 Hz), 8.11 (s, 1H), 8.16 (s, 1H), 9.89 (s, 1H) (one secondary amine proton (NH) signal not observed). HRMS (ESI) m/z [M+H]$^+$ calcd. for C$_{30}$H$_{38}$N7$^+$, 496.3187.

(1s,4s)-N$^1$-(5-Methyl-4-(6-phenylimidazo[1,2-a]pyridin-3-yl)pyrimidin-2-yl)cyclohexane-1,4-diamine (91)

(1s,4s)-N$^1$-(4-(6-Bromoimidazo[1,2-a]pyridin-3-yl)-5-methylpyrimidin-2-yl)cyclohexane-1,4-diamine (100 mg, 0.25 mmol) and 4,4,5,5-tetramethyl-2-phenyl-1,3,2-dioxaborolane (51.0 mg, 0.25 mmol) were reacted according to general synthetic procedure C. The product was further purified by preparative HPLC to give 91 as a yellow solid (70.0 mg, 70%). $^1$H-NMR (MeOD-$d_4$): δ 1.69-1.72 (m, 6H), 1.89-1.92 (m, 2H), 2.45 (s, 3H), 3.12 (br, 1H), 4.05 (br, 1H), 7.46 (t, 1H, J=7.0 Hz), 7.54 (t, 2H, J=7.0 Hz), 7.68 (d, 2H, J=7.5 Hz), 7.80 (s, 2H), 8.24, (s, 1H), 8.29 (s, 1H), 10.05 (s, 1H) (two primary amine protons (NH$_2$) and one secondary amine proton (NH) signals not observed). HRMS (ESI) m/z [M+H]$^+$ 399.2297.

(1s,4s)-N$^1$-(5-Methyl-4-(6-(pyridin-3-ylamino)imidazo[1,2-a]pyridin-3-yl)pyrimidin-2-yl)cyclohexane-1,4-diamine (92)

(1s,4s)-N$^1$-(4-(6-Bromoimidazo[1,2-a]pyridin-3-yl)-5-methylpyrimidin-2-yl)cyclohexane-1,4-diamine (200 mg, 0.50 mmol) and pyridin-3-amine (47.0 mg, 0.50 mmol) were reacted according to general synthetic procedure B. The product was further purified by preparative HPLC to give 92 as a yellow solid (40 mg, 20%). $^1$H-NMR (D$_2$O-$d_2$): δ 1.35

(br, 2H), 1.48-1.58 (m, 6H), 1.90 (s, 3H), 3.16 (br, 1H), 3.32 (br, 1H), 6.97 (d, 1H, J=9.5 Hz), 7.15 (t, 1H, J=8.0 Hz), 7.19 (d, 1H, J=7.5 Hz), 7.25 (d, 1H, J=9.5 Hz), 7.69 (s, 1H), 7.71 (s, 1H), 7.92 (d, 1H, J=4.0 Hz), 8.01 (s, 1H), 8.42 (s, 1H), 9.16 (s, 1H) (two primary amine protons (NH$_2$) and one secondary amine proton (NH) signals not observed). HRMS (ESI) m/z [M+H]$^+$ 415.2356.

(1s,4s)-N$^1$-(5-Methyl-4-(6-(pyrimidin-5-ylamino)imidazo[1,2-a]pyridin-3-yl)pyrimidin-2-yl)cyclohexane-1,4-diamine (93)

(1s,4s)-N$^1$-(4-(6-Bromoimidazo[1,2-a]pyridin-3-yl)-5-methylpyrimidin-2-yl)cyclohexane-1,4-diamine (200 mg, 0.50 mmol) and pyrimidin-5-amine (48.0 mg, 0.50 mmol) were reacted according to general synthetic procedure B. The product was further purified by preparative HPLC to 93 as a yellow solid (60 mg, 29%). $^1$H-NMR (MeOD-d$_4$): δ 1.40-1.44 (m, 2H), 1.54-1.59 (m, 4H), 1.73-1.77 (m, 2H), 2.83 (br, 1H), 3.42 (s, 3H), 3.92 (br, 1H), 5.42 (d, 1H, J=7.5 Hz), 7.21 (d, 1H, J=9.5 Hz), 7.32 (s, 1H), 7.63 (d, 1H, J=9.5 Hz), 8.07 (s, 1H), 8.14 (s, 1H), 8.45 (s, 2H), 8.67 (s, 1H), 9.75 (s, 1H) (two primary amine protons (NH$_2$) signals not observed). HRMS (ESI) m/z [M+H]$^+$ calcd. for C$_{22}$H$_{26}$N9$^+$, 416.23010.

N$^1$-(5-Methyl-4-(6-phenylimidazo[1,2-a]pyridin-3-yl)pyrimidin-2-yl)cyclohexane-1,3-diamine (94)

N$^1$-(4-(6-Bromoimidazo[1,2-a]pyridin-3-yl)-5-methylpyrimidin-2-yl)cyclohexane-1,3-diamine (100 mg, 0.25 mmol) and 4,4,5,5-tetramethyl-2-phenyl-1,3,2-dioxaborolane (51.0 mg, 0.25 mmol) were reacted according to general synthetic procedure C. The product was further purified by preparative HPLC to give 94 as a yellow sticky liquid (40.0 mg, 40%). $^1$H-NMR (MeOD-d$_4$): δ 0.99 (s, 1H), 1.22-1.29 (m, 3H), 1.69-1.75 (m, 2H), 2.04 (d, 1H, J=11.5 Hz), 2.39-2.42 (s, 4H), 2.55 (br, 1H), 3.76 (br, 1H), 7.47 (t, 1H, J=7.0 Hz), 7.55 (t, 2H, J=7.0 Hz), 7.68 (d, 2H, J=7.5 Hz), 7.77 (s, 2H), 8.21, (s, 1H), 8.25 (s, 1H), 10.03 (s, 1H) (two primary amine protons (NH$_2$) and one secondary amine proton (NH) signals not observed). HRMS (ESI) m/z [M+H]$^+$ calcd. for C$_{24}$H$_{27}$N6$^+$, 399.2297.

N$^1$-(5-Methyl-4-(6-(pyridin-3-ylamino)imidazo[1,2-a]pyridin-3-yl)pyrimidin-2-yl)cyclohexane-1,3-diamine (95)

N$^1$-(4-(6-Bromoimidazo[1,2-a]pyridin-3-yl)-5-methylpyrimidin-2-yl)cyclohexane-1,3-diamine (150 mg, 0.38 mmol) and pyridin-3-amine (36.0 mg, 0.38 mmol) were reacted according to general synthetic procedure B. The product was further purified by preparative HPLC to give 95 as a yellow solid (45 mg, 29%). $^1$H-NMR (MeOD-d$_4$): δ 1.26-1.36 (m, 4H), 1.84 (s, 1H), 1.93 (s, 1H), 2.01 (s, 1H), 2.42 (s, 4H), 2.97 (br, 1H), 3.78 (br, 1H), 7.34 (t, 1H, J=6.5 Hz), 7.47 (d, 1H, J=9.5 Hz), 7.55 (d, 1H, J=8.0 Hz), 7.73 (d, 1H, J=9.0 Hz), 8.07 (d, 1H, J=3.5 Hz), 8.18, (s, 1H), 8.25 (s, 1H), 8.35 (s, 1H), 8.46 (s, 1H), 9.87 (s, 1H) (two primary amine protons (NH$_2$) and one secondary amine proton (NH) signals not observed). HRMS (ESI) m/z [M+H]$^+$ 415.2355.

N$^1$-(5-Methyl-4-(6-(pyrimidin-5-ylamino)imidazo[1,2-a]pyridin-3-yl)pyrimidin-2-yl)cyclohexane-1,3-diamine (96)

N$^1$-(4-(6-Bromoimidazo[1,2-a]pyridin-3-yl)-5-methylpyrimidin-2-yl)cyclohexane-1,3-diamine (150 mg, 0.38 mmol) and pyrimidin-5-amine (36.0 mg, 0.38 mmol) were reacted according to general synthetic procedure B. The product was further purified by preparative HPLC to give 96 as a yellow solid (60 mg, 38%). $^1$H-NMR (MeOD-d$_4$): δ 1.26-1.42 (m, 4H), 1.87 (s, 1H), 2.01-2.04 (m, 2H), 2.34 (s, 3H), 2.43 (d, 1H, J=10.5 Hz), 3.11 (br, 1H), 3.77-3.82 (m, 1H), 7.43 (d, 1H, J=9.5 Hz), 7.68 (d, 1H, J=9.5 Hz), 8.12 (s, 1H), 8.17 (s, 1H), 8.52 (s, 1H), 8.58 (s, 2H), 8.64 (s, 1H), 9.83 (s, 1H) (two primary amine protons (NH$_2$) and one secondary amine proton (NH) signals not observed). HRMS (ESI) m/z [M+H]$^+$ 416.2310.

N$^1$,N$^1$-Dimethyl-N$^4$-(5-methyl-4-(6-phenylimidazo[1,2-$^a$]pyridin-3-yl)pyrimidin-2-yl)cyclohexane-1,4-diamine (97)

N$^1$-(4-(6-Bromoimidazo[1,2-a]pyridin-3-yl)-5-methylpyrimidin-2-yl)-N$^4$,N$^4$-dimethylcyclohexane-1,4-diamine (100 mg, 0.23 mmol) and 4,4,5,5-tetramethyl-2-phenyl-1,3,2-dioxaborolane (47.0 mg, 0.23 mmol) were reacted according to general synthetic procedure C. The product was further purified by preparative HPLC to give 97 as a yellow sticky liquid (70.0 mg, 71%). $^1$H-NMR (CDCl$_3$): δ 0.99-1.01 (m, 2H), 1.27 (q, 2H, J=12.5 Hz), 1.80-1.82 (m, 2H), 2.21 (d, 2H, J=10.5 Hz), 2.42 (s, 9H), 2.91-2.93 (m, 1H), 3.68-3.70 (m, 1H), 5.42 (s, 1H), 7.43 (t, 1H, J=7.0 Hz), 7.50 (t, 2H, J=7.0 Hz), 7.59-7.63 (m, 3H), 7.83 (d, 1H, J=9.0 Hz), 8.16 (s, 1H), 8.19 (s, 1H), 9.88 (s, 1H). HRMS (ESI) m/z [M+H]$^+$ 427.2609.

N$^1$,N$^1$-Dimethyl-N$^4$-(5-Methyl-4-(6-(pyridin-3-ylamino)imidazo[1,2-a]pyridin-3-yl)pyrimidin-2-yl)cyclohexane-1,4-diamine (98)

N$^1$-(4-(6-Bromoimidazo[1,2-a]pyridin-3-yl)-5-methylpyrimidin-2-yl)-N$^4$,N$^4$-dimethylcyclohexane-1,4-diamine (200 mg, 0.47 mmol) and pyridin-3-amine (44.0 mg, 0.47 mmol) were reacted according to general synthetic procedure B to give 98 as an orange solid (100 mg, 48%). $^1$H-NMR (CDCl$_3$): δ 1.21-1.329 (m, 4H), 2.14-2.21 (m, 10H), 2.38 (s, 3H), 3.68-3.70 (m, 1H), 4.90 (d, 1H, J=8.0 Hz), 5.78 (d, 1H, J=4.5 Hz), 7.18 (t, 1H, J=7.5 Hz), 7.21-7.24 (m, 2H), 7.70 (d, 1H, J=9.0 Hz), 8.13 (s, 1H), 8.17 (d, 1H, J=4.0 Hz), 8.19 (s, 1H), 8.44 (s, 1H), 9.78 (s, 1H) (one carbon proton (CH) signal not observed). HRMS (ESI) m/z [M+H]$^+$ 443.2230.

N$^1$,N$^1$-Dimethyl-N$^4$-(5-Methyl-4-(6-(pyrimidin-5-ylamino)imidazo[1,2-a]pyridin-3-yl)pyrimidin-2-yl)cyclohexane-1,4-diamine (99)

N$^1$-(4-(6-Bromoimidazo[1,2-a]pyridin-3-yl)-5-methylpyrimidin-2-yl)-N$^4$,N$^4$-dimethylcyclohexane-1,4-diamine (200 mg, 0.47 mmol) and pyrimidin-5-amine (45.0 mg, 0.47 mmol) were reacted according to general synthetic procedure B to give 99 as an orange solid (100 mg, 48%). $^1$H-NMR (DMSO-d$_6$): δ 1.06-1.19 (m, 2H), 1.54-1.56 (m, 2H), 1.92-2.00 (m, 10H), 2.34 (s, 3H), 3.51-3.53 (m, 1H), 4.12-4.13 (m, 1H), 6.89 (s, 1H), 7.41 (d, 1H, J=9.0 Hz), 7.76 (d, 1H, J=9.5 Hz), 8.20 (s, 1H), 8.24 (s, 1H), 8.54 (s, 2H), 8.61 (s, 1H), 8.64 (s, 1H), 9.80 (s, 1H). HRMS (ESI) m/z [M+H]$^+$ 444.2623.

(1 s,3R,5S,7r)-3,5-Dimethyl-7-((5-methyl-4-(6-phenylimidazo[1,2-a]pyridin-3-yl)pyrimidin-2-yl)amino)adamantan-1-ol (100)

(1 s,3r,5R,7S)-3-((4-(6-Bromoimidazo[1,2-a]pyridin-3-yl)-5-methylpyrimidin-2-yl)amino)adamantan-1-ol (100 mg, 0.22 mmol) and 4,4,5,5-tetramethyl-2-phenyl-1,3,2-dioxaborolane (45.0 mg, 0.22 mmol) were reacted according to general synthetic procedure C. The product was further purified by preparative HPLC to give 100 as a yellow solid (80.0 mg, 76%). $^1$H-NMR (DMSO-d$_6$): δ 1.13-1.16 (m, 2H), 1.34 (br, 4H), 1.76-1.83 (m, 4H), 1.83 (br, 2H), 1.98 (br, 1H), 2.00 (br, 1H), 2.33 (s, 3H), 4.34 (s, 1H), 6.63 (s, 1H), 7.42 (t, 1H, J=7.0 Hz), 7.50 (t, 2H, J=7.0 Hz), 7.72 (d, 2H, J=7.5 Hz), 7.77 (d, 1H, J=9.0 Hz), 7.84 (d, 1H, J=9.0 Hz), 8.17, (s, 1H), 8.29 (s, 1H), 9.54 (s, 1H). HRMS (ESI) m/z [M+H]$^+$ 480.2763.

(1 s,3R,5S,7r)-3,5-Dimethyl-7-((5-methyl-4-(6-(pyridin-3-ylamino)imidazo[1,2-a]pyridin-3-yl)pyrimidin-2-yl)amino)adamantan-1-ol (101)

(1 s,3r,5R,7S)-3-((4-(6-Bromoimidazo[1,2-a]pyridin-3-yl)-5-methylpyrimidin-2-yl)amino)adamantan-1-ol (160 mg, 0.35 mmol) and pyridin-3-amine (33.0 mg, 0.35 mmol) were reacted according to general synthetic procedure B to give 101 as a yellow solid (60.0 mg, 35%). $^1$H-NMR (DMSO-d$_6$): δ 1.38-1.52 (m, 6H), 1.88-2.02 (m, 9H), 2.31 (s, 3H), 4.57 (s, 1H), 6.32 (s, 1H), 7.25 (t, 1H, J=7.5 Hz), 7.37 (d, 1H, J=9.5 Hz), 7.46 (d, 1H, J=7.5 Hz), 7.72 (d, 1H, J=9.5 Hz), 8.11 (s, 1H), 8.24 (s, 1H), 8.37 (s, 2H), 9.45 (s, 1H). HRMS (ESI) m/z [M+H]$^+$496.2822.

(1 s,3R,5S,7r)-3,5-Dimethyl-7-((5-methyl-4-(6-(pyrimidin-5-ylamino)imidazo[1,2-a]pyridin-3-yl)pyrimidin-2-yl)amino)adamantan-1-ol (102)

(1 s,3r,5R,7S)-3-((4-(6-Bromoimidazo[1,2-a]pyridin-3-yl)-5-methylpyrimidin-2-yl)amino)adamantan-1-ol (160 mg, 0.35 mmol) and pyrimidin-5-amine (35.0 mg, 0.35 mmol) were reacted according to general synthetic procedure B to give 102 as a yellow solid (80.0 mg, 46%). $^1$H-NMR (DMSO-d$_6$): δ 1.38-1.52 (m, 6H), 1.86-2.01 (m, 9H), 2.32 (s, 3H), 4.56 (s, 1H), 6.37 (s, 1H), 7.42 (d, 1H, J=9.5 Hz), 7.75 (d, 1H, J=9.5 Hz), 8.14 (s, 1H), 8.25 (s, 1H), 8.56 (s, 3H), 8.66 (s, 1H), 9.50 (s, 1H). HRMS (ESI) m/z [M+H]$^+$ 497.2777.

3-(5-Methyl-2-((tetrahydro-2H-pyran-4-yl)amino)pyrimidin-4-yl)-N-(pyridin-3-yl)imidazo[1,2-a]pyridin-6-amine (103)

4-(6-Bromoimidazo[1,2-a]pyridin-3-yl)-5-methyl-N-(tetrahydro-2H-pyran-4-yl)pyrimidin-2-amine (194 mg, 0.50 mmol) and pyridin-3-amine (47.2 mg, 0.50 mmol) were reacted according to general synthetic procedure B. The product was further purified by preparative HPLC to give 103 as a yellow sticky liquid (70 mg, 35%). $^1$H-NMR (CDCl$_3$): δ 1.64-1.70 (m, 2H), 1.93 (d, 2H, J=11.0 Hz), 2.39 (s, 3H), 3.39 (br, 2H), 3.92-3.94 (m, 3H), 6.07 (s, 1H), 7.23-7.30 (m, 3H), 7.77 (d, 1H, J=9.5 Hz), 8.16-8.17 (m, 3H), 8.25 (s, 1H), 8.46 (s, 1H), 9.82 (s, 1H). HRMS (ESI) m/z [M+H]$^+$ 402.2042.

3-(5-Methyl-2-((tetrahydro-2H-pyran-4-yl)amino)pyrimidin-4-yl)-N-(pyrimidin-5-yl)imidazo[1,2-a]pyridin-6-amine (104)

4-(6-Bromoimidazo[1,2-a]pyridin-3-yl)-5-methyl-N-(tetrahydro-2H-pyran-4-yl)pyrimidin-2-amine (180 mg, 0.46 mmol) and pyrimidin-5-amine (45.0 mg, 0.46 mmol) were reacted according to general synthetic procedure B. The product was further purified by preparative HPLC to give 104 as a yellow sticky liquid (30 mg, 16%). H-NMR (CDCl$_3$): δ 1.70-1.72 (m, 2H), 1.92 (d, 2H, J=11.0 Hz), 2.35 (s, 3H), 3.42 (br, 2H), 3.89-3.96 (m, 3H), 6.60 (s, 1H), 7.25 (br, 1H), 7.74 (d, 1H, J=9.5 Hz), 8.14 (s, 1H), 8.15 (s, 1H), 8.24 (s, 1H), 8.54 (s, 2H), 8.76 (s, 1H), 9.81 (s, 1H). HRMS (ESI) m/z [M+H]$^+$ calcd. for C$_{21}$H$_{23}$N$_8$O$^+$, 403.1991.

(1r,4r)-4-((5-Methyl-4-(6-phenylimidazo[1,2-a]pyridin-3-yl)pyrimidin-2-yl)amino)cyclohexan-1-ol (105)

(1r,4r)-4-((4-(6-Bromoimidazo[1,2-a]pyridin-3-yl)-5-methylpyrimidin-2-yl)amino)cyclohexan-1-ol (100 mg, 0.25 mmol) and 4,4,5,5-tetramethyl-2-phenyl-1,3,2-dioxaborolane (51.0 mg, 0.25 mmol) were reacted according to general synthetic procedure C to give 105 as a white solid (70.0 mg, 70%). $^1$H-NMR (CDCl$_3$): δ 1.19-1.25 (m, 4H), 1.80 (d, 2H, J=10.0 Hz), 2.10 (d, 2H, J=11.5 Hz), 2.41 (s, 3H), 3.49-3.52 (m, 2H), 3.71-3.73 (m, 1H), 4.89 (d, 1H, J=7.0 Hz), 7.42 (t, 1H, J=7.0 Hz), 7.50 (t, 2H, J=7.0 Hz), 7.56-7.60 (m, 3H), 7.79 (d, 1H, J=9.5 Hz), 8.15 (s, 1H), 8.20 (s, 1H), 9.95 (s, 1H). HRMS (ESI) m/z [M+H]$^+$ 400.2137.

(1r,4r)-4-((5-Methyl-4-(6-(pyridin-3-ylamino)imidazo[1,2-a]pyridin-3-yl)pyrimidin-2-yl)amino)cyclohexan-1-ol (106) and (1r,4r)-4-((4-(Imidazo[1,2-a]pyridin-3-yl)-5-methylpyrimidin-2-yl)amino)cyclohexan-1-ol (107)

(1r,4r)-4-((4-(6-Bromoimidazo[1,2-a]pyridin-3-yl)-5-methylpyrimidin-2-yl)amino)cyclohexan-1-ol (200 mg, 0.50 mmol) and pyridin-3-amine (47.0 mg, 0.50 mmol) were reacted according to general synthetic procedure B to give: 106 as a yellow solid (40 mg, 19%). $^1$H-NMR (MeOD-d$_4$): δ 1.4-1.29 (m, 4H), 1.89-1.91 (m, 2H), 1.98-2.00 (m, 2H), 2.39 (s, 3H), 3.61-3.65 (m, 3H), 7.22 (s, 1H), 7.30-7.32 (m, 2H), 7.79 (d, 1H, J=9.5 Hz), 8.09 (s, 2H), 8.20 (s, 1H), 8.25 (s, 1H), 8.44 (s, 1H), 9.90 (s, 1H) (one secondary amine proton (NH) signal not observed). HRMS (ESI) m/z [M+H]$^+$ 416.2198.107 as a white solid (40 mg, 28%). $^1$H-NMR (DMSO-d$_6$): δ 1.25-1.35 (m, 4H), 1.89 (d, 2H, J=10.5 Hz), 1.97 (d, 2H, J=10.0 Hz), 2.34 (s, 3H), 3.43-3.45 (m, 1H), 3.68-3.69 (m, 1H), 4.58 (s, 1H), 6.99 (d, 1H, J=8.0 Hz), 7.09 (t, 1H, J=7.0 Hz), 7.49 (t, 1H, J=7.5 Hz), 7.77 (d, 1H, J=9.0 Hz), 8.24 (s, 1H), 8.25 (s, 1H), 9.90 (s, 1H). HRMS (ESI) m/z [M+H]$^+$ 324.1826.

(1r,4r)-4-((5-Methyl-4-(6-(pyrimidin-5-ylamino)imidazo[1,2-a]pyridin-3-yl)pyrimidin-2-yl)amino)cyclohexan-1-ol (108)

(1r,4r)-4-((4-(6-Bromoimidazo[1,2-a]pyridin-3-yl)-5-methylpyrimidin-2-yl)amino)cyclohexan-1-ol (200 mg, 0.50 mmol) and pyrimidin-5-amine (48.0 mg, 0.50 mmol) were reacted according to general synthetic procedure B to give 108 as an orange solid (35 mg, 17%). $^1$H-NMR (MeOD-d$_4$): δ 1.28-1.33 (m, 4H), 1.87-1.90 (m, 2H), 1.98-2.00 (m, 2H), 2.38 (s, 3H), 3.38 (s, 1H), 3.51-3.56 (m, 1H), 3.65-3.67 (m, 1H), 7.47 (d, 1H, J=9.5 Hz), 7.72 (d, 1H, J=9.5 Hz), 8.17 (s, 1H), 8.18 (s, 1H), 8.58 (s, 2H), 8.63 (s, 1H), 9.91 (s, 1H) (two secondary amine proton (NH) signals not observed). HRMS (ESI) m/z [M+H]$^+$ 417.2149.

N$^1$-Methyl-N$^4$-(5-Methyl-4-(6-(pyrimidin-5-ylamino)imidazo[1,2-a]pyridin-3-yl)pyrimidin-2-yl)cyclohexane-1,4-diamine (109)

N$^1$-(4-(6-Bromoimidazo[1,2-a]pyridin-3-yl)-5-methylpyrimidin-2-yl)-N$^4$-methylcyclohexane-1,4-diamine (100 mg, 0.24 mmol) and pyrimidin-5-amine (23.0 mg, 0.24 mmol) were reacted according to general synthetic procedure B. The product was further purified by preparative HPLC to give 109 as a yellow solid (60 mg, 58%). $^1$H-NMR (MeOD-d$_4$): δ 1.39-1.46 (m, 2H), 1.65-1.67 (m, 1H), 1.78-1.82 (m, 1H), 1.88 (br s, 1H), 1.97-1.99 (m, 2H), 2.15 (br s, 2H), 2.35-2.37 (m, 3H), 3.05-3.09 (m, 1H), 3.72-3.74 (m, 1H), 3.93-3.95 (m, 1H), 7.42 (d, 1H, J=9.5 Hz), 7.69 (t, 1H, J=9.0 Hz), 8.11-8.21 (m, 2H), 8.55-8.64 (m, 3H), 9.83 (s, 1H) (three secondary amine proton (NH) signals not observed). HRMS (ESI) m/z [M+H]$^+$ 430.2468.

(1s,3r,5R,7S)-3-((5-Fluoro-4-(6-phenylimidazo[1,2-a]pyridin-3-yl)pyrimidin-2-yl)amino)-5,7-dimethyl-adamantan-1-ol (110)

(1 s,3r,5R,7S)-3-((4-(6-Bromoimidazo[1,2-a]pyridin-3-yl)-5-fluoropyrimidin-2-yl)amino)adamantan-1-ol (80 mg, 0.18 mmol) and 4,4,5,5-tetramethyl-2-phenyl-1,3,2-dioxaborolane (36.0 mg, 0.18 mmol) were reacted according to general synthetic procedure C to give 110 as a yellow solid (80.0 mg, 92%). $^1$H-NMR (DMSO-d$_6$): δ 1.21-1.23 (m, 2H), 1.38-1.40 (m, 4H), 1.82-1.92 (m, 6H), 2.01-2.04 (m, 2H), 3.18-3.19 (m, 1H), 4.40 (s, 1H), 6.94 (s, 1H), 7.45 (t, 1H, J=7.0 Hz), 7.53 (t, 2H, J=7.0 Hz), 7.58 (d, 2H, J=7.0 Hz), 7.83 (d, 1H, J=9.0 Hz), 7.90 (d, 1H, J=9.0 Hz), 8.30 (s, 1H), 8.45 (s, 1H), 9.90 (s, 1H). HRMS (ESI) m/z [M+H]$^+$ 484.2513.

(1 s,3r,5R,7S)-3-((5-Fluoro-4-(6-(pyrimidin-5-ylamino)imidazo[1,2-a]pyridin-3-yl)pyrimidin-2-yl)amino)-5,7-dimethyladamantan-1-ol (111)

(1 s,3r,5R,7S)-3-((4-(6-Bromoimidazo[1,2-a]pyridin-3-yl)-5-fluoropyrimidin-2-yl)amino)adamantan-1-ol (120 mg, 0.26 mmol) and pyrimidin-5-amine (25.0 mg, 0.26 mmol) were reacted according to general synthetic procedure B to give 111 as a yellow solid (60.0 mg, 46%). $^1$H-NMR (DMSO-d$_6$): δ 1.42-1.56 (m, 6H), 1.91-2.07 (m, 8H), 3.17-3.19 (m, 3H), 4.10-4.11 (m, 1H), 4.55 (s, 1H), 6.53 (s, 1H), 7.50 (d, 1H, J=9.0 Hz), 7.80 (d, 1H, J=9.5 Hz), 8.27 (d, 1H, J=4.0 Hz), 8.41 (d, 1H, J=3.0 Hz), 8.59 (s, 2H), 8.60 (s, 1H), 8.68 (s, 1H), 9.91 (s, 1H). HRMS (ESI) m/z [M+H]$^+$ 501.2526.

N$^1$-(5-Methyl-4-(6-(pyrimidin-5-ylamino)imidazo[1,2-a]pyridin-3-yl)pyrimidin-2-yl)-N$^4$-(2,2,2-trifluoroethyl)cyclohexane-1,4-diamine (112)

N$^1$-(4-(6-Bromoimidazo[1,2-a]pyridin-3-yl)-5-methylpyrimidin-2-yl)-N$^4$-(2,2,2-trifluoroethyl)cyclohexane-1,4-diamine (100 mg, 0.21 mmol) and pyrimidin-5-amine (20.0 mg, 0.21 mmol) were reacted according to general synthetic procedure B. The product was further purified by preparative HPLC to give 112 as a yellow solid (20 mg, 19%). $^1$H-NMR (MeOD-d$_4$): δ 1.10-1.12 (m, 2H), 1.30-1.37 (m, 2H), 1.92-1.94 (m, 2H), 2.05-2.07 (m, 2H), 2.41 (s, 3H), 2.57 (t, 1H, J=12.5 Hz), 3.25 (q, 2H, J=13.5 Hz), 3.72 (t, 1H, J=12.5 Hz), 7.50 (d, 1H, J=9.0 Hz), 7.75 (d, 1H, J=9.0 Hz), 8.20 (s, 2H), 8.22 (s, 1H), 8.57 (s, 2H), 8.67 (s, 1H), 9.90 (s, 1H) (two secondary amine protons (NH) signals not observed). HRMS (ESI) m/z [M+H]$^+$ 498.2339.

N-(4-((5-Methyl-4-(6-(pyrimidin-5-ylamino)imidazo[1,2-a]pyridin-3-yl)pyrimidin-2-yl)amino)cyclohexyl)acetamide (113)

To a solution of (1r,4r)-N$^1$-(5-methyl-4-(6-(pyrimidin-5-ylamino)imidazo[1,2-a]pyridin-3-yl)pyrimidin-2-yl)cyclohexane-1,4-diamine (380 mg, 0.92 mmol) and triethylamine (1 mL) in dioxane (3 mL) was added acetyl chloride (71 μL, 1.00 mmol). The reaction was stirred overnight, concentrated under reduced pressure and purified by flash column chromatography starting with 100% DCM ramping to 6% MeOH+1% NH$_3$ (32% in water).to give 113 as a yellow solid (200 mg, 48%). $^1$H-NMR (MeOD-d$_4$): δ 1.22-1.24 (m, 2H), 1.31-1.36 (m, 2H), 1.86-1.89 (m, 2H), 1.94 (s, 3H), 2.00-2.04 (m, 2H), 2.32 (s, 3H), 3.61-3.64 (m, 2H), 7.46 (d, 1H, J=9.0 Hz), 7.70 (d, 1H, J=9.5 Hz), 8.14 (s, 3H), 8.55 (s, 2H), 8.64 (s, 1H), 9.83 (s, 1H) (two secondary amine protons (NH) signals not observed). HRMS (ESI) m/z [M+H]$^+$ 458.2418.

(1r,4r)-N$^1$-(4-(6-Bromo-7-(trifluoromethyl)imidazo[1,2-a]pyridin-3-yl)-5-methylpyrimidin-2-yl)cyclohexane-1,4-diamine (114)

6-Bromo-3-(2-chloro-5-methylpyrimidin-4-yl)-7-(trifluoromethyl) imidazo[1,2-a]pyridine (200 mg, 0.51 mmol) and (1r,4r)-cyclohexane-1,4-diamine (176 mg, 1.54 mmol) were reacted according to general synthetic procedure A(ii) to give 114 as a yellow powder (80.0 mg, 34%). $^1$H-NMR (CDCl$_3$): δ 1.34-1.36 (m, 4H), 1.94-1.96 (m, 2H), 2.18-2.20 (m, 2H), 2.37 (s, 3H), 2.73-2.76 (m, 1H), 3.81-3.83 (m, 1H), 5.00 (d, 1H, J=7.5 Hz), 8.11 (s, 1H), 8.22 (s, 1H), 8.24 (s, 1H), 10.09 (s, 1H) (two primary amine protons (NH$_2$) signals not observed). HRMS (ESI) m/z [M+H]$^+$ 469.0962.

(1r,4r)-N$^1$-(5-Methyl-4-(6-(pyrimidin-5-ylamino)imidazo[1,2-a]pyridin-3-yl)pyrimidin-2-yl)cyclohexane-1,4-diamine (115)

(1r,4r)-N$^1$-(4-(6-Bromoimidazo[1,2-a]pyridin-3-yl)-5-methylpyrimidin-2-yl)cyclohexane-1,4-diamine (400 mg, 1.00 mmol) and pyrimidin-5-amine (96 mg, 1.00 mmol) were reacted according to general synthetic procedure B. The product was further purified by preparative HPLC to give 115 as a yellow solid (290 mg, 70%). $^1$H-NMR (DMSO-d$_6$): δ 1.26-1.29 (m, 4H), 1.88-1.92 (m, 4H), 2.33 (s, 3H), 2.91-2.93 (m, 1H), 3.60-3.63 (m, 1H), 6.83 (s, 1H), 7.41 (d, 1H, J=9.5 Hz), 7.76 (d, 1H, J=9.5 Hz), 8.20 (s, 1H), 8.24 (s, 1H), 8.55 (s, 2H), 8.59 (s, 1H), 8.64 (s, 1H), 9.69 (s, 1H) (two primary amine protons (NH$_2$) signals not observed). HRMS (ESI) m/z [M+H]$^+$ 416.2310.

(1r,4r)-N$^1$-(5-Methyl-4-(6-(pyrimidin-4-ylamino)imidazo[1,2-a]pyridin-3-yl)pyrimidin-2-yl)cyclohexane-1,4-diamine (116)

(1r,4r)-N$^1$-(4-(6-Bromoimidazo[1,2-a]pyridin-3-yl)-5-methylpyrimidin-2-yl)cyclohexane-1,4-diamine (200 mg, 0.50 mmol) and pyrimidin-4-amine (47 mg, 0.50 mmol) were reacted according to general synthetic procedure B. The product was further purified by preparative HPLC to give 116 as a yellow solid (20 mg, 19%). $^1$H-NMR (MeOD-d$_4$): δ 1.43-1.45 (m, 4H), 2.02-2.05 (m, 2H), 2.20-2.22 (m, 2H), 2.41 (s, 3H), 3.10-3.13 (m, 1H), 3.90-3.93 (m, 1H), 6.90 (d, 1H, J=6.0 Hz), 7.55 (d, 1H, J=10.0 Hz), 7.70 (d, 1H, J=9.5 Hz), 8.13 (s, 1H), 8.28 (s, 1H), 8.30 (s, 1H), 8.49 (s, 1H), 8.67 (s, 1H), 10.60 (s, 1H) (two primary amine protons (NH$_2$) and one secondary amine proton (NH) signals not observed). HRMS (ESI) m/z [M+H]$^+$ 416.2311.

(4-(3-(2-(((1r,4r)-4-Aminocyclohexyl)amino)-5-fluoropyrimidin-4-yl)imidazo[1,2-a]pyridin-6-yl)phenyl)(piperazin-1-yl)methanone (117)

(1r,4r)-N$^1$-(4-(6-Bromoimidazo[1,2-a]pyridin-3-yl)-5-fluoropyrimidin-2-yl)cyclohexane-1,4-diamine (150 mg, 0.37 mmol) and tert-butyl 4-(4-(4,4,5,5-tetramethyl-1,3,2-dioxaborolan-2-yl)benzoyl)piperazine-1-carboxylate (154 mg, 0.37 mmol)) were reacted according to general synthetic procedure C to give tert-butyl 4-(4-(3-(2-(((r,4r)-4-aminocyclohexyl)amino)-5-fluoropyrimidin-4-yl)imidazo[1,2-a]pyridin-6-yl)benzoyl)piperazine-1-carboxylate (205 mg). The latter was heated at reflux in 3M HCl (4 mL) and MeOH (4 mL) for 6 h, basified with 2M NaOH, and extracted with DCM (3×100 mL). Organic extracts were combined, concentrated under reduced pressure and purified by preparative HPLC to give 117 as a yellow solid (90 mg, 47%). $^1$H-NMR (DMSO-$d_6$): δ 1.04-1.07 (m, 2H), 1.20-1.27 (m, 2H), 1.65-1.69 (m, 2H), 1.91-1.94 (m, 2H), 2.27-2.29 (m, 3H), 3.33-3.36 (m, 4H), 3.74-3.80 (m, 3H), 7.27 (t, 1H, J=6.5 Hz), 7.33-7.38 (m, 5H), 7.73 (d, 1H, J=9.5 Hz), 8.13 (s, 1H), 8.24 (s, 1H), 10.38 (s, 1H). HRMS (ESI) m/z [M+H]$^+$ 515.2685.

(1r,4r)-N$^1$-(5-Chloro-4-(7-(pyrimidin-5-ylamino)imidazo[1,2-a]pyridin-3-yl)pyrimidin-2-yl)cyclohexane-1,4-diamine (118)

(1r,4r)-N$^1$-(4-(7-Bromoimidazo[1,2-a]pyridin-3-yl)-5-chloro pyrimidin-2-yl)cyclohexane-1,4-diamine (200 mg, 0.48 mmol) and pyrimidin-5-amine (45 mg, 0.48 mmol) were reacted according to general synthetic procedure B. The product was further purified by preparative HPLC to give 118 as a yellow solid (110 mg, 53%). $^1$H-NMR (DMSO-$d_6$): δ 1.17-1.22 (m, 2H), 1.33-1.35 (m, 2H), 1.83-1.85 (m, 2H), 1.97-2.00 (m, 2H), 2.60-2.62 (m, 1H), 3.65-3.67 (m, 1H), 6.93 (s, 1H), 7.24 (s, 1H), 7.42 (d, 1H, J=8.0 Hz), 8.34 (s, 1H), 8.64 (s, 1H), 8.81 (s, 2H), 8.86 (s, 1H), 9.28 (s, 1H), 9.86 (s, 1H) (two primary amine protons (NH$_2$) signals not observed). HRMS (ESI) m/z [M+H]$^+$ 436.1763.

3-(2-(((1r,4r)-4-(Aziridin-1-yl)cyclohexyl)amino)-5-methylpyrimidin-4-yl)-N-(pyrimidin-5-yl)imidazo[1,2-a]pyridin-7-amine (119)

A suspension of N$^1$-(5-methyl-4-(6-(pyrimidin-5-ylamino) imidazo[1,2-$_a$]pyridin-3-yl)pyrimidin-2-yl)cyclohexane-1,4-diamine (160 mg, 0.39 mmol) and K$_3$PO$_4$ (409 mg, 1.93 mmol) in 1-bromo-2-chloroethane (0.5 mL) and MeCN (3 mL) was heated in a pressurised tube at 120° C. for 3 h, concentrated under reduced pressure and purified by flash column chromatography starting with 100% DCM ramping to 5% MeOH+0.5% NH$_3$ (32% in water) to afford 119 as a yellow powder (20 mg, 12%). $^1$H-NMR (MeOD-$d_4$): δ 1.15-1.37 (m, 6H), 1.70-1.72 (m, 2H), 1.86-1.88 (m, 2H), 2.00-2.04 (m, 2H), 2.37 (s, 3H), 3.68-3.73 (m, 1H), 7.45 (dd, 1H, J=9.5 & 2.0 Hz), 7.71 (d, 1H, J=9.5 Hz), 8.14 (s, 1H), 8.18 (s, 1H), 8.56 (s, 2H), 8.61 (s, 1H), 9.85 (d, 1H, J=2.0 Hz) (two secondary amine (NH) protons and one CH proton signals not observed). HRMS (ESI) m/z [M+H]$^+$ 442.2466.

N$^1$-(4-(6-((5-Fluoropyridin-3-yl)amino)imidazo[1,2-a]pyridin-3-yl)-5-methylpyrimidin-2-yl)-N$^4$,N$^4$-dimethylcyclohexane-1,4-diamine (120)

N$^1$-(4-(6-Bromoimidazo[1,2-a]pyridin-3-yl)-5-methylpyrimidin-2-yl)-N$^4$,N$^4$-dimethylcyclohexane-1,4-diamine (100 mg, 0.23 mmol) and 5-fluoropyridin-3-amine (26 mg, 0.23 mmol) were reacted according to general synthetic procedure B. The product was further purified by preparative HPLC to give 120 as a yellow solid (50 mg, 47%). $^1$H-NMR (MeOD-$d_4$): δ 1.25-1.34 (m 4H), 1.83-1.85 (m, 2H), 2.10-2.12 (m, 2H), 2.21 (s, 6H), 2.30 (t, 1H, J=11.5 Hz), 2.40 (s, 3H), 3.68 (t, 1H, J=11.0 Hz), 7.27 (dt, 1H, J=11.0 & 2.5 Hz), 7.48 (dd, 1H, J=9.5 & 2.5 Hz), 7.73 (d, 1H, J=9.5 Hz), 7.91 (t, 1H, J=2.5 Hz), 8.17 (s, 1H), 8.18 (s, 1H), 8.20 (s, 1H), 9.91 (s, 1H). HRMS (ESI) m/z [M+H]$^+$ 460.2503.

(1r,4r)-N$^1$-Isopropyl-N$^4$-(5-methyl-4-(6-(pyrimidin-5-ylamino)imidazo[1,2-a]pyridin-3-yl)pyrimidin-2-yl)cyclohexane-1,4-diamine (121)

(1r,4r)-N$^1$-(5-Methyl-4-(6-(pyrimidin-5-ylamino) imidazo[1,2-a]pyridin-3-yl)pyrimidin-2-yl)cyclohexane-1,4-diamine (85 mg, 0.20 mmol) and acetone (73 μL, 1.00 mmol) were reacted according to general synthetic procedure D to give 121 as a white powder (40 mg, 45%). $^1$H-NMR (MeOd-$d_4$): δ 1.08-1.11 (m, 8H), 1.30-1.34 (m, 2H), 1.93-1.95 (m, 2H), 2.04-2.07 (m, 2H), 2.40 (s, 3H), 2.61-2.63 (m, 1H), 2.96-2.98 (m, 1H), 3.68-3.70 (m, 1H), 7.49 (dd, 1H, J=9.5 & 2.0 Hz), 7.74 (d, 1H, J=9.5 Hz), 8.18 (s, 1H), 8.21 (s, 1H), 8.56 (s, 2H), 8.65 (s, 1H), 9.87 (d, 1H, J=2.0 Hz) (three secondary amine proton (NH) signals not observed). HRMS (ESI) m/z [M+H]$^+$ 443.2545.

(1r,4r)-N$^1$-(5-Methyl-4-(6-(methyl(pyridin-3-yl)amino)imidazo[1,2-a]pyridin-3-yl)pyrimidin-2-yl)cyclohexane-1,4-diamine (122)

(1r,4r)-N$^1$-(4-(6-Bromoimidazo[1,2-a]pyridin-3-yl)-5-methylpyrimidin-2-yl)cyclohexane-1,4-diamine (220 mg, 0.55 mmol) and N-methylpyridin-3-amine (56 μL, 0.55 mmol) were reacted according to general synthetic procedure B to give 122 as a yellow solid (30 mg, 13%). $^1$H-NMR (CDCl$_3$): δ 1.01 (br s, 2H), 1.23 (q, 2H, J=14.5 Hz), 1.79 (d, 2H, J=12.0 Hz), 2.06 (d, 2H, J=12.0 Hz), 2.38 (s, 3H), 2.60 (t, 1H, J=10.0 Hz), 3.38 (s, 3H), 3.70 (t, 1H, J=10.0 Hz), 4.85 (d, 1H, J=8.0 Hz), 7.12-7.18 (m, 2H), 7.22 (dd, 1H, J=9.5 & 2.0 Hz), 7.73 (d, 1H, J=9.5 Hz), 8.12 (d, 1H, J=5.0 Hz), 8.14 (s, 1H), 8.19 (s, 1H), 8.30 (s, 1H), 9.66 (s, 1H) (two primary amine protons (NH$_2$) signals not observed). HRMS (ESI) m/z [M+H]$^+$ 429.2518.

(1r,4r)-N$^1$-(4-(6-((6-Fluoropyridin-3-yl)amino)imidazo[1,2-a]pyridin-3-yl)-5-methylpyrimidin-2-yl)cyclohexane-1,4-diamine (123)

(1r,4r)-N$^1$-(4-(6-Bromoimidazo[1,2-a]pyridin-3-yl)-5-methylpyrimidin-2-yl)cyclohexane-1,4-diamine (200 mg, 0.50 mmol) and 6-fluoropyridin-3-amine (56 mg, 0.50 mmol) were reacted according to general synthetic procedure B to give 123 as an orange solid (90 mg, 42%). $^1$H-NMR (MeOD-$d_4$): δ 1.18 (br s, 2H), 1.33 (q, 2H, J=11.5 Hz), 1.87 (d, 2H, J=10.0 Hz), 2.02 (d, 2H, J=11.0 Hz), 2.36 (s, 3H), 2.69 (br s, 1H), 3.65 (t, 1H, J=11.0 Hz), 6.98 (dd, 1H, J=9.0 & 3.0 Hz), 7.38 (dd, 1H, J=9.5 & 2.0 Hz), 7.62-7.69 (m, 2H), 7.99 (br s, 1H), 8.10 (s, 1H), 8.17 (s, 1H), 9.72 (d, 1H, J=2.0 Hz). HRMS (ESI) m/z [M+H]$^+$ 432.2190.

8-(4-(Imidazo[1,2-a]pyridin-3-yl)-5-methylpyrimidin-2-yl)-2,8-diazaspiro[4.5]decan-1-on (124)

8-(4-(6-Bromoimidazo[1,2-a]pyridin-3-yl)-5-methylpyrimidin-2-yl)-2,8-diazaspiro[4.5]decan-1-one (200 mg, 0.45 mmol) and pyrimidin-5-amine (44 mg, 0.45 mmol) were reacted according to general synthetic procedure B. The product was further purified by preparative HPLC to give 124 as a yellow solid (50 mg, 31%). $^1$H-NMR (CDCl$_3$): δ 1.54 (d, 2H, J=13.5 Hz), 1.96 (ddd, 2H, J=14.0, 11.5 & 4.5 Hz), 2.15 (t, 2H, J=7.0 Hz), 2.35 (s, 3H), 3.29 (ddd, 2H, J=13.5, 11.0 & 3.0 Hz), 3.40 (t, 2H, J=7.0 Hz), 4.54 (td, 2H, J=13.5 & 4.0 Hz), 6.96 (dt, 1H, J=7.0 & 0.5 Hz), 7.01 (s, 1H), 7.39 (ddd, 1H, J=7.5, 7.0 & 0.5 Hz), 7.82 (d, 1H, J=9.0 Hz), 8.20 (s, 1H), 8.26 (s, 1H), 9.49 (d, 1H, J=7.0 Hz). HRMS (ESI) m/z [M+H]$^+$ 363.1972.

8-(5-Methyl-4-(6-phenylimidazo[1,2-a]pyridin-3-yl)pyrimidin-2-yl)-2,8-diazaspiro[4.5]decan-1-one (125)

8-(4-(6-Bromoimidazo[1,2-a]pyridin-3-yl)-5-methylpyrimidin-2-yl)-2,8-diazaspiro[4.5]decan-1-one (100 mg, 0.23 mmol) and 4,4,5,5-tetramethyl-2-phenyl-1,3,2-dioxaborolane (46.0 mg, 0.23 mmol) were reacted according to general synthetic procedure C to give 125 as a yellow solid (50.0 mg, 50%). $^1$H-NMR (DMSO-d): δ 1.40 (d, 2H, J=13.5 Hz), 1.69 (dt, 2H, J=13.0 & 4.0 Hz), 2.06 (t, 2H, J=6.5 Hz), 2.38 (s, 3H), 3.16-3.28 (m, 4H), 4.50 (td, 2H, J=13.5 & 3.5 Hz), 7.44 (t, 1H, J=7.5 Hz), 7.50 (t, 2H, J=7.0 Hz), 7.63 (s, 1H), 7.70 (d, 2H, J=7.0 Hz), 7.82 (dd, 1H, J=9.0 & 1.5 Hz), 7.87 (d, 1H, J=9.0 Hz), 8.30 (s, 1H), 8.38 (s, 1H), 9.91 (s, 1H). HRMS (ESI) m/z [M+H]$^+$ 439.2245.

N-((1r,4r)-4-((5-Methyl-4-(6-(pyrimidin-5-ylamino)imidazo[1,2-a]pyridin-3-yl)pyrimidin-2-yl)amino)cyclohexyl)methanesulfonamide (126)

To a solution of (1r,4r)-N$^1$-(5-methyl-4-(6-(pyrimidin-5-ylamino)imidazo[1,2-a]pyridin-3-yl)pyrimidin-2-yl)cyclohexane-1,4-diamine (80 mg, 0.19 mmol) and triethylamine (32 µL, 0.39 mmol) in DCE (5 mL) cooled on an ice bath was added methanesulfonyl chloride (32 µL, 0.39 mmol). The reaction was stirred overnight, concentrated under reduced pressure and purified by flash column chromatography starting with 100% DCM ramping to 6% MeOH+1% NH$_3$ (32% in water).to give 126 as a white solid (20 mg, 21%). $^1$H-NMR (DMSO-d$_6$): δ 1.25-1.28 (m, 4H), 1.85-1.88 (m, 4H), 2.33 (s, 3H), 2.90 (s, 3H), 3.01-3.04 (m, 1H), 3.52-3.54 (m, 1H), 6.91 (s, 2H), 7.41 (d, 1H, J=9.0 Hz), 7.76 (d, 1H, J=9.5 Hz), 8.18 (s, 1H), 8.25 (s, 1H), 8.59 (s, 3H), 8.67 (s, 1H), 9.73 (s, 1H). HRMS (ESI) m/z [M+H]$^+$ 494.2088.

(1r,4r)-N$^1$-(4-(6-((6-Methoxypyridin-3-yl)amino)imidazo[1,2-a]pyridin-3-yl)-5-methylpyrimidin-2-yl)cyclohexane-1,4-diamine (127)

(1r,4r)-N$^1$-(4-(6-Bromoimidazo[1,2-a]pyridin-3-yl)-5-methylpyrimidin-2-yl)cyclohexane-1,4-diamine (600 mg, 1.50 mmol) and 6-methoxypyridin-3-amine (186 mg, 2.50 mmol) were reacted according to general synthetic procedure B. The product was further purified by preparative HPLC to give 127 as an orange solid (200 mg, 30%). $^1$H-NMR (MeOD-d$_4$): δ 1.26-1.55 (m, 4H), 2.06 (dd, 4H, J=27.0 & 12.0 Hz), 2.35 (s, 3H), 3.02-3.15 (m, 1H), 3.60-3.74 (m, 1H), 3.90 (s, 3H), 6.81 (d, 1H, J=8.5 Hz), 7.32 (dd, 1H, J=9.5 & 2.0 Hz), 7.60 (d, 1H, J=9.5 Hz), 7.63 (dd, 1H, J=9.0 & 3.0 Hz), 8.01 (d, 1H, J=3.0 Hz), 8.03 (s, 1H), 8.19 (s, 1H), 8.45 (s, 1H), 9.39 (s, 1H). HRMS (ESI) m/z [M+H]$^+$ 445.2463.

(1r,4r)-N$^1$-(5-Methyl-4-(6-(pyridin-2-ylamino)imidazo[1,2-a]pyridin-3-yl)pyrimidin-2-yl)cyclohexane-1,4-diamine (128)

(1r,4r)-N$^1$-(4-(6-Bromoimidazo[1,2-a]pyridin-3-yl)-5-methylpyrimidin-2-yl)cyclohexane-1,4-diamine (150 mg, 0.38 mmol) and pyridin-2-amine (35 mg, 0.38 mmol) were reacted according to general synthetic procedure B. The product was further purified by preparative HPLC to give 128 as an orange solid (40 mg, 25%). $^1$H-NMR (MeOD-d$_4$): δ 1.03 (br s, 2H), 1.26-1.33 (m, 2H), 1.78 (br s, 2H), 2.08 (d, 2H, J=11.5 Hz), 2.39 (s, 3H), 2.60 (t, 1H, J=11.0 Hz), 3.87 (br s, 1H), 6.79 (dd, 1H, J=7.0 & 5.5 Hz), 6.86 (d, 1H, J=8.5 Hz), 7.47 (d, 1H, J=9.0 Hz), 7.59 (ddd, 1H, J=9.0, 8.0 & 2.0 Hz), 7.61 (d, 1H, J=9.5 Hz), 8.04 (s, 1H), 8.14 (d, 1H, J=4.0 Hz), 8.23 (s, 1H), 8.45 (br s, 1H), 10.47 (d, 1H, J=1.5 Hz) (two primary amine protons (NH$_2$) and one secondary amine proton (NH) signals not observed). HRMS (ESI) m/z [M+H]$^+$ 415.2357.

(1r,4r)-N$^1$-(2-Methoxyethyl)-N$^4$-(5-methyl-4-(6-phenylimidazo[1,2-a]pyridin-3-yl)pyrimidin-2-yl)cyclohexane-1,4-diamine (129) and (1 s,4s)-N$^1$-(2-Methoxyethyl)-N$^4$-(5-methyl-4-(6-phenylimidazo[1,2-a]pyridin-3-yl)pyrimidin-2-yl)cyclohexane-1,4-diamine (130)

4-((5-Methyl-4-(6-phenylimidazo[1,2-a]pyridin-3-yl)pyrimidin-2-yl)amino)cyclohexan-1-one (130 mg, 0.33 mmol) and 2-methoxyethan-1-amine (29 µL, 0.38 mmol) were reacted according to general synthetic procedure D. The product was purified by preparative HPLC to give: 129 as a white solid (25 mg, 17%). $^1$H-NMR (CDCl$_3$): δ 1.01 (br s, 2H), 1.20 (q, 2H, J=12.5 Hz), 1.60 (br s, 2H), 2.14 (d, 2H, J=11.5 Hz), 2.39 (s, 3H), 2.74 (br s, 1H), 2.87 (s, 2H), 3.38 (s, 3H), 3.58 (s, 2H), 3.71 (br s, 1H), 5.18 (br s, 1H), 7.42 (t, 1H, J=7.0 Hz), 7.49 (t, 2H, J=7.5 Hz), 7.55-7.61 (m, 3H), 7.80 (d, 1H, J=9.0 Hz), 8.14 (s, 1H), 8.18 (s, 1H), 8.40 (s, 1H), 9.85 (s, 1H). HRMS (ESI) m/z [M+H]$^+$ 457.2714. 130 as a white solid (15 mg, 10%). H-NMR (CDCl$_3$): δ 1.60 (br s, 2H), 1.72 (br s, 4H), 1.87 (br s, 2H), 2.39 (s, 3H), 2.85 (br s, 1H), 2.99 (s, 2H), 3.35 (s, 3H), 3.60 (s, 2H), 4.14 (br s, 1H), 5.84 (br s, 1H), 7.40 (t, 1H, J=7.5 Hz), 7.46 (t, 2H, J=7.0 Hz), 7.57 (d, 2H, J=7.5 Hz), 7.60 (dd, 1H, J=9.0 & 1.5 Hz), 7.79 (d, 1H, J=9.5 Hz), 8.16 (s, 2H), 8.43 (br s, 1H), 9.96 (br s, 1H). HRMS (ESI) m/z [M+H]$^+$ 457.2715.

(1r,4r)-N$^1$-Ethyl-N$^4$-(5-methyl-4-(6-phenylimidazo[1,2-a]pyridin-3-yl)pyrimidin-2-yl)cyclohexane-1,4-diamine (131) and (1s,4s)-N$^1$-ethyl-N$^4$-(5-Methyl-4-(6-phenylimidazo[1,2-a]pyridin-3-yl)pyrimidin-2-yl)cyclohexane-1,4-diamine (132)

4-((5-Methyl-4-(6-phenylimidazo[1,2-a]pyridin-3-yl)pyrimidin-2-yl)amino)cyclohexan-1-one (150 mg, 0.38 mmol) and ethanamine (2M in THF, 130 µL, 0.33 mmol) were reacted according to general synthetic procedure D. The product was purified by preparative HPLC to give: 131 as a white solid (30 mg, 19%). $^1$H-NMR (CDCl$_3$): δ 1.10-1.40 (m, 7H), 1.94 (br s, 2H), 2.16 (d, 2H, J=11.0 Hz), 2.38 (s, 3H, CH$_3$), 2.78 (br s, 2H), 3.76 (s, 1H), 4.93 (d, 1H, J=7.0 Hz), 7.40 (t, 1H, J=7.5 Hz), 7.48 (t, 2H, J=7.5 Hz), 7.57 (d, 3H, J=7.5 Hz), 7.78 (d, 1H, J=9.5 Hz), 8.10 (s, 1H), 8.21 (s, 1H), 8.47 (s, 1H), 9.71 (s, 1H). HRMS (ESI) m/z [M+H]$^+$ 427.2609. 132 as a white solid (25 mg, 16%). $^1$H-NMR (CDCl$_3$): δ 1.31 (t, 3H, J=7.0 Hz), 1.45-2.00 (m, 8H), 2.36 (s, 3H), 2.80-2.98 (m, 2H), 3.60-3.70 (m, 1H), 4.14 (br s, 1H), 5.94 (d, 1H, J=7.0 Hz), 7.38 (t, 1H, J=7.0 Hz), 7.45 (t, 2H, J=7.0 Hz), 7.56 (d, 2H, J=9.0 Hz), 7.59 (dd, 1H, J=11.5 & 1.5 Hz), 7.78 (d, 1H, J=9.0 Hz), 8.14 (s, 1H), 8.15 (s, 1H), 8.53 (s, 1H), 9.96 (s, 1H). HRMS (ESI) m/z [M+H]$^+$ 427.2607.

(1r,4r)-N$^1$-Methyl-N$^4$-(5-methyl-4-(6-phenylimidazo[1,2-a]pyridin-3-yl)pyrimidin-2-yl)cyclohexane-1,4-diamine (133)

4-((5-Methyl-4-(6-phenylimidazo[1,2-a]pyridin-3-yl)pyrimidin-2-yl)amino)cyclohexan-1-one (150 mg, 0.38 mmol) and methanamine hydrochloride (26 mg, 0.38 mmol) were reacted according to general synthetic procedure D. The product was purified by preparative HPLC to give 133 as a white solid (30 mg, 19%). $^1$H-NMR (CDCl$_3$): δ 1.10-1.40 (m, 4H), 1.94 (br s, 2H), 2.17 (d, 2H, J=9.0 Hz), 2.39 (s, 3H), 2.42 (s, 3H), 2.75 (br s, 1H), 3.77 (br s, 1H), 4.99 (br s, 1H), 7.41 (t, 1H, J=7.0 Hz), 7.48 (t, 2H, J=8.0 Hz), 7.53-7.62 (m, 3H), 7.79 (d, 1H, J=9.0 Hz), 8.11 (s, 1H), 8.21 (s, 1H), 8.46 (s, 1H), 9.71 (s, 1H). HRMS (ESI) m/z [M+H]$^+$ 413.2453.

(1r,4r)-N$^1$-(5-Methyl-4-(6-(pyridin-4-ylamino)imidazo[1,2-a]pyridin-3-yl)pyrimidin-2-yl)cyclohexane-1,4-diamine (134)

(1r,4r)-N$^1$-(4-(6-Bromoimidazo[1,2-a]pyridin-3-yl)-5-methylpyrimidin-2-yl)cyclohexane-1,4-diamine (150 mg, 0.38 mmol) and pyridin-4-amine (35 mg, 0.38 mmol) were reacted according to general synthetic procedure B. The product was further purified by preparative HPLC to give 134 as an orange solid (40 mg, 25%). $^1$H-NMR (DMSO-d$_6$): δ 1.31 (br s, 4H), 1.92 (br s, 4H), 2.33 (s, 3H), 2.92 (br s, 1H), 3.65 (br s, 1H), 6.70 (br s, 1H), 6.95 (d, 1H, J=8.0 Hz), 7.41 (d, 1H, J=9.5 Hz), 7.78 (d, 1H, J=9.5 Hz), 8.21 (s, 1H), 8.26 (s, 1H), 8.33 (br s, 2H), 9.04 (br s, 1H), 9.67 (s, 1H). HRMS (ESI) m/z [M+H]$^+$ 415.2357.

N-((1r,4r)-4-(Azetidin-1-yl)cyclohexyl)-5-methyl-4-(6-phenylimidazo[1,2-a]pyridin-3-yl)pyrimidin-2-amine (135) and N-((1s,4s)-4-(azetidin-1-yl)cyclohexyl)-5-methyl-4-(6-phenylimidazo[1,2-a]pyridin-3-yl)pyrimidin-2-amine (136)

4-((5-Methyl-4-(6-phenylimidazo[1,2-a]pyridin-3-yl)pyrimidin-2-yl)amino)cyclohexan-1-one (150 mg, 0.38 mmol) and azetidine (25 µL, 0.38 mmol) were reacted according to general synthetic procedure D. The product was purified by preparative HPLC to give: 135 as a yellow solid (45 mg, 27%). $^1$H-NMR (CDCl$_3$): δ 1.00-1.30 (m, 4H), 1.66 (br s, 2H), 2.14 (d, 2H, J=7.0 Hz), 2.30-2.40 (m, 2H), 2.37 (s, 3H), 2.58 (br s, 1H), 3.74 (br s, 5H), 5.33 (br s, 1H), 7.39 (t, 1H, J=7.0 Hz), 7.48 (t, 2H, J=7.5 Hz), 7.55 (d, 2H, J=7.5 Hz), 7.57 (dd, 1H, J=9.0 & 1.5 Hz), 7.79 (d, 1H, J=9.5 Hz), 8.10 (s, 1H), 8.18 (s, 1H), 9.64 (s, 1H). HRMS (ESI) m/z [M+H]$^+$ 439.2610. 136 as a yellow solid (15 mg, 10%). $^1$H-NMR (CDCl$_3$): δ 1.52 (br s, 4H), 1.62-1.78 (m, 2H), 1.84-1.96 (m, 2H), 2.25-2.35 (m, 2H), 2.39 (s, 3H), 2.52 (br s, 1H), 3.20-4.10 (m, 4H), 4.17 (br s, 1H), 5.89 (d, 1H, J=8.0 Hz), 7.38-7.43 (m, 1H), 7.47 (t, 2H, J=7.5 Hz), 7.56-7.64 (m, 3H), 7.78 (d, 1H, J=9.0 Hz), 8.15 (s, 1H), 8.20 (s, 1H), 9.96 (s, 1H). HRMS (ESI) m/z [M+H]$^+$ 439.2609.

5-Fluoro-4-(6-phenylimidazo[1,2-a]pyridin-3-yl)-N-((1r,4r)-4-(pyrrolidin-1-yl)cyclohexyl)pyrimidin-2-amine (137)

(1r,4r)-N$^1$-(5-Fluoro-4-(6-phenylimidazo[1,2-a]pyridin-3-yl)pyrimidin-2-yl)cyclohexane-1,4-diamine (95 mg, 0.24 mmol) and 1,4-dibromobutane (30 µL, 0.25 mmol) were reacted according to general synthetic procedure E to give 137 as a yellow solid (40 mg, 37%). $^1$H-NMR (CDCl$_3$): δ 1.24-1.31 (m, 2H), 1.49-1.52 (m, 2H), 1.97 (s, 2H), 2.14-2.17 (m, 2H), 2.23-2.25 (m, 2H), 2.31-2.34 (m, 2H), 2.64 (br s, 2H), 309-3.14 (m, 1H), 3.61 (br s, 2H), 3.75-3.77 (m, 1H), 4.89 (d, 1H, J=7.5 Hz), 7.47 (t, 1H, J=7.5 Hz), 7.55 (t, 2H, J=7.0 Hz), 7.62-7.65 (m, 3H), 7.84 (d, 1H, J=9.5 Hz), 8.24 (d, 1H, J=3.5 Hz), 8.48 (d, 1H, J=3.5 Hz), 10.11 (s, 1H). HRMS (ESI) m/z [M+H]$^+$ 457.2516.

N-((1r,4r)-4-(Azetidin-1-yl)cyclohexyl)-5-fluoro-4-(6-phenylimidazo[1,2-a]pyridin-3-yl)pyrimidin-2-amine (138)

(1r,4r)-N$^1$-(5-Fluoro-4-(6-phenylimidazo[1,2-a]pyridin-3-yl)pyrimidin-2-yl)cyclohexane-1,4-diamine (80 mg, 0.20 mmol) and 1-bromo-3-chloropropane (22 µL, 0.22 mmol) were reacted according to general synthetic procedure E to give 138 as a yellow solid (15 mg, 17%). $^1$H-NMR (CDCl$_3$): δ 1.00-1.40 (m, 4H), 1.70-1.80 (m, 2H), 2.24 (d, 2H, J=11.0 Hz), 2.28-2.43 (m, 2H), 2.56-2.70 (m, 1H), 3.75 (br s, 4H), 4.95 (d, 1H, J=7.0 Hz), 7.44 (t, 1H, J=7.5 Hz), 7.53 (t, 2H, J=7.5 Hz), 7.60 (d, 2H, J=8.5 Hz), 7.62 (dd, 1H, J=9.5 & 2.0 Hz), 7.84 (d, 1H, J=9.0 Hz), 8.21 (d, 1H, J=3.5 Hz), 8.46 (d, 1H, J=3.5 Hz), 8.49 (s, 1H), 10.3 (s, 1H). HRMS (ESI) m/z [M+H]$^+$ 443.2357.

3-(2-(((1r,4r)-4-(Azetidin-1-yl)cyclohexyl)amino)-5-methylpyrimidin-4-yl)-N-(5-fluoropyridin-3-yl)imidazo[1,2-a]pyridin-6-amine (139)

(1r,4r)-N$^1$-(4-(7-((5-Fluoropyridin-3-yl)amino)imidazo[1,2-a]pyridin-3-yl)-5-methylpyrimidin-2-yl)cyclohexane-1,4-diamine (160 mg, 0.37 mmol) and 1-bromo-3-chloropropane (44 µL, 0.44 mmol) were reacted according to general synthetic procedure E to give 139 as a yellow solid (20 mg, 12%). $^1$H-NMR (MeOD-d$_4$): δ 1.10-1.45 (m, 4H), 1.96 (br s, 2H), 2.13 (d, 2H, J=12.0 Hz), 2.37 (s, 3H), 2.35-2.50 (m, 2H), 3.04 (br s, 1H), 3.66-3.78 (m, 1H), 4.02 (t, 4H, J=7.5 Hz), 7.28 (td, 1H, J=11.0 & 2.5 Hz), 7.45 (dd, 1H, J=9.5 & 2.0 Hz), 7.70 (d, 1H, J=9.5 Hz), 7.91 (d, 1H, J=2.5 Hz), 8.14 (s, 1H), 8.18 (s, 1H), 8.21 (s, 1H), 8.54 (s, 1H), 9.74 (s, 1H). HRMS (ESI) m/z [M+H]$^+$ 473.2577.

5-Methyl-4-(6-phenylimidazo[1,2-a]pyridin-3-yl)-N-((1r,4r)-4-(pyrrolidin-1-yl)cyclohexyl)pyrimidin-2-amine (140)

(1r,4r)-N$^1$-(5-Methyl-4-(6-phenylimidazo[1,2-a]pyridin-3-yl)pyrimidin-2-yl)cyclohexane-1,4-diamine (160 mg, 0.38 mmol) and 1,4-dibromobutane (67 µL, 0.56 mmol) were reacted according to general synthetic procedure E. The product was further purified by preparative HPLC to give 140 as a yellow solid (90 mg, 52%). $^1$H-NMR (CDCl$_3$): δ 1.20-1.40 (m, 4H), 1.85 (br s, 2H), 1.95 (s, 4H), 2.18 (d, 2H, J=8.5 Hz), 2.39 (s, 3H), 2.88 (s, 2H), 3.01 (br s, 2H), 3.72 (br s, 1H), 5.59 (br s, 1H), 7.40 (t, 1H, J=7.0 Hz), 7.48 (t, 2H, J=7.5 Hz), 7.58 (d, 2H, J=7.5 Hz), 7.60 (dd, 1H, J=9.5 & 1.5 Hz), 7.82 (d, 1H, J=9.0 Hz), 8.13 (s, 1H), 8.17 (s, 1H), 8.38 (s, 2H), 9.78 (s, 1H). HRMS (ESI) m/z [M+H]$^+$ 453.2766.

3-(2-(((1r,4r)-4-(Azetidin-1-yl)cyclohexyl)amino)-5-methylpyrimidin-4-yl)-N-(pyrimidin-5-yl)imidazo[1,2-a]pyridin-6-amine (141)

(1r,4r)-N$^1$-(5-Methyl-4-(7-(pyrimidin-5-ylamino)imidazo[1,2-a]pyridin-3-yl)pyrimidin-2-yl)cyclohexane-1,4-diamine (150 mg, 0.36 mmol) and 1-bromo-3-chloropropane (54 µL, 0.54 mmol) were reacted according to general synthetic procedure E to give 141 as a yellow solid (30 mg, 18%). $^1$H-NMR (MeOD-d$_4$): δ 1.20-1.42 (m, 4H), 1.99 (d, 2H, J=7.0 Hz), 2.12 (d, 2H, J=11.5 Hz), 2.34 (s, 3H), 2.45 (br s, 2H), 3.06-3.20 (m, 1H), 3.66-3.75 (m, 1H), 4.11 (t, 4H, J=8.0 Hz), 7.43 (dd, 1H, J=9.5 & 2.0 Hz), 7.68 (d, 1H, J=9.0 Hz), 8.11 (s, 1H), 8.18 (s, 1H), 8.33 (s, 2H), 8.57 (s, 2H), 8.62 (s, 1H), 9.75 (s, 1H). HRMS (ESI) m/z [M+H]$^+$ 456.2625.

3-(5-Methyl-2-(((1r,4r)-4-(pyrrolidin-1-yl)cyclohexyl)amino)pyrimidin-4-yl)-N-(pyrimidin-5-yl)imidazo[1,2-a]pyridin-6-amine (142)

(1r,4r)-N-(5-Methyl-4-(7-(pyrimidin-5-ylamino)imidazo[1,2-a]pyridin-3-yl)pyrimidin-2-yl)cyclohexane-1,4-diamine (150 mg, 0.36 mmol) and 1,4-dibromobutane (65 μL, 0.54 mmol) were reacted according to general synthetic procedure E. The product was further purified by preparative HPLC to give 142 as a yellow solid (30 mg, 18%). $^1$H-NMR (MeOD-d$_4$): δ 1.30-1.44 (m, 2H), 1.46-1.64 (m, 2H), 2.06 (s, 4H), 2.15 (d, 4H, J=10.5 Hz), 2.34 (s, 3H, CH$_3$), 3.11 (t, 1H, J=11.5 Hz), 3.22-3.42 (m, 2H), 3.67-3.78 (m, 1H), 7.42 (dd, 1H, J=9.5 & 2.0 Hz), 7.67 (d, 1H, J=9.5 Hz), 8.10 (s, 1H), 8.17 (s, 1H), 8.39 (s, 2H), 8.57 (s, 2H), 8.62 (s, 1H), 9.76 (s, 1H). HRMS (ESI) m/z [M+H]$^+$ 470.2780.

5-Fluoro-4-(6-phenylimidazo[1,2-a]pyridin-3-yl)-N-(piperidin-4-yl)pyrimidin-2-amine (143)

tert-Butyl 4-((4-(6-bromoimidazo[1,2-a]pyridin-3-yl)-5-fluoropyrimidin-2-yl)amino)piperidine-1-carboxylate (860 mg, 1.76 mmol) and 4,4,5,5-tetramethyl-2-phenyl-1,3,2-dioxaborolane (359 mg, 1.76 mmol) were reacted according to general synthetic procedure C to give tert-butyl 4-((5-fluoro-4-(6-phenylimidazo[1,2-a]pyridin-3-yl)pyrimidin-2-yl)amino)piperidine-1-carboxylate (800 mg). The latter was stirred at room temperature in 6 M HCl (10 mL) overnight, basified with 6 M NaOH, and extracted with DCM (2×400 mL). Organic extracts were combined, concentrated under reduced pressure and purified by flash column chromatography starting with 100% DCM ramping to 4% MeOH+ 0.05% NH$_3$ (32% in water) to afford 143 as a white solid (550 mg, 81%). $^1$H-NMR (CDCl$_3$): δ 1.32-1.44 (m, 2H), 2.05 (d, 2H, J=10.5 Hz), 2.41 (br s, 2H), 2.95 (d, 2H, J=12.5 Hz), 3.82-3.93 (m, 1H), 5.02 (d, 1H, J=8.0 Hz), 7.45 (t, 1H, J=7.5 Hz), 7.51 (t, 2H, J=7.0 Hz), 7.59-7.66 (m, 3H), 7.83 (d, 1H, J=9.5 Hz), 8.21 (d, 1H, J=3.5 Hz), 8.50 (d, 1H, J=4.0 Hz), 10.20 (s, 1H). HRMS (ESI) m/z [M+H]$^+$ 389.1887.

5-Fluoro-N-(1-Methylpiperidin-4-yl)-4-(6-phenylimidazo[1,2-a]pyridin-3-yl)pyrimidin-2-amine (144)

4-(6-Bromoimidazo[1,2-a]pyridin-3-yl)-5-fluoro-N-(1-methylpiperidin-4-yl)pyrimidin-2-amine (100 mg, 0.25 mmol) and 4,4,5,5-tetramethyl-2-phenyl-1,3,2-dioxaborolane (359 mg, 1.76 mmol) were reacted according to general synthetic procedure C. The product was further purified by preparative HPLC to give 144 as a beige solid (65 mg, 65%). $^1$H-NMR (CDCl$_3$): δ 1.74-1.90 (m, 2H), 2.15 (d, 3H, J=11.5 Hz), 2.36 (s, 3H), 3.06 (br s, 1H), 3.87 (br s, 1H), 5.26 (d, 1H, J=6.5 Hz), 7.48 (t, 1H, J=7.0 Hz), 7.55 (t, 2H, J=7.5 Hz), 7.59-7.66 (m, 3H), 7.85 (d, 1H, J=9.0 Hz), 8.22 (d, 1H, J=3.5 Hz), 8.40 (s, 1H), 8.52 (d, 1H, J=4.0 Hz), 10.19 (s, 1H). HRMS (ESI) m/z [M+H]$^+$ 403.2044.

N-(1-(Cyclopropylmethyl)piperidin-4-yl)-5-fluoro-4-(6-phenylimidazo[1,2-a]pyridin-3-yl)pyrimidin-2-amine (145)

A solution of 5-fluoro-4-(6-phenylimidazo[1,2-a]pyridin-3-yl)-N-(piperidin-4-yl)pyrimidin-2-amine (100 mg, 0.26 mmol), (bromomethyl)cyclopropane (89 μL, 0.78 mmol), Triethylamine (0.2 mL, 2.27 mmol) in DMF (5 mL) was stirred at 90° C. overnight. The reaction mixture was concentrated under reduced pressure and purified by purified by flash column chromatography starting with 100% DCM ramping to 3% MeOH to afford 145 as a white solid (15 mg, 13%). $^1$H-NMR (CDCl$_3$): δ 0.25 (s, 2H), 0.60-0.70 (m, 2H), 0.96 (br s, 1H), 1.85-2.10 (m, 2H), 2.21 (d, 2H, J=12.0 Hz), 2.58 (br s, 2H), 3.44 (br s, 2H), 3.94 (br s, 1H), 4.94 (s, 2H), 5.61 (s, 1H), 7.45 (t, 1H, J=7.0 Hz), 7.54 (t, 2H, J=7.5 Hz), 7.59-7.66 (m, 3H), 7.86 (d, 1H, J=9.5 Hz), 8.22 (d, 1H, J=3.5 Hz), 8.52 (d, 1H, J=3.5 Hz), 10.21 (s, 1H). HRMS (ESI) m/z [M+H]$^+$ 443.2360.

N-(1-(Cyclopentylmethyl)piperidin-4-yl)-5-fluoro-4-(6-phenylimidazo[1,2-a]pyridin-3-yl)pyrimidin-2-amine (146)

5-Fluoro-4-(6-phenylimidazo[1,2-a]pyridin-3-yl)-N-(piperidin-4-yl)pyrimidin-2-amine (100 mg, 0.26 mmol) and cyclopropanecarbaldehyde (28 μL, 0.26 mmol) were reacted according to general synthetic procedure D to give 146 as a white solid (100 mg, 82%). $^1$H-NMR (CDCl$_3$): δ 1.09-1.21 (m, 2H), 1.45-1.65 (m, 6H), 1.66-1.78 (m, 2H), 1.82 (br s, 1H), 1.90-2.00 (m, 1H), 2.05 (s, 3H), 2.10-2.23 (m, 2H), 2.76 (br s, 2H), 3.70-3.85 (m, 1H), 5.11 (d, 1H, J=4.0 Hz), 7.44 (t, 1H, J=7.5 Hz), 7.52 (t, 2H, J=7.5 Hz), 7.59-7.65 (m, 3H), 7.84 (d, 1H, J=9.0 Hz), 8.20 (d, 1H, J=4.0 Hz), 8.50 (d, 1H, J=3.5 Hz), 10.21 (s, 1H). HRMS (ESI) m/z [M+H]$^+$ 471.2672.

5-Fluoro-N-(1-(methylsulfonyl)piperidin-4-yl)-4-(6-phenylimidazo[1,2-a]pyridin-3-yl)pyrimidin-2-amine (147)

To a solution of 5-fluoro-4-(6-phenylimidazo[1,2-a]pyridin-3-yl)-N-(piperidin-4-yl)pyrimidin-2-amine (130 mg, 0.33 mmol) and triethylamine (44 μL, 0.50 mmol) in DCM (10 mL) cooled on an ice bath was added methanesulfonyl chloride (57 μL, 0.98 mmol). The reaction was stirred overnight, concentrated under reduced pressure and purified by flash column chromatography starting with 100% DCM ramping to 3% MeOH. The product was further purified by preparative HPLC to give 147 as a yellow solid (40 mg, 26%). $^1$H-NMR (DMSO-d$_6$): δ 1.54 (q, 2H, J=10.0 Hz), 1.99 (d, 2H, J=11.0 Hz), 2.68 (br s, 2H), 2.31-2.38 (m, 2H), 3.75-3.92 (m, 1H), 7.44 (d, 1H, J=8.0 Hz), 7.47 (t, 1H, J=7.5 Hz), 7.57 (t, 2H, J=7.5 Hz), 7.79 (d, 2H, J=7.5 Hz), 7.84 (d, 1H, J=9.0 Hz), 7.92 (d, 1H, J=9.0 Hz), 8.39 (d, 1H, J=4.0 Hz), 8.48 (d, 1H, J=3.5 Hz), 10.16 (s, 1H) (three methyl protons signals not observed). HRMS (ESI) m/z [M+H]$^+$ 467.1668.

4-(3-(5-Fluoro-2-((1-methylpiperidin-4-yl)amino)pyrimidin-4-yl)imidazo[1,2-a]pyridin-6-yl)-N,N-dimethylbenzenesulfonamide (148)

4-(6-Bromoimidazo[1,2-a]pyridin-3-yl)-5-fluoro-N-(1-methylpiperidin-4-yl)pyrimidin-2-amine (100 mg, 0.25 mmol) and N,N-dimethyl-4-(4,4,5,5-tetramethyl-1,3,2-dioxaborolan-2-yl)benzenesulfonamide (78 mg, 0.25 mmol)

were reacted according to general synthetic procedure C. The product was further purified by preparative HPLC to give 148 as a yellow solid (110 mg, 86%). $^1$H-NMR (DMSO-$d_6$): δ 1.52 (br s, 4H), 1.85-1.93 (m, 2H), 2.03 (br s, 2H), 2.54-2.74 (s, 6H), 3.64 (br s, 1H), 7.37 (d, 1H, J=7.0 Hz), 7.86-8.00 (m, 4H), 8.06 (d, 2H, J=8.0 Hz), 8.40 (d, 1H, J=4.0 Hz), 8.47 (d, 1H, J=3.5 Hz), 10.24 (s, 1H) (three methyl protons signals not observed). HRMS (ESI) m/z [M+H]$^+$ 510.2088.

3-(5-Fluoro-2-((1-methylpiperidin-4-yl)amino)pyrimidin-4-yl)-N-(pyrimidin-5-yl)imidazo[1,2-a]pyridin-6-amine (149)

4-(6-Bromoimidazo[1,2-a]pyridin-3-yl)-5-fluoro-N-(1-methylpiperidin-4-yl)pyrimidin-2-amine (200 mg, 0.50 mmol) and pyrimidin-5-amine (48 mg, 0.50 mmol) were reacted according to general synthetic procedure B. The product was further purified by preparative HPLC to give 149 as a grey solid (65 mg, 31%). $^1$H-NMR (CDCl$_3$): δ 2.11-2.15 (m, 2H), 2.27-2.30 (m, 2H), 2.75 (s, 3H), 2.89 (br s, 2H), 3.47 (br s, 2H), 4.05 (br s, 1H), 7.37-7.39 (m, 1H), 7.76 (d, 1H, J=9.5 Hz), 8.16 (d, 1H, J=3.5 Hz), 8.40 (s, 1H), 8.44 (d, 1H, J=3.5 Hz), 8.55 (s, 2H), 8.76 (s, 1H), 10.06 (s, 1H) (one secondary amine proton (NH) not observed). HRMS (ESI) m/z [M+H]$^+$ 467.1668. HRMS (ESI) m/z [M+H]$^+$ 420.2061.

(1r,4r)-N$^1$-(5-Methyl-4-(6-phenyl-7-(trifluoromethyl)imidazo[1,2-a]pyridin-3-yl)pyrimidin-2-yl)cyclohexane-1,4-diamine (150)

(1r,4r)-N$^1$-(4-(6-Bromo-7-(trifluoromethyl)imidazo[1,2-a]pyridin-3-yl)-5-methylpyrimidin-2-yl)cyclohexane-1,4-diamine (100 mg, 0.21 mmol) and phenylboronic acid (26 mg, 0.21 mmol) were reacted according to general synthetic procedure C. The product was further purified by preparative HPLC to give 150 as a white solid (45 mg, 46%). $^1$H-NMR (CDCl$_3$): δ 1.08-1.22 (m, 2H), 1.29 (br s, 2H), 1.85-2.15 (m, 4H), 2.86-3.00 (m, 1H), 3.66 (br s, 1H), 5.13 (br s, 1H), 6.06 (br s, 4H), 7.36-7.48 (m, 5H), 8.16 (s, 1H), 8.20 (s, 1H), 8.22 (s, 1H), 9.37 (s, 1H) (two primary amine protons (NH$_2$) not observed. HRMS (ESI) m/z [M+H]$^+$ 467.2172.

5-Methyl-N-((11r,4r)-4-methylcyclohexyl)-4-(6-phenylimidazo[1,2-a]pyridin-3-yl)pyrimidin-2-amine (151)

4-(6-Bromoimidazo[1,2-a]pyridin-3-yl)-5-methyl-N-((1r,4r)-4-methylcyclohexyl)pyrimidin-2-amine (100 mg, 0.25 mmol) and phenylboronic acid (31 mg, 0.25 mmol) were reacted according to general synthetic procedure C. The product was further purified by preparative HPLC to give 151 as a white solid (60 mg, 61%). $^1$H-NMR (DMSO-$d_6$): δ 0.47 (br s, 1H), 0.62 (s, 4H), 1.05-1.25 (m, 3H), 1.39 (s, 2H), 1.89 (d, 2H, J=11.0 Hz), 2.36 (s, 3H), 3.53 (br s, 1H), 6.92 (d, 1H, J=7.5 Hz), 7.44 (t, 1H, J=7.0 Hz), 7.52 (t, 2H, J=7.5 Hz), 7.70-7.78 (m, 3H), 7.85 (d, 1H, J=9.0 Hz), 8.25 (s, 1H), 8.26 (s, 1H), 9.99 (s, 1H). HRMS (ESI) m/z [M+H]$^+$ 398.2345.

3-(5-Methyl-2-(((1r,4r)-4-methylcyclohexyl)amino) pyrimidin-4-yl)-N-(pyrimidin-5-yl) imidazo[1,2-a]pyridin-6-amine (152)

4-(6-Bromoimidazo[1,2-a]pyridin-3-yl)-5-methyl-N-((1r,4r)-4-methylcyclohexyl)pyrimidin-2-amine (200 mg, 0.50 mmol) and pyrimidin-5-amine (48 mg, 0.50 mmol) were reacted according to general synthetic procedure B. The product was further purified by preparative HPLC to give 152 as an orange solid (70 mg, 34%). $^1$H-NMR (DMSO-$d_6$): δ 0.64 (br s, 2H), 1.05-1.35 (m, 2H), 1.47 (br s, 2H), 1.86 (d, 2H, J=6.0 Hz), 2.34 (s, 3H), 3.19 (d, 3H, J=5.5 Hz), 3.50 (br s, 1H), 4.11 (q, 1H, J=5.5 Hz), 6.82 (br s, 1H), 7.42 (dd, 1H, J=9.5 & 2.0 Hz), 7.78 (d, 1H, J=9.5 Hz), 8.22 (d, 2H, J=11.5 Hz), 8.51 (s, 2H), 8.58 (s, 1H), 8.63 (s, 1H), 9.85 (br s, 1H). HRMS (ESI) m/z [M+H]$^+$ 415.2357.

2-(((1r,4r)-4-((5-Methyl-4-(6-(pyrimidin-5-ylamino) imidazo[1,2-a]pyridin-3-yl)pyrimidin-2-yl)amino) cyclohexyl)amino)acetamide (153) and 2,2'-(((1r,4r)-4-((5-Methyl-4-(6-(pyrimidin-5-ylamino)imidazo [1,2-a]pyridin-3-yl)pyrimidin-2-yl)amino) cyclohexyl)azanediyl)diacetamide (154)

A suspension of (1r,4r)-N$^1$-(5-methyl-4-(6-(pyrimidin-5-ylamino)imidazo[1,2-a]pyridin-3-yl)pyrimidin-2-yl)cyclohexane-1,4-diamine (100 mg, 0.24 mmol), 3-bromopropanamide (50 mg, 0.36 mmol) and K$_2$CO$_3$ (50 mg, 0.36 mmol) in DMF was stirred at room temperature overnight. The reaction mixture was concentrated under reduced pressure and purified by flash column chromatography starting with 100% DCM ramping to 8% MeOH+1% NH$_3$ (32% in water). The products were further purified by preparative HPLC to give: 153 as a yellow solid (30 mg, 26%). $^1$H-NMR (MeOD-$d_4$): δ 1.37-1.48 (m, 4H), 2.09-2.16 (m, 4H), 3.38 (s, 3H), 3.09 (t, 1H, J=12.5 Hz), 3.73-3.77 (m, 3H), 7.45 (dd, 1H, J=9.0 & 2.0 Hz), 7.71 (d, 1H, J=9.5 Hz), 8.14 (s, 1H), 8.22 (s, 1H), 8.34 (s, 2H), 8.60 (s, 2H), 8.64 (s, 1H), 9.76 (br s, 1H) (two primary amine protons (NH$_2$) and one secondary amine (NH) signals not observed). HRMS (ESI) m/z [M+H]$^+$ 473.2743. 154 as a brown solid (15 mg, 12%). $^1$H-NMR (MeOD-$d_4$): δ 1.15-1.40 (m, 4H), 1.70-1.92 (m, 2H), 2.00-2.15 (m, 2H), 2.38 (s, 3H), 2.45-2.62 (m, 1H), 3.16 (br s, 4H), 3.54-3.63 (m, 1H), 7.45 (dd, 1H, J=9.0 & 2.0 Hz), 7.72 (d, 1H, J=9.5 Hz), 8.16 (s, 1H), 8.19 (s, 1H), 8.57 (s, 2H), 8.63 (s, 1H), 9.86 (d, 1H, J=1.5 Hz) (four primary amine protons (NH$_2$) and two secondary amine protons (NH) signals not observed). HRMS (ESI) m/z [M+H]$^+$ 530.2741.

N-(4,4-Difluorocyclohexyl)-5-methyl-4-(6-phenylimidazo[1,2-a]pyridin-3-yl)pyrimidin-2-amine (155)

4-(6-Bromoimidazo[1,2-a]pyridin-3-yl)-N-(4,4-difluorocyclohexyl)-5-methylpyrimidin-2-amine (160 mg, 0.38 mmol) and phenylboronic acid (45 mg, 0.38 mmol) were reacted according to general synthetic procedure C. The product was further purified by preparative HPLC to give 155 as a white solid (65 mg, 41%). $^1$H-NMR (CDCl$_3$): δ 1.35-1.55 (m, 2H), 1.50-1.62 (m, 2H), 1.80-1.95 (m, 2H), 1.95-2.10 (m, 2H), 2.42 (s, 3H), 3.80-3.92 (m, 1H), 5.35 (br s, 1H), 7.41-7.46 (m, 1H), 7.46-7.52 (m, 2H), 7.54-7.59 (m, 2H), 7.61 (dd, 1H, J=2.0 & 9.5 Hz), 7.82 (dd, 1H, J=1.0 & 9.5 Hz), 8.18 (s, 1H), 8.20 (s, 1H), 9.93 (s, 1H). HRMS (ESI) m/z [M+H]$^+$ 420.1998.

N-(4,4-Difluorocyclohexyl)-4-(imidazo[1,2-a]pyridin-3-yl)-5-methylpyrimidin-2-amine (156)

4-(6-Bromoimidazo[1,2-a]pyridin-3-yl)-N-(4,4-difluorocyclohexyl)-5-methylpyrimidin-2-amine (240 mg, 0.57 mmol) and pyrimidin-5-amine (55 mg, 0.57 mmol) were reacted according to general synthetic procedure B. The product was further purified by preparative HPLC to give 156 as a white solid (30 mg, 15%). $^1$H-NMR (CDCl$_3$): δ 1.65-1.75 (m, 2H), 1.83-2.03 (m, 2H), 2.10-2.23 (m, 4H), 2.34 (s, 3H), 3.95-4.05 (m, 1H), 4.94 (d, 1H, J=7.5 Hz), 6.94 (dt, 1H, J=7.0 & 1.0 Hz), 7.33-7.39 (m, 1H), 7.74 (d, 1H, J=9.0 Hz), 8.14 (s, 1H), 8.23 (s, 1H), 9.66 (d, 1H, J=7.0 Hz). HRMS (ESI) m/z [M+H]$^+$ 344.1688.

Methyl (1r,4r)-4-((5-methyl-4-(6-(pyrimidin-5-ylamino)imidazo[1,2-a]pyridin-3-yl)pyrimidin-2-yl)amino)cyclohexane-1-carboxylate (157)

Methyl (1r,4r)-4-((4-(6-bromoimidazo[1,2-a]pyridin-3-yl)-5-methylpyrimidin-2-yl)amino)cyclohexane-1-carboxylate (600 mg, 1.35 mmol) and pyrimidin-5-amine (130 mg, 1.35 mmol) were reacted according to general synthetic procedure B. The product was further purified by preparative HPLC to give 157 as an orange solid (200 mg, 32%). $^1$H-NMR (MeOD-d$_4$): δ 1.27-1.31 (m, 4H), 1.85-2.00 (m, 2H), 2.00-2.15 (m, 2H), 2.20-2.35 (m, 1H), 2.40 (s, 3H), 3.62-3.70 (m, 4H), 7.47 (dd, 1H, J=9.0 & 2.0 Hz), 7.73 (d, 1H, J=9.5 Hz), 8.19 (s, 1H), 8.20 (s, 1H), 8.51 (s, 2H), 8.61 (s, 1H), 9.98 (s, 1H) (two secondary amine protons (NH) signals not observed). HRMS (ESI) m/z [M+H]$^+$ 459.2258.

(1r,4r)-4-((5-Methyl-4-(6-(pyrimidin-5-ylamino)imidazo[1,2-a]pyridin-3-yl)pyrimidin-2-yl)amino)cyclohexane-1-carboxylic acid (158)

A solution of methyl (1r,4r)-4-((5-methyl-4-(6-(pyrimidin-5-ylamino)imidazo[1,2-a]pyridin-3-yl)pyrimidin-2-yl)amino)cyclohexane-1-carboxylate (135 mg, 0.29 mmol) in 2M NaOH (8 mL) and MeOH (8 mL) was stirred at room temperature overnight. The reaction mixture was washed with DCM (2×100 mL). The aqueous phase was acidified to pH 3. The resulting precipitate was filtered, and purified by preparative HPLC to give 158 as a yellow solid (50 mg, 39%). $^1$H-NMR (DMSO-d$_6$): δ 0.90-1.40 (m, 4H), 1.60-2.10 (m, 4H), 2.07 (s, 1H), 2.34 (s, 3H), 3.53 (br s, 1H), 6.82 (s, 1H), 7.39 (d, 1H, J=8.5 Hz), 7.76 (d, 1H, J=9.5 Hz), 8.19 (s, 1H), 8.25 (s, 1H), 8.54 (s, 2H), 8.59 (s, 1H), 8.64 (s, 1H), 9.81 (s, 1H), 12.05 (br s, 1H). HRMS (ESI) m/z [M+H]$^+$ 445.2099.

(1r,4r)-N$^1$-(4-(7-Fluoro-6-phenylimidazo[1,2-a]pyridin-3-yl)-5-methylpyrimidin-2-yl)cyclohexane-1,4-diamine (159)

(1r,4r)-N$^1$-(4-(6-Bromo-7-fluoroimidazo[1,2-a]pyridin-3-yl)-5-methylpyrimidin-2-yl)cyclohexane-1,4-diamine (100 mg, 0.24 mmol) and phenylboronic acid (29 mg, 0.24 mmol) were reacted according to general synthetic procedure C. The product was further purified by preparative HPLC to give 159 as a white solid (20 mg, 20%). $^1$H-NMR (CDCl$_3$): δ 1.17-1.21 (m, 4H), 1.92 (br s, 2H), 2.09-2.11 (m, 2H), 2.37 (s, 3H), 2.88 (br s, 1H), 3.72 (br s, 1H), 5.11 (br s, 1H), 7.45-7.53 (m, 6H), 8.10 (s, 1H), 8.18 (s, 1H), 9.68 (d, 1H, J=7.5 Hz) (two primary amine protons (NH$_2$) signals not observed). HRMS (ESI) m/z [M+H]$^+$ 417.2204.

(1r,4r)-N$^1$-(5-Fluoro-4-(6-phenylimidazo[1,2-a]pyridin-3-yl)pyrimidin-2-yl)-N$^4$-(1-methylpiperidin-4-yl)cyclohexane-1,4-diamine (160)

(1r,4r)-N$^1$-(5-Fluoro-4-(6-phenylimidazo[1,2-a]pyridin-3-yl)pyrimidin-2-yl)cyclohexane-1,4-diamine (100 mg, 0.25 mmol) and 1-methylpiperidin-4-one (29 μL, 0.25 mmol) were reacted according to general synthetic procedure D. The product was further purified by preparative HPLC to give 160 as a yellow sticky liquid (50 mg, 40%). $^1$H-NMR (CDCl$_3$): δ 0.82-0.89 (m, 2H), 1.16-1.25 (m, 2H), 1.75-1.83 (m, 4H), 2.01-2.04 (m, 2H), 2.17-2.19 (m, 2H), 2.54-2.67 (m, 5H), 2.88 (br s, 2H), 3.23 (br s, 2H), 3.71 (s, 1H), 5.08 (br s, 1H), 7.44 (t, 1H, J=7.5 Hz), 7.53 (t, 2H, J=7.5 Hz), 7.61-7.64 (m, 3H), 7.85 (d, 1H, J=9.0 Hz), 8.20 (d, 1H, J=3.5 Hz), 8.50 (d, 1H, J=3.5 Hz), 10.19 (s, 1H) (one secondary amine proton (NH) not observed). HRMS (ESI) m/z [M+H]$^+$ 500.2938.

(1r,4r)-N$^1$-(5-fluoro-4-(6-phenylimidazo[1,2-a]pyridin-3-yl)pyrimidin-2-yl)-N$^4$-(tetrahydro-2H-pyran-4-yl)cyclohexane-1,4-diamine (161)

(1r,4r)-N$^1$-(5-Fluoro-4-(6-phenylimidazo[1,2-a]pyridin-3-yl)pyrimidin-2-yl)cyclohexane-1,4-diamine (100 mg, 0.25 mmol) and tetrahydro-4H-pyran-4-one (23 μL, 0.25 mmol) were reacted according to general synthetic procedure D. The product was further purified by preparative HPLC to give 161 as a yellow solid (55 mg, 45%). $^1$H-NMR (CDCl$_3$): δ 1.21-1.34 (m, 4H), 1.73-1.80 (m, 2H), 1.85-1.88 (m, 2H), 1.99-2.01 (m, 2H), 2.22-2.24 (m, 2H), 2.92 (br s, 1H), 3.06 (br s, 1H), 3.35-3.40 (m, 2H), 3.76 (br s, 1H), 4.01-4.04 (m, 2H), 4.99 (s, 1H), 7.45 (t, 1H, J=7.0 Hz), 7.54 (t, 2H, J=7.0 Hz), 7.61-7.64 (m, 3H), 7.84 (d, 1H, J=9.5 Hz), 8.21 (d, 1H, J=3.5 Hz), 8.47 (d, 1H, J=4.0 Hz), 10.09 (s, 1H) (one secondary amine proton (NH) not observed). HRMS (ESI) m/z [M+H]$^+$ 487.2622.

N-(1-(Ethylsulfonyl)piperidin-4-yl)-5-fluoro-4-(6-phenylimidazo[1,2-a]pyridin-3-yl)pyrimidin-2-amine (163)

To a solution of 5-fluoro-4-(6-phenylimidazo[1,2-a]pyridin-3-yl)-N-(piperidin-4-yl)pyrimidin-2-amine (92 mg, 0.24 mmol) and triethylamine (32 μL, 0.36 mmol) in DCM (10 mL) cooled on an ice bath was added ethanesulfonyl chloride (68 μL, 0.72 mmol). The reaction was stirred overnight, concentrated under reduced pressure and purified by flash column chromatography starting with 100% DCM ramping to 3% MeOH to give 163 as a yellow solid (65 mg, 56%). $^1$H-NMR (DMSO-d$_6$): δ 1.17 (t, 3H, J=7.0 Hz), 1.47-1.51 (m, 2H), 1.97 (d, 2H, J=10.5 Hz), 2.82 (br s, 2H), 3.45 (br s, 2H), 3.82 (br s, 1H), 7.44-7.49 (m, 2H), 7.58 (t, 2H, J=7.5 Hz), 7.78 (d, 2H, J=7.5 Hz), 7.82-7.85 (m, 1H), 7.92 (d, 1H, J=9.0 Hz), 8.39 (d, 1H, J=3.5 Hz), 8.47 (d, 1H, J=3.5 Hz), 10.16 (s, 1H). HRMS (ESI) m/z [M+H]$^+$ 481.1822.

(1r,4r)-4-((5-Chloro-4-(6-(4-fluorophenyl)imidazo[1,2-a]pyridin-3-yl)pyrimidin-2-yl)amino)cyclohexan-1-ol (165)

(1r,4r)-4-((4-(6-Bromoimidazo[1,2-a]pyridin-3-yl)-5-chloropyrimidin-2-yl)amino)cyclohexan-1-ol (150 mg, 0.36 mmol) and (4-fluorophenyl)boronic acid (50 mg, 0.36 mmol) were reacted according to general synthetic procedure C to give 165 as a white solid (115 mg, 73%). $^1$H-NMR (DMSO-d$_6$): δ 0.73 (br s, 1H), 1.27 (br s, 3H), 1.57 (br s, 1H), 1.86 (br s, 3H), 3.22 (br s, 1H), 3.56 (br s, 1H), 4.38 (s, 1H), 7.33-7.36 (m, 2H), 7.46 (s, 1H), 7.79-7.82 (m, 3H), 7.87 (d, 1H, J=9.0 Hz), 8.44 (s, 1H), 8.56 (s, 1H), 9.81 (s, 1H). HRMS (ESI) m/z [M+H]$^+$ 438.1498.

(1r,4r)-4-((5-Chloro-4-(6-(pyridin-3-yl)imidazo[1,2-a]pyridin-3-yl)pyrimidin-2-yl)amino)cyclohexan-1-ol (166)

(1r,4r)-4-((4-(6-Bromoimidazo[1,2-a]pyridin-3-yl)-5-chloropyrimidin-2-yl)amino)cyclohexan-1-ol (150 mg, 0.36 mmol) and pyridin-3-ylboronic acid (44 mg, 0.36 mmol) were reacted according to general synthetic procedure C to give 166 as a white solid (95 mg, 63%). $^1$H-NMR (DMSO-$d_6$): δ 0.68 (br s, 1H), 1.24-1.27 (m, 3H), 1.51 (br s, 1H), 1.85-1.93 (m, 3H), 3.22 (br s, 1H), 3.56 (br s, 1H), 4.33 (s, 1H), 7.48 (s, 1H), 7.53-7.56 (m, 1H), 7.87-7.93 (m, 2H), 8.20 (d, 1H, J=7.5 Hz), 8.45 (s, 1H), 8.58 (s, 1H), 8.63-8.65 (m, 1H), 9.00 (s, 1H), 9.89 (s, 1H). HRMS (ESI) m/z [M+H]$^+$ 421.1544.

(1r,4r)-4-((5-Chloro-4-(6-(6-methoxypyridin-3-yl)imidazo[1,2-a]pyridin-3-yl)pyrimidin-2-yl)amino)cyclohexan-1-ol (167)

(1r,4r)-4-((4-(6-Bromoimidazo[1,2-a]pyridin-3-yl)-5-chloropyrimidin-2-yl)amino)cyclohexan-1-ol (500 mg, 1.19 mmol) and (6-methoxypyridin-3-yl)boronic acid (182 mg, 1.19 mmol) were reacted according to general synthetic procedure C to give 167 as a white solid (430 mg, 80%). $^1$H-NMR (DMSO-$d_6$): δ 0.75 (br s, 1H), 1.28 (br s, 3H), 1.56 (br s, 1H), 1.87 (br s, 3H), 3.28 (br s, 1H), 3.57 (br s, 1H), 3.93 (s, 3H), 4.33 (s, 1H), 6.97 (d, 1H, J=8.5 Hz), 7.47 (s, 1H), 7.81-7.90 (m, 2H), 8.11 (d, 1H, J=7.5 Hz), 8.44 (s, 1H), 8.59 (s, 1H), 9.89 (s, 1H) (one secondary amine proton (NH) not observed). HRMS (ESI) m/z [M+H]$^+$ 451.1650.

4-(4-((5-Methyl-4-(6-(pyrimidin-5-ylamino)imidazo[1,2-a]pyridin-3-yl)pyrimidin-2-yl)amino)cyclohexyl)piperazin-2-one (168)

4-((5-Methyl-4-(6-(pyrimidin-5-ylamino)imidazo[1,2-a]pyridin-3-yl)pyrimidin-2-yl)amino)cyclohexan-1-one (200 mg, 0.48 mmol) and piperazin-2-one (48 mg, 0.48 mmol) were reacted according to general synthetic procedure D. The product was further purified by preparative HPLC to give 168 as a yellow solid (30 mg, 13%). $^1$H-NMR (MeOD-$d_4$): δ 1.26-1.36 (m, 2H), 1.59 (br s, 2H), 1.74-1.76 (m, 1H), 1.87-1.88 (m, 2H), 2.12-2.14 (m, 1H), 2.36 (br s, 1H), 2.42 (s, 3H), 2.66 (s, 1H), 2.77-2.80 (m, 1H), 3.19 (s, 1H), 3.28 (s, 1H), 3.28-3.30 (m, 1H), 3.66-3.69 (m, 1H), 3.90-3.92 (m, 1H), 7.47-7.52 (m, 1H), 7.75 (d, 1H, J=9.5 Hz), 8.21-8.24 (m, 2H), 8.58 (s, 2H), 8.65 (s, 1H), 9.94 (s, 1H) (three secondary amine proton (NH) signals not observed). HRMS (ESI) m/z [M+H]$^+$ 499.2682.

1-Methyl-3-((1r,4r)-4-((5-methyl-4-(6-phenylimidazo[1,2-a]pyridin-3-yl)pyrimidin-2-yl)amino)cyclohexyl)urea (169)

A solution of (1r,4r)-N$^1$-(5-Methyl-4-(6-phenylimidazo[1,2-a]pyridin-3-yl)pyrimidin-2-yl)cyclohexane-1,4-diamine (50 mg, 0.13 mmol), methylcarbamic chloride (18 mg, 0.15 mmol) and Triethylamine (35 μL, 0.25 mmol) in DCM (10 mL) was stirred at room temperature for 2 h. The reaction mixture was purified by preparative HPLC to give 169 as a yellow solid (40 mg, 68%). $^1$H-NMR (DMSO-$d_6$): δ 0.86 (br s, 2H), 1.25-1.34 (m, 2H), 1.64 (br s, 2H), 1.89-1.91 (m, 2H), 2.34 (s, 3H), 3.18 (br s, 1H), 3.32 (br s, 1H), 3.67 (br s, 1H), 5.64 (d, 1H, J=4.5 Hz), 6.96 (d, 1H, J=8.0 Hz), 7.46 (t, 1H, J=7.5 Hz), 7.53 (t, 2H, J=7.0 Hz), 7.73-7.78 (m, 2H), 7.85 (d, 1H, J=9.0 Hz), 8.16 (s, 1H), 8.23 (s, 1H), 8.28 (s, 1H), 9.82 (s, 1H). HRMS (ESI) m/z [M+H]$^+$ 456.2510.

5-Fluoro-4-(7-phenylimidazo[1,2-a]pyridin-3-yl)-N-(piperidin-4-yl)pyrimidin-2-amine (170)

4-(7-Chloroimidazo[1,2-a]pyridin-3-yl)-5-fluoro-N-(piperidin-4-yl)pyrimidin-2-amine (147 mg, 0.42 mmol) and 4,4,5,5-tetramethyl-2-phenyl-1,3,2-dioxaborolane (86 mg, 0.42 mmol) were reacted according to general synthetic procedure C. The product was further purified by preparative HPLC to give 170 as a white solid (100 mg, 61%). $^1$H-NMR (DMSO-$d_6$): δ 1.50-1.54 (m, 2H), 2.03-2.05 (m, 2H), 3.11-3.16 (m, 2H), 3.28-3.33 (m, 1H), 4.61-4.63 (m, 2H), 7.49 (t, 1H, J=7.5 Hz), 7.56 (t, 2H, J=7.5 Hz), 7.72-7.74 (m, 1H), 7.95 (d, 1H, J=7.5 Hz), 8.18 (s, 1H), 8.35 (s, 1H), 8.42 (d, 1H, J=3.5 Hz), 8.54 (d, 1H, J=3.5 Hz), 9.81 (d, 1H, J=7.5 Hz) (two secondary amine protons (NH) signals not observed). HRMS (ESI) m/z [M+H]$^+$ 389.1888.

5-Fluoro-N-(1-(methylsulfonyl)piperidin-4-yl)-4-(7-phenylimidazo[1,2-a]pyridin-3-yl)pyrimidin-2-amine (171)

To a solution of 5-fluoro-4-(7-phenylimidazo[1,2-a]pyridin-3-yl)-N-(piperidin-4-yl)pyrimidin-2-amine (70 mg, 0.18 mmol) and triethylamine (24 μL, 0.27 mmol) in DCM (10 mL) cooled on an ice bath was added methanesulfonyl chloride (32 μL, 0.55 mmol). The reaction was stirred overnight, concentrated under reduced pressure and purified by flash column chromatography starting with 100% DCM ramping to 3% MeOH. The product was further purified by preparative HPLC to give 171 as a yellow solid (55 mg, 66%). $^1$H-NMR (DMSO-$d_6$): δ 1.47-1.54 (m, 2H), 1.99-2.02 (m, 2H), 2.99 (s, 3H), 3.22-3.27 (m, 2H), 3.52-3.54 (m, 1H), 4.48-4.51 (m, 2H), 7.19 (d, 1H, J=7.0 Hz), 7.49 (t, 1H, J=7.5 Hz), 7.57 (t, 2H, J=7.5 Hz), 7.73-7.75 (m, 1H), 7.95-7.97 (m, 2H), 8.18 (d, 1H, J=1.5 Hz), 8.42 (d, 1H, J=3.5 Hz), 8.53 (d, 1H, J=3.5 Hz), 9.82 (d, 1H, J=7.5 Hz). HRMS (ESI) m/z [M+H]$^+$ 467.1666.

1-Methyl-3-((1r,4r)-4-((5-methyl-4-(6-(pyrimidin-5-ylamino)imidazo[1,2-a]pyridin-3-yl)pyrimidin-2-yl)amino)cyclohexyl)urea (172)

(1r,4r)-N$^1$-(5-methyl-4-(6-(pyrimidin-5-ylamino)imidazo[1,2-a]pyridin-3-yl)pyrimidin-2-yl)cyclohexane-1,4-diamine (128 mg, 0.31 mmol), methylcarbamic chloride (44 mg, 0.46 mmol) and Triethylamine (130 μL, 0.93 mmol) in DCM (10 mL) was stirred at room temperature for 2 h. The resulting solid was filtered, washed with H$_2$O and MeOH to give 172 as a beige solid (100 mg, 68%). $^1$H-NMR (DMSO-$d_6$): δ 0.84 (br s, 2H), 1.10-1.17 (m, 2H), 1.63-1.85 (m, 4H), 2.33 (s, 1H), 2.55 (d, 3H, J=4.5 Hz), 3.26 (br s, 1H), 3.53-3.59 (m, 1H), 5.64 (br s, 2H), 6.68 (s, 1H), 7.40 (d, 1H, J=9.0 Hz), 7.76 (d, 1H, J=9.5 Hz), 8.18 (s, 1H), 8.25 (s, 1H), 8.55-8.57 (m, 3H), 8.66 (s, 1H), 9.76 (s, 1H) (two secondary amine proton (NH) signals not observed). HRMS (ESI) m/z [M+H]$^+$ 473.2528

Example 2 Biological Activity

Kinase Assays

Eurofins Pharma Discovery or Reaction Biology Corporation Kinase Profiler services were used to measure inhibition of CDKs and other kinases by radiometric assay.

Inhibition of CDK4/D1, CDK6/D3 and CDK9/T1 were also determined in-house using ADP Glo Kinase assays (Promega Corporation, Madison, USA). Briefly, the kinase reaction for CDK4/D1 and CDK6/D3 was performed with kinase reaction buffer (40 nM Tris base pH 7.5, 20 mM $MgCl_2$, 0.4 mM DTT), 0.1 mg/ml BSA and RB-CTF substrate (retinoblastoma protein 1 C-terminal fraction). For CDK9/CyclinT1, the kinase reaction was performed with standard assay buffer and Kinase Dilution Buffer and RBER-IRStide substrate. Serial dilutions of 1:3 were prepared for test compounds for 10 concentrations (from 10 µM to 0.5 nM). The kinase reactions were started by addition of ATP, incubated for 40 min at 37° C. and then stopped by adding 10 µL of ADP Glo reagent. After incubation at room temperature in the dark for 40 min, 20 µL of kinase detection reagent was added per well and incubated for 40 min. Luminescence was measured using an EnVision Multilabel plate reader (PerkinElmer, Buckinghamshire, UK). Positive and negative controls were performed in the presence and absence of CDK kinases, respectively. Half-maximal inhibition ($IC_{50}$) values were calculated using a 4-parameter logistic non-linear regression model with Graphpad prism (Version 6.0). Apparent inhibition constants ($K_i$) values were calculated from $K_m$ (ATP) and $IC_{50}$ values for the respective kinases. The results are shown in Table 2.

Cell Viability Assay

Compounds from Example 1 were subjected to a standard MTT (3-(4,5-dimethylthiazol-2-yl)-2,5-diphenyltetrazolium bromide) and resazurin assays on solid tumour cell lines and leukemia cell lines, respectively, as previously reported (Wang S et al., *J Med Chem* 47:1662-1675, 2004 and Diab S. et al. *CheMedChem* 9:962-972, 2014). Compound concentrations required to inhibit 50% of cell growth ($GI_{50}$) were calculated using non-linear regression analysis. The results are shown in Tables 2 and 3.

TABLE 2

Inhibition of cyclin-dependant kinases and anti-proliferative activity (72 h, $GI_{50}$ µM) of representative compounds

| | CDK inhibition, $K_i$ (µM)/ or residual activity (%) at 10 µM | | | | | | 72 h Growth inhibition $GI_{50}$ (µM) |
|---|---|---|---|---|---|---|---|
| Cmpd | CDK1B | CDK2A | CDK4D1 | CDK6D3 | CDK7H | CDK9T1 | MV4-11 |
| 1 | 0.077 | 0.018 | 0.025 | 23% | 0.026 | 0.006 | 0.046 ± 0.005 |
| 2 | 0.085 | 0.012 | — | 5% | 0.034 | 0.005 | 0.006 ± 0.001 |
| 3 | 0.084 | 0.023 | 0% | 46% | 0.019 | 0.006 | <0.001 |
| 4 | 1% | 2% | 0% | 2% | — | 0.003 | 0.004 ± 0.001 |
| 5 | 0.014 | 0.006 | 0% | 16% | 0.075 | 0.002 | 0.003 ± 0.001 |
| 6 | 0.013 | 0.009 | 11% | 16% | 0.016 | 0.003 | 0.002 ± 0.0005 |
| 7 | 0.42 | 0.24 | 0.691 | 1.71 | 0.73 | 0.006 | 0.075 ± 0.011 |
| 8 | 3.81 | 0.35 | 11% | 34% | 0.38 | 0.035 | 0.066 ± 0.007 |
| 9 | 0.266 | 0.08 | 45% | 58% | 0.23 | 0.009 | 0.008 ± 0.002 |
| 10 | 1.53 | 0.43 | 2.62 | 1.54 | 0.60 | 0.008 | 0.059 ± 0.008 |
| 11 | 75% | 63% | 40% | 27% | 26% | 0.291 | 0.009 ± 0.001 |
| 12 | 0.121 | 0.013 | 4% | 41% | 0.032 | 0.008 | 0.006 ± 0.001 |
| 13 | 0.329 | 0.063 | 0% | 59% | 0.052 | 0.024 | 0.022 ± 0.002 |
| 14 | 0.755 | 0.115 | 3% | 17% | 0.040 | 0.007 | 0.368 ± 0.129 |
| 15 | 0.070 | 0.027 | 0% | 13% | 0.15 | 0.014 | 0.050 ± 0.009 |
| 16 | 0.000 | 0.001 | — | 32% | 50% | 0.029 | 0.010 ± 0.001 |
| 17 | 0.004 | 0.0004 | 1% | 26% | 0.001 | 0.062 | <0.001 |
| 18 | 0.028 | 0.007 | 9% | 41% | 0.001 | 0.148 | 6.108 ± 1.141 |
| 19 | 0.795 | 0.527 | 0.004 | — | 0.27 | 0.078 | 0.084 ± 0.008 |
| 20 | 56% | 54% | 29% | — | 1.75 | 0.829 | 0.092 ± 0.010 |
| 21 | 0.479 | 0.321 | -11% | — | 0.60 | 0.069 | 0.003 ± 0.001 |
| 22 | 1.06 | 1.12 | 2% | 42% | 0.437 | 0.095 | 0.041 ± 0.012 |
| 23 | 0.258 | 0.155 | 0% | 39% | 0.885 | 0.063 | 0.280 ± 0.049 |
| 24 | -1% | -1% | -16% | 18% | 0.281 | 0.141 | 0.506 ± 0.104 |
| 25 | 3% | 2% | 4% | 4% | 1% | 0.003 | <0.001 |
| 26 | 7% | 5% | 9% | 24% | 0% | 0.003 | <0.001 |
| 27 | -1% | 4% | 4% | 15% | 2% | 0.003 | <0.001 |
| 28 | 4% | 8% | 95% | 100% | 2% | 0.85 | 0.042 ± 0.017 |
| 29 | 3.57 | 1.83 | 17% | 45% | 2.73 | 0.051 | 0.101 ± 0.039 |
| 30 | 67% | 49% | 17% | 39% | 13% | 0.12 | 0.017 ± 0.006 |
| 31 | 32% | 145 | 45 | 11% | 13% | 0.018 | 0.005 ± 0.002 |
| 32 | >10 | 0.63 | 16% | 36% | 5.39 | 0.094 | 0.066 ± 0.014 |
| 33 | 11% | 13% | 7% | 12% | 7% | 0.022 | 0.004 ± 0.001 |
| 34 | 2.16 | 0.09 | 2.80 | 1.05 | 2.24 | 0.005 | 0.095 ± 0.031 |
| 35 | 0.88 | 0.26 | 0.79 | 0.394 | 0.27 | 0.007 | 0.011 ± 0.002 |
| 36 | 0.065 | 0.016 | 4% | 48% | 0.094 | 0.016 | 0.004 ± 0.001 |
| 37 | 0.17 | 0.044 | 7% | 96% | 1.18 | 0.12 | 0.013 ± 0.002 |
| 38 | 2.56 | 0.91 | 0% | 80% | 0.58 | 0.065 | 0.052 ± 0.011 |
| 39 | 7.36 | 4.74 | 36% | 100% | 5.60 | 0.165 | 0.082 ± 0.020 |
| 40 | 0.88 | 0.73 | 30% | 72% | 0.038 | 0.014 | 0.005 ± 0.001 |
| 41 | 2.66 | 0.059 | 40% | 55% | 0.958 | 0.045 | 0.013 ± 0.002 |
| 42 | 0.460 | 0.046 | 0% | 45% | 0.024 | 0.061 | 0.007 ± 0.001 |
| 43 | 4% | 1% | 0% | 2% | 3% | 0.008 | 0.004 ± 0.001 |
| 44 | 0% | 0% | 2% | 1% | 2% | 0.007 | <0.001 |
| 45 | 0% | 0% | 5% | 0% | 2% | 0.006 | <0.001 |
| 46 | 0% | 0% | 0% | 1% | 3% | 0.004 | <0.001 |
| 47 | 5% | 2% | 4% | 16% | 0.075 | 0.004 | 0.003 ± 0.001 |
| 48 | 13% | 3% | 4% | 45% | 8% | 0.004 | 0.002 ± 0.000 |
| 49 | 1% | 0% | 0% | 5% | 3% | 0.003 | — |

TABLE 2-continued

Inhibition of cyclin-dependant kinases and anti-proliferative activity (72 h, $GI_{50}$ μM) of representative compounds

| | CDK inhibition, $K_i$ (μM)/ or residual activity (%) at 10 μM | | | | | | 72 h Growth inhibition $GI_{50}$ (μM) |
|---|---|---|---|---|---|---|---|
| Cmpd | CDK1B | CDK2A | CDK4D1 | CDK6D3 | CDK7H | CDK9T1 | MV4-11 |
| 50 | 1% | 0% | 14% | 4% | 4% | 0.003 | — |
| 51 | 4% | 4% | 0% | 22% | 6% | 0.006 | 0.001 ± 0.000 |
| 52 | 6% | 7% | 4% | 21% | 6% | 0.013 | 0.008 ± 0.003 |
| 53 | 18% | 3% | 0% | 0% | 5% | 0.049 | 0.002 ± 0.001 |
| 54 | 29% | 5% | 0% | 0% | 6% | 0.110 | 0.018 ± 0.004 |
| 55 | 24% | 5% | 5% | 2% | 8% | 0.069 | 0.558 ± 0.130 |
| 56 | 39% | 12% | 0% | 5% | 22% | 0.051 | — |
| 57 | 47% | 31% | 45% | 39% | 17% | 0.069 | 0.067 ± 0.014 |
| 58 | 71% | 70% | 69% | 86% | 22% | 0.17 | 0.177 ± 0.005 |
| 59 | 2.68 | 0.92 | 55% | 91% | 2.39 | 0.072 | 0.274 ± 0.064 |
| 60 | 57% | 62% | 115 | 89% | 37% | 0.41 | 0.057 ± 0.006 |
| 61 | 79% | 63% | 17% | 89% | 37% | 0.49 | 0.083 ± 0.035 |
| 62 | 87% | 72% | 63% | 87% | 60% | 0.497 | 0.025 ± 0.009 |
| 63 | 18% | 6% | 38% | 29% | 18% | 0.054 | 0.095 ± 0.031 |
| 64 | 2.37 | 0.59 | 1% | 38% | 1.44 | 0.016 | 0.155 ± 0.054 |
| 65 | 32% | 12% | 125 | 24% | 31% | 0.024 | — |
| 66 | 1.26 | 0.18 | 0.76 | 0.33 | 3.25 | 0.007 | — |
| 67 | 38% | 10% | 31% | 29% | 52% | 0.017 | 0.128 ± 0.04 |
| 68 | 2.18 | 0.35 | 37% | 23% | 0.71 | 0.033 | 0.127 ± 0.002 |
| 69 | 2.95 | 0.61 | 24% | 25% | 0.95 | 0.023 | 0.199 ± 0.02 |
| 70 | 4.32 | 1.42 | 31% | 70% | 3.28 | 0.62 | 0.212 ± 0.104 |
| 71 | 6.05 | 2.66 | 35% | 66% | 5.19 | 0.203 | 0.383 ± 0.119 |
| 72 | 69% | 52% | 77% | 85% | 57% | 0.194 | 1.457 ± 0.476 |
| 73 | 75% | 62% | 53% | 49% | 63% | 0.469 | 0.752 ± 0.055 |
| 74 | 39% | 11% | 41% | 46% | 50% | 0.020 | 0.349 ± 0.086 |
| 75 | 52% | 22% | 41% | 46% | 50% | 0.034 | — |
| 76 | 72% | 59% | 91% | 89% | 92% | 0.485 | — |
| 77 | 5% | 0% | 5% | 6% | 3% | 0.011 | — |
| 78 | 7% | 0% | 10% | 3% | 3% | 0.019 | — |
| 79 | 0.27 | 0.071 | 13% | 80% | 0.079 | 0.004 | 0.008 ± 0.001 |
| 80 | — | — | 61% | 54% | — | 0.200 | 0.243 ± 0.053 |
| 81 | 2.01 | 0.51 | 1.58 | 1.01 | 0.21 | 0.008 | 0.025 ± 0.011 |
| 82 | 0.82 | 0.22 | 20% | 99% | 0.15 | 0.018 | 0.054 ± 0.015 |
| 83 | 2.56 | 0.91 | 27% | 80% | 0.58 | 0.065 | 0.052 ± 0.011 |
| 84 | 51% | 39% | 9% | 12% | 10% | 0.033 | 0.035 ± 0.006 |
| 85 | 7.44 | 0.77 | 75% | 43% | 0.048 | 0.13 | 1.324 ± 0.549 |
| 86 | 2.64 | 0.25 | 25% | 47% | 0.044 | 0.216 | 0.086 ± 0.005 |
| 87 | 31% | 19% | 73% | 39% | 14% | 0.073 | 0.135 ± 0.057 |
| 88 | 0.16 | 0.019 | 0.06 | 0.034 | 1.26 | 0.002 | — |
| 89 | 10% | 7% | 21% | 225 | 12% | 0.027 | 0.003 ± 0.001 |
| 90 | 57% | 44% | 24% | 80% | 295 | 0.211 | 0.229 ± 0.015 |
| 91 | 5% | 7% | 17% | 41% | 19% | 0.082 | 0.014 ± 0.007 |
| 92 | 22% | 27% | 37% | 58% | 27% | 0.089 | 0.179 ± 0.061 |
| 93 | 35% | 31% | 28% | 69% | 49% | 0.071 | 0.336 ± 0.082 |
| 94 | 20% | 12% | 25% | 45% | 10% | 0.388 | 0.748 ± 0.063 |
| 95 | 59% | 28% | 76% | 76% | 33% | 0.198 | 0.646 ± 0.129 |
| 96 | 63% | 37% | 49% | 90% | 63% | 0.193 | >10 |
| 97 | 28% | 32% | 54% | 39% | 9% | 0.016 | 0.058 ± 0.002 |
| 98 | 1.50 | 0.31 | 0.78 | 0.53 | 1.67 | 0.004 | 0.153 ± 0.021 |
| 99 | 1.66 | 0.48 | 1.16 | 0.51 | 3.10 | 0.006 | 0.265 ± 0.034 |
| 100 | 87% | 79% | 96% | 84% | 98% | >5 | >10 |
| 101 | 60% | 41% | 97% | 100% | 85% | 0.561 | >10 |
| 102 | 36% | 22% | 73% | 100% | 85% | 0.109 | 0.059 ± 0.019 |
| 103 | 4% | 1% | 30% | 45% | 40% | 0.203 | >10 |
| 104 | 4% | 2% | 70% | 73% | 57% | 0.155 | 4.76 ± 1.16 |
| 105 | 7% | 3% | 93% | 94% | 15% | 0.188 | 0.748 ± 0.063 |
| 106 | 5% | 2% | 43% | 71% | 25% | 0.042 | 0.851 ± 0.048 |
| 107 | 47% | 5% | 37% | 54% | 34% | 0.161 | 1.416 ± 0.652 |
| 108 | 0.16 | 0.035 | 70% | 68% | 4.76 | 0.018 | >10 |
| 109 | 1.26 | 0.18 | 0.94 | 0.21 | >10 | 0.008 | — |
| 110 | 66% | 61% | 99% | 100% | 87% | >5 | — |
| 111 | 20% | 11% | 29% | 89% | 86% | 0.108 | — |
| 112 | 1.73 | 0.49 | >5 | 45% | >5 | 0.205 | 2.55 ± 1.70 |
| 113 | 0.82 | 0.45 | 28% | 39% | 2.59 | 1.01 | >10 |
| 114 | 53% | 28% | 8% | 40% | 0.075 | 0.005 | 0.026 ± 0.009 |
| 115 | 1.35 | 0.14 | 1.24 | 1.11 | 4 | 0.006 | 0.552 ± 0.166 |
| 116 | — | — | 18% | 86% | — | 0.106 | 0.885 ± 0.137 |
| 117 | 10% | 4% | 0% | 12% | 5% | 0.004 | 0.045 ± 0.004 |
| 118 | 0.154 | 0.026 | 0% | 6% | 0.018 | 0.036 | — |
| 119 | 0.623 | 0.14 | 0.64 | 0.54 | 0.12 | 0.004 | — |
| 120 | 31% | 4% | 0.87 | — | 29% | 0.015 | 0.023 ± 0.010 |
| 121 | 0.78 | 0.86 | 2.21 | 47% | 3.86 | 0.032 | — |

TABLE 2-continued

Inhibition of cyclin-dependant kinases and anti-proliferative activity (72 h, GI$_{50}$ μM) of representative compounds

| | CDK inhibition, K$_i$ (μM)/ or residual activity (%) at 10 μM | | | | | | 72 h Growth inhibition GI$_{50}$ (μM) |
|---|---|---|---|---|---|---|---|
| Cmpd | CDK1B | CDK2A | CDK4D1 | CDK6D3 | CDK7H | CDK9T1 | MV4-11 |
| 122 | 1.71 | 1.15 | 71% | 44% | 1.16 | 0.30 | — |
| 123 | 1.53 | 0.30 | 31% | 155 | 0.89 | 0.011 | — |
| 124 | 87% | 34% | — | — | 91% | >5 | >5 |
| 125 | >5 | 3.94 | 100% | 92% | 4.56 | 2.88 | — |
| 126 | 2% | 0.089 | 14% | — | 94% | 0.111 | >5 |
| 127 | 34% | 0% | 32% | — | 39% | 0.045 | — |
| 128 | 45% | 0.706 | 38% | — | 34% | 0.31 | 0.068 ± 0.006 |
| 129 | 42% | 0% | 32% | — | 18% | 0.12 | — |
| 130 | 25% | 23% | 23% | — | 40% | 1.12 | 0.172 ± 0.001 |
| 131 | 29% | 44% | 24% | — | 20% | 0.320 | 0.132 ± 0.059 |
| 132 | 25% | 23% | 16% | — | 40% | 1.12 | 0.012 ± 0.008 |
| 133 | 22% | 40% | 60% | — | 10% | 0.14 | — |
| 134 | 43% | 22% | 11% | — | 28% | 0.12 | — |
| 135 | 61% | 57% | 28% | — | 13% | 1.14 | 0.564 ± 0.047 |
| 136 | 22% | 59% | 48% | — | 36% | 2.77 | 0.297 ± 0.001 |
| 137 | 3% | 0% | 7% | — | 0.040 | 0.003 | <0.01 |
| 138 | 0.076 | 0.111 | 6% | — | 0% | 0.006 | <0.001 |
| 139 | 31% | 4% | 14% | — | 15% | 0.044 | — |
| 140 | 39% | 61% | 65% | — | 0.597 | 0.53 | 0.242 ± 0.132 |
| 141 | 0.532 | 0.064 | 15% | — | 30% | 0.011 | — |
| 142 | 23% | 15% | 8% | — | 39% | 0.025 | 0.064 ± 0.017 |
| 143 | 3% | 4% | 4% | — | 0.088 | 0.108 | 0.003 ± 0.001 |
| 144 | 0.047 | 8% | 20% | — | 0.072 | 0.138 | 0.005 ± 0.003 |
| 145 | 0.222 | 22% | 41% | — | 0.199 | 0.402 | 0.0011 ± 0.001 |
| 146 | 16% | 34% | 34% | — | 0.37 | 1.823 | 0.026 ± 0.003 |
| 147 | 0.334 | 0.015 | 70% | — | 54% | 0.711 | 0.620 ± 0.260 |
| 148 | 27% | 46% | 70% | — | 18% | 0.261 | 0.023 ± 0.007 |
| 149 | 9% | 20% | 3% | — | 0.313 | 0.178 | 0.145 ± 0.001 |
| 150 | 45% | 11% | 21% | — | 0.372 | 0.149 | 0.420 ± 0.020 |
| 151 | 96% | 87% | 93% | — | 94% | >5 | 8.643 ± 0.010 |
| 152 | 34% | 5% | 20% | — | 55% | 0.181 | 2.856 ± 0.290 |
| 153 | 0.632 | 14% | 0% | — | 49% | 0.010 | 9.317 ± 0.730 |
| 154 | 14% | 7% | 3% | — | 37% | 0.022 | >10 |
| 155 | 100% | 100% | 96% | — | 99% | >5 | 7.003 ± 2.030 |
| 156 | 77% | 34% | 51% | — | 80% | >5 | 3.301 ± 0.310 |
| 157 | 69% | 38% | 32% | — | 90% | 0.527 | 2.399 ± 0.090 |
| 158 | 94% | 85% | 92% | — | 98% | 0.185 | >10 |
| 159 | 31% | 11% | 43% | — | 20% | 0.061 | — |
| 160 | 3% | 7% | 0% | — | 0.099 | 0.014 | — |
| 161 | 0.074 | 6% | 3% | — | 0.094 | 0.016 | — |
| 163 | — | 0% | 61% | — | 5% | 4.57 | — |
| 165 | — | 51% | 61% | — | 24% | 0.93 | — |
| 166 | — | 8% | 54% | — | 33% | 1.28 | — |
| 167 | — | 4% | 66% | — | 49% | 0.49 | — |
| 168 | — | 11% | 22% | — | 55% | 0.181 | — |
| 169 | — | 31% | 81% | — | 35% | 1.88 | — |
| 170 | — | 7% | 5% | — | 18% | >5 | — |
| 171 | — | 35% | 47% | — | 65% | >5 | — |
| 172 | — | 2% | 6% | — | 21% | 0.005 | — |

TABLE 3

Antiproliferative activity of representative compounds

| Human cancer cell lines | | 72 h Antiproliferative activity, GI$_{50}$ (μmol/L) ± SD | |
|---|---|---|---|
| Origin | Destination | 7 | 10 |
| Breast | T47D | 0.616 ± 0.086 | 0.834 ± 0.066 |
|  | MCF-7 | 0.218 ± 0.013 | 0.247 ± 0.014 |
|  | MDA-MB-231 | 0.035 ± 0.008 | 0.418 ± 0.123 |
|  | MDA-MB-453 | 0.931 ± 0.269 | 0.049 ± 0.012 |
|  | MDA-MB-468 | 0.080 ± 0.015 | 0.420 ± 0.070 |
| Ovarian | A2780 | 0.274 ± 0.030 | 0.278 ± 0.032 |
| Prostate | PC3 | 0.087 ± 0.040 | 0.289 ± 0.098 |
|  | LNCap | — | 0.202 ± 0.052 |
| Leukaemia | MOLM13 | 0.015 ± 0.006 | 0.019 ± 0.001 |
|  | NB4 | 0.160 ± 0.052 | 0.153 ± 0.051 |
|  | U937 | 0.156 ± 0.061 | 0.156 ± 0.050 |

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

Please note that the following claims are provisional claims only, and are provided as examples of possible claims and are not intended to limit the scope of what may be claimed in any future patent applications based on the present application. Integers may be added to or omitted from the example claims at a later date so as to further define or re-define the invention.

The invention claimed is:
1. A compound of Formula I:

Formula (I)

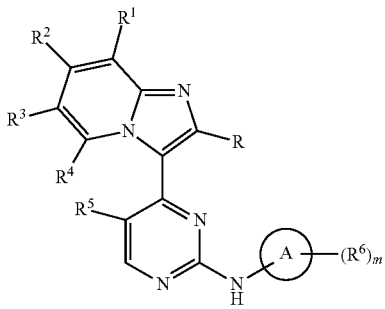

or a pharmaceutically acceptable salt, wherein:

A is a cycloalkyl or heterocycloalkyl, optionally substituted by one or more $R^6$ groups such that m is an integer from 0 to 5 inclusive, and wherein said heterocycloalkyl has 1-2 heteroatoms selected from N, O and S; and wherein R and $R^6$ are each independently selected from the group consisting of H, alkyl, alkyl-$R^7$, cycloalkyl, heterocycloalkyl, aryl, heteroaryl, $CH_2$-heteroaryl, aralkyl, halogen, $NO_2$, CN, $CF_3$, OH, O-alkyl, O-alkyl-$R^7$, O-cycloalkyl, O-heterocycloalkyl, O-aryl, O-heteroaryl, $NH_2$, NH-alkyl, NH-alkyl-$R^7$, NH-cycloalkyl, NH-heterocycloalkyl, NH-aryl, NH-heteroaryl, NH—$R^7$, NHO-aryl, $NHCH_2$-aryl, N-(alkyl)$_2$, N-(cycloalkyl)$_2$, N-(heterocycloalkyl)$_2$, N-(aryl)$_2$, N-(heteroaryl)$_2$, N-(alkyl)($R^7$), N-(cycloalkyl)($R^7$), N-(heterocycloalkyl)($R^7$), N-(aryl)($R^7$), N-(heteroaryl)($R^7$), COOH, $CONH_2$, CONH-alkyl, CONH-aryl, CON-(alkyl)($R^7$), CON(aryl)($R^7$), CON(heteroaryl)($R^7$), CONH—$R^7$, $SO_3H$, $SO_2$-alkyl, $SO_2$-alkyl-$R^7$, $SO_2$-aryl, $SO_2$-aryl-$R^7$, $SO_2NH_2$, $SO_2NH$-$R^7$, CO-alkyl, CO-alkyl-$R^7$, CO-aryl, CO-aryl-$R^7$, CO—$R^7$, and $COOR^7$;

$R^1$, $R^2$, $R^3$, and $R^4$ are each independently selected from the group consisting of H, cycloalkyl, heterocycloalkyl, aryl, heteroaryl, $CH_2$-heteroaryl, aralkyl, O-cycloalkyl, O-heterocycloalkyl, O-aryl, O-heteroaryl, NH-cycloalkyl, NH-heterocycloalkyl, NH-aryl, NH-heteroaryl, NHO-aryl, $NHCH_2$-aryl, N-(cycloalkyl)$_2$, N-(heterocycloalkyl)$_2$, N-(aryl)$_2$, N-(heteroaryl)$_2$, N-(cycloalkyl)($R^7$), N-(heterocycloalkyl)($R^7$), N-(aryl)($R^7$), N-(heteroaryl)($R^7$), CONH-aryl, CON(aryl)($R^7$), CON(heteroaryl)($R^7$), S-(heteroaryl)($R^7$), CONH-aryl, $SO_2$-aryl, $SO_2$-aryl-$R^7$, CO-aryl, and CO-aryl-$R^7$, with the proviso that at least one of $R^1$, $R^2$, $R^3$ and $R^4$ is not H; and wherein $R^7$ is selected from the group consisting of H, alkyl, cycloalkyl, heterocycloalkyl, aryl, heteroaryl, aralkyl, halogen, $NO_2$, CN, $CF_3$, OH, O-alkyl, O-cycloalkyl, O-heterocycloalkyl, O-aryl, O-heteroaryl, $NH_2$, NH-alkyl, NH-cycloalkyl, NH-heterocycloalkyl, NH-aryl, NH-heteroaryl, NH—$R^{10}$, N-(alkyl)$_2$, N-(cycloalkyl)$_2$, N-(heterocycloalkyl)$_2$, N-(aryl)$_2$, N-(heteroaryl)$_2$, COOH, COO-alkyl, $CONH_2$, CONH-alkyl, CONH-aryl, $SO_3H$, $SO_2$-alkyl, $SO_2$-aryl, $SO_2NH_2$, CO-alkyl, CO-aryl;

$R^5$ is selected from alkyl, O-alkyl, CN, and halogen; and wherein said heterocycloalkyl and heteroaryl groups comprise 1-2 heteroatoms selected from N, S and O, and wherein said alkyl, cycloalkyl, heterocycloalkyl, aralkyl, aryl and heteroaryl groups may be optionally substituted with one or more groups selected from halogen, alkyl, CN, OH, O-methyl, O-ethyl, O-$CF_3$, $NH_2$, COOH, $CONH_2$, heterocycloalkyl, CO-heterocycloalkyl, $CF_3$, and $SO_2N(CH_3)_2$.

2. The compound according to claim 1, wherein A is a 5- to 7-membered cycloalkyl or heterocycloalkyl group optionally substituted with one or more $R^6$ groups.

3. The compound according to claim 1, wherein R is H.

4. The compound according to claim 1, wherein R is selected from the group consisting of H, alkyl, cycloalkyl, heterocycloalkyl, aryl, heteroaryl, $CH_2$-heteroaryl, halogen, $NO_2$, $CF_3$, OH, O-alkyl, O—$C_{3-8}$ cycloalkyl, O-aryl, O-heteroaryl, $NH_2$, NH-alkyl, NH-cycloalkyl, NH-heterocycloalkyl, NH-aryl, NH-heteroaryl, NH—$C_{1-3}$O-aryl, NHO-aryl, NHO-heteroaryl, $NHCH_2$-aryl, N(alkyl)$_2$, N(cycloalkyl)$_2$, N(heterocycloalkyl)$_2$, and N-(alkyl)(aryl); wherein said heterocycloalkyl and heteroaryl groups have 1-2 heteroatoms selected from N, S and O, and wherein said alkyl, cycloalkyl, heterocycloalkyl, aralkyl, aryl, and heteroaryl groups may be optionally substituted with one or more groups selected from halogen, alkyl, CN, OH, O-methyl, O-ethyl, O—$HCF_2$, $NH_2$, COOH, $CONH_2$, heterocycloalkyl, CO-heterocycloalkyl, $CF_3$, and $SO_2N(CH_3)_2$.

5. The compound according to claim 1, wherein either or both of $R^1$ and $R^4$ is H.

6. The compound according to claim 1, wherein $R^1$, $R^2$, $R^3$ and $R^4$ are independently selected from the group consisting of H, aryl, heteroaryl, $CH_2$-heteroaryl, NH-aryl, NH-heteroaryl, O-aryl, O-heteroaryl, NH—$C_{1-3}$O-aryl, NHO-aryl, NHO-heteroaryl, $NHCH_2$-aryl, and N-(alkyl)(aryl)(arylaryl); wherein said heteroaryl groups have 1-2 heteroatoms selected from N, S and O, and wherein said aryl and heteroaryl groups may be optionally substituted with one or more groups selected from halogen, alkyl, CN, OH, O-methyl, O-ethyl, O—$HCF_2$, $NH_2$, COOH, $CONH_2$, heterocycloalkyl, CO-heterocycloalkyl, $CF_3$, and $SO_2N(CH_3)_2$; but with the proviso that at least one of $R^1$, $R^2$, $R^3$ and $R^4$ is not H.

7. The compound according to claim 1, wherein $R^2$ or $R^3$ is phenyl.

8. The compound according to claim 1, wherein $R^5$ is methyl or halogen.

9. The compound according to claim 1, wherein $R^6$ is independently selected from the group consisting of H, alkyl, OH, halogen, O-alkyl, $CO_2$-alkyl, COOH, $C_{1-3}$-heterocycloalkyl, $NH_2$, NH-alkyl, NH-cycloalkyl, NH—$R^7$ where $R^7$ is CO(NH-alkyl), $SO_2$-alkyl, NH-alkyl-$R^7$ where $R^7$ is $CF_3$, O-alkyl, CO($NH_2$), $CO_2$-alkyl, N-(alkyl)$_2$, N-(alkyl)($R^7$) where $R^7$ is $SO_2$-alkyl, $SO_2NH_2$, alkyl-$R^7$ where $R^7$ is $CO_2$-alkyl, and COO$R^7$ where $R^7$ is a $C_{1-3}$ alkyl or $C_{1-6}$ alkyl; wherein said heterocycloalkyl and heteroaryl groups have 1-2 two heteroatoms selected from N, S and O, and wherein said alkyl, cycloalkyl, heterocycloalkyl, aralkyl, aryl, and heteroaryl groups may be optionally substituted with one or more groups selected from halogen, alkyl, CN, OH, O-methyl, O-ethyl, O—$HCF_2$, $NH_2$, COOH, $CONH_2$, heterocycloalkyl, CO-heterocycloalkyl, $CF_3$, and $SO_2N(CH_3)_2$.

10. The compound according to claim 1, wherein $R^6$ is independently selected from the group consisting of heterocycloalkyl, $NH_2$, NH—$C_{1-3}$ alkyl, NH—$R^7$ where $R^7$ is CO(NH-alkyl), $SO_2$-$C_{1-3}$ alkyl, or $SO_2NH_2$; wherein said heterocycloalkyl has 1-2 N heteroatoms, and wherein said alkyl and heterocycloalkyl groups may be optionally substituted with one or more groups selected from halogen, alkyl, CN, OH, O-methyl, O-ethyl, O—$HCF_2$, $NH_2$, COOH, $CONH_2$, $CF_3$, and $SO_2N(CH_3)_2$.

11. The compound according to claim 1, wherein $R^6$ is independently selected from the group consisting of azetidine, $NH_2$, NH—$C_{1-3}$ alkyl substituted with O-methyl or O-ethyl, $SO_2$-$C_{1-3}$ alkyl, and $SO_2NH_2$.

12. The compound according to claim 1, wherein m is selected from 1, 2 and 3.

13. The compound according to claim 1, wherein m is 1.

14. The compound according to claim 1, wherein A is cyclohexane, adamantane, tetrahydro-2H-pyran or piperidine optionally substituted with at least one of $R^6$.

15. A pharmaceutical composition or medicament comprising a compound according to claim 1 and a pharmaceutically acceptable carrier, diluent and/or excipient.

16. A method of treating a cancer selected from breast cancer, ovarian cancer, prostate cancer and leukaemia, the method comprising administering to said subject a therapeutically effective amount of a compound according to claim 1 or a pharmaceutically acceptable salt or thereof, optionally in combination with a pharmaceutically acceptable carrier, diluent and/or excipient.

17. A compound selected from the group consisting of:
(1r,4r)-$N^1$-(5-Fluoro-4-(6-((4-fluorobenzyl)amino)imidazo[1,2-a]pyridin-3-yl)pyrimidin-2-yl)cyclohexane-1,4-diamine,
(1r,4r)-$N^1$-(5-Methyl-4-(6-phenylimidazo[1,2-a]pyridin-3-yl)pyrimidin-2-yl)cyclohexane-1,4-diamine,
(1r,4r)-$N^1$-(5-Fluoro-4-(6-((3-fluorophenyl)amino)imidazo[1,2-a]pyridin-3-yl)pyrimidin-2-yl)cyclohexane-1,4-diamine,
(1r,4r)-$N^1$-(5-Fluoro-4-(6-(pyridin-3-yl)imidazo[1,2-a]pyridin-3-yl)pyrimidin-2-yl)cyclohexane-1,4-diamine,
(1r,4r)-$N^1$-(5-Fluoro-4-(6-(3-fluoropyridin-2-yl)imidazo[1,2-a]pyridin-3-yl)pyrimidin-2-yl)cyclohexane-1,4-diamine,
(1r,4r)-$N^1$-(5-Methyl-4-(6-(phenylamino)imidazo[1,2-a]pyridin-3-yl)pyrimidin-2-yl)cyclohexane-1,4-diamine,
(1r,4r)-$N^1$-(5-Methyl-4-(6-(pyridin-3-ylamino)imidazo[1,2-a]pyridin-3-yl)pyrimidin-2-yl)cyclohexane-1,4-diamine,
$N^1$,$N^1$-Dimethyl-$N^4$-(5-Methyl-4-(6-(pyridin-3-ylamino)imidazo[1,2-a]pyridin-3-yl)pyrimidin-2-yl)cyclohexane-1,4-diamine,
$N^1$,$N^1$-dimethyl-$N^4$-(5-Methyl-4-(6-(pyrimidin-5-ylamino)imidazo[1,2-a]pyridin-3-yl)pyrimidin-2-yl)cyclohexane-1,4-diamine,
(1r,4r)-$N^1$-(5-Chloro-4-(7-(pyrimidin-5-ylamino)imidazo[1,2-a]pyridin-3-yl)pyrimidin-2-yl)cyclohexane-1,4-diamine,
3-(2-(((1r,4r)-4-(Aziridin-1-yl)cyclohexyl)amino)-5-methylpyrimidin-4-yl)-N-(pyrimidin-5-yl)imidazo[1,2-a]pyridin-7-amine,
(1r,4r)-$N^1$-(2-Methoxyethyl)-$N^4$-(5-methyl-4-(6-phenylimidazo[1,2-a]pyridin-3-yl)pyrimidin-2-yl)cyclohexane-1,4-diamine,
(1s,4s)-$N^1$-(2-Methoxyethyl)-$N^4$-(5-methyl-4-(6-phenylimidazo[1,2-a]pyridin-3-yl)pyrimidin-2-yl)cyclohexane-1,4-diamine,
(1r,4r)-$N^1$-Ethyl-$N^4$-(5-methyl-4-(6-phenylimidazo[1,2-a]pyridin-3-yl)pyrimidin-2-yl)cyclohexane-1,4-diamine,
(1s,4s)-$N^1$-ethyl-$N^4$-(5-Methyl-4-(6-phenylimidazo[1,2-a]pyridin-3-yl)pyrimidin-2-yl)cyclohexane-1,4-diamine,
N-((1r,4r)-4-(Azetidin-1-yl)cyclohexyl)-5-methyl-4-(6-phenylimidazo[1,2-a]pyridin-3-yl)pyrimidin-2-amine,
N-((1s,4s)-4-(Azetidin-1-yl)cyclohexyl)-5-methyl-4-(6-phenylimidazo[1,2-a]pyridin-3-yl)pyrimidin-2-amine,
5-Fluoro-4-(6-phenylimidazo[1,2-a]pyridin-3-yl)-N-((1r,4r)-4-(pyrrolidin-1-yl)cyclohexyl)pyrimidin-2-amine,
N-((1r,4r)-4-(Azetidin-1-yl)cyclohexyl)-5-fluoro-4-(6-phenylimidazo[1,2-a]pyridin-3-yl)pyrimidin-2-amine,
5-Fluoro-N-(1-(methylsulfonyl)piperidin-4-yl)-4-(6-phenylimidazo[1,2-a]pyridin-3-yl)pyrimidin-2-amine,
N-(1-(Ethylsulfonyl)piperidin-4-yl)-5-fluoro-4-(6-phenylimidazo[1,2-a]pyridin-3-yl)pyrimidin-2-amine,
(1r,4r)-N-Cyclopropyl-4-((5-methyl-4-(6-(pyrimidin-5-ylamino)imidazo[1,2-a]pyridin-3-yl)pyrimidin-2-yl)amino)cyclohexane-1-carboxamide, and
4-((5-fluoro-4-(6-phenylimidazo[1,2-a]pyridin-3-yl)pyrimidin-2-yl)amino)cyclohexane-1-sulfonamide.

18. A method of treating a cancer selected from breast cancer, ovarian cancer, prostate cancer and leukaemia, the method comprising administering to said subject a therapeutically effective amount of a compound according to claim 17 or a pharmaceutically acceptable salt or thereof, optionally in combination with a pharmaceutically acceptable carrier, diluent and/or excipient.

* * * * *